US008361961B2

(12) United States Patent
DeFrees et al.

(10) Patent No.: US 8,361,961 B2
(45) Date of Patent: Jan. 29, 2013

(54) O-LINKED GLYCOSYLATION OF PEPTIDES

(75) Inventors: Shawn DeFrees, North Wales, PA (US);
David A. Zopf, Wayne, PA (US);
Zhi-Guang Wang, Dresher, PA (US);
Henrik Clausen, Holte (DK)

(73) Assignee: BioGeneriX AG, Ulm (DE)

( * ) Notice: Subject to any disclaimer, the term of this patent is extended or adjusted under 35 U.S.C. 154(b) by 1199 days.

(21) Appl. No.: 10/585,385

(22) PCT Filed: Jan. 10, 2005

(86) PCT No.: PCT/US2005/000799
§ 371 (c)(1),
(2), (4) Date: Aug. 12, 2008

(87) PCT Pub. No.: WO2005/070138
PCT Pub. Date: Aug. 4, 2005

(65) Prior Publication Data
US 2009/0169509 A1    Jul. 2, 2009

Related U.S. Application Data

(60) Provisional application No. 60/535,284, filed on Jan. 8, 2004, provisional application No. 60/544,411, filed on Feb. 12, 2004, provisional application No. 60/546,631, filed on Feb. 20, 2004, provisional application No. 60/555,813, filed on Mar. 23, 2004, provisional application No. 60/570,891, filed on May 12, 2004.

(51) Int. Cl.
*A61K 38/14* (2006.01)
*A61K 38/18* (2006.01)
(52) U.S. Cl. ........................ 514/7.6; 514/20.9
(58) Field of Classification Search .................. None
See application file for complete search history.

(56) References Cited

U.S. PATENT DOCUMENTS

| | | | |
|---|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,496,689 A | 1/1985 | Mitra |
| 4,565,653 A | 1/1986 | Ives et al. |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,925,796 A | 5/1990 | Bergh et al. |
| 5,032,519 A | 7/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,169,933 A | 12/1992 | Anderson et al. |
| 5,182,107 A | 1/1993 | Friden |
| 5,194,376 A | 3/1993 | Kang |
| 5,202,413 A | 4/1993 | Spinu |
| 5,219,564 A | 6/1993 | Zalipsky et al. |
| 5,281,698 A | 1/1994 | Nitecki |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot et al. |
| 5,369,017 A | 11/1994 | Wong et al. |
| 5,374,541 A | 12/1994 | Wong et al. |
| 5,374,655 A | 12/1994 | Kashem et al. |
| 5,399,345 A | 3/1995 | Schumacher et al. |
| 5,405,753 A | 4/1995 | Brossmer et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,583,042 A | 12/1996 | Roth |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |

(Continued)

FOREIGN PATENT DOCUMENTS

CA    2324616 A1    9/1999
CA    2500389 A1    4/2004

(Continued)

OTHER PUBLICATIONS

Alpin, et al., "Preparation, Properties, and Applications of Carbohydrate Conjugates of Proteins and Lipids," *CRC Crit. Rev. Biochem.*, pp. 259-306 (1981).

(Continued)

*Primary Examiner* — Christina Bradley
(74) *Attorney, Agent, or Firm* — Leydig, Voit & Mayer, Ltd.

(57) ABSTRACT

The present invention provides polypeptides that include an O-linked glycosylation site that is not present in the wild-type peptide. The polypeptides of the invention include glycoconjugates in which a species such as a water-soluble polymer, a therapeutic agent of a biomolecule is covalently linked through an intact O-linked glycosyl residue to the polypeptide. Also provided are methods of making the peptides of the invention and methods, pharmaceutical compositions containing the peptides and methods of treating, ameliorating or preventing diseased in mammals by administering an amount of a peptide of the invention sufficient to achieve the desired response.

15 Claims, 23 Drawing Sheets

U.S. PATENT DOCUMENTS

| | | |
|---|---|---|
| 5,705,367 A | 1/1998 | Gotschlich |
| 5,716,812 A | 2/1998 | Withers et al. |
| 5,723,121 A | 3/1998 | Takenaga et al. |
| 5,728,554 A | 3/1998 | Bayer et al. |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,874,075 A | 2/1999 | Collins et al. |
| 5,876,980 A | 3/1999 | DeFrees et al. |
| 5,922,577 A | 7/1999 | DeFrees et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,342,382 B1 | 1/2002 | Gotschlich |
| 6,348,558 B1 | 2/2002 | Harris et al. |
| 6,361,977 B1 * | 3/2002 | Bauer et al. .................. 435/69.52 |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,063,015 B2 | 11/2011 | DeFrees et al. |
| 8,207,112 B2 | 6/2012 | Hinderer et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | DeFrees et al. |
| 2005/0100982 A1 | 5/2005 | DeFrees et al. |
| 2005/0106658 A1 | 5/2005 | DeFrees et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0030521 A1 | 2/2006 | DeFrees et al. |
| 2006/0035224 A1 | 2/2006 | Johansen |
| 2006/0111279 A1 | 5/2006 | DeFrees et al. |
| 2006/0177892 A1 | 8/2006 | DeFrees |
| 2006/0182714 A1 | 8/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |

| | | |
|---|---|---|
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |
| 2008/0015142 A1 | 1/2008 | DeFrees et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |

FOREIGN PATENT DOCUMENTS

| | | |
|---|---|---|
| CA | 2511814 A1 | 7/2004 |
| DE | 19852729 A1 | 5/2000 |
| EP | 0370205 A2 | 5/1990 |
| EP | 0459630 A2 | 12/1991 |
| EP | 0474313 A2 | 3/1992 |
| EP | 0585109 A2 | 3/1994 |
| EP | 0605963 A2 | 7/1994 |
| EP | 1270642 A1 | 1/2003 |
| EP | 1428878 A1 | 6/2004 |
| JP | H03-503759 A | 8/1991 |
| JP | H10-307356 A | 11/1998 |
| JP | 2001-519784 A | 10/2001 |
| RU | 2005/101348 A | 8/2005 |
| WO | WO 87/00056 | 1/1987 |
| WO | WO 87/00056 A | 1/1987 |
| WO | WO 87/05330 | 9/1987 |
| WO | WO 89/06546 A1 | 7/1989 |
| WO | WO 89/10134 A1 | 11/1989 |
| WO | WO 90/07572 A1 | 7/1990 |
| WO | WO 90/08164 A1 | 7/1990 |
| WO | WO 90/08823 A1 | 8/1990 |
| WO | WO 90/13540 | 11/1990 |
| WO | WO 91/14697 A1 | 10/1991 |
| WO | WO 92/01055 A1 | 1/1992 |
| WO | WO 92/18135 A1 | 10/1992 |
| WO | WO 92/22310 A1 | 12/1992 |
| WO | WO 93/15189 | 8/1993 |
| WO | WO 94/04193 | 3/1994 |
| WO | WO 94/05332 A2 | 3/1994 |
| WO | WO 94/09027 | 4/1994 |
| WO | WO 94/15625 | 7/1994 |
| WO | WO 94/17039 | 8/1994 |
| WO | WO 94/18247 | 8/1994 |
| WO | WO 94/28024 A1 | 12/1994 |
| WO | WO 95/02421 A1 | 1/1995 |
| WO | WO 95/04278 A1 | 2/1995 |
| WO | WO 96/11953 A1 | 4/1996 |
| WO | WO 96/21468 A1 | 7/1996 |
| WO | WO 96/21469 | 7/1996 |
| WO | WO 96/32491 A1 | 10/1996 |
| WO | WO 96/36357 A1 | 11/1996 |
| WO | WO 96/40731 | 12/1996 |
| WO | WO 96/40881 A1 | 12/1996 |
| WO | WO 97/05330 A1 | 2/1997 |
| WO | WO 98/05363 A2 | 2/1998 |
| WO | WO 98/31826 | 7/1998 |
| WO | WO 98/41562 A1 | 9/1998 |
| WO | WO 98/51784 A1 | 11/1998 |
| WO | WO 98/58964 A1 | 12/1998 |
| WO | WO 99/00150 A2 | 1/1999 |
| WO | WO 99/14259 | 3/1999 |
| WO | WO 99/22764 A1 | 5/1999 |
| WO | WO 99/34833 | 7/1999 |
| WO | WO 99/45964 | 9/1999 |
| WO | WO 99/48515 A1 | 9/1999 |
| WO | WO 99/55376 A1 | 11/1999 |
| WO | WO 00/23114 A2 | 4/2000 |
| WO | WO 00/26354 A1 | 5/2000 |
| WO | WO 00/65087 A1 | 11/2000 |
| WO | WO 01/02017 A2 | 1/2001 |
| WO | WO 01/05434 A2 | 1/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/88117 A2 | 11/2001 |
| WO | WO 02/02597 A2 | 1/2002 |
| WO | WO 02/02764 A2 | 1/2002 |
| WO | WO 02/13843 A2 | 2/2002 |
| WO | WO 02/13873 A2 | 2/2002 |
| WO | WO 02/44196 A1 | 6/2002 |

| WO | WO 02/053580 A2 | 7/2002 |
| --- | --- | --- |
| WO | WO 02/074806 A2 | 9/2002 |
| WO | WO 02/092619 A2 | 11/2002 |
| WO | WO 03/017949 A2 | 3/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 2004/000366 A1 | 12/2003 |
| WO | WO 2004/009838 A2 | 1/2004 |
| WO | WO 2004/010327 A2 | 1/2004 |
| WO | WO 2004/022004 A2 | 3/2004 |
| WO | WO 2004/033651 A2 | 4/2004 |
| WO | WO 2004/046222 A1 | 6/2004 |
| WO | WO 2004/067566 A1 | 8/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/096148 A2 | 11/2004 |
| WO | WO 2004/099231 A2 | 11/2004 |
| WO | WO 2004/103275 A2 | 12/2004 |
| WO | WO 2005/012484 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/091944 A2 | 10/2005 |
| WO | WO 2005/121331 A2 | 12/2005 |
| WO | WO 2006/010143 A2 | 1/2006 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2007/022512 A2 | 2/2007 |
| WO | WO 2007/056191 A2 | 5/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Bennett, et al., "A Novel Human UDP-*N*-acetyl-D-galactosamine: Polypeptide *N*Acetylgalactosaminyltransferase, GalNAc-T7, with Specificity for Partial GalNAc-glycosylated Acceptor Substrates," *FEBS Letters* 460:226-230 (1999).

Bennett, et al.,"Cloning of a Human UDP-*N*-Acetyl-α-D-Galactosamine: Polypeptide *N*-Acetylgalactosaminyltransferase That Complements Other GalNAc-Transferases in Complete *O*-Glycosylation of the MUC1 Tandem Repeat," *J. Biol. Chem.*, 273(46):30472-30481 (1998).

Bhadra, et al., "Pegnology: A Review of PEG-ylated Systems," *Pharmazie*, 57:5-29 (2002).

Bouizar, et al., Bouizar, et al., "Purification and Characterization of Calcitonin Receptors in Rat Kidney Membranes by Covalent Cross-linking Techniques," *Eur. J. Biochem.*, 155:141-147 (1986).

Browning, et al., "Studies on the Differing Effects of Tumor Recrosis Factor and Lymphotoxin on the Growth of Several Human Tumor Lines," *J. Immunol.*, 143-1859-1867 (1989).

Chaffee, et al., "IgG Antibody Response to Polyethylene Glycol-modified Adenosine Deaminase in Patients with Adenosine Deaminase Deficiency," *J. Clin. Invest.*, 89:1643-1651 (May 1992).

Charter, et al., "Biosynthetic Incorporation of Unnatural Sialic Acids Into Polysialic Acid on Neural Cells," *Glycobiology*, 10(10): 1049-1056 (2000).

Chrisey et al., "Covalent Attachment of Synthetic DNA to Self-assembled Monolayer Films," *Nucleic Acids Research*, 24(15):3031-3039 (1996).

Cohn, et al., "Biodegradable PEO/PLA Block Copolymers," *J. Biomed. Mater. Res.*, 22:993-1009 (1988).

Delgado, et al., "The Uses of Properties of PEG-Linked Proteins," *Critical Reviews in Therapeutic Drug Carrier Systems*, 9(3,4):249-304 (1992).

Dunn, et al., "Polymeric Drugs and Drug Delivery Systems," *ACS Symposium Series 469, Americal Chemical Society* (1991).

Edge, et al., "Deglycosylation of Glycoproteins by Trifluoromethanesulfonic Acid," *Anal. Biochem.*, 118:131-137 (1981).

Hagen, et al., "Cloning and Characterization of a Ninth Member of the UDP-GalNAc:Polypeptide *N*-Acetylgalactosaminyltransferase Family, ppGaNTase-T9," *J. Biol. Chem.*, 276(20): 17395-17404 (2001).

Harris, Milton J., "Laboratory Synthesis of Polyethylene Glycol Derivatives," *Macronol. Chem. Phys.*, C25(3):325-373 (1985).

Harris, Milton J., "Poly(ethylene Glycol Chemistry; Biotechnical and Biomedical Applications," *Plenum Press*, New York (1992).

Harris, et al., "Poly(ethylene Glycol): Chemistry and Biological Applications," *ACS Symposium Series No. 680, American Chemical Society* (1997).

Hassan, et al., "The Lectin Domain of UDP-*N*-acetyl-D-galactosamine: Polypeptide *N*-acetylgalactosaminyltransferase-T4 Directs Its Glycopeptide Specificities," *J. Biol. Chem.*, 275:38197-38205 (2000).

Hassan, et al., "16 Control of Mucin-Type *O*-Glycosylation: *O*-Glycan Occupancy is Directed by Substate Specificities of Polypeptide GalNAc-Transferases," *Carbohydrates in Chemistry and Biology*, Part II, vol. 3, pp. 273-292 (2000).

Hermanson, Greg T., "Bioconjugate Techniques," *Academic Press*, San Diego, (1996).

Herscovics, et al.., "Glycoprotein Biosynthesis in Yeast," *FASEB J*, 7:540-550 (1993).

Hounsell, et al., "O-linked Protein Glycosylation Structure and Function," *Glycoconj. J*, 13:19-26 (1996).

Joshi, et al., "ATP Synthase Complex from Bovine Heart Mitochondria," *J. Biol. Chem.*, 265:14518-14525 (1990).

Jung, et al., "Crosslinking of Platelet Glycoprotein Ib by *N*-Succinimidy1(4-Azidophenyldithio) Propionate and 3,3'-Dithiobis (Sulfosucdinimidyl Propionate)," *Biochimica et Biophysica Acta*, 761:152-162 (1983).

Katre, et al., "Chemical Modification of Recombinant Interleukin 2 by Polyethylene Glycol Increases Its Potency in the Murine Meth A Sarcoma Model," *Proc. Natl. Acad. Sci. USA*, 84:1487-1491 (Mar. 1987).

Keana, et al., "New Reagents for Photoaffinity Labeling: Synthesis and Photolysis of Functionalized Perfluorophenyl Azides," *J. Org. Chem.*, 55:3640-3647 (1990).

Keppler, et al., "Biochemical Engineering of the *N*-acyl Side Chain of Sialic Acid: Biological Implications," *Glycobiology*, 11(2):11R-18R (2001).

Kitamura, et al., "Polyethylene Glycol Modification of the Monoclonal Antibody A7 Enhances its Tumor Localization," *Biochem. Biophys. Res. Commun.*, 171(3):1387-1394 (Sep. 28, 1990).

Kodama, et al., "Synthesis of UDP-6-Deoxy- and -6-Fluoro-D-galactoses and Their Enzymatic Glycosyl Transfer to Mono-and Biantennary Carbohydrate Chains," *Tetrahedron Lett.* 34(40):6419-6422 (1993).

Kornfield, et al., "Assembly of Asparagine-linked Oligosaccharides," *Ann Rev Biochem*, 54:631-664 (1985).

Kukuruzinska, et al., "Protein Glycosylation in Yeast: Transcript Heterogeneity of the ALG7 Gene," *Proc. Natl. Acad. Sci. USA*, 84:2145-2149 (1987).

Langer, Robert, "New Methods of Drug Delivery," *Science*, 249:1527-1533 (1990).

Lougheed, et al., "Glycosyl Fluorides Can Function as Substrates for Nucleotide Phosphosugar-dependent Glycosyltransferases," *J. Biol. Chem.*, 274:37717-37722 (1999).
Müller, et al., "Localization of O-Glycosylation Sites on Glycopeptide Fragments from Lactation-associated MUC1," *J. Biol. Chem.*, 272:24780-24793 (1997).
Müller, et al., "High Density O-Glycosylation on Tandem Repeat Peptide from Secretory MUC1 of T47D Breast Cancer Cells," *J. Biol. Chem.*, 274:18165-18172 (1999).
Park, et al., "Characterization of the Cell Surface Receptor for a Multi-lineage Colony-stimulating Factor (CSF-2α)," *J. Biol. .Chem.*, 261:205-210 (1986).
Pyatak, et al., "Preparation of a Polyethylene Glycol: Superoxide Dismutase Adduct, and an Examination of its Blood Circulating Life and Anti-Inflammatory Activity," *Res. Commun. Chem. Pathol. Pharmacol.*, 29(1):2-16 (Jul. 1980).
Scouten, William H., "[2] A Survey of Enzyme Coupling Techniques," *Methods in Enzymology*, 135:30-65 (1987).
Shen, et al.; "Cis-aconityl Spacer Between Daunomycin and Macromolecular Carriers: A Model of pH-Sensitive Linkage Releasing Drug From a Lysosomotropic Conjugate," *Biochem. Biophys. Res. Commun.*, 102(3):1048-1054 (Oct. 15, 1981).
Sojar, et al., "A Chemical Method for the Deglycosylation of Proteins," *Arch. Biochem. Biophys.*, 259(1):52-57 (1987).
Stemmer, Willem P. C., "Rapid Evolution of a Protein in vitro by DNA Shuffling," *Letters to Nature*, 370:389-391 (1994).
Stemmer, William P. C., "DNA Shuffling by Random Fragmentation and Reassembly: In vitro Recombination for Molecular Evolution," *Proc. Natl. Acad. Sci. USA*, 91:10747-10751 (Oct. 1994).
Takeda, et al., "GPI-anchor Biosynthesis," *Trends Biochem. Sci.*, 20:367-371 (1995).
Tanner, et al., "Protein Glycosylation in Yeast," *Biochim. Biophys. Acta.*, 906:81-91 (1987).
Tenno, et al., "The Lectin Domain of UDP-GalNAc: Polypeptide N-Acetylgalactosaminyltransferase 1 is Involved in O-Glycosylation of a Polypeptide with Multiple Acceptor Sites," *J. Biol. Chem.*, 277(49):47088-47096 (2002).
Thotakura, et al., "[28] Enzymatic Deglycosylation of Glycoproteins," *Meth. Enzymol.*, 138:350-359 (1987).
Udenfriend, "How Glycosyl-phosphatidylinositol-anchored Membrane Proteins are Made," *Ann. Rev. Biochem.*, 64:593-591 (1995).
Veronese, et al., "Surface Modification of Proteins: Activation of Monomethoxy-polyethylene Glycols by Phenylchloroformates and Modification of Ribonuclease and Superoxide Dismutase," *App. Biochem. Biotech.*, 11:141-152.
Vocadlo, et al., "Glycosidase-catalysed Oligosaccharide Synthesis," *Carbohydrates in Chemistry and Biology*, Part I, vol. 2, pp. 723-844 (2000).
Wong, et al., "Chemical Crosslinking and the Stabilization of Proteins and Enzymes," *Enzyme Microb. Technol.*, 14:866-874 (1992).
Yamada, et al., "Selective Modification of Aspartis Acid-101 in Lysozyme by Carbodiimide Reaction," *Biochemistry*, 20:4836-4842 (1981).
Younes, et al., "Morphological Study of Biodegradable PEO/PLA block Copolymers," *J. Biomed. Mater. Res.*, 21:1301-1316 (1987).
Zalipsky, Samuel, "Functionalized Poly(ethylene glycol) for Preparation of Biologically Relevant Conjugates," *Bioconjugate Chem.*, 6:150-165 (1995).
Zarling, et al., "Mapping of Lymphocyte Surface Polypeptide Antigens by Chemical Cross-linking with Bsocoes," *J. Immunol.*, 124(2):913-920 (1980).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.

Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4,2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated 27 Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.

Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Abeijon et al.,"3' -0-(4-Benzoyl)benzoylcytidine 5'-Triphosphate A Substrate and Photoaffinity Label for Cmp-N-Acetylneuraminic Acid Synthetase," *J. Biol. Chem.*, 261(24): 11374-11377 (1986).
Abuchowski et al., "Alteration of Immunological Properties of Bovine Serum Albumin by Covalent Attachment of Polyethylene Glycol," *J. Biol. Chem.*, 252(11): 3578-3581 (1977).
Abuchowski et al., "Effect of Covalent Attachment of Polyethylene Glycol on Immunogenicity and Circulating Life of Bovine Liver Catalase," *J. Biol. Chem.*, 252(11): 3582-3586 (1977).
Abuchowski et al.,"Cancer Therapy With Chemically Modified Enzymes. I. Antitumor . Properties of Polyethylene Glycol-Asparaginase Conjugates," *Cancer Biochem. Biophys.*, 7(2): 175-186 (1984).
Adelhorst et al.,"Structure-Activity Studies of Glucagon-like Peptide-1," *J. Biol. Chem.*, 269(9): 6275-6278 (1994).
Ailor et al., "N-Glycan Patterns of Human Transferrin Produced in *Trichoplusia Ni* Insect Cells: Effects of Mammalian Galactosyltransferase," *Glycobiology*, 10(8): 837-847 (2000).
Alam et al., "Expression and Purification of a Mutant Human Growth Hormone That Is Resistant to Proteolytic Cleavage by Thrombin, Plasmin and Human Plasma In Vitro," *J. Biotechnol.*, 65(2-3): 183-190 (1998).
Allegre et al., "Cholesterol Removal by Nanofiltration: Applications in Nutraceutics and Nutritional Supplements," *J. Memb. Sci.*, 269(1-2): 109-117 (2006).
Altmann et al., "Insect Cells As Hosts for the Expression of Recombinant Glycoproteins," *Glycoconj. J.*, 16(2): 109-123 (1999).
Amersham Pharmacia Biotech, "Hydrophobic Interaction Chromatography: Principles and Methods," 104 pp. (2000).
Aplin et al., "Preparation, Properties, and Applications of Carbohydrate Conjugates of Proteins and Lipids," *CRC Crit. Rev. Biochem.*, 10(4): 259-306 (1981).
Arslan et al., "Mobilization of Peripheral Blood Stem Cells," *Transf. Apher. Sci.*, 37: 179-185 (2007).
Barrios et al., "Length of the Antibody Heavy Chain Complementarity Determining Region 3 As A Specificity~Determining Factor," *J. Mol. Recognit.*, 17(4):332-338 (2004).
Beauchamp et al., "A New Procedure for the Synthesis of Polyethylene Glycol-Protein Adducts; Effects on Function, Receptor Recognition, and Clearance of Superoxide Dismutase, Lactoferrin, and α 2-Macroglobulin," *Anal. Biochem.*, 131(1): 25-33 (1983).
Bedard et al., "Maximization of Recombinant Protein Yield in the Insect Cel/baculovirus System By One-Time Addition of Nutrients to High-Density Batch Cultures," *Cytotechnology*, 15(1-3):129-138 (1994).
Berger et al., "Preparation of Polyethylene Glycol-Tissue Plasminogen Activator Adducts That Retain Functional Activity: Characteristics and Behavior in Three Animal Species." *Blood*, 71(6): 1641-1647 (1988).
Berg-Fussman et al., "Human Acid ,B-Glucosidase N-Glycosylation Site Occupancy and the Effect of Glycosylation on Enzymatic Activity," *J. Biol. Chem.*, 268(20): 14861-14866 (1993).
Bhatia et al., "Use of Thiol-Terminal Silanes and Heterobifunctional Crosslinkers for Immobilization of Antibodies on Silica Surfaces," *Anal. Biochem.*, 178(2): 408-413 (1989).

Bickel et al., "Delivery of Peptides and Proteins Through the Blood-Brain Barrier,"*Adv. Drug Deliv. Rev.*, 46(1-3): 247-279 (2001).

Bijsterbosch et al., "Quantitative analysis of the targeting of mannose-terminal glucocerebrosidase: Predominant uptake by liver endothelial cells," *Eur. J. Biochem.*, 237(2): 344-349 (1996).

Bjoern et al., "Human Plasma and Recombinant Factor VII. Characterization of O-Glycosylations At Serine Residues 52 and 60 and Effects of Site-Directed Mutagenesis of Serine 52 to Alanine,"*J. Biol. Chem.*, 266(17): 11051-11057 (1991).

Boccu et al., "Coupling of Monomethoxypolyethyleneglycols to Proteins Via Active Esters," *Z. Naturforsch.*, 38c: 94-99 (1983).

Boime et al., "Glycoprotein Hormone Structure-Function and Analog Design," *Recent Prog. Horm. Res.*, 54: 271-289 (1999).

Boissel et al., "Erythropoietin Structure-Function Relationships: Mutant Proteins That Test a Model of Tertiary Structure," *J. Biol. Chem.*, 268(21): 15983-15993 (1993).

Bork et al., "Go Hunting in Sequence Databases But Watch Out for the Traps," *Trends Genet.*, 12(10): 425-427 (1996).

Bork, "Powers and Pitfalls in Sequence Analysis: The 70% Hurdle," *Genome Res.*, 10(4): 398-400 (2000).

Boyd et al., "The Effect of the Removal of Sialic Acid, Galactose and Total Carbohydrate on the Functional Activity of Campath-1H,"*Mol. Immunol.*, 32(17-18): 1311-1318 (1995).

Brenner, "Errors in Genome Annotation," *Trends Genet.*, 15(4): 132-133 (1999).

Brockhausen et al., "Glycoproteins and Their Relationship to Human Disease," *Acta Anatomica*, 161: 36-78 (1998).

Brockhausen et al., "Enzymatic Basis for Sialyl-Tn Expression in Human Colon Cancer Cells," *Glycoconj. J.*, 15: 595-603 (1998).

Broun et al., "Catalytic Plasticity of Fatty Acid Modification Enzymes Underlying Chemical Diversity of Plant Lipids," *Science*, 282(5392): 1315-1317 (1998).

Broxmeyer et al., "Rapid Mobilization of Murine and Human Hematopoietic Stem and Progenitor Cells With AMD3100, A CXCR4 Antagonist," *J. Exp. Med.*, 201(8): 1307-1318 (2005).

Brumeanu et al., "Enzymatically Mediated, Glycosidic Conjugation of Immunoglobulins With Viral Epitopes," *J. Immunol. Meth.*, 183: 185-197 (1995).

Bückmann et al., "Functionalization of Poly(Ethylene Glycol) and Monomethoxy-Poly(Ethylene Glycol)," *Makromol. Chem.*, 182(5): 1379-1384 (1981).

Burns et al., "Purification and Characterization of the Yeast-Expressed Erythropoietin Mutant Epo (R103A), A Specific Inhibitor of Human Primary Hematopoietic Cell Erythropoiesis," *Blood*, 99(12): 4400-4405 (2002).

Butnev et al., "Hormone-Specific Inhibitory Influence of Alpha-Subunit Asn56 Oligosaccharide on In Vitro Subunit Association and Follicle-Stimulating Hormone Receptor Binding of Equine Gonadotropins," *Biol. Reprod.*, 58(2): 458-469 (1998).

Byun et al., "Binding Kinetics of Thrombin and Antithrombin III With Immobilized Heparin Using a Spacer," *ASAIO J.*, 38(3): M649-M653 (1992).

Cantin et al., "Polyethylene Glycol Conjugation At Cys232 Prolongs The Half-Life of Alpha1 Proteinase Inhibitor," *Am. J. Respir. Cell Mol. Biol.*, 27(6): 659-665 (2002).

Capoccia et al., "G-Csf and Amd3100 Mobilize Monocytes Into the Blood That Stimulate Angiogenesis In Vivo Through a Paracrine Mechanism," *Blood*, 108(7): 2438-2445 (2006).

Casares et al., "Antigen-Specific Downregulation of T Cells by Doxorubicin Delivered Through a Recombinant MHC II-Peptide Chimera," *Nat. Biotechnol.*, 19(2): 142-147 (2001).

Cashen et al., "Mobilizing Stem Cells From Normal Donors: Is It Possible to Improve Upon G-CSF," *Bone Marrow Trans.*, 39: 577-588 (2007).

Chern et al., "Structural Role of Amino Acids 99-110 in Recombinant Human Erythropoietin," *Eur. J. Biochem.*, 202(2): 225-229 (1991).

Chiba et al., "Cloning and Expression of the Carboxypeptidase Gene From Aspergillus Saitoi and Determination of the Catalytic Residues by Site-Directed Mutagenesis," *Biochem. J.*, 308(2): 405-409 (1995).

Clark et al., "Long-Acting Growth Hormones Produced by Conjugation With Polyethylene Glycol," *J. Biol. Chem.*, 271(36): 21969-21977 (1996).

Cointe et al., "Unusual N-Glycosylation of A Recombinant Human Erythropoietin Expressed in a Human Lymphoblastoid Cell Line Does Not Alter Its Biological Properties," *Glycobiology*, 10(5): 511-519 (2000).

Conradt et al., "Structure of the Carbohydrate Moiety of Human Interferon-Beta Secreted by a Recombinant Chinese Hamster Ovary Cell Line," *J. Biol. Chem.*, 262(30): 14600-14605 (1987).

Cope et al., "Molecular Cloning of a Gene Involved in Lipooligosaccharide Biosynthesis and Virulence Expression by Haemophilus Influenzae Type B," *Mol. Microbiol.*, 5(5): 1113-1124 (1991).

Copeland, "Enzymes: A Practical Introduction to Structure, Mechanism and Data Analysis" 2nd ed., Wiley-VCH, New York, pp. 146-150 (2000).

Costa et al., "Stable Expression of the Golgi Form and Secretory Variants of Human Fucosyltransferase III From BHK-21 Cells. Purification and Characterization of an Engineered Truncated Form From the Culture Medium," *J. Biol. Chem.*, 272(17): 11613-11621 (1997).

Crout et al., "Glycosidases and Glycosyl Transferases in Glycoside and Oligosaccharide Synthesis," *Curr. Opin. Chem. Biol.*, 2(1): 98-111 (1998).

Culajay et al., "Thermodynamic Characterization of Mutants of Human Fibroblast Growth Factor 1 With an Increased Physiological Half-Life," *Biochem.*, 39: 7153-7158 (2000).

Deacon, "Therapeutic Strategies Based on Glucagon-Like Peptide 1," *Diabetes*, 54: 2181-2189 (2004).

Defrees et al., "Glycopegylation of Recombinant Therapeutic Proteins Produced in *Escherichia coli*," *Glycobiology*, 16(9): 833-843 (2006).

Delgado et al., "Coupling of Poly(Ethylene Glycol) to Albumin Under Very Mild Conditions by Activation With Tresyl Chloride: Characterization of the Conjugate by Partitioning in Aqueous Two-Phase Systems," *Biotechnol. Appl. Biochem.*, 12(2): 119-128 (1990).

De Vries et al, "Acceptor Specificity of Different Length Constructs of Human Recombinant Alpha 1,3/4-Fucosyltransferases: Replacement of the Stem Region and the Transmembrane Domain of Fucosyltransferase V by Protein A Results in an Enzyme With GDP-Fucose Hydrolyzing Activity," *J. Biol. Chem.*, 270(15): 8712-8722 (1995).

De Vries et al., "Acceptor Specificity of GDP-Fuc:Gal Beta 1→4glcnac-R Alpha 3-Fucosyltransferase VI (Fuct VI) Expressed in Insect Cells As Soluble, Secreted Enzyme," *Glycobiology*, 7(7): 921-927 (1997).

Dinter et al., "Glycosylation Engineering in Chinese Hamster Ovary Cells Using Tricistronic Vectors," *Biotechnol. Lett.*, 22(1): 25-30 (2000).

Doerks et al., "Protein Annotation: Detective Work for Function Prediction," *Trends Genet.*, 14(6): 248-250 (1998).

Douglas et al., "Polymer-Supported Solution Synthesis of Oligosaccharides," *J. Am. Chem. Soc.*, 113(13): 5095-5097 (1991).

Dubé et al., "Glycosylation At Specific Sites of Erythropoietin Is Essential for Biosynthesis, Secretion, and Biological Function," *J. Biol. Chem.*, 263(33): 17516-17521 (1988).

Dumas et al., "Enzymatic Synthesis of Sialyl Le$^x$ and Derivatives Based on a Recombinant Fucosyltransferase," *Bioorg. Med. Chem. Lett.*, 1(8): 425-428 (1991).

Durieux et al., "Synthesis of Biotinylated Glycosulfopeptides by Chemoselective Ligation," *Tetrahedron Lett.*, 42(12): 2297-2299 (2001).

Dwek et al., "Glycobiology: 'The Function of Sugar in the Igg Molecule'," *J. Anat.*, 187(Pt. 2): 279-292 (1995).

Eavarone et al., "Targeted Drug Delivery to C6 Glioma by Transferrin-Coupled Liposomes," *J. Biomed. Mater. Res.*, 51(1): 10-14 (2000).

Elhalabi et al., "Synthesis and Applications for Unnatural Sugar Nucleotides,"*Curr. Med. Chem.*, 6(2): 93-116 (1999).

Espuelas et al., "Synthesis of an Amphiphilic Tetraantennary Mannosyl Conjugate and Incorporation Into Liposome Carriers," *Bioorg. Med. Chem. Lett.*, 13(15): 2557-2560 (2003).

Fairhall et al., "Growth Hormone (GH) Binding Protein and GH Interactions In Vivo in the Guinea Pig," *Endocrinology*, 131(4): 1963-1969 (1992).

Fan et al., "Detailed Studies on Substrate Structure Requirements of Glycoamidases A and F," *J. Biol. Chem.*, 272(43): 27058-27064 (1997).

Feldman et al., "Engineering N-Linked Protein Glycosylation with Diverse O Antigen Lipopolysaccharide Structures in *Escherichia Coli,*" *Proc. Natl. Acad. Sci. USA*, 102(8): 3016-3021 (2005).

Felix et al., "Synthesis of Symmetrically and Asymmetrically Branched Pegylating Reagents," *J. Peptide Res.*, 63: 85-90 (2004).

Fibi et al., "N- and O-glycosylation Muteins of Recombinant Human Erythropoietin Secreted From BHK-21 Cells," *Blood*, 85(5): 1229-1236 (1995).

Fischer et al., "Recombinant Coagulation Factor IX: Glycosylation Analysis and In Vitro Conversion into Human-Like Sialylation Pattern," *Thromb. Res.*, 89(3): 147-150 (1998).

Flomenberg et al., "The Use of AMD3100 plus G-CSF for Autologous Hematopoietic Progenitor Cell Mobilization is Superior to G-CSF Alone," *Blood*, 106(5): 1867-1874 (2005).

Flynn et al., "Campath-1H Monoclonal Antibody Therapy," *Curr. Opin. Oncol.*, 12(6): 574-581 (2000).

Francis et al.,"PEGylation of Cytokines and other Therapeutic Protiens and Peptides: the Importance of Biological Optimisation of Coupling Techniques," *Intl. J. Hematol.*, 68(1): 1-18 (1998).

Fritz et al., "The Beginnings of Mucin Biosynthesis: the Crystal Structure of UDP-GalNAc:Polypeptide Alpha-N-Acetylgalactosaminyltransferase-T1," *Proc. Natl. Acad. Sci. USA*, 101(43): 15307-15312 (2004).

Fritz et al., "Dynamic Association Between the Catalytic and Lectin Domains of Human UDP-Galnac:Polypeptide Alpha-N-Acetylgalactosaminyltransferase-2," *J. Biol. Chem.*, 281(13): 8613-8619 (2006).

Garnett et al., "Targeted Drug Conjugates: Principles and Progress," *Adv. Drug Deliv. Rev.*, 53(2): 171-216 (2002).

Gatot et al., "Conservative Mutations in the Immunosuppressive Region of the Bovine Leukemia Virus Transmembrane Protein Affect Fusion But Not Infectivity In Vivo," *J. Biol. Chem.*, 273(21): 12870-12880 (1998).

Ge et al., "Cloning and Heterologous Expression of an Alpha1,3-Fucosyltransferase Gene from the Gastric Pathogen Helicobacter Pylori," *J. Biol. Chem.*, 272(34): 21357-21363 (1997).

GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).

Gervais et al., "Glycosylation of Human Recombinant Gonadotrophins: Characterization and Batch-To-Batch Consistency," *Glycobiology*, 13(3): 179-189 (2003).

Gilbert et al., "Effect of Lipids on Insect Cell Growth and Expression of Recombinant Proteins in Serum-Free Medium," *Cytotechnology*, 22(1-3): 211-216 (1996).

Gillis et al., "Production of Recombinant Human Colony Stimulating Factors in Yeast," *Behring Inst. Mitt.*, 83: 1-7 (1988).

Ginns, PEG Glucocerebrosidase, Internet page from www.gaucher.org.uk/peg2.prg, Nov. 1994, printed Jun. 21, 2002.

Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).

Gotschlich, "Genetic Locus for the Biosynthesis of the Variable Portion of Neisseria Gonorrhoeae Lipooligosaccharide," *J. Exp. Med.*, 180(6): 2181-2190 (1994).

Grabenhorst et al., "Biosynthesis and Secretion of Human Interleukin 2 Glycoprotein Variants From Baculovirus-Infected Sf21 Cells. Characterization of Polypeptides and Posttranslational Modifications," *Eur. J. Biochem.*, 215(1): 189-197 (1993).

Grabenhorst et al., "The Cytoplasmic, Transmembrane, and Stem Regions of Glycosyltransferases Specify Their In Vivo Functional Sublocalization and Stability in the Golgi," *J. Biol. Chem.*, 274(51): 36107-36116 (1999).

Grodberg et al.,"Alanine Scanning Mutagenesis of Human Erythropoietin Identifies Four Amino Acids Which are Critical for Biological Activity," *Eur. J. Biochem.*, 218(2): 597-601 (1993).

Gross et al., "Enzymatic Introduction of a Fluorescent Sialic Acid Into Oligosaccharide Chains of Glycoproteins," *Eur. J. Biochem.*, 177(3): 583-589 (1988).

Gross et al., "Transfer of Synthetic Sialic Acid Analogues to N- and O-Linked Glycoprotein Glycans Using Four Different Mammalian Sialyltransferases," *Biochemistry*, 28(18): 7386-7392 (1989).

Gross, "Fluorescent CMP-Sialic Acids as a Tool to Study the Specificity of the CMP-Sialic Acid Carrier and the glycoconjugate Sialylation in Permeabilized Cells," *Eur. J. Biochem.*, 203(1-2): 269-275 (1992).

Guo et al., "Utilization of Glycosyltransferases to Change Oligosaccharide Structures," *Appl. Biochem. Biotechnol.*, 68(1-2): 1-20 (1997).

Hagen et al., "Structure-Function Analysis of the UDP-N-acetyl-D-Galactosamine:Polypeptide N-acetylgalactosaminyltransferase. Essential residues Lie in a Predicted Active Site Cleft Resembling a Lactose Repressor Fold," *J. Biol. Chem.*, 274(10): 6797-6803 (1999).

Hall, "Immunotoxin Treatment of Brain Tumors," *Methods Mol. Biol.*, 166: 139-154 (2001).

Hällgren et al., "An Animated GDP-Fucose Analog Useful in the Fucosyltransferase Catalyzed Addition of Biologocial Probes onto Oligosaccharide Chains," *J. Carb. Chem.*, 14(4-5): 453-464 (1995).

Haneda et al., "Transglycosylation of Intact Sialo Complex-Type Oligosaccharides to the N-Acetylglucosamine Moieties of Glycopeptides by Mucor Hiemalis Endo-Beta-N-Acetylglucosaminidase," *Carbohydr. Res.*, 292: 61-70 (1996).

Hang et al., "Ketone Isosteres of 2-N-Acetamidosugars as Substrates for Metabolic Cell Surface Engineering," *J. Am. Chem. Soc.*, 123(6): 1242-1243 (2001).

Hansen et al., "Prediction of O-Glycosylation of Mammalian Proteins: Specificity Patterns of UDP-Galnac:Polypeptide N-Acetylgalactosaminyltransferase," *Biochem J.*, 308: 801-813 (1995).

Haro et al., "Glycosylated Human Growth Hormone (Hgh): A Novel 24 Kda Hgh-N Variant," *Biochem. Biophys. Res. Comm.*, 228(2): 549-556 (1996).

Harris et al., "Effect of pegylation on pharmaceuticals," *Nat. Rev. Drug Discov.*, 2(3): 214-221 (2003).

Harris et al., Abstracts of Papers of the American Chemical Society, V 201, APR, p. 64-POLY, pp. 154-155 (1991).

Harris (ed.), "Poly(Ethylene Glycol) Chemistry: Biotechnical and Biomedical Applications", Plenum Press, New York (1992) (Title Pages only).

Harris et al. (eds.), "Poly(ethylene glycol): Chemistry and Biological Applications," ACS Symposium Series, vol. 680, American Chemical Society (1997) (Title Pages only).

Hayes et al., "The Biosynthesis of Oligosaccharides in Intact Golgi Preparations from Rat Liver. Analysis of N-linked and O-Linked Glycans Labeled by UDP-[6-3H]N-Acetylgalactosamine," *J. Biol. Chem.*, 268(22): 16170-16178 (1993).

Hellstrom et al., "Development and Activities of the BR96-Doxorubicin Immunoconjugate," *Methods Mol. Biol.*, 166: 3-16 (2001).

Hermanson et al., *Immobilized Affinity Ligand Techniques*, Academic Press (1992) (Table of Contents).

Hermanson, *Bioconjugate Techniques*, Academic Press, San Diego (1996) (Table of Contents).

Hermentin, et al., "The Hypothetical N-Glycan Charge: a Number That Characterizes Protein Glycosylation," *Glycobiology*, 6(2): 217-230 (1996).

Hill et al., "Allogeneic Stem Cell Transplantation with peripheral Blood Stem Cells Mobilized by Pegylated G-CSF," *Biol. Blood Marrow Trans.*, 12: 603-607 (2006).

Hills et al., "Control of Therapeutic Monoclonal Antibody Glycosylation Through the Addition of Sugar Media Components andIn Vitro Remodling," *Am. Biotechnol. Lab.*, 20(11): 30 (2002).

Hink et al., "Expression of Three Recombinant Proteins Using Baculovirus Vectors in 23 Insect Cell Lines," *Biotechnol. Prog.*, 7(1): 9-14 (1991).

Höglund, "Glycosylated and Non-Glycosylated Recombinant Human Granulocyte Colony-Stimulating Factor (rhG-CSF)—What is the Difference?," *Med. Oncol.*, 15(4): 229-233 (1998).

Hollister et al., "Engineering Lepidopteran Insect Cells for Sialoglycoprotein Production by Genetic Transformation with Mammalian Beta 1,4-Galactosyltransferase and Alpha 2,6-Sialyltransferase Genes," *Glycobiology*, 11(1): 1-9 (2001).

Hu et al., "FGF-18, A Novel Member of the Fibroblast Growth Factor Family, Stimulates Hepatic and Intestinal Proliferation," *Mol. Cell. Biol.*, 18(10): 6063-6074 (1998).

Hübel et al., "Clinical Applications of Granulocyte Colony-Stimulating Factor: an Update and Summary," *Ann. Hematol.*, 82: 207-213 (2003).

Ichikawa et al., "Chemical-Enzymatic Synthesis and Conformational Analysis of Sialyl Lewis x and Derivatives," *J. Am. Chem. Soc.*, 114(24): 9283-9298 (1992).

Ikonomou et al., "Design of an Efficient Medium for Insect Cell Growth and Recombinant Protein Production," In Vitro *Cell. Dev. Biol. Anim.*, 37(9): 549-559 (2001).

Inlow et al., "Insect Cell Culture and Baculovirus Propagation in Protein-Free Medium," *J. Tissue Cult. Methods*, 12(1): 13-16 (1989).

Inoue et al., "The Production of Recombinant Human Erythropoietin," *Biotechnol. Annu. Rev.*, 1: 297-313 (1995).

Ito et al., "Synthesis of Bioactive Sialosides," *Pure Appl. Chem.*, 65(4): 753-762 (1993).

Jackson et al., "Synthesis, Isolation, and Characterization of Conjugates of Ovalbumin with Monomethoxypolyethylene Glycol Using Cyanuric Chloride as the Coupling Agent," *Anal. Biochem.*, 165(1): 114-127 (1987).

Jarvis et al., "Engineering N-Glycosylation Pathways in the Baculovirus-Insect Cell System," *Curr. Opin. Biotechnol.*, 9(5): 528-533 (1998).

Jezek et al., "Solid Phase Synthesis of Glycopeptide Dendrimers with Tn Antigenic Structure and Their Biological Activites. Part 1," *J. Peptide Sci.*, 5: 46-55 (1999).

Joppich et al., "Peptides Flanked by Two Polymer Chains, 1," *Makromol. Chem.*, 180: 1381-1384 (1979).

Kajihara et al., "Enzymatic Synthesis of Kdn Oligosaccharides by a Bacterial Alpha-(2→6)-Sialyltransferase," *Carbohydrate Research*, 315: 137-141 (1999).

Kalsner et al., "Insertion into Aspergillus Nidulans of Functional UDP-GlcNAc: Alpha 3-D-Mannoside Beta-1,2-N-Acetylglucosaminyl-Transferase I, the Enzyme Catalysing the First Committed Step from Oligomannose to Hybrid and Complex N-Glycans," *Glycoconj. J.*, 12(3): 360-370 (1995).

Kaneko et al., "Assignment of the Human Alpha 1,3-fucosyltransferase IX Gene (FUT9) to Chromosome Band 6q16 by in Situ Hybridization," *Cytogenet. Cell Genet.*, 86(3-4): 329-330 (1999).

Kaneko et al., "Alpha1,3-fucosyltransferase IX (Fuc-TIX) is Very Highly Conserved Between Human and Mouse; Molecular Cloning, Characterization and Tissue Distribution of Human Fuc-TIX," *FEBS Lett.*, 452(3): 237-242 (1999).

Kasina et al., "Simplified Preformed Chelate Protein Radiolabeling with Technetium-99m Mercaptoacetamidoadipoylglycylglycine (N3S-adipate)," *Bioconjug. Chem.*, 9(1): 108-117 (1998).

Katre et al., "Chemical Modification of Recombinant Interleukin 2 By Polyethylene Glycol Increases Its Potency in the Murine Meth A Sarcoma Model," *Proc. Natl. Acad. Sci. USA*, 84(6): 1487-1491 (1987).

Kawasaki et al., "Application of Liquid Chromatography/Mass Spectrometry and Liquid Chromatography With Tandem Mass Spectrometry to the Analysis of the Site-Specific Carbohydrate Heterogeneity in Erythropoietin," *Anal. Biochem.*, 285: 82-91 (2000).

Keene et al., "Expression of Biologically Active Human Follitropin in Chinese Hamster Ovary Cells," *J. Biol. Chem.*, 264(9): 4769-4775 (1989).

Kennedy, "Hydrophobic-Interaction Chromatography," in *Current Protocols in Protein Science*, pp. 8.4.1-8.4.21, Wiley (1995).

Keppler et al., "Biochemical Engineering of the N-Acyl Side Chain of Sialic Acid: Biological Implications," *Glycobiology*, 11(2): 11R-18R (2001).

Kimura et al., "Reconstitution of Functional L-Selectin Ligands on a Cultured Human Endothelial Cell Line by Cotransfection of Alpha1→3 Fucosyltransferase VII and Newly Cloned Glcnacbeta:6-Sulfotransferase Cdna," *Proc. Natl. Acad. Sci. USA*, 96(8): 4530-4535 (1999).

Kisselev, "Polypeptide Release Factors in Prokaryotes and Eukaryotes: Same Function, Different Structure," *Structure*, 10(1): 8-9 (2002).

Kitamura et al., "Chemical Engineering of the Monoclonal Antibody A7 by Polyethylene Glycol for Targeting Cancer Chemotherapy," *Cancer Res.*, 51(16): 4310-4315 (1991).

Kobayashi et al., "Monoclonal Antibody-Dendrimer Conjugates Enable Radiolabeling of Antibody With Markedly High Specific Activity With Minimal Loss of Immunoreactivity," *Eur. J. Nucl. Med.*, 27(9):1334-1339 (2000).

Koeller et al., "Emerging Themes in Medicinal Glycoscience," *Nat. Biotechnol.*, 18(8): 835-841 (2000).

Koeller et al., "Enzymes for Chemical Synthesis," *Nature*, 409(6817): 232-240 (2001).

Koide et al., "Modification of Amino Groups in Porcine Pancreatic Elastase With Polyethylene Glycol in Relation to Binding Ability Towards Anti-Serum and to Enzymic Activity," *Biochem. Biophys. Res. Commun.*, 111(2): 659-667 (1983).

Kornfeld et al., "Assembly of Asparagine-Linked Oligosaccharides," *Ann. Rev. Biochem.*, 54: 631-664 (1985).

Kreitman, "Toxin-Labeled Monoclonal Antibodies," *Curr. Pharm. Biotechnol.*, 2(4): 313-325 (2001).

Kroschinsky et al., "The Role of Pegfilgrastim in Mobilization of Hematopoietic Stem Cells," *Trans. Apher. Sci.*, 38: 237-244 (2008).

Krystal et al., "Purification of Human Erythropoietin to Homogeneity by a Rapid Five-Step Procedure," *Blood*, 67(1): 71-99 (1986).

Kuhn et al., "Active Site and Oligosaccharide Recognition Residues of Peptide-N4-(N-Acetyl-Beta-D-Glucosaminyl)Asparagine Amidase F," *J. Biol. Chem.*, 270(49): 29493-29497 (1995).

Kukowska-Latallo et al., "A Cloned Human Cdna Determines Expression of a Mouse Stage-Specific Embryonic Antigen and the Lewis Blood Group Alpha(1,3/1,4)Fucosyltransferase," *Genes Dev.*, 4(8): 1288-1303 (1990).

Lai et al, "Structural Characterization of Human Erythropoietin," *J. Biol. Chem.*, 261(7): 3116-3121 (1986).

Lau et al., "Quantitative Competitive Reverse Transcription-PCR As a Method to Evaluate Retrovirus Removal During Chromatography Procedures," *J. Biotechnol.*, 75(2-3): 105-115 (1999).

Lee et al., "Efficient Coupling of Glycopeptides to Proteins With A Heterobifunctional Reagent," *Biochemistry*, 28(4): 1856-1861 (1989).

Lee-Huang et al., "Cloning and Expression of Human Erythropoietin Cdna in *Escherichia coli*," *Proc. Natl. Acad. Sci. USA*, 81(9): 2708-2712 (1984).

Legault et al., "Human Alpha(1,3/1,4)-Fucosyltransferases Discriminate Between Different Oligosaccharide Acceptor Substrates Through a Discrete Peptide Fragment," *J. Biol. Chem.*, 270(36): 20987-20996 (1995).

Leist et al., "Derivatives of Erythropoietin That Are Tissue Protective But Not Erythropoietic," *Science*, 305: 239-242 (2004).

Leiter et al., "Purification, Cdna Cloning, and Expression of GDP-L-Fuc:Asn-Linked Glcnac Alpha1,3-Fucosyltransferase From Mung Beans," *J. Biol. Chem.*, 274(31): 21830-21839 (1999).

Leung, "Engineering a Unique Glycosylation Site for Site-Specific Conjugation of Haptens to Antibody Fragments," *J. Immunol.* 154(11): 5919-5926 (1995).

Lewis et al., "Structure and Properties of Members of the Hgh Family: A Review," *Endocr. J.*, 47(Suppl.): S1-S8 (2000).

Li et al., "The Role of the Transferrin-Transferrin-Receptor System in Drug Delivery and Targeting," *Trends Pharmacol. Sci.*, 23(5): 206-209 (2002).

Li et al., "Transferrin/Transferrin Receptor-Mediated Drug Delivery," *Med. Res. Rev.*, 22(3): 225-250 (2002).

Licari et al., "Modeling the Population Dynamics of Baculovirus-Infected Insect Cells: Optimizing Infection Strategies for Enhanced Recombinant Protein Yields," *Biotechnol. Bioeng.*, 39(4): 432-441 (1992).

Licari et al., "Production of a Discrete, Heterogeneous Population of Beta-Galactosidase Polypeptides Using Baculovirus Expression Vectors," *Biotechnol. Bioeng.*, 39(9): 932-944 (1992).

Liles et al., "Augmented Mobilization and Collection of CD34+ Hematopoietic Cells From Normal Human Volunteers Stimulated With Granulocyte-Colony-Stimulating Factor by Single-Dose Administration of AMD3100, A CXCR4 Antagonist," *Transfusion*, 45: 295-300 (2005).

Lin et al., "Cloning and Expression of the Human Erythropoietin Gene," *Proc. Natl. Acad. Sci. USA*, 82: 7580-7584 (1985).

Liu et al., "A Paradigm Case for the Merging of Glycal and Enzymatic Assembly Methods in Glycoconjugate Synthesis: A Highly Efficient Chemo-Enzymatic Synthesis of GM$_3$," *Chem. Eur. J.*, 2(11): 1359-1362 (1996).

Long et al., "Design of Homogeneous, Monopegylated Erythropoietin Analogs With Preserved In Vitro Bioactivity," *Exp. Hematol.*, 34(6): 697-704 (2006).

Lönnberg, "Solid-Supported Synthesis of Glycoconjugates," *Curr. Org. Synth.*, 6(4): 400-425 (2009)

Lord et al., "Kinetics of Neutrophil Production in Normal and Neutropenic Animals During the Response to Filgrastim (R-Methu G-CSF) or Filgrastim SD/01 (PEG-R-Methu G-CSF)," *Clin. Cancer Res.*, 7(7): 2085-2090 (2001).

Luckow et al., "Baculovirus Systems for the Expression of Human Gene Products," *Curr. Opin. Biotechnol.*, 4(5): 564-572 (1993).

Lund et al., "Oligosaccharide-Protein Interactions in Igg Can Modulate Recognition by Fc Gamma Receptors," *FASEB J.*, 9(1): 115-119 (1995).

Lund et al., "Multiple Interactions of Igg With Its Core Oligosaccharide Can Modulate Recognition by Complement and Human Fc Gamma Receptor I and Influence the Synthesis of Its Oligosaccharide Chains," *J. Immunol.*, 157(11): 4963-4969 (1996).

Mahal et al., "Engineering Chemical Reactivity on Cell Surfaces Through Oligosaccharide Biosynthesis," *Science*, 276(5315): 1125-1128 (1997).

Malissard et al., "Expression of Functional Soluble Forms of Human Beta-1, 4-Galactosyltransferase I, Alpha-2,6-Sialyltransferase, and Alpha-1, 3-Fucosyltransferase VI in the Methylotrophic Yeast Pichia Pastoris," *Biochem. Biophys. Res. Commun.*, 267(1): 169-173 (2000).

Maranga et al., "Virus-Like Particle Production At Low Multiplicities of Infection With the Baculovirus Insect Cell System," *Biotechnol. Bioeng.*, 84(2): 245-253 (2003).

Maras et al., "Molecular Cloning and Enzymatic Characterization of a Trichoderma Reesei 1,2-Alpha-D-Mannosidase," *J Biotechnol.*, 77(2-3): 255-263 (2000).

Meynial-Salles et al., "In Vitro Glycosylation of Proteins: An Enzymatic Approach," *J. Biotechnol.*, 46(1): 1-14 (1996).

Miller, "Baculoviruses: High-Level Expression in Insect Cells," *Curr. Opin. Genet. Dev.*, 3(1): 97-101 (1993).

Min et al., "Site-Directed Mutagenesis of Recombinant Equine Chorionic Gonadotropin/Luteinizing Hormone: Differential Role of Oligosaccharides in Luteinizing Hormone- and Follicle-Stimulating Hormone-Like Activities," *Endocr. J.*, 43(5): 585-593 (1996).

Mistry et al., "Therapeutic Delivery of Proteins to Macrophages: Implications for Treatment of Gaucher's Disease," *Lancet*, 348(9041): 1555-1559 (1996).

Mollicone et al., "Acceptor Specificity and Tissue Distribution of Three Human Alpha-3-Fucosyltransferases," *Eur. J. Biochem.*, 191(1): 169-176 (1990).

Monaco et al., "Expression of Recombinant Human Granulocyte Colony-Stimulating Factor in CHO Dhfr-Cells: New Insights Into the In Vitro Amplification Expression System," *Gene*, 180: 145-150 (1996).

Morimoto et al., "Biological and Physicochemical Characterization of Recombinant Human Erythropoietins Fractionated by Mono Q Column Chromatography and Their Modification With Sialyltransferase," *Glycoconj. J.*, 13(6): 1013-1020 (1996).

Nagata et al., "The Chromosomal Gene Structure and Two mRNAs for Human Granulocyte Colony-Stimulating Factor," *EMBO J.*, 5(3): 575-581 (1986).

Natsuka et al., "Molecular Cloning of a cDNA Encoding a Novel Human Leukocyte Alpha-1,3-fucosyltransferase Capable of Synthesizing the Sialyl Lewis X Determinant," *J. Biol. Chem.*, 269(24): 16789-16794 (1994).

NCBI—Accession No. NCAA26095 (2 pgs.) (2006).

NCBI—Accession No. NP_058697 (3 pgs.) (2007).

NCBI—Accession No. NP_999299 (2 pgs.) (2007).

NCBI Database hits for erythropoietin protein sequences (3 pgs.) (2007).

Ngo et al., "The Protein Folding Problem and Tertiary Structure Prediction, Chapter 14: Computational Complexity Protein Structure Prediction, and the Levinthal Paradox," pp. 433-440 and 492-495 (1994).

Nilsson et al., "Immobilization of Ligands with Organic Sulfonyl Chlorides," *Methods Enzymol.*, 104: 56-69 (1984).

Nunez et al., "The Synthesis and Characterization of α- and β-L-Fucopyranosyl phosphates and GDP Fucose[1]," *Can. J. Chem.*, 59(14): 2086-2095 (1981).

O'Connell et al., "The Influence of Flanking Sequence on the O-Glycosylation of Threonine In Vitro," *J. Biol. Chem.*, 267(35): 25010-25018 (1992).

Oetke et al., "Versatile Biosynthetic Engineering of Sialic Acid in Living Cells Using Synthetic Sialic Acid Analogues," *J. Biol. Chem.*, 277(8): 6688-6695 (2002).

Oh-Eda et al., "O-Linked Sugar Chain of Human Granulocyte Colony-Stimulating Factor Protects it Against Polymerization and Denaturation Allowing it to Retain its Biological Activity," *J. Biol. Chem.*, 265: 11432-11435 (1990).

Olson et al., "Structural Basis for Recognition of Phosphorylated High Mannose Oligosaccharides by the Cation-Dependent Mannose 6-Phosphate Receptor," *J. Biol. Chem.*, 274(42): 29889-29896 (1999).

Orlean, "Vol. III: The Molecular and Cellular Biology of the Yeast Saccharomyces: Cell Cycle and Cell Biology", in *Biogenesis of Yeast Wall and Surface Components*, Chapter 3, pp. 229-362, Cold Spring Harbor Laboratory Press (1997).

Orskov et al., "Complete Sequences of Glucagon-Like Peptide-1 from Human and Pig Small Intestine," *J. Biol. Chem.*, 264(22): 12826-12829 (1989).

O'Shannessy et al., "Specific Conjugation Reactions of the Oligosaccharide Moieties of Immunoglobulins," *J. Appl. Biochem.*, 7: 347-355 (1985).

Palacpac et al., "Stable Expression of Human Beta1,4-Galactosyltransferase in Plant Cells Modifies N-linked Glycosylation Patterns,"*Proc. Natl. Acad. Sci. USA*, 96(8): 4692-4697 (1999).

Palcic et al., "Enzymic Synthesis of Oligosaccharides Terminating in the Tumor-Associated Sialyl-Lewis-a Determinant," *Carbohydr. Res.*, 190(1): 1-11 (1989).

Paulson et al., "Reactivation of Asialo-Rabbit Liver Binding Protein by Resialylation with Beta-D-Galactoside Alpha2 Leads to 6 Sialyltransferase," *J. Biol. Chem.*, 252(23): 8624-8628 (1977).

Plummer et al., "Novel, Specific O-Glycosylation of Secreted Flavobacterium Meningosepticum Proteins. Asp-Ser and Asp-Thr-Thr Consensus Sites," *J. Biol. Chem.*, 270(22): 13192-13196 (1995).

PNGase-F Amidase Sequence from F. Meningosepticum (RN 128688-70-0) (2007).

PNGase-F Amidase Sequence from F. Meningosepticum (RN 128688-71-1) (2007).

Prati et al., "Engineering of Coordinated Up- and Down-Regulation of Two Glycosyltransferases of the O-Glycosylation Pathway in Chinese Hamster Ovary (CHO) Cells," *Biotech and Bioeng.*, 79(5): 580-585 (2002).

Prieels et al., "Co-Purification of the Lewis Blood Group N-Acetylglucosaminide Alpha 1 goes to 4 Fucosyltransferase and an N-Acetylglucosaminide Alpha 1 goes to 3 Fucosyltransferase From Human Milk," *J. Biol. Chem.*, 256(20): 10456-10463 (1981).

Pyatak et al., "Preparation of a Polyethylene Glycol: Superoxide Dismutase Adduct, and an Examination of its Blood Circulation Life and Anti-Inflammatory Activity," *Res. Commun. Chem. Pathol. Pharmacol.*, 29(1): 113-127 (1980).

Quelle et al., "High-level Expression and Purification of a Recombinant Human Erythropoietin Produced Using a Baculovirus Vector," *Blood*, 74(2): 652-657 (1989).

Rabouille et al., "The Drosophila GMII Gene Encodes a Golgi Alpha-Mannosidase II," *J Cell Sci.*, 112(Pt. 19): 3319-3330 (1999).

Rasko et al., "Cloning and Characterization of the Alpha(1,3/4) Fucosyltransferase of Helicobacter pylori," *J. Biol. Chem.*, 275(7): 4988-4994 (2000).

R & D Systems, Fibroblast Growth Factors (FGFs), Internet page from www.rndsystems.com/mini_review_detail_objectname_MR01_FGFs.aspx, 2001, printed Mar. 10, 2011.

Rathnam et al., "Conjugation of a Fetuin Glycopeptide to Human Follicle-Stimulating Hormone and its Subunits by Photoactivation," *Biochim. Biophys. Acta*, 624(2): 436-442 (1980).

Reff et al., "Future of Monoclonal Antibodies in the Treatment of Hematologic Malignancies," *Cancer Control*, 9(2): 152-166 (2002).

Rosenthal et al., "Isolation of Peptidoglycan and Soluble Peptidoglycan Fragments," *Methods Enzymol.*, 235: 253-285 (1994).

Rotondaro et al., "Purification and Characterization of Two Recombinant Human Granulocyte Colony-Stimulating Factor Glycoforms," *Mol. Biotech.*, 11: 117-128 (1999).

Rudikoff et al., "Single Amino Acid Substitution Altering Antigen-Binding Specificity," *Proc. Natl. Acad. Sci. USA*, 79(6):1979-1983 (1982).

Sadler et al., "Purification of Mammalian Glycosyltransferases," *Methods Enzymol.*, 83: 458-514 (1982).

Sandberg et al., "Structural and Functional Characterization of B-Domain Deleted Recombinant Factor VIII," *Semin. Hematol.*, 38(2 Suppl. 4): 4-12 (2001).

Saneyoshi et al., "Equine Follicle-Stimulating Hormone: Molecular Cloning of Beta Subunit and Biological Role of the Asparagine-Linked Oligosaccharide at Asparagine(56) of Alpha Subunit," *Biol. Reprod.*, 65(6): 1686-1690 (2001).

Sasaki et al., "Carbohydrate Structure of Erythropoietin Expressed in Chinese Hamster Ovary Cells by a Human Erythropoietin CdnA," *J. Biol. Chem.*, 262(25): 12059-12076 (1987).

Sasaki et al., "Expression Cloning of a Novel Alpha 1,3-Fucosyltransferase that is Involved in Biosynthesis of the Sialyl Lewis X Carbohydrate Determinants in Leukocytes," *J.Biol. Chem.*, 269(20): 14730-14737 (1994).

Saxon et al., "Cell Surface Engineering by a Modified Staudinger Reaction," *Science*, 287(5460): 2007-2010 (2000).

Saxon et al., "Investigating Cellular Metabolism of Synthetic Azidosugars with the Staudinger Ligation," *J. Am. Chem. Soc.*, 124(50): 14893-14902 (2002).

Schlaeger, "Medium Design for Insect Cell Culture," *Cytotechnology*, 20(1-3): 57-70 (1996).

Schwarz et al., "Transfer of 131I and Fluoresceinyl Sialic Acid Derivatives into the Oligosaccharide Chains of IgG: a New Method for Site-Specific Labeling of Antibodies," *Nucl. Med. Biol.*, 26(4):383-388 (1999).

Schwientek et al., "Efficient intra- and Extracellular Production of Human Beta-1,4-Galactosyltransferase in Saccharomyces Cerevisiae is Mediated by Yeast Secretion Leaders," *Gene*, 145(2): 299-303 (1994).

Schwientek et al., "Functional Conservation of Subfamilies of Putative UDP-N-Acetylgalactosamine:Polypeptide N-Acetylgalactosaminyltransferases in Drosophila, Caenorhabditis Elegans, and Mammals. One Subfamily Composed of I(2)35Aa is Essential in Drosophila," *J. Biol. Chem.*, 277(25): 22623-22638 (2002).

Scouten, "A Survey of Enzyme Coupling Techniques," *Methods Enzymol.*, 135: 30-65 (1987).

Seely et al., "Use of Ion-Exchange Chromatography and Hydrophobic Interaction Chromatography in the Preparation and Recovery of Polyethylene Glycol-Linked Proteins," *J. Chromatog.*, 908: 235-241 (2001).

Seffernick et al., "Melamine Deaminase and Atrazine Chlorohydrolase: 98 Percent Identical but Functionally Different," *J. Bacteriol.*, 183(8): 2405-2410 (2001).

Seitz, "Glycopeptide Synthesis and the Effects of Glycosylation on Protein Structure and Activity," *Chembiochem.*, 1(4): 214-246 (2000).

Shah et al., "Transcellular Delivery of an Insulin-Transferrin Conjugate in Enterocyte-Like Caco-2 Cells," *J. Pharm. Sci.*, 85(12): 1306-1311 (1996).

Shapiro et al., "The Safety and Efficacy of Recombinant Human Blood Coagulation Factor IX in Previously Untreated Patients with Severe or Moderately Severe Hemophilia B," *Blood*, 105(2): 518-525 (2005).

Shen et al., "Cis-Aconityl Spacer Between Daunomycin and Macromolecular Carriers: a Model of pH-Sensitive Linkage Releasing Drug from a Lysosomotropic Conjugate," *Biochem. Biophys. Res. Commun.*, 102(3): 1048-1054 (1981).

Shinkai et al., "Protein Expression and Purification," *Prot. Exp. Purif.*, 10: 379-385 (1997).

Sinclair et al., "Glycoengineering: the Effect of Glycosylation on the Properties of Therapeutic Proteins," *J. Pharm. Sci.*, 94: 1626-1635 (2005).

Singh et al., "Glycosidase-catalysed synthesis of oligosaccharides: a two-step synthesis of the core trisaccharide of N•linked glycoproteins using the β-*N*acetylhexosaminidase and the β-mannosidase from *Aspergillus oryzae*," *Chem. Commun.*, 1996(8): 993-994 (1996).

Sinha et al., "Release of Soluble Peptidoglycan from Growing Conococci: Demonstration of Anhydro-Muramyl-Containing Fragments," *Infect. Immun.*, 29(3): 914-925 (1980).

Skolnick et al., "From Genes to Protein Structure and Function: Novel Applications of Computational Approaches in the Genomic Era," *Trends Biotechnol.*, 18(1): 34-39 (2000).

Smith et al., "The Challenges of Genome Sequence Annotation or "the Devil is in the Details"," *Nat. Biotechnol.*, 15(12): 1222-1223 (1997).

Snider et al., "Characterization of the Heterogeneity of Polyethylene Glycol-Modified Superoxide Dismutase by Chromatographic and Electrophoretic Techniques," *J. Chromatogr.*, A 599(1-2): 141-155 (1992).

Sojar et al., "A Chemical Method for the Deglycosylation of Proteins," *Arch. Biochem. Biophys.*, 259(1): 52-57 (1987).

Song et al., "Enhanced Neuroprotective Effects of Basic Fibroblast Growth Factor in Regional Brain ischemia After Conjugation to a Blood-Brain Barrier Delivery Vector," *J. Pharmacol. Exp. Ther.*, 301(2): 605-610 (2002).

Srinivasachar et al., "New Protein Cross-Linking Reagents that are Cleaved by Mild Acid," *Biochemistry*, 28(6): 2501-2509 (1989).

Srivastava et al., "Enzymatic Transfer of a Preassembled Trisaccharide Antigen to Cell Surfaces Using a Fucosyltransferase," *J. Biol. Chem.*, 267(31): 22356-22361 (1992).

Staudacher, "α 1,3 Fucosyltransferases," *Trends Glycosci. Glycotechnol.*, 8(44): 391-408 (1996).

Stephens et al., "The Pyruvate Dehydrogenase Complex of *Escherichia coli* K12. Nucleotide Sequence Encoding the Pyruvate Dehydrogenase Component," *Eur. J. Biochem.*, 133(1): 155-162 (1983).

Stephens et al., "The Pyruvate Dehydrogenase Complex of *Escherichia Coli* K12. Nucleotide Sequence Encoding the Dihydrolipoamide Acetyltransferase Component," *Eur. J. Biochem.*, 133(3): 481-489 (1983).

Stephens et al., "Nucleotide Sequence of the Lipoamide Dehydrogenase Gene of *Escherichia coli* K12,"*Eur. J. Biochem.*, 135(3): 519-527 (1983).

Strausberg et al., "Generation and Initial Analysis of More Than 15,000 Full-Length Human and Mouse cDNA Sequences," *Proc Natl Acad Sci USA*, 99(26): 16899-16903 (2002).

Takane et al., "Chronopharmacology of Antitumor Effect Induced by Interferon-Beta in Tumor-Bearing Mice," *J Pharmacol Exp Ther.*, 294(2): 746-752 (2000).

Takeuchi et al., "Role of Sugar Chains in the In Vitro Biological Activity of Human Erythropoietin Produced in Recombinant Chinese Hamster Ovary Cells," *J. Biol. Chem.*, 265(21): 12127-12130 (1990).

Taniguchi et al., "A Glycomic Approach to the Identification and Characterization of Glycoprotein Function in Cells Transfected with Glycosyltransferase Genes," *Proteomics*, 1(2): 239-247 (2001).

Taylor et al., Protein Immobilization Fundamentals and Applications, Manual (1991).

Ten Hagen et al., "Characterization of a UDP-GalNAc:Polypeptide N-Acetylgalactosaminyltransferase that Displays Glycopeptide N-Acetylgalactosaminyltransferase Activity," *J. Biol. Chem.*, 274(39): 27867-27874 (1999).

Tom et al., "Reproducible Production of a PEGylated Dual-Acting Peptide for Diabetes," *AAPS Journal*, 9(2): E227-E234 (2007).

Trottein et al., "Molecular Cloning of a Putative Alpha3-Fucosyltransferase from Schistosoma Mansoni," *Mol. Biochem. Parasitol.*, 107(2): 279-287 (2000).

Tsuboi et al., "Acquisition of P-Selectin Binding Activity by En Bloc Transfer of Sulfo Le(x) Trisaccharide to the Cell Surface: Comparison to a Sialyl Le(x) Tetrasaccharide Transferred on the Cell Surface," *Arch. Biochem. Biophys.*, 374(1): 100-106 (2000).

Tsunoda et al., "Enhanced Antitumor Potency of Polyethylene Glycolylated Tumor Necrosis Factor-α: A Novel Polymer-Conjugation Technique with a Reversible Amino-Protective Reagent[1]," *J. Pharmacol. Exp. Ther.*, 209(1): 368-372 (1999).

Tuddenham"RNA as Drug and Antidote," *Nature*, 419(6902): 23-24 (2002).

Ulloa-Aguirre et al., "Role of Glycosylation in Function of Follicle-Stimulating Hormone," *Endocrine*, 11(3): 205-215 (1999).

Uludag et al., "Targeting Systemically Administered Proteins to Bone by Bisphosphonate Conjugation," *Biotechnol. Prog.*, 18(3): 604-611 (2002).

Uptima, Detergents: Solubilization of Biomolecules, Internet page from www.interchim.com/interchim/bio/produits_uptima/product_line/p1p_detergents.htm, 2001, printed Nov. 14, 2011.

Urdal et al, "Lymphokine Purification by Reversed-Phase High-Performance Liquid Chromatography," *J. Chromatogr.*, 296: 171-179 (1984).

Van Berkel et al., "Heterogeneity in Utilization of N-Glycosylation Sites Asn624 and Asn138 in Human Lactoferrin: a Study With Glycosylation-Site Mutants," *Biochem. J.*, 319(Pt. 1): 117-122 (1996).

Van Reis et al., "Industrial Scale Harvest of Proteins From Mammalian Cell Culture by Tangential Flow Filtration," *Biotechnol. Bioeng.*, 38(4): 413-422 (1991).

Van Tetering et al., "Characterization of a Core Alpha→3-Fucosyltransferase from the Snail Lymnaea Stagnalis that is Involved in the Synthesis of Complex-Type N-Glycans," *FEBS Lett.*, 461(3): 311-314 (1999).

Veronese, "Peptide and Protein PEGylation: a Review of Problems and Solutions," *Biomaterials*, 22(5): 405-417 (2001).

Vitetta et al., "Immunology. Considering Therapeutic Antibodies," *Science*, 313: 308-309 (2006).

Vyas et al., "Ligand-Receptor-Mediated Drug Delivery: An Emerging Paradigm in Cellular Drug Targeting," *Crit. Rev. Ther. Drug Carrier Syst.*, 18(1): 1-76 (2001).

Wang et al., "Identification of a GDP-L-Fucose:Polypeptide Fucosyltransferase and Enzymatic Addition of O-Linked Fucose to EGF Domains," *Glycobiology*, 6(8): 837-842 (1996).

Wang et al., "Chemoenzymatic Synthesis of a High-Mannose-Type N-Glycopeptide Analog With C-Glycosidic Linkage," *Tetrahedron Lett.*, 37(12): 1975-1978 (1996).

Wang et al., "Single-Chain Fv With Manifold N-Glycans As Bifunctional Scaffolds for Immunomolecules," *Protein Eng.*, 11(12): 1277-1283 (1998).

Wang et al., "Novel Helicobacter Pylori Alpha1,2-Fucosyltransferase, a Key Enzyme in the Synthesis of Lewis Antigens," *Microbiol.*, 145(Pt. 11): 3245-3253 (1999).

Wellhöner et al., "Uptake and Concentration of Bioactive Macromolecules by K562 Cells Via the Transferrin Cycle Utilizing an Acid-Labile Transferrin Conjugate," *J. Biol. Chem.*, 266(7): 4309-4314 (1991).

Wells, "Additivity of Mutational Effects in Proteins," *Biochemistry*, 29(37): 8509-8517 (1990).

Weston et al., "Isolation of a Novel Human Alpha (1,3)Fucosyltransferase Gene and Molecular Comparison to the Human Lewis Blood Group Alpha (1,3/1,4)Fucosyltransferase Gene. Syntenic, Homologous, Nonallelic Genes Encoding Enzymes With Distinct Acceptor Substrate Specificities," *J. Biol. Chem.*, 267(6): 4152-4160 (1992).

Weston et al., "Molecular Cloning of a Fourth Member of a Human Alpha (1,3)Fucosyltransferase Gene Family," *J. Biol. Chem.*, 267(34): 24575-24584 (1992).

White et al., "Purification and Cdna Cloning of a Human UDP-N-Acetyl-Alpha-D-Galactosamine:Polypeptide N-Acetylgalactosaminyltransferase," *J. Biol. Chem.*, 270(41): 24156-24165 (1995).

Wishart et al., "A Single Mutation Converts a Novel Phosphotyrosine Binding Domain Into a Dual-Specificity Phosphatase," *J. Biol. Chem.*, 270(45): 26782-26785 (1995).

Witkowski et al., "Conversion of a Beta-Ketoacyl Synthase to a Malonyl Decarboxylase by Replacement of the Active-Site Cysteine With Glutamine," *Biochemistry*, 38(36): 11643-11650 (1999).

Witte et al., "Enzymatic Glycoprotein Synthesis: Preparation of Ribonuclease Glycoforms Via Enzymatic Glycopeptide Condensation and Glycosylation," *J. Am. Chem. Soc.*, 119(9): 2114-2118 (1997).

Witte et al., "Monoclonal Antibodies Targeting the VEGF Receptor-2 (Flk1/KDR) As an Anti-Angiogenic Therapeutic Strategy," *Cancer and Metastasis Rev.*, 17: 155-161 (1998).

Woghiren et al., "Protected Thiol-Polyethylene Glycol: A New Activated Polymer for Reversible Protein Modification," *Bioconjug. Chem.*, 4(5): 314-318 (1993).

Wong et al., "Enzyme-Catalyzed Synthesis of N-Acetyllactosamine With In Situ Regeneration of Uridine 5'-Diphosphate Glucose and Uridine 5'-Diphosphate Galactose," *J. Org. Chem.*, 47(27): 5416-5418 (1982).

Wong et al., "Low Multiplicity Infection of Insect Cells With a Recombinant Baculovirus: The Cell Yield Concept," *Biotechnol. Bioeng.*, 49(6): 659-666 (1996).

Woods et al., "Transferrin Receptors and Cation-Independent Mannose-6-Phosphate Receptors Deliver Their Ligands to Two Distinct Subpopulations of Multivesicular Endosomes," *Eur. J. Cell Biol.*, 50(1): 132-143 (1989).

Wright et al., "Effect of C2-Associated Carbohydrate Structure On Ig Effector Function: Studies With Chimeric Mouse-Human Igg1 Antibodies in Glycosylation Mutants of Chinese Hamster Ovary Cells," *J. Immunol.*, 160(7): 3393-3402 (1998).

Wu et al., "Pharmacokinetics and Brain Uptake of Biotinylated Basic Fibroblast Growth Factor Conjugated to a Blood-Brain Barrier Drug Delivery System," *J. Drug Target.*, 10(3): 239-245 (2002).

Xing et al., "Design of a Transferrin-Proteinase Inhibitor Conjugate to Probe for Active Cysteine Proteinases in Endosomes," *Biochem. J.*, 336(Pt. 3): 667-673 (1998).

Yamamoto et al., "Chemoenzymatic Synthesis of a Novel Glycopeptide Using a Microbial Endoglycosidase," *Carbohydr. Res.*, 305(3-4): 415-422 (1998).

Yarema et al., "Metabolic Delivery of Ketone Groups to Sialic Acid Residues. Application to Cell Surface Glycoform Engineering," *J. Biol. Chem.*, 273(47): 31168-31179 (1998).

Yin et al., "Effects of Antioxidants on the Hydrogen Peroxide-Mediated Oxidation of Methionine Residues in Granulocyte Colony-Stimulating Factor and Human Parathyroid Hormone Fragment 13-34," *Pharm. Res.*, 21(12): 2377-2383 (2004).

Yoshida et al., "Expression and Characterization of Rat UDP-N-Acetylglucosamine: Alpha-3-D-Mannoside Beta-1,2-N-Acetylglucosaminyltransferase I in Saccharomyces Cerevisiae," *Glycobiology*, 9(1): 53-58 (1999).

Yoshitake et al., "Nucleotide Sequence of the Gene for Human Factor IX (Antihemophilic Factor B)," *Biochemistry*, 24(14): 3736-3750 (1985).

Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).

Zhang et al., "Stable Expression of Human Alpha-2,6-Sialyltransferase in Chinese Hamster Ovary Cells: Functional Consequences for Human Erythropoietin Expression and Bioactivity," *Biochim. Biophys. Acta*, 1425: 441-452 (1998).

Zheng et al., "Optimized Production of Recombinant Bluetongue Core-Like Particles Produced by the Baculovirus Expression System," *Biotechnol. Bioeng.*, 65(5): 600-604 (1999).

Zhou et al., "Lipooligosaccharide Biosynthesis in Neisseria Gonorrhoeae: Cloning, Identification and Characterization of the Alpha 1,5 Heptosyltransferase I Gene (Rfac)," *Mol. Microbiol.*, 14(4): 609-618 (1994).

\* cited by examiner

FIGURE 10A

| Protein | Organism | EC# | GenBank / GenPept | | SwissProt | PDB / 3D |
|---|---|---|---|---|---|---|
| At1g08280 | Arabidopsis thaliana | n.d. | AC011438 BT004583 NC_003070 | AAF18241.1 AAO42829.1 NP_172305.1 | Q84W00 Q9SGD2 | |
| At1g08660/F22O13.14 | Arabidopsis thaliana | n.d. | AC003981 AY064135 AY124807 NC_003070 NM_180609 | AAF99778.1 AAL36042.1 AAM70516.1 NP_172342.1 NP_850940.1 | Q8VZJ0 Q9FRR9 | |
| At3g48820/T21J18_90 | Arabidopsis thaliana | n.d. | AY080589 AY133816 AL132963 NM_114741 | AAL85966.1 AAM91750.1 CAB87910.1 NP_190451.1 | Q8RY00 Q9M301 | |
| α-2,3-sialyltransferase (ST3GAL-IV) | Bos taurus | n.d. | AJ584673 | CAE48298.1 | | |
| α-2,3-sialyltransferase (St3Gal-V) | Bos taurus | n.d. | AJ585768 | CAE51392.1 | | |
| α-2,6-sialyltransferase (Siat7b) | Bos taurus | n.d. | AJ620651 | CAF05850.1 | | |
| α-2,8-sialyltransferase (SIAT8A) | Bos taurus | 2.4.99.8 | AJ699418 | CAG27880.1 | | |
| α-2,8-sialyltransferase (Siat8D) | Bos taurus | n.d. | AJ699421 | CAG27883.1 | | |
| α-2,8-sialyltransferase ST8Siα-III (Siat8C) | Bos taurus | n.d. | AJ704563 | CAG28696.1 | | |
| CMP α-2,6-sialyltransferase (ST6Gal I) | Bos taurus | 2.4.99.1 | Y15111 NM_177517 | CAA75385.1 NP_803483.1 | O18974 | |
| sialyltransferase 8 (fragment) | Bos taurus | n.d. | AF450088 | AAL47018.1 | Q8WN13 | |
| sialyltransferase ST3Gal-II (Siat4B) | Bos taurus | n.d. | AJ748841 | CAG44450.1 | | |
| sialyltransferase ST3Gal-III (Siat6) | Bos taurus | n.d. | AJ748842 | CAG44451.1 | | |
| sialyltransferase ST3Gal-VI (Siat10) | Bos taurus | n.d. | AJ748843 | CAG44452.1 | | |
| ST3Gal I | Bos taurus | n.d. | AJ305086 | CAC24698.1 | Q9BEG4 | |
| St6GalNAc-VI | Bos taurus | n.d. | AJ620949 | CAF06586.1 | | |
| CDS4 | Branchiostoma floridae | n.d. | AF391289 | AAM18873.1 | Q8T771 | |
| polysialyltransferase (PST) (fragment) ST8Sia IV | Cercopithecus aethiops | 2.4.99.- | AF210729 | AAF17105.1 | Q9TT09 | |
| polysialyltransferase (STX) (fragment) ST8Sia II | Cercopithecus aethiops | 2.4.99.- | AF210318 | AAF17104.1 | Q9TT10 | |
| α-2,3-sialyltransferase ST3Gal I (Siat4) | Ciona intestinalis | n.d. | AJ626815 | CAF25173.1 | | |
| α-2,3-sialyltransferase ST3Gal I (Siat4) | Ciona savignyi | n.d. | AJ626814 | CAF25172.1 | | |
| α-2,8-polysialyltransferase ST8Sia IV | Cricetulus griseus | 2.4.99.- | - Z46801 | AAE28634 CAA86822.1 | Q64690 | |
| Gal β-1,3/4-GlcNAc α-2,3-sialyltransferase St3Gal I | Cricetulus griseus | n.d. | AY266675 | AAP22942.1 | Q80WL0 | |
| Gal β-1,3/4-GlcNAc α-2,3-sialyltransferase St3Gal II (fragment) | Cricetulus griseus | n.d. | AY266676 | AAP22943.1 | Q80WK9 | |
| α-2,3-sialyltransferase ST3Gal I (Siat4) | Danio rerio | n.d. | AJ783740 | CAH04017.1 | | |
| α-2,3-sialyltransferase ST3Gal II (Siat5) | Danio rerio | n.d. | AJ783741 | CAH04018.1 | | |

FIGURE 10B

| Protein | Organism | EC# | GenBank / GenPept | SwissProt | PDB / 3D |
|---|---|---|---|---|---|
| α-2,3-sialyltransferase ST3Gal III (Siat6) | Danio rerio | n.d. | AJ626821 | CAF25179.1 | |
| α-2,3-sialyltransferase ST3Gal IV (Siat4c) | Danio rerio | n.d. | AJ744809 | CAG32845.1 | |
| α-2,3-sialyltransferase ST3Gal V-r (Siat5-related) | Danio rerio | n.d. | AJ783742 | CAH04019.1 | |
| α-2,6-sialyltransferase ST6Gal I (Siat1) | Danio rerio | n.d. | AJ744801 | CAG32837.1 | |
| α-2,6-sialyltransferase ST6GalNAc II (Siat7B) | Danio rerio | n.d. | AJ634459 | CAG25680.1 | |
| α-2,6-sialyltransferase ST6GalNAc V (Siat7E) (fragment) | Danio rerio | n.d. | AJ646874 | CAG26703.1 | |
| α-2,6-sialyltransferase ST6GalNAc VI (Siat7F) (fragment) | Danio rerio | n.d. | AJ646883 | CAG26712.1 | |
| α-2,8-sialyltransferase ST8Sia I (Siat 8A) (fragment) | Danio rerio | n.d. | AJ715535 | CAG29374.1 | |
| α-2,8-sialyltransferase ST8Sia III (Siat 8C) (fragment) | Danio rerio | n.d. | AJ715543 | CAG29382.1 | |
| α-2,8-sialyltransferase ST8Sia IV (Siat 8D) (fragment) | Danio rerio | n.d. | AJ715545 | CAG29384.1 | |
| α-2,8-sialyltransferase ST8Sia V (Siat 8E) (fragment) | Danio rerio | n.d. | AJ715546 | CAG29385.1 | |
| α-2,8-sialyltransferase ST8Sia VI (Siat 8F) (fragment) | Danio rerio | n.d. | AJ715551 | CAG29390.1 | |
| β-galactosamide α-2,6-sialyltransferase II (ST6Gal II) | Danio rerio | n.d. | AJ627627 | CAF29495.1 | |
| N-glycan α-2,8-sialyltransferase | Danio rerio | n.d. | BC050483 AY055462 NM_153662 | AAH50483.1 AAL17875.1 NP_705948.1 | Q7ZU51 Q8QH83 | |
| ST3Gal III-related (siat6r) | Danio rerio | n.d. | BC053179 AJ626820 NM_200355 | AAH53179.1 CAF25178.1 NP_956649.1 | Q7T3B9 | |
| St3Gal-V | Danio rerio | n.d. | AJ619960 | CAF04061.1 | | |
| st6GalNAc-VI | Danio rerio | n.d. | BC060932 AJ620947 | AAH60932.1 CAF06584.1 | | |
| α-2,6-sialyltransferase (CG4871) ST6Gal I | Drosophila melanogaster | 2.4.99.1 | AE003465 AF218237 AF397532 AE003465 NM_079129 NM_166684 | AAF47256.1 AAG13185.1 AAK92126.1 AAM70791.1 NP_523853.1 NP_726474.1 | Q9GU23 Q9W121 | |
| α-2,3-sialyltransferase (ST3Gal-VI) | Gallus gallus | n.d. | AJ585767 AJ627204 | CAE51391.1 CAF25503.1 | | |
| α-2,3-sialyltransferase ST3Gal I | Gallus gallus | 2.4.99.4 | X80503 NM_205217 | CAA56666.1 NP_990548.1 | Q11200 | |
| α-2,3-sialyltransferase ST3Gal IV (fragment) | Gallus gallus | 2.4.99.- | AF035250 | AAC14163.1 | O73724 | |
| α-2,3-sialyltransferase (ST3GAL-II) | Gallus gallus | n.d. | AJ585761 | CAE51385.2 | | |
| α-2,6-sialyltransferase (Siat7b) | Gallus gallus | n.d. | AJ620653 | CAF05852.1 | | |
| α-2,6-sialyltransferase ST6Gal I | Gallus gallus | 2.4.99.1 | X75558 NM_205241 | CAA53235.1 NP_990572.1 | Q92182 | |
| α-2,6-sialyltransferase | Gallus gallus | 2.4.99.3 | - | AAE68028.1 | Q92183 | |

FIGURE 10C

| Protein | Organism | EC# | GenBank / GenPept | | SwissProt | PDB / 3D |
|---|---|---|---|---|---|---|
| ST6GalNAc I | | | X74946<br>NM_205240 | AAE68029.1<br>CAA52902.1<br>NP_990571.1 | | |
| α-2,6-sialyltransferase ST6GalNAc II | Gallus gallus | 2.4.99.- | X77775<br>NM_205233 | AAE68030.1<br>CAA54813.1<br>NP_990564.1 | Q92184 | |
| α-2,6-sialyltransferase ST6GalNAc III (SIAT7C) (fragment) | Gallus gallus | n.d. | AJ634455 | CAG25677.1 | | |
| α-2,6-sialyltransferase ST6GalNAc V (SIAT7E) (fragment) | Gallus gallus | n.d. | AJ646877 | CAG26706.1 | | |
| α-2,8-sialyltransferase (GD3 Synthase) ST8Sia I | Gallus gallus | 2.4.99.- | U73176 | AAC28888.1 | P79783 | |
| α-2,8-sialyltransferase (SIAT8B) | Gallus gallus | n.d. | AJ699419 | CAG27881.1 | | |
| α-2,8-sialyltransferase (SIAT8C) | Gallus gallus | n.d. | AJ699420 | CAG27882.1 | | |
| α-2,8-sialyltransferase (SIAT8F) | Gallus gallus | n.d. | AJ699424 | CAG27886.1 | | |
| α-2,8-syalyltransferase ST8Siα-V (SIAT8C) | Gallus gallus | n.d. | AJ704564 | CAG28697.1 | | |
| β-galactosamide α-2,6-sialyltransferase II (ST6Gal II) | Gallus gallus | n.d. | AJ627629 | CAF29497.1 | | |
| GM3 synthase (SIAT9) | Gallus gallus | 2.4.99.9 | AY515255 | AAS83519.1 | | |
| polysialyltransferase ST8Sia IV | Gallus gallus | 2.4.99.- | AF008194 | AAB95120.1 | O42399 | |
| α-2,3-sialyltransferase ST3Gal I | Homo sapiens | 2.4.99.4 | L29555<br>AF059321<br>L13972<br>AF155238<br>AF186191<br>BC018357<br>NM_003033<br>NM_173344 | AAA36612.1<br>AAC17874.1<br>AAC37574.1<br>AAD39238.1<br>AAG29876.1<br>AAH18357.1<br>NP_003024.1<br>NP_775479.1 | Q11201<br>O60677<br>Q9UN51 | |
| α-2,3-sialyltransferase ST3Gal II | Homo sapiens | 2.4.99.4 | U63090<br>BC036777<br>X96667<br>NM_006927 | AAB40389.1<br>AAH36777.1<br>CAA65447.1<br>NP_008858.1 | Q16842<br>O00654 | |
| α-2,3-sialyltransferase ST3Gal III (SiaT6) | Homo sapiens | 2.4.99.6 | L23768<br>BC050380<br>AF425851<br>AF425852<br>AF425853<br>AF425854<br>AF425855<br>AF425856<br>AF425857<br>AF425858<br>AF425859<br>AF425860<br>AF425861<br>AF425862<br>AF425863<br>AF425864<br>AF425865<br>AF425866<br>AF425867<br>AY167992<br>AY167993<br>AY167994 | AAA35778.1<br>AAH50380.1<br>AAO13859.1<br>AAO13860.1<br>AAO13861.1<br>AAO13862.1<br>AAO13863.1<br>AAO13864.1<br>AAO13865.1<br>AAO13866.1<br>AAO13867.1<br>AAO13868.1<br>AAO13869.1<br>AAO13870.1<br>AAO13871.1<br>AAO13872.1<br>AAO13873.1<br>AAO13874.1<br>AAO13875.1<br>AAO38806.1<br>AAO38807.1<br>AAO38808.1 | Q11203<br>Q86UR6<br>Q86UR7<br>Q86UR8<br>Q86UR9<br>Q86US0<br>Q86US1<br>Q86US2<br>Q8IX43<br>Q8IX44<br>Q8IX45<br>Q8IX46<br>Q8IX47<br>Q8IX48<br>Q8IX49<br>Q8IX50<br>Q8IX51<br>Q8IX52<br>Q8IX53<br>Q8IX54<br>Q8IX55<br>Q8IX56 | |

FIGURE 10D

| Protein | Organism | EC# | GenBank / GenPept | | SwissProt | PDB / 3D |
|---|---|---|---|---|---|---|
| | | | AY167995 | AAO38809.1 | Q8IX57 | |
| | | | AY167996 | AAO38810.1 | Q8IX58 | |
| | | | AY167997 | AAO38811.1 | | |
| | | | AY167998 | AAO38812.1 | | |
| | | | NM_006279 | NP_006270.1 | | |
| | | | NM_174964 | NP_777624.1 | | |
| | | | NM_174965 | NP_777625.1 | | |
| | | | NM_174966 | NP_777626.1 | | |
| | | | NM_174967 | NP_777627.1 | | |
| | | | NM_174969 | NP_777629.1 | | |
| | | | NM_174970 | NP_777630.1 | | |
| | | | NM_174972 | NP_777632.1 | | |
| α-2,3-sialyltransferase ST3Gal IV | Homo sapiens | 2.4.99.- | L23767 | AAA16460.1 | Q11206 | |
| | | | AF035249 | AAC14162.1 | O60497 | |
| | | | BC010645 | AAH10645.1 | Q96QQ9 | |
| | | | AY040826 | AAK93790.1 | Q8N6A6 | |
| | | | AF516602 | AAM66431.1 | Q8N6A7 | |
| | | | AF516603 | AAM66432.1 | Q8NFD3 | |
| | | | AF516604 | AAM66433.1 | Q8NFG7 | |
| | | | AF525084 | AAM81378.1 | | |
| | | | X74570 | CAA52662.1 | | |
| | | | CR456858 | CAG33139.1 | | |
| | | | NM_006278 | NP_006269.1 | | |
| α-2,3-sialyltransferase ST3Gal VI | Homo sapiens | 2.4.99.4 | AF119391 | AAD39131.1 | Q9Y274 | |
| | | | BC023312 | AAH23312.1 | | |
| | | | AB022918 | BAA77609.1 | | |
| | | | AX877828 | CAE89895.1 | | |
| | | | AX886023 | CAF00161.1 | | |
| | | | NM_006100 | NP_006091.1 | | |
| α-2,6-sialyltransferase (ST6Gal II ; KIAA1877) | Homo sapiens | n.d. | BC008680 | AAH08680.1 | Q86Y44 | |
| | | | AB058780 | BAB47506.1 | Q8IUG7 | |
| | | | AB059555 | BAC24793.1 | Q96HE4 | |
| | | | AJ512141 | CAD54408.1 | Q96JF0 | |
| | | | AX795193 | CAE48260.1 | | |
| | | | AX795193 | CAE48261.1 | | |
| | | | NM_032528 | NP_115917.1 | | |
| α-2,6-sialyltransferase (ST6GALNAC III) | Homo sapiens | n.d. | BC059363 | AAH59363.1 | Q8N259 | |
| | | | AY358540 | AAQ88904.1 | Q8NDV1 | |
| | | | AK091215 | BAC03611.1 | | |
| | | | AJ507291 | CAD45371.1 | | |
| | | | NM_152996 | NP_694541.1 | | |
| α-2,6-sialyltransferase (ST6GalNAc V) | Homo sapiens | n.d. | BC001201 | AAH01201.1 | Q9BVH7 | |
| | | | AK056241 | BAB71127.1 | | |
| | | | AL035409 | CAB72344.1 | | |
| | | | AJ507292 | CAD45372.1 | | |
| | | | NM_030965 | NP_112227.1 | | |
| α-2,6-sialyltransferase (SThM) ST6GalNAc II | Homo sapiens | 2.4.99.- | U14550 | AAA52228.1 | Q9UJ37 | |
| | | | BC040455 | AAH40455.1 | Q12971 | |
| | | | AJ251053 | CAB61434.1 | | |
| | | | NM_006456 | NP_006447.1 | | |
| α-2,6-sialyltransferase ST6Gal I | Homo sapiens | 2.4.99.1 | BC031476 | AAH31476.1 | P15907 | |
| | | | BC040009 | AAH40009.1 | | |
| | | | A17362 | CAA01327.1 | | |
| | | | A23699 | CAA01686.1 | | |
| | | | X17247 | CAA35111.1 | | |
| | | | X54363 | CAA38246.1 | | |
| | | | X62822 | CAA44634.1 | | |
| | | | NM_003032 | NP_003023.1 | | |
| | | | NM_173216 | NP_775323.1 | | |
| α-2,6-sialyltransferase ST6GalNAc I | Homo sapiens | 2.4.99.3 | BC022462 | AAH22462.1 | Q8TBJ6 | |
| | | | AY096001 | AAM22800.1 | Q9NSC7 | |
| | | | AY358918 | AAQ89277.1 | Q9NXQ7 | |
| | | | AK000113 | BAA90953.1 | | |
| | | | Y11339 | CAA72179.2 | | |

FIGURE 10E

| Protein | Organism | EC# | GenBank / GenPept | | SwissProt | PDB / 3D |
|---|---|---|---|---|---|---|
| | | | NM_018414 | NP_060884.1 | | |
| α-2,8-polysialyltransferase ST8Sia IV | Homo sapiens | 2.4.99.- | L41680<br>BC027866<br>BC053657<br>NM_005668 | AAC41775.1<br>AAH27866.1<br>AAH53657.1<br>NP_005659.1 | Q8N1F4<br>Q92187<br>Q92693 | |
| α-2,8-sialyltransferase (GD3 synthase) ST8Sia I | Homo sapiens | 2.4.99.8 | L32867<br>L43494<br>BC046158<br>-<br>AY569975<br>D26360<br>X77922<br>NM_003034 | AAA62366.1<br>AAC37586.1<br>AAH46158.1<br>AAQ53140.1<br>AAS75783.1<br>BAA05391.1<br>CAA54891.1<br>NP_003025.1 | Q86X71<br>Q92185<br>Q93064 | |
| α-2,8-sialyltransferase ST8Sia II | Homo sapiens | 2.4.99.- | L29556<br>U82762<br>U33551<br>BC069584<br>NM_006011 | AAA36613.1<br>AAB51242.1<br>AAC24458.1<br>AAH69584.1<br>NP_006002.1 | Q92186<br>Q92470<br>Q92746 | |
| α-2,8-sialyltransferase ST8Sia III | Homo sapiens | 2.4.99.- | AF004668<br>AF003092<br>NM_015879 | AAB87642.1<br>AAC15901.2<br>NP_056963.1 | O43173<br>Q9NS41 | |
| α-2,8-sialyltransferase ST8Sia V | Homo sapiens | 2.4.99.- | U91641<br>CR457037<br>NM_013305 | AAC51727.1<br>CAG33318.1<br>NP_037437.1 | O15466 | |
| ENSP00000020221 (fragment) | | n.d. | AC023295 | - | | |
| lactosylceramide α-2,3-sialyltransferase (ST3Gal V) | Homo sapiens | 2.4.99.9 | AF105026<br>AF119415<br>BC065936<br>AY152815<br>AAP65066<br>AY359105<br>AB018356<br>AX876536<br>NM_003896 | AAD14634.1<br>AAF66146.1<br>AAH65936.1<br>AAO16866.1<br>AAP65066.1<br>AAQ89463.1<br>BAA33950.1<br>CAE89320.1<br>NP_003887.2 | Q9UNP4<br>O94902 | |
| N-acetylgalactosaminide α-2,6-sialyltransferase (ST6GalNAc VI) | Homo sapiens | 2.4.99.- | BC006564<br>BC007802<br>BC016299<br>AY358672<br>AB035173<br>AK023900<br>AJ507293<br>AX880950<br>CR457318<br>NM_013443 | AAH06564.1<br>AAH07802.1<br>AAH16299.1<br>AAQ89035.1<br>BAA87035.1<br>BAB14715.1<br>CAD45373.1<br>CAE91145.1<br>CAG33599.1<br>NP_038471.2 | Q969X2<br>Q9H8A2<br>Q9ULB8 | |
| N-acetylgalactosaminide α-2,6-sialyltransferase IV (ST6GalNAc IV) | Homo sapiens | 2.4.99.- | AF127142<br>BC036705<br>-<br>AB035172<br>AK000600<br>Y17461<br>AJ271734<br>AX061620<br>AX068265<br>AX969252<br>NM_014403<br>NM_175039 | AAF00102.1<br>AAH36705.1<br>AAP63349.1<br>BAA87034.1<br>BAA91281.1<br>CAB44354.1<br>CAC07404.1<br>CAC24981.1<br>CAC27250.1<br>CAF14360.1<br>NP_055218.3<br>NP_778204.1 | Q9H4F1<br>Q9NWU6<br>Q9UKU1<br>Q9ULB9<br>Q9Y3G3<br>Q9Y3G4 | |
| ST8SIA-VI (fragment) | Homo sapiens | n.d. | AJ621583<br>XM_291725 | CAF21722.1<br>XP_291725.2 | | |
| unnamed protein product | Homo sapiens | n.d. | AK021929<br>AX881696 | BAB13940.1<br>CAE91353.1 | Q9HAA9 | |
| Gal β-1,3/4-GlcNAc α- | Mesocricetus | 2.4.99.6 | AJ245699 | CAB53394.1 | Q9QXF6 | |

FIGURE 10F

| Protein | Organism | EC# | GenBank / GenPept | | SwissProt | PDB / 3D |
|---|---|---|---|---|---|---|
| 2,3-sialyltransferase (ST3Gal III) | | | auratus | | | |
| Gal β-1,3/4-GlcNAc α-2,3-sialyltransferase (ST3Gal IV) | | 2.4.99.6 | AJ245700 | CAB53395.1 | Q9QXF5 | |
| GD3 synthase (fragment) ST8Sia I | | n.d. | AF141657 | AAD33879.1 | Q9WUL1 | |
| polysialyltransferase (ST8Sia IV) | | 2.4.99.- | AJ245701 | CAB53396.1 | Q9QXF4 | |
| α-2,3-sialyltransferase ST3Gal I | St3gal1 | Mus musculus | 2.4.99.4 | AF214028<br>AK031344<br>AK078469<br>X73523<br>NM_009177 | AAF60973.1<br>BAC27356.1<br>BAC37290.1<br>CAA51919.1<br>NP_033203.1 | P54751<br>Q11202<br>Q9JL30 |
| α-2,3-sialyltransferase ST3Gal II | St3gal2 | Mus musculus | 2.4.99.4 | BC015264<br>BC066064<br>AK034554<br>AK034863<br>AK053827<br>X76989<br>NM_009179<br>NM_178048 | AAH15264.1<br>AAH66064.1<br>BAC28752.1<br>BAC28859.1<br>BAC35543.1<br>CAA54294.1<br>NP_033205.1<br>NP_835149.1 | Q11204<br>Q8BPL0<br>Q8BSA0<br>Q8BSE9<br>Q91WH6 |
| α-2,3-sialyltransferase ST3Gal III | St3gal3 | Mus musculus | 2.4.99.- | BC006710<br>AK005053<br>AK013016<br>X84234<br>NM_009176 | AAH06710.1<br>BAB23779.1<br>BAB28598.1<br>CAA59013.1<br>NP_033202.2 | P97325<br>Q922X5<br>Q9CZ48<br>Q9DBB6 |
| α-2,3-sialyltransferase ST3Gal IV | St3gal4 | Mus musculus | 2.4.99.4 | BC011121<br>BC050773<br>D28941<br>AK008543<br>AB061305<br>X95809<br>NM_009178 | AAH11121.1<br>AAH50773.1<br>BAA06068.1<br>BAB25732.1<br>BAB47508.1<br>CAA65076.1<br>NP_033204.2 | P97354<br>Q61325<br>Q91Y74<br>Q921R5<br>Q9CVE8 |
| α-2,3-sialyltransferase ST3Gal VI | St3gal6 | Mus musculus | 2.4.99.4 | AF119390<br>BC052338<br>AB063326<br>AK033562<br>AK041173<br>NM_018784 | AAD39130.1<br>AAH52338.1<br>BAB79494.1<br>BAC28360.1<br>BAC30851.1<br>NP_061254 | Q80UR7<br>Q8BLV1<br>Q8VIB3<br>Q9WVG2 |
| α-2,6-sialyltransferase ST6GalNAc II | St6galnac2 | Mus musculus | 2.4.99.- | NM_009180<br>BC010208<br>AB027198<br>AK004613<br>X93999<br>X94000<br>NM_009180 | 6667963<br>AAH10208.1<br>BAB00637.1<br>BAB23410.1<br>CAA63821.1<br>CAA63822.1<br>NP_033206.2 | P70277<br>Q9DC24<br>Q9JJM5 |
| α-2,6-sialyltransferase ST6Gal I | St6gal1 | Mus musculus | 2.4.99.1 | -<br>BC027833<br>D16106<br>AK034768<br>AK084124<br>NM_145933 | AAE68031.1<br>AAH27833.1<br>BAA03680.1<br>BAC28828.1<br>BAC39120.1<br>NP_666045.1 | Q64685<br>Q8BM62<br>Q8K1L1 |
| α-2,6-sialyltransferase ST6Gal II | St6gal2 | Mus musculus | n.d. | AK082566<br>AB095093<br>AK129462<br>NM_172829 | BAC38534.1<br>BAC87752.1<br>BAC98272.1<br>NP_766417.1 | Q8BUU4 |
| α-2,6-sialyltransferase ST6GalNAc I | St6galnac1 | Mus musculus | 2.4.99.3 | Y11274<br>NM_011371 | CAA72137.1<br>NP_035501.1 | Q9QZ39<br>Q9JJP5 |
| α-2,6-sialyltransferase ST6GalNAc III | St6galnac3 | Mus musculus | n.d. | BC058387<br>AK034804<br>Y11342<br>Y11343 | AAH58387.1<br>BAC28836.1<br>CAA72181.2<br>CAB95031.1 | Q9WUV2<br>Q9JHP5 |

FIGURE 10G

| Protein | Organism | EC# | GenBank / GenPept | | SwissProt | PDB / 3D |
|---|---|---|---|---|---|---|
| | | | NM_011372 | NP_035502 | | |
| α-2,6-sialyltransferase ST6GalNAc IV | St6galnac4 | Mus musculus | 2.4.99.7 | BC056451 AK085730 AJ007310 Y15779 Y15780 Y19055 Y19057 NM_011373 | AAH56451.1 BAC39523.1 CAA07446.1 CAB43507.1 CAB43514.1 CAB93946.1 CAB93948.1 NP_035503.1 | Q8C3J2 Q9JHP2 Q9R2B6 O88725 Q9JHP0 Q9QUP9 Q9R2B5 |
| α-2,8-sialyltransferase (GD3 synthase) ST8Sia I | St8sia1 | Mus musculus | 2.4.99.8 | L38677 BC024821 AK046188 AK052444 X84235 AJ401102 NM_011374 | AAA91869.1 AAH24821.1 BAC32625.1 BAC34994.1 CAA59014.1 CAC20706.1 NP_035504.1 | Q64468 Q64687 Q8BL76 Q8BWI0 Q8K1C1 Q9EPK0 |
| α-2,8-sialyltransferase (ST8Sia VI) | St8sia6 | Mus musculus | n.d. | AB059554 AK085105 NM_145838 | BAC01265.1 BAC39367.1 NP_665837.1 | Q8BI43 Q8K4T1 |
| α-2,8-sialyltransferase ST8Sia II | St8sia2 | Mus musculus | 2.4.99.- | X83562 X99646 X99647 X99648 X99649 X99650 X99651 NM_009181 | CAA58548.1 CAA67965.1 CAA67965.1 CAA67965.1 CAA67965.1 CAA67965.1 CAA67965.1 NP_033207.1 | O35696 |
| α-2,8-sialyltransferase ST8Sia IV | St8sia4 | Mus musculus | 2.4.99.8 | BC060112 AK003690 AK041723 AJ223956 X86000 Y09484 NM_009183 | AAH60112.1 BAB22941.1 BAC31044.1 CAA11685.1 CAA59992.1 CAA70692.1 NP_033209.1 | Q64692 Q8BY70 |
| α-2,8-sialyltransferase ST8Sia V | St8sia5 | Mus musculus | 2.4.99.- | BC034855 AK078670 X98014 X98014 X98014 NM_013666 NM_153124 NM_177416 | AAH34855.1 BAC37354.1 CAA66642.1 CAA66643.1 CAA66644.1 NP_038694.1 NP_694764.1 NP_803135.1 | P70126 P70127 P70128 Q8BJW0 Q8JZQ3 |
| α-2,8-sialyltransferase ST8Sia III | St8sia3 | Mus musculus | 2.4.99.- | BC075645 AK015874 X80502 NM_009182 | AAH75645.1 BAB30012.1 CAA56665.1 NP_033208.1 | Q64689 Q9CUJ6 |
| GD1 synthase (ST6GalNAc V) | St6galnac5 | Mus musculus | n.d. | BC055737 AB030836 AB028840 AK034387 AK038434 AK042683 NM_012028 | AAH55737.1 BAA85747.1 BAA89292.1 BAC28693.1 BAC29997.1 BAC31331.1 NP_036158.2 | Q8CAM7 Q8CBX1 Q9QYJ1 Q9R0K6 |
| GM3 synthase (α-2,3-sialyltransferase) ST3Gal V | St3gal5 | Mus musculus | 2.4.99.9 | AF119416 - AB018048 AB013302 AK012961 Y15003 NM_011375 | AAF66147.1 AAP65063.1 BAA33491.1 BAA76467.1 BAB28571.1 CAA75235.1 NP_035505.1 | O88829 Q9CZ65 Q9QWF9 |
| N-acetylgalactosaminide α-2,6-sialyltransferase (ST6GalNAc VI) | St6galnac6 | Mus musculus | 2.4.99.- | BC036985 AB035174 AB035123 AK030648 | AAH36985.1 BAA87036.1 BAA95940.1 BAC27064.1 | Q8CDC3 Q8JZW3 Q9JM95 Q9R0G9 |

FIGURE 10H

| Protein | Organism | EC# | GenBank / GenPept | | SwissProt | PDB / 3D |
|---|---|---|---|---|---|---|
| | | | NM_016973 | NP_058669.1 | | |
| M138L | Myxoma virus | n.d. | U46578<br>AF170726<br>NC_001132 | AAD00069.1<br>AAE61323.1<br>AAE61326.1<br>AAF15026.1<br>NP_051852.1 | | |
| α-2,3-sialyltransferase (St3Gal-I) | Oncorhynchus mykiss | n.d. | AJ585760 | CAE51384.1 | | |
| α-2,6-sialyltransferase (Siat1) | Oncorhynchus mykiss | n.d. | AJ620649 | CAF05848.1 | | |
| α-2,8-polysialyltransferase IV (ST8Sia IV) | Oncorhynchus mykiss | n.d. | AB094402 | BAC77411.1 | Q7T2X5 | |
| GalNAc α-2,6-sialyltransferase (RtST6GalNAc) | Oncorhynchus mykiss | n.d. | AB097943 | BAC77520.1 | Q7T2X4 | |
| α-2,3-sialyltransferase ST3Gal IV | Oryctolagus cuniculus | 2.4.99.- | AF121967 | AAF28871.1 | Q9N257 | |
| OJ1217_F02.7 | Oryza sativa (japonica cultivar-group) | n.d. | AP004084 | BAD07616.1 | | |
| OSJNBa0043L24.2 or OSJNBb0002J11.9 | Oryza sativa (japonica cultivar-group) | n.d. | AL731626<br>AL662969 | CAD41185.1<br>CAE04714.1 | | |
| P0683f02.18 or P0489B03.1 | Oryza sativa (japonica cultivar-group) | n.d. | AP003289<br>AP003794 | BAB63715.1<br>BAB90552.1 | | |
| α-2,6-sialyltransferase ST6GalNAc V (Siat7E) (fragment) | Oryzias latipes | n.d. | AJ646876 | CAG26705.1 | | |
| α-2,3-sialyltransferase ST3Gal I (Siat4) | Pan troglodytes | n.d. | AJ744803 | CAG32839.1 | | |
| α-2,3-sialyltransferase ST3Gal II (Siat5) | Pan troglodytes | n.d. | AJ744804 | CAG32840.1 | | |
| α-2,3-sialyltransferase ST3Gal III (Siat6) | Pan troglodytes | n.d. | AJ626819 | CAF25177.1 | | |
| α-2,3-sialyltransferase ST3Gal IV (Siat4c) | Pan troglodytes | n.d. | AJ626824 | CAF25182.1 | | |
| α-2,3-sialyltransferase ST3Gal VI (Siat10) | Pan troglodytes | n.d. | AJ744808 | CAG32844.1 | | |
| α-2,6-sialyltransferase (Sia7A) | Pan troglodytes | n.d. | AJ748740 | CAG38615.1 | | |
| α-2,6-sialyltransferase (Sia7B) | Pan troglodytes | n.d. | AJ748741 | CAG38616.1 | | |
| α-2,6-sialyltransferase ST6GalNAc III (Siat7C) | Pan troglodytes | n.d. | AJ634454 | CAG25676.1 | | |
| α-2,6-sialyltransferase ST6GalNAc IV (Siat7D) (fragment) | Pan troglodytes | n.d. | AJ646870 | CAG26699.1 | | |
| α-2,6-sialyltransferase ST6GalNAc V (Siat7E) | Pan troglodytes | n.d. | AJ646875 | CAG26704.1 | | |
| α-2,6-sialyltransferase ST6GalNAc VI (Siat7F) (fragment) | Pan troglodytes | n.d. | AJ646882 | CAG26711.1 | | |
| α-2,8-sialyltransferase 8A (Siat8A) | Pan troglodytes | 2.4.99.8 | AJ697658 | CAG26896.1 | | |
| α-2,8-sialyltransferase 8B (Siat8B) | Pan troglodytes | n.d. | AJ697659 | CAG26897.1 | | |
| α-2,8-sialyltransferase 8C (Siat8C) | Pan troglodytes | n.d. | AJ697660 | CAG26898.1 | | |
| α-2,8-sialyltransferase 8D (Siat8D) | Pan troglodytes | n.d. | AJ697661 | CAG26899.1 | | |
| α-2,8-sialyltransferase | Pan troglodytes | n.d. | AJ697662 | CAG26900.1 | | |

FIGURE 10I

| Protein | Organism | EC# | GenBank / GenPept | | SwissProt | PDB / 3D |
|---|---|---|---|---|---|---|
| 8E (Siat8E) | | | | | | |
| α-2,8-sialyltransferase 8F (Siat8F) | Pan troglodytes | n.d. | AJ697663 | CAG26901.1 | | |
| β-galactosamide α-2,6-sialyltransferase I (ST6Gal I; Siat1) | Pan troglodytes | 2.4.99.1 | AJ627624 | CAF29492.1 | | |
| β-galactosamide α-2,6-sialyltransferase II (ST6Gal II) | Pan troglodytes | n.d. | AJ627625 | CAF29493.1 | | |
| GM3 synthase ST3Gal V (Siat9) | Pan troglodytes | n.d. | AJ744807 | CAG32843.1 | | |
| S138L | Rabbit fibroma virus Kasza | n.d. | NC_001266 | NP_052025 | | |
| α-2,3-sialyltransferase ST3Gal III | Rattus norvegicus | 2.4.99.6 | M97754 NM_031697 | AAA42146.1 NP_113885.1 | Q02734 | |
| α-2,3-sialyltransferase ST3Gal IV (Siat4c) | Rattus norvegicus | n.d. | AJ626825 | CAF25183.1 | | |
| α-2,3-sialyltransferase ST3Gal VI | Rattus norvegicus | n.d. | AJ626743 | CAF25053.1 | | |
| α-2,6-sialyltransferase ST3Gal II | Rattus norvegicus | 2.4.99.- | X76988 NM_031695 | CAA54293.1 NP_113883.1 | Q11205 | |
| α-2,6-sialyltransferase ST6Gal I | Rattus norvegicus | 2.4.99.1 | M18769 M83143 | AAA41196.1 AAB07233.1 | P13721 | |
| α-2,6-sialyltransferase ST6GalNAc I (Siat7A) | Rattus norvegicus | n.d. | AJ634458 | CAG25684.1 | | |
| α-2,6-sialyltransferase ST6GalNAc II (Siat7B) | Rattus norvegicus | n.d. | AJ634457 | CAG25679.1 | | |
| α-2,6-sialyltransferase ST6GalNAc III | Rattus norvegicus | 2.4.99.- | L29554 BC072501 NM_019123 | AAC42086.1 AAH72501.1 NP_061996.1 | Q64686 | |
| α-2,6-sialyltransferase ST6GalNAc IV (Siat7D) (fragment) | Rattus norvegicus | n.d. | AJ646871 | CAG26700.1 | | |
| α-2,6-sialyltransferase ST6GalNAc V (Siat7E) | Rattus norvegicus | n.d. | AJ646872 | CAG26701.1 | | |
| α-2,6-sialyltransferase ST6GalNAc VI (Siat7F) (fragment) | Rattus norvegicus | n.d. | AJ646881 | CAG26710.1 | | |
| α-2,8-sialyltransferase (GD3 synthase) ST8Sia I | Rattus norvegicus | 2.4.99.- | U53883 D45255 | AAC27541.1 BAA08213.1 | P70554 P97713 | |
| α-2,8-sialyltransferase (SIAT8E) | Rattus norvegicus | n.d. | AJ699422 | CAG27884.1 | | |
| α-2,8-sialyltransferase (SIAT8F) | Rattus norvegicus | n.d. | AJ699423 | CAG27885.1 | | |
| α-2,8-sialyltransferase ST8Sia II | Rattus norvegicus | 2.4.99.- | L13445 NM_057156 | AAA42147.1 NP_476497.1 | Q07977 Q64688 | |
| α-2,8-sialyltransferase ST8Sia III | Rattus norvegicus | 2.4.99.- | U55938 NM_013029 | AAB50061.1 NP_037161.1 | P97877 | |
| α-2,8-sialyltransferase ST8Sia IV | Rattus norvegicus | 2.4.99.- | U90215 | AAB49989.1 | O08563 | |
| β-galactosamide α-2,6-sialyltransferase II (ST6Gal II) | Rattus norvegicus | n.d. | AJ627626 | CAF29494.1 | | |
| GM3 synthase ST3Gal V | Rattus norvegicus | n.d. | AB018049 NM_031337 | BAA33492.1 NP_112627.1 | O88830 | |

FIGURE 10J

| Protein | Organism | EC# | GenBank / GenPept | | SwissProt | PDB / 3D |
|---|---|---|---|---|---|---|
| sialyltransferase ST3Gal-I (Siat4A) | Rattus norvegicus | n.d. | AJ748840 | CAG44449.1 | | |
| α-2,3-sialyltransferase (St3Gal-II) | Silurana tropicalis | n.d. | AJ585763 | CAE51387.1 | | |
| α-2,6-sialyltransferase (Siat7b) | Silurana tropicalis | n.d. | AJ620650 | CAF05849.1 | | |
| α-2,6-sialyltransferase (St6galnac) | Strongylocentrotus purpuratus | n.d. | AJ699425 | CAG27887.1 | | |
| α-2,3-sialyltransferase (ST3GAL-III) | Sus scrofa | n.d. | AJ585765 | CAE51389.1 | | |
| α-2,3-sialyltransferase (ST3GAL-IV) | Sus scrofa | n.d. | AJ584674 | CAE48299.1 | | |
| α-2,3-sialyltransferase ST3Gal I | Sus scrofa | 2.4.99.4 | M97753 | AAA31125.1 | Q02745 | |
| α-2,6-sialyltransferase (fragment) ST6Gal I | Sus scrofa | 2.4.99.1 | AF136746 | AAD33059.1 | Q9XSG8 | |
| β-galactosamide α-2,6-sialyltransferase (ST6GalNAc-V) | Sus scrofa | n.d. | AJ620948 | CAF06585.2 | | |
| sialyltransferase (fragment) ST6Gal I | sus scrofa | n.d. | AF041031 | AAC15633.1 | O62717 | |
| ST6GALNAC-V | Sus scrofa | n.d. | AJ620948 | CAF06585.1 | | |
| α-2,3-sialyltransferase (Siat5-r) | Takifugu rubripes | n.d. | AJ744805 | CAG32841.1 | | |
| α-2,3-sialyltransferase ST3Gal I (Siat4) | Takifugu rubripes | n.d. | AJ626816 | CAF25174.1 | | |
| α-2,3-sialyltransferase ST3Gal II (Siat5) (fragment) | Takifugu rubripes | n.d. | AJ626817 | CAF25175.1 | | |
| α-2,3-sialyltransferase ST3Gal III (Siat6) | Takifugu rubripes | n.d. | AJ626818 | CAF25176.1 | | |
| α-2,6-sialyltransferase ST6Gal I (Siat1) | Takifugu rubripes | n.d. | AJ744800 | CAG32836.1 | | |
| α-2,6-sialyltransferase ST6GalNAc II (Siat7B) | Takifugu rubripes | n.d. | AJ634460 | CAG25681.1 | | |
| α-2,6-sialyltransferase ST6GalNAc II B (Siat7B-related) | Takifugu rubripes | n.d. | AJ634461 | CAG25682.1 | | |
| α-2,6-sialyltransferase ST6GalNAc III (Siat7C) (fragment) | Takifugu rubripes | n.d. | AJ634456 | CAG25678.1 | | |
| α-2,6-sialyltransferase ST6GalNAc IV (siat7D) (fragment) | Takifugu rubripes | 2.4.99.3 | Y17466 AJ646869 | CAB44338.1 CAG26698.1 | Q9W6U6 | |
| α-2,6-sialyltransferase ST6GalNAc V (Siat7E) (fragment) | Takifugu rubripes | n.d. | AJ646873 | CAG26702.1 | | |
| α-2,6-sialyltransferase ST6GalNAc VI (Siat7F) (fragment) | Takifugu rubripes | n.d. | AJ646880 | CAG26709.1 | | |
| α-2,8-sialyltransferase ST8Sia I (Siat 8A) (fragment) | Takifugu rubripes | n.d. | AJ715534 | CAG29373.1 | | |
| α-2,8-sialyltransferase ST8Sia II (Siat 8B) (fragment) | Takifugu rubripes | n.d. | AJ715538 | CAG29377.1 | | |
| α-2,8-sialyltransferase ST8Sia III (Siat 8C) (fragment) | Takifugu rubripes | n.d. | AJ715541 | CAG29380.1 | | |
| α-2,8-sialyltransferase ST8Sia IIIr (Siat 8Cr) | Takifugu rubripes | n.d. | AJ715542 | CAG29381.1 | | |
| α-2,8-sialyltransferase ST8Sia V (Siat 8E) | Takifugu rubripes | n.d. | AJ715547 | CAG29386.1 | | |

FIGURE 10K

| Protein | Organism | EC# | GenBank / GenPept | | SwissProt | PDB / 3D |
|---|---|---|---|---|---|---|
| (fragment) | | | | | | |
| α-2,8-sialyltransferase ST8Sia VI (Siat 8F) (fragment) | Takifugu rubripes | n.d. | AJ715549 | CAG29388.1 | | |
| α-2,8-sialyltransferase ST8Sia VIr (Siat 8Fr) | Takifugu rubripes | n.d. | AJ715550 | CAG29389.1 | | |
| α-2,3-sialyltransferase (Siat5-r) | Tetraodon nigroviridis | n.d. | AJ744806 | CAG32842.1 | | |
| α-2,3-sialyltransferase ST3Gal I (Siat4) | Tetraodon nigroviridis | n.d. | AJ744802 | CAG32838.1 | | |
| α-2,3-sialyltransferase ST3Gal III (Siat6) | Tetraodon nigroviridis | n.d. | AJ626822 | CAF25180.1 | | |
| α-2,6-sialyltransferase ST6GalNAc II (Siat7B) | Tetraodon nigroviridis | n.d. | AJ634462 | CAG25683.1 | | |
| α-2,6-sialyltransferase ST6GalNAc V (Siat7E) (fragment) | Tetraodon nigroviridis | n.d. | AJ646879 | CAG26708.1 | | |
| α-2,8-sialyltransferase ST8Sia I (Siat 8A) (fragment) | Tetraodon nigroviridis | n.d. | AJ715536 | CAG29375.1 | | |
| α-2,8-sialyltransferase ST8Sia II (Siat 8B) (fragment) | Tetraodon nigroviridis | n.d. | AJ715537 | CAG29376.1 | | |
| α-2,8-sialyltransferase ST8Sia III (Siat 8C) (fragment) | Tetraodon nigroviridis | n.d. | AJ715539 | CAG29378.1 | | |
| α-2,8-sialyltransferase ST8Sia IIIr (Siat 8Cr) (fragment) | Tetraodon nigroviridis | n.d. | AJ715540 | CAG29379.1 | | |
| α-2,8-sialyltransferase ST8Sia V (Siat 8E) (fragment) | Tetraodon nigroviridis | n.d. | AJ715548 | CAG29387.1 | | |
| α-2,3-sialyltransferase (St3Gal-II) | Xenopus laevis | n.d. | AJ585762 | CAE51386.1 | | |
| α-2,3-sialyltransferase (St3Gal-VI) | Xenopus laevis | n.d. | AJ585766 | CAE51390.1 | | |
| α-2,3-sialyltransferase St3Gal-III (Siat6) | Xenopus laevis | n.d. | AJ585764 AJ626823 | CAE51388.1 CAF25181.1 | | |
| α-2,8-polysialyltransferase | Xenopus laevis | 2.4.99.- | AB007468 | BAA32617.1 | O93234 | |
| α-2,8-sialyltransferase ST8Siα-I (Siat8A;GD3 synthase) | Xenopus laevis | n.d. | AY272056 AY272057 AJ704562 | AAQ16162.1 AAQ16163.1 CAG28695.1 | | |
| Unknown (protein for MGC:81265) | Xenopus laevis | n.d. | BC068760 | AAH68760.1 | | |
| α-2,3-sialyltransferase (3Gal-VI) | Xenopus tropicalis | n.d. | AJ626744 | CAF25054.1 | | |
| α-2,3-sialyltransferase (Siat4c) | Xenopus tropicalis | n.d. | AJ622908 | CAF22058.1 | | |
| α-2,6-sialyltransferase ST6GalNAc V (Siat7E) (fragment) | Xenopus tropicalis | n.d. | AJ646878 | CAG26707.1 | | |
| α-2,8-sialyltransferase ST8Sia III (Siat 8C) (fragment) | Xenopus tropicalis | n.d. | AJ715544 | CAG29383.1 | | |
| β-galactosamide α-2,6-sialyltransferase II (ST6Gal II) | Xenopus tropicalis | n.d. | AJ627628 | CAF29496.1 | | |
| sialytransferase St8Sial | Xenopus tropicalis | n.d. | AY652775 | AAT67042 | | |
| poly-α-2,8-sialosyl sialyltransferase (NeuS) | Escherichia coli K1 | 2.4.-.- | M76370 X60598 | AAA24213.1 CAA43053.1 | Q57269 | |
| polysialyltransferase | Escherichia coli K92 | 2.4.-.- | M88479 | AAA24215.1 | Q47404 | |

FIGURE 10L

| Protein | Organism | EC# | GenBank / GenPept | | SwissProt | PDB / 3D |
|---|---|---|---|---|---|---|
| α-2,8 polysialyltransferase SiaD | Neisseria meningitidis B1940 | 2.4.-.- | M95053 X78068 | AAA20478.1 CAA54985.1 | Q51281 Q51145 | |
| SynE | Neisseria meningitidis FAM18 | n.d. | U75650 | AAB53842.1 | O06435 | |
| polysialyltransferase (SiaD)(fragment) | Neisseria meningitidis M1019 | n.d. | AY234192 | AAO85290.1 | | |
| SiaD (fragment) | Neisseria meningitidis M209 | n.d. | AY281046 | AAP34769.1 | | |
| SiaD (fragment) | Neisseria meningitidis M3045 | n.d. | AY281044 | AAP34767.1 | | |
| polysialyltransferase (SiaD)(fragment) | Neisseria meningitidis M3315 | n.d. | AY234191 | AAO85289.1 | | |
| SiaD (fragment) | Neisseria meningitidis M3515 | n.d. | AY281047 | AAP34770.1 | | |
| polysialyltransferase (SiaD)(fragment) | Neisseria meningitidis M4211 | n.d. | AY234190 | AAO85288.1 | | |
| SiaD (fragment) | Neisseria meningitidis M4642 | n.d. | AY281048 | AAP34771.1 | | |
| polysialyltransferase (SiaD)(fragment) | Neisseria meningitidis M5177 | n.d. | AY234193 | AAO85291.1 | | |
| SiaD | Neisseria meningitidis M5178 | n.d. | AY281043 | AAP34766.1 | | |
| SiaD (fragment) | Neisseria meningitidis M980 | n.d. | AY281045 | AAP34768.1 | | |
| NMB0067 | Neisseria meningitidis MC58 | n.d. | NC_003112 | NP_273131 | | |
| Lst | Aeromonas punctata Sch3 | n.d. | AF126256 | AAS66624.1 | | |
| ORF2 | Haemophilus influenzae A2 | n.d. | M94855 | AAA24979.1 | | |
| HI1699 | Haemophilus influenzae Rd | n.d. | U32842 NC_000907 | AAC23345.1 NP_439841.1 | Q48211 | |
| α-2,3-sialyltransferase | Neisseria gonorrhoeae F62 | 2.4.99.4 | U60664 | AAC44539.1 AAE67205.1 | P72074 | |
| α-2,3-sialyltransferase | Neisseria meningitidis 126E, NRCC 4010 | 2.4.99.4 | U60662 | AAC44544.2 | | |
| α-2,3-sialyltransferase | Neisseria meningitidis 406Y, NRCC 4030 | 2.4.99.4 | U60661 | AAC44543.1 | | |
| α-2,3-sialyltransferase (NMB0922) | Neisseria meningitidis MC58 | 2.4.99.4 | U60660 AE002443 NC_003112 | AAC44541.1 AAF41330.1 NP_273962.1 | P72097 | |
| NMA1118 | Neisseria meningitidis Z2491 | n.d. | AL162755 NC_003116 | CAB84380.1 NP_283887.1 | Q9JUV5 | |
| PM0508 | Pasteurella multocida PM70 | n.d. | AE006086 NC_002663 | AAK02592.1 NP_245445.1 | Q9CNC4 | |
| WaaH | Salmonella enterica SARB25 | n.d. | AF519787 | AAM82550.1 | Q8KS93 | |
| WaaH | Salmonella enterica SARB3 | n.d. | AF519788 | AAM82551.1 | Q8KS92 | |
| WaaH | Salmonella enterica SARB39 | n.d. | AF519789 | AAM82552.1 | | |
| WaaH | Salmonella enterica SARB53 | n.d. | AF519790 | AAM82553.1 | | |
| WaaH | Salmonella enterica SARB57 | n.d. | AF519791 | AAM82554.1 | Q8KS91 | |
| WaaH | Salmonella enterica SARB71 | n.d. | AF519793 | AAM82556.1 | Q8KS89 | |
| WaaH | Salmonella enterica | n.d. | AF519792 | AAM82555.1 | Q8KS90 | |

FIGURE 10M

| Protein | Organism | EC# | GenBank / GenPept | SwissProt | PDB / 3D |
|---|---|---|---|---|---|
| | SARB8 | | | | |
| WaaH | Salmonella enterica SARC10V | n.d. | AF519779 | AAM88840.1 | Q8KS99 |
| WaaH (fragment) | Salmonella enterica SARC12 | n.d. | AF519781 | AAM88842.1 | |
| WaaH (fragment) | Salmonella enterica SARC13I | n.d. | AF519782 | AAM88843.1 | Q8KS98 |
| WaaH (fragment) | Salmonella enterica SARC14I | n.d. | AF519783 | AAM88844.1 | Q8KS97 |
| WaaH | Salmonella enterica SARC15II | n.d. | AF519784 | AAM88845.1 | Q8KS96 |
| WaaH | Salmonella enterica SARC16II | n.d. | AF519785 | AAM88846.1 | Q8KS95 |
| WaaH (fragment) | Salmonella enterica SARC3I | n.d. | AF519772 | AAM88834.1 | Q8KSA4 |
| WaaH (fragment) | Salmonella enterica SARC4I | n.d. | AF519773 | AAM88835.1 | Q8KSA3 |
| WaaH | Salmonella enterica SARC5IIa | n.d. | AF519774 | AAM88836.1 | |
| WaaH | Salmonella enterica SARC6IIa | n.d. | AF519775 | AAM88837.1 | Q8KSA2 |
| WaaH | Salmonella enterica SARC8 | n.d. | AF519777 | AAM88838.1 | Q8KSA1 |
| WaaH | Salmonella enterica SARC9V | n.d. | AF519778 | AAM88839.1 | Q8KSA0 |
| UDP-glucose : α-1,2-glucosyltransferase (WaaH) | Salmonella enterica subsp. arizonae SARC 5 | 2.4.1.- | AF511116 | AAM48166.1 | |
| bifunctional α-2,3/-2,8-sialyltransferase (Cst-II) | Campylobacter jejuni ATCC 43449 | n.d. | AF401529 | AAL06004.1 | Q93CZ5 |
| Cst | Campylobacter jejuni 81-176 | n.d. | AF305571 | AAL09368.1 | |
| α-2,3-sialyltransferase (Cst-III) | Campylobacter jejuni ATCC 43429 | 2.4.99.- | AY044156 | AAK73183.1 | |
| α-2,3-sialyltransferase (Cst-III) | Campylobacter jejuni ATCC 43430 | 2.4.99.- | AF400047 | AAK85419.1 | |
| α-2,3-sialyltransferase (Cst-II) | Campylobacter jejuni ATCC 43432 | 2.4.99.- | AF215659 | AAG43979.1 | Q9F0M9 |
| α-2,3/8-sialyltransferase (CstII) | Campylobacter jejuni ATCC 43438 | n.d. | AF400048 | AAK91725.1 | Q93MQ0 |
| α-2,3-sialyltransferase cst-II | Campylobacter jejuni ATCC 43446 | 2.4.99.- | AF167344 | AAF34137.1 | |
| α-2,3-sialyltransferase (Cst-II) | Campylobacter jejuni ATCC 43456 | 2.4.99.- | AF401528 | AAL05990.1 | Q93D05 |
| α-2,3-/α-2,8-sialyltransferase (CstII) | Campylobacter jejuni ATCC 43460 | 2.4.99.- | AY044868 | AAK96001.1 | Q938X6 |
| α-2,3/8-sialyltransferase (Cst-II) | Campylobacter jejuni ATCC 700297 | n.d. | AF216647 | AAL36462.1 | |
| ORF | Campylobacter jejuni GB11 | n.d. | AY422197 | AAR82875.1 | |
| α-2,3-sialyltransferase cstIII | Campylobacter jejuni MSC57360 | 2.4.99.- | AF195055 | AAG29922.1 | |
| α-2,3-sialyltransferase cstIII Cj1140 | Campylobacter jejuni NCTC 11168 | 2.4.99.- | AL139077 NC_002163 | CAB73395.1 NP_282288.1 | Q9PNF4 |
| α-2,3/α-2,8-sialyltransferase II (cstII) | Campylobacter jejuni O:10 | n.d. | - AX934427 | AAO96669.1 CAF04167.1 | |
| α-2,3/α-2,8-sialyltransferase II (CstII) | Campylobacter jejuni O:19 | n.d. | AX934431 | CAF04169.1 | |
| α-2,3/α-2,8-sialyltransferase II (CstII) | Campylobacter jejuni O:36 | n.d. | AX934436 | CAF04171.1 | |
| α-2,3/α-2,8- | Campylobacter | n.d. | AX934434 | CAF04170.1 | |

FIGURE 10N

| Protein | Organism | EC# | GenBank / GenPept | | SwissProt | PDB / 3D |
|---|---|---|---|---|---|---|
| sialyltransferase II (CstII) | jejuni O:4 | | | | | |
| α-2,3/α-2,8-sialyltransferase II (CstII) | Campylobacter jejuni O:41 | n.d. | -<br>-<br>AX934429 | AAO96670.1<br>AAT17967.1<br>CAF04168.1 | | |
| α-2,3-sialyltransferase cst-I | Campylobacter jejuni OH4384 | 2.4.99.- | AF130466<br>- | AAF13495.1<br>AAS36261.1 | Q9RGF1 | |
| bifunctional α-2,3/-2,8-sialyltransferase (Cst-II) | Campylobacter jejuni OH4384 | 2.4.99.- | AF130984<br>AX934425 | AAF31771.1<br>CAF04166.1 | | 1RO7 C<br>1RO8 A |
| HI0352 (fragment) | Haemophilus influenzae Rd | n.d. | U32720<br>X57315<br>NC_000907 | AAC22013.1<br>CAA40567.1<br>NP_438516.1 | P24324 | |
| PM1174 | Pasteurella multocida PM70 | n.d. | AE006157<br>NC_002663 | AAK03258.1<br>NP_246111.1 | Q9CLP3 | |
| Sequence 10 from patent US 6503744 | Unknown. | n.d. | - | AAO96672.1 | | |
| Sequence 10 from patent US 6699705 | Unknown. | n.d. | - | AAT17969.1 | | |
| Sequence 12 from patent US 6699705 | Unknown. | n.d. | - | AAT17970.1 | | |
| Sequence 2 from patent US 6709834 | Unknown. | n.d. | - | AAT23232.1 | | |
| Sequence 3 from patent US 6503744 | Unknown. | n.d. | - | AAO96668.1 | | |
| Sequence 3 from patent US 6699705 | Unknown. | n.d. | - | AAT17965.1 | | |
| Sequence 34 from patent US 6503744 | Unknown. | n.d. | - | AAO96684.1 | | |
| Sequence 35 from patent US 6503744 (fragment) | Unknown. | n.d. | -<br>- | AAO96685.1<br>AAS36262.1 | | |
| Sequence 48 from patent US 6699705 | Unknown. | n.d. | - | AAT17988.1 | | |
| Sequence 5 from patent US 6699705 | Unknown. | n.d. | - | AAT17966.1 | | |
| Sequence 9 from patent US 6503744 | Unknown. | n.d. | - | AAO96671.1 | | |

O-LINKED GLYCOSYLATION OF PEPTIDES

CROSS-REFERENCES TO RELATED APPLICATIONS

The present application is a U.S. National Phase application of PCT Application No. PCT/US2004/040709, filed Dec. 3, 2004, and claims priority to U.S. Provisional Patent Application No. 60/535,284, filed Jan. 8, 2004, U.S. Provisional Patent Application No. 60/544,411, filed Feb. 12, 2004; U.S. Provisional Patent Application No. 60/546,631, filed Feb. 20, 2004; U.S. Provisional Patent Application No. 60/555,813, filed Mar. 23, 2004, and U.S. Provisional Patent Application No. 60/570,891, filed May 12, 2004, each of which are incorporated herein by reference in their entirety for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 98,552 bytes ASCII (Text) file named "ReplacementSequenceListing" created Nov. 10, 2011.

FIELD OF THE INVENTION

The present invention relates to O-linked glycosylated glycopeptides, particularly therapeutic peptides and peptide mutants that include O-linked glycosylation sites not present in the wild-type peptide.

The administration of glycosylated and non-glycosylated peptides for engendering a particular physiological response is well known in the medicinal arts. For example, both purified and recombinant hGH are used for treating conditions and diseases due to hGH deficiency, e.g., dwarfism in children, interferon has known antiviral activity and granulocyte colony stimulating factor stimulates the production of white blood cells.

A principal factor that has limited the use of therapeutic peptides is the difficulty inherent in engineering an expression system to express a peptide having the glycosylation pattern of the wild-type peptide. As is known in the art, improperly or incompletely glycosylated peptides can be immunogenic, leading to neutralization of the peptide and/or leading to the development of an allergic response. Other deficiencies of recombinantly produced glycopeptides include suboptimal potency and rapid clearance rates.

One approach to solving the problems inherent in the production of glycosylated peptide therapeutics has been to modify the peptides in vitro after they are expressed. Post-expression in vitro modification has been used to both modify of glycan structures and introduce of glycans at novel sites. A comprehensive toolbox of recombinant eukaryotic glycosyltransferases has become available, making in vitro enzymatic synthesis of mammalian glycoconjugates with custom designed glycosylation patterns and glycosyl structures possible. See, for example, U.S. Pat. Nos. 5,876,980; 6,030,815; 5,728,554; 5,922,577; and WO/9831826; US2003180835; and WO 03/031464.

In addition to manipulating the structure of glycosyl groups on polypeptides, glycopeptides can be prepared with one or more non-saccharide modifying groups, such as water soluble polymers. An exemplary polymer that has been conjugated to peptides is poly(ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332).

In these non-specific methods, poly(ethyleneglycol) is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous product is superior.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labeled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. Carbohydr. Res. 305: 415-422 (1998) and U.S. Patent Application Publication 20040137557 which is incorporated herein by reference).

Carbohydrates are attached to glycopeptides in several ways of which N-linked to asparagine and mucin-type O-linked to serine and threonine are the most relevant for recombinant glycoprotein therapeutics. Unfortunately, not all polypeptide comprise an N- or O-linked glycosylation site as part of their primary amino acid sequence. In other cases an existing glycosylation site may be inconvenient for the attachment of a modifying group (e.g., a water-soluble or water-insoluble polymers, therapeutic moieties, and or biomolecules) to the polypeptide, or attachment of such moieties at that site may cause an undesirable decrease in biological activity of the polypeptide. Thus there is a need in the art for methods that permit both the precise creation of glycosylation sites and the ability to precisely direct the modification of those sites.

SUMMARY OF THE INVENTION

It is a discovery of the present invention that enzymatic glycoconjugation reactions can be specifically targeted to O-linked glycosylation sites and to glycosyl residues that are attached to O-linked glycosylation sites. The targeted O-linked glycosylation sites can be sites native to a wild-type peptide or, alternatively, they can be introduced into a peptide by mutation. Accordingly, the present invention provides polypeptides comprising mutated sites suitable for O-linked glycosylation and pharmaceutical compositions thereof. In addition, the present invention provides methods of making such polypeptides and using such polypeptides and/or pharmaceutical compositions thereof for therapeutic treatments.

Thus, in a first aspect, the invention provides an isolated polypeptide comprising a mutant peptide sequence, wherein the mutant peptide sequence encodes an O-linked glycosylation site that does not exist in the corresponding wild-type polypeptide.

In one embodiment, the isolated polypeptide is a G-CSF polypeptide.

In one embodiment, the G-CSF polypeptide comprises a mutant peptide sequence with the formula of $M^1X_nTPLGP$ (SEQ ID NO: 214) or $M^1B_oPZ_mX_nTPLGP$ (SEQ ID NO: 215). In this embodiment, the superscript, 1, denotes the first position of the amino acid sequence of the wild-type G-CSF sequence (SEQ ID NO: 143), the subscripts n, o, and m are integers selected from 0 to 3, and at least one of X and B is threonine or serine, and when more than one of X and B is threonine or serine, the identity of these moieties is independently selected. Also in this embodiment, Z is selected from glutamate, any uncharged amino acid or dipeptide combination including MQ, GQ, and MV. In another embodiment, the G-CSF polypeptide comprises a mutant peptide sequence selected from the sequences consisting of MVTPLGP (SEQ ID NO: 1), MQTPLGP (SEQ ID NO: 2), MIATPLGP (SEQ ID NO: 3), MATPLGP (SEQ ID NO: 4), MPTQGAMPLGP (SEQ ID NO: 5), MVQTPLGP (SEQ ID NO: 6), MQSTPLGP (SEQ ID NO: 7), MGQTPLGP (SEQ ID NO: 8), MAPTSSSPLGP (SEQ ID NO: 9), and MAPTPLGPA (SEQ ID NO: 10).

In another embodiment, the G-CSF polypeptide comprises a mutant peptide sequence with the formula of $M^1TPXBO_rP$ (SEQ ID NO: 225). In this embodiment the superscript, 1, denotes the first position of the amino acid sequence of the wild-type G-CSF sequence (SEQ ID NO: 143), and the subscript r is an integer selected from 0 to 3, and at least one of X, B and O is threonine or serine, and when more than one of X, B and O is threonine or serine, the identity of these moieties is independently selected. In another embodiment, the G-CSF polypeptide comprises a mutant peptide sequence selected from the sequences consisting of: MTPTLGP (SEQ ID NO: 228), MTPTQLGP (SEQ ID NO: 11), MTPTSLGP (SEQ ID NO: 12), MTPTQGP (SEQ ID NO: 13), MTPTSSP (SEQ ID NO: 14), $M^1$TPQTP (SEQ ID NO: 15), $M^1$TPTGP (SEQ ID NO: 16), $M^1$TPLTP (SEQ ID NO: 17), $M^1$TPNTGP (SEQ ID NO: 18), MTPLGP (SEQ ID NO: 19), $M^1$TPVTP (SEQ ID NO: 20), $M^1$TPMVTP (SEQ ID NO: 21), and $MT^1P^2TQGL^3G^4P^5A^6S^7$ (SEQ ID NO: 22).

In another embodiment, the G-CSF polypeptide comprises a mutant peptide sequence with the formula of $LGX^{53}B_oLGI$ (SEQ ID NO: 217), wherein the superscript denotes the position of the amino acid in the wild type G-CSF amino acid sequence, and X is histidine, serine, arginine, glutamic acid or tyrosine, and B is either threonine or serine, and o is an integer from 0 to 3. In another embodiment, the G-CSF polypeptide comprises a mutant peptide sequence selected from the sequences consisting of: LGHTLGI (SEQ ID NO: 23), LGSSLGI (SEQ ID NO: 24), LGYSLGI (SEQ ID NO: 25), LGESLGI (SEQ ID NO: 26), and LGSTLGI (SEQ ID NO: 27).

In another embodiment, the G-CSF polypeptide comprises a mutant peptide sequence with the formula of $P^{129}Z_mJ_qO_rX_nPT$ (SEQ ID NO: 218) wherein the superscript denotes the position of the amino acid in the wild type G-CSF amino acid sequence, and Z, J, O and X are independently selected from threonine or serine, and m, q, r, and n are integers independently selected from 0 to 3. In another embodiment, the G-CSF polypeptide comprises a mutant peptide sequence selected from the sequences consisting of: $P^{129}$ATQPT (SEQ ID NO: 28), $P^{129}$TLGPT (SEQ ID NO: 29), $P^{129}$TQGPT (SEQ ID NO: 30), P129TSSPT (SEQ ID NO: 31), $P^{129}$TQGAPT (SEQ ID NO: 32), $P^{129}$NTGPT (SEQ ID NO: 33), PALQPTQT (SEQ ID NO: 34), $P^{129}$ALTPT (SEQ ID NO: 35), $P^{129}$MVTPT (SEQ ID NO: 36), $P^{129}$ASSTPT (SEQ ID NO: 37), $P^{129}$TTQP (SEQ ID NO: 38), $P^{129}$NTLP (SEQ ID NO: 39), $P^{129}$TLQP (SEQ ID NO: 40), $MAP^{129}$ATQPTQGAM (SEQ ID NO: 41), and $MP^{129}$ATTQPTQGAM (SEQ ID NO: 42).

In another embodiment, the G-CSF polypeptide comprises a mutant peptide sequence with the formula of $PZ_mU_sJ_qP^{61}O_rX_mB_oC$ (SEQ ID NO: 219) wherein the superscript denotes the position of the amino acid in the wild type G-CSF amino acid sequence, and at least one of Z, J, O, and U is selected from threonine or serine, and when more than one of Z, J, O and U is threonine or serine, each is independently selected, X and B are any uncharged amino acid or glutamate, and m, s, q, r, n, and o are integers independently selected from 0 to 3. In another embodiment the G-CSF polypeptide comprises a mutant peptide sequence selected from the sequences consisting of: $P^{61}$TSSC (SEQ ID NO: 43), $P^{61}$TSSAC (SEQ ID NO: 44), $LGIPTAP^{61}LSSC$ (SEQ ID NO: 45), $LGIPTQP^{61}LSSC$ (SEQ ID NO: 46), $LGIPTQGP^{61}LSSC$ (SEQ ID NO: 47), $LGIPQTP^{61}LSSC$ (SEQ ID NO: 48), $LGIPTSP^{61}LSSC$ (SEQ ID NO: 49), $LGIPTQP^{61}LSSC$ (SEQ ID NO: 50), $LGTPWAP^{61}LSSC$ (SEQ ID NO: 51), $LGTPFAP^{61}LSSC$ (SEQ ID NO: 52), $P^{61}$FTP (SEQ ID NO: 53), and $SLGAP^{58}TAP^{61}LSS$ (SEQ ID NO: 54).

In another embodiment the G-CSF polypeptide comprises a mutant peptide sequence with the formula of $Ø_aG_pJ_qO_rP^{175}X_nB_oZ_mU_sΨ_t$ (SEQ ID NO: 220) wherein the superscript denotes the position of the amino acid in SEQ ID NO: 143, and at least one of Z, U, O, J, G, Ø, B and X is threonine or serine and when more than one of Z, U, O, J, G, Ø, B and X are threonine or serine, they are independently selected. 0 is optionally R, and G is optionally H. The symbol Ψ represents any uncharged amino acid residue or glutamate, and a, p, q, r, n, o, m, s, and t are integers independently selected from 0 to 3. In another embodiment the G-CSF polypeptide comprises a mutant peptide sequence selected from the sequences consisting of: $RHLAQTP^{175}$ (SEQ ID NO: 55), $RHLAGQTP^{175}$ (SEQ ID NO: 56), $QP^{175}TQGAMP$ (SEQ ID NO: 57), $RHLAQTP^{175}AM$ (SEQ ID NO: 58), $QP^{175}TSSAP$ (SEQ ID NO: 59), $QP^{175}TSSAP$ (SEQ ID NO: 60), $QP^{175}TQGAMP$ (SEQ ID NO: 61), $QP^{175}TQGAM$ (SEQ ID NO: 62), $QP^{175}TQGA$ (SEQ ID NO: 63), $QP^{175}TVM$ (SEQ ID NO: 64), $QP^{175}NTGP$ (SEQ ID NO: 65), and $QP^{175}QTLP$ (SEQ ID NO: 66).

In another embodiment the G-CSF polypeptide comprises a mutant peptide sequence selected from the sequences $P^{133}TQTAMP^{139}$ (SEQ ID NO:67) $P^{133}TQGTMP$ (SEQ ID NO:68), $P^{133}TQGTNP$ (SEQ ID NO:69), $P^{133}TQGTLP$ (SEQ ID NO:70), and $PALQP^{133}TQTAMPA$ (SEQ ID NO:71).

In another embodiment, the isolated polypeptide is an hGH polypeptide.

In one embodiment, the hGH polypeptide comprises a mutant peptide sequence with the formula of $P^{133}JXBOZUK^{140}QTYS$ (SEQ ID NO: 221), wherein superscripts denote the position of the amino acid in (SEQ ID NO: 160); and J is selected from threonine and arginine; X is selected from alanine, glutamine, isoleucine, and threonine; B is selected from glycine, alanine, leucine, valine, asparagine, glutamine, and threonine; 0 is selected from tyrosine, serine, alanine, and threonine; and Z is selected from isoleucine and methionine; and U is selected from phenylalanine and proline. In another embodiment, the hGH polypeptide comprises a mutant peptide sequence selected from the sequences consisting of: PTTGQIFK (SEQ ID NO: 72), PTTAQIFK (SEQ ID NO: 73), PTTLQIFK (SEQ ID NO: 74), PTTLYVFK (SEQ ID NO: 75), PTTVQIFK (SEQ ID NO: 76), PTTVSIFK (SEQ ID NO: 77), PTTNQIFK (SEQ ID NO: 78), PTTQQIFK (SEQ ID NO: 79), PTATQIFK (SEQ ID NO: 80), PTQGQIFK (SEQ ID NO: 81), PTQGAIFK (SEQ ID NO: 82), PTQGAMFK (SEQ ID NO: 83), PTIGQIFK (SEQ ID NO: 84), PTINQIFK (SEQ ID NO: 85), PTINTIFK (SEQ ID NO: 86), PTILQIFK (SEQ ID NO: 87), PTIVQIFK (SEQ ID NO: 88), PTIQQIFK (SEQ ID NO: 89), PTIAQIFK (SEQ ID NO: 90), $P^{133}TTTQIFK^{140}QTYS$ (SEQ ID NO: 91), and $P^{133}TQGAMPK^{140}QTYS$ (SEQ ID NO: 92).

In another embodiment, the hGH polypeptide comprises a mutant peptide sequence with the formula of $P^{133}RTGQIPTQBYS$ (SEQ ID NO: 222) wherein superscripts denote the position of the amino acid in SEQ ID NO: 160; and B is selected from alanine and threonine. In another embodiment, the hGH polypeptide comprises a mutant peptide sequence selected from the sequences consisting of: PRTGQIPTQTYS (SEQ ID NO: 93) and PRTGQIPTQAYS (SEQ ID NO: 94).

In another embodiment, the hGH polypeptide comprises a mutant peptide sequence with the formula of $L^{128}XTBOP^{133}UTG$ (SEQ ID NO: 223) wherein superscripts denote the position of the amino acid in SEQ ID NO: 160; and X is selected from glutamic acid, valine and alanine; B is selected from glutamine, glutamic acid, and glycine; O is selected from serine and threonine; and U is selected from arginine, serine, alanine and leucine. In another embodiment, the hGH polypeptide comprises a mutant peptide sequence selected from the sequences consisting of: $LETQSP^{133}RTG$ (SEQ ID NO: 95), $LETQSP^{133}STG$ (SEQ ID NO: 96), $LETQS^{133}ATG$ (SEQ ID NO: 97), $LETQSP^{133}LTG$ (SEQ ID NO: 98), $LETETP^{133}R$ (SEQ ID NO: 99), $LETETP^{133}A$ (SEQ ID NO: 100), $LVTQSP^{133}RTG$ (SEQ ID NO: 101), $LVTETP^{133}RTG$ (SEQ ID NO: 102), $LVTETP^{133}ATG$ (SEQ ID NO: 103), and $LATGSP^{133}RTG$ (SEQ ID NO: 104).

In another embodiment the hGH polypeptide comprises a mutant peptide sequence with the formula of $M^1BPTX_nZ_mOPLSRL$ (SEQ ID NO: 224) wherein the superscript 1, denotes the position of the amino acid in SEQ ID NO: 159; and B is selected from phenylalanine, valine and alanine or a combination thereof; X is selected from glutamate, valine and proline Z is threonine; O is selected from leucine and isoleucine; and when X is proline, Z is threonine; and wherein n and m are integers selected from 0 and 2. In another embodiment, the hGH polypeptide comprises a mutant peptide sequence selected from the sequences consisting of: $M^1FPTEIPLSRL$ (SEQ ID NO: 105), $M^1FPTV LPLSRL$ (SEQ ID NO: 106), and $M^1APTPTIPLSRL$ (SEQ ID NO: 107).

In still another embodiment the hGH polypeptide comprises the following mutant peptide sequence: $M^1VTPTIPLSRL$ (SEQ ID NO:108).

In still another embodiment the hGH polypeptide comprises a mutant peptide sequence selected from $M^1APTSSPTIPL^7SR^9$ (SEQ ID NO:109) and $DGSP^{133}NTGQIFK^{140}$ (SEQ ID NO:110).

In another embodiment the isolated polypeptide is an IFN alpha polypeptide.

In one embodiment, the INF alpha polypeptide has a peptide sequence comprising a mutant amino acid sequence, and the peptide sequence corresponds to a region of INF alpha 2 having a sequence as shown in SEQ NO:180, and wherein the mutant amino acid sequence contains a mutation at a position corresponding to $T^{106}$ of INF alpha 2. In another embodiment the IFN alpha polypeptide is selected from the group consisting of IFN alpha, IFN alpha 4, IFN alpha 5, IFN alpha 6, IFN alpha 7, IFN alpha 8, IFN alpha 10, IFN alpha 14, IFN alpha 16, IFN alpha 17, and IFN alpha 21. In yet another embodiment, the IFN alpha polypeptide is an IFN alpha polypeptide comprising a mutant amino acid sequence selected from the group consisting of $^{99}CVMQEERVTETPLMNADSIL^{118}$ (SEQ ID NO:111) $^{99}CVMQEEGVTETPLMNADSIL^{118}$ (SEQ ID NO:112), and $^{99}CVMQGVGVTETPLMNADSIL^{118}$ (SEQ ID NO:113). In still another embodiment, the IFN alpha polypeptide is an IFN alpha 4 polypeptide comprising a mutant amino acid sequence selected from the group consisting of: $^{99}CVIQEVGVTETPLMNVDSIL^{118}$ (SEQ ID NO:114), and $^{99}CVIQGVGVTETPLMKEDSIL^{118}$ (SEQ ID NO:115). In another embodiment, the IFN alpha polypeptide is an IFN alpha 5 polypeptide comprising a mutant amino acid sequence selected from the group consisting of: $^{99}CMMQEVGVTDTPLMNVDSIL^{118}$ (SEQ ID NO:116), $^{99}CMMQEVGVTETPLMNVDSIL^{118}$ (SEQ ID NO:117) and $^{99}CMMQGVGVTDTPLMNVDSIL^{118}$ (SEQ ID NO:118). In an another embodiment, the IFN alpha polypeptide is an IFN alpha 6 polypeptide comprising a mutant amino acid sequence selected from the group consisting of: $^{99}CVMQEVWVTGTPLMNEDSIL^{118}$ (SEQ ID NO:119), $^{99}CVMQEVGVTGTPLMNEDSIL^{118}$ (SEQ ID NO:120) and $^{99}CVMQGVGVTETPLMNEDSIL^{118}$ (SEQ ID NO:121). In yet an another embodiment, the IFN alpha polypeptide is an IFN alpha 7 polypeptide comprising a mutant amino acid sequence selected from the group consisting of: $^{99}CVIQEVGVTETPLMNEDFIL^{118}$ (SEQ ID NO:122), and $^{99}CVIQGVGVTETPLMNEDFIL^{118}$ (SEQ ID NO:123). In still another embodiment, the IFN alpha polypeptide is an IFN alpha 8 polypeptide comprising a mutant amino acid sequence selected from the group consisting of: $^{99}CVMQEVGVTESPLMYEDSIL^{118}$ (SEQ ID NO:124), and $^{99}CVMQGVGVTESPLMYEDSIL^{118}$ (SEQ ID NO:125). In another embodiment, the IFN alpha polypeptide is an IFN alpha 10 polypeptide comprising a mutant amino acid sequence selected from the group consisting of: $^{99}CVIQEVGVTETPLMNEDSIL^{118}$ (SEQ ID NO:126) and $^{99}CVIQGVGVTETPLMNEDSIL^{118}$ (SEQ ID NO:127). In another embodiment, the IFN alpha polypeptide is an IFN alpha 14 polypeptide comprising a mutant amino acid sequence selected from the group consisting of: $^{99}CVIQEVGVTETPLMNEDSIL^{118}$ (SEQ ID NO:128), and $^{99}CVIQGVGVTETPLMNEDSIL^{118}$ (SEQ ID NO:129). In another embodiment, the IFN alpha polypeptide is an IFN alpha 16 polypeptide comprising a mutant amino acid sequence selected from the group consisting of: $^{99}CVTQEVGVTEIPLMNEDSIL^{118}$ (SEQ ID NO:130), $^{99}CVTQEVGVTETPLMNEDSIL^{118}$ (SEQ ID NO:131), and $^{99}CVTQGVGVTETPLMNEDSIL^{118}$ (SEQ ID NO:132). In still another embodiment, the IFN alpha polypeptide is an IFN alpha 17 polypeptide comprising a mutant amino acid sequence selected from the group consisting of: $^{99}CVIQEVGMTETPLMNEDSIL^{118}$ (SEQ ID NO:133), $^{99}CVIQEVGVTETPLMNEDSIL^{118}$ (SEQ ID NO:134), and $^{99}CVIQGVGMTETPLMNEDSIL^{118}$ (SEQ ID NO:135). In one more embodiment, the IFN alpha polypeptide is an IFN alpha 21 polypeptide comprising a mutant amino acid sequence selected from the group consisting of:

[99]CVIQEVGVTETPLMNVDSIL[118] (SEQ ID NO:136), and
[99]CVIQGVGVTETPLMNVDSIL[118] (SEQ ID NO:137).

In a second aspect, the invention provides an isolated nucleic acid encoding a polypeptide comprising a mutant peptide sequence, wherein the mutant peptide sequence encodes an O-linked glycosylation site that does not exist in the corresponding wild-type polypeptide. In one embodiment the nucleic acid encoding a polypeptide comprising a mutant peptide sequence is comprised within an expression cassette. In another related embodiment, the present invention provides a cell comprises the nucleic acid of the present invention.

In a third aspect, the isolated polypeptide comprising a mutant peptide sequence, that encodes an O-linked glycosylation site that not existing in the corresponding wild-type polypeptide, has a formula selected from:

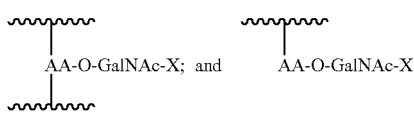

AA-O-GalNAc-X; and    AA-O-GalNAc-X wherein AA is an amino acid side chain that comprises a hydroxyl moiety that is within the mutant polypeptide sequence; and X is a modifying group or a saccharyl moiety. In one embodiment X comprises a group selected from sialyl, galactosyl and Gal-Sia moieties, wherein at least one of said sialyl, galactosyl and Gal-Sia comprises a modifying group.

In another embodiment X comprises the moiety:

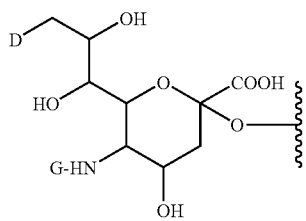

wherein D is a member selected from —OH and $R^1$-L-HN—; G is a member selected from $R^1$-L- and —C(O)(C$_1$-C$_6$)alkyl; $R^1$ is a moiety comprising a member selected a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is $R^1$-L-, and when G is —C(O)(C$_1$-C$_6$)alkyl, D is $R^1$-L-NH—.

In another embodiment X comprises the structure:

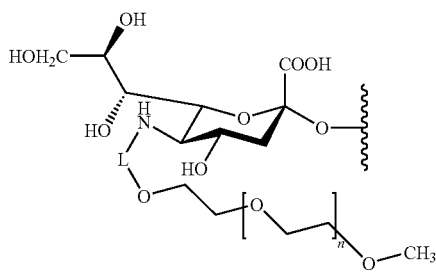

in which L is a substituted or unsubstituted alkyl or substituted or unsubstituted heteroalkyl group; and n is selected from the integers from 0 to about 500.

In another embodiment, X comprises the structure:

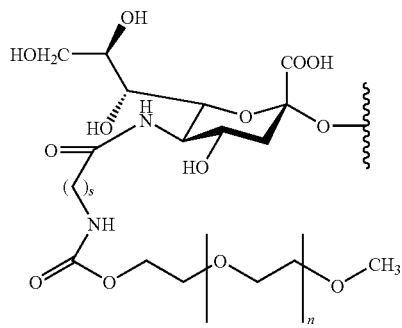

in which s is selected from the integers from 0 to 20.

In a fourth aspect the invention provides a method for making a glycoconjugate of an isolated polypeptide comprising a mutant peptide sequence encoding an O-linked glycosylation site that does not existing in the corresponding wild-type polypeptide, comprising the steps of:
(a) recombinantly producing the mutant polypeptide, and
(b) enzymatically glycosylating the mutant polypeptide with a modified sugar at said O-linked glycosylation site.

In a fifth aspect the invention provides a pharmaceutical composition of an isolated polypeptide comprising a mutant peptide sequence, wherein the mutant peptide sequence encodes an O-linked glycosylation site that does not exist in the corresponding wild-type polypeptide.

In one embodiment the pharmaceutical composition comprises an effective amount of a G-CSF polypeptide of the invention glycoconjugated with a modified sugar. In a related embodiment, the modified sugar is modified with a member selected from poly(ethylene glycol) and methoxy-poly(ethylene glycol) (m-PEG).

In another embodiment the pharmaceutical composition comprises an effective amount of an hGH polypeptide of the invention glycoconjugated with a modified sugar. In a related embodiment, the modified sugar is modified with a member selected from poly(ethylene glycol) and methoxy-poly(ethylene glycol) (m-PEG).

In another embodiment the pharmaceutical composition comprises an effective amount of an granulocyte macrophage colony stimulating factor polypeptide of the invention glycoconjugated with a modified sugar. In a related embodiment, the modified sugar is modified with a member selected from poly(ethylene glycol) and methoxy-poly(ethylene glycol) (m-PEG).

In another embodiment the pharmaceutical composition comprises an effective amount of an IFN alpha polypeptide of the invention glycoconjugated with a modified sugar. In a related embodiment, the modified sugar is modified with a member selected from poly(ethylene glycol) and methoxy-poly(ethylene glycol) (m-PEG).

In a sixth aspect the invention provides a method of providing therapy to a subject in need of said therapy, wherein the method comprises, administering to said subject an effective amount a pharmaceutical composition of the invention. In one embodiment, the therapy provided is G-CSF therapy. In another embodiment the therapy provided is granulocyte macrophage colony stimulating factor therapy. In another embodiment the therapy provided is interferon alpha therapy. In still another embodiment the therapy provided is Growth Hormone therapy.

Additional aspects, advantages and objects of the present invention will be apparent from the detailed description that follows.

BRIEF DESCRIPTION OF THE DRAWINGS

FIG. 10 shows representative sialyltransferases of use in the present invention.

DETAILED DESCRIPTION OF THE INVENTION

Abbreviations

Figure 1:
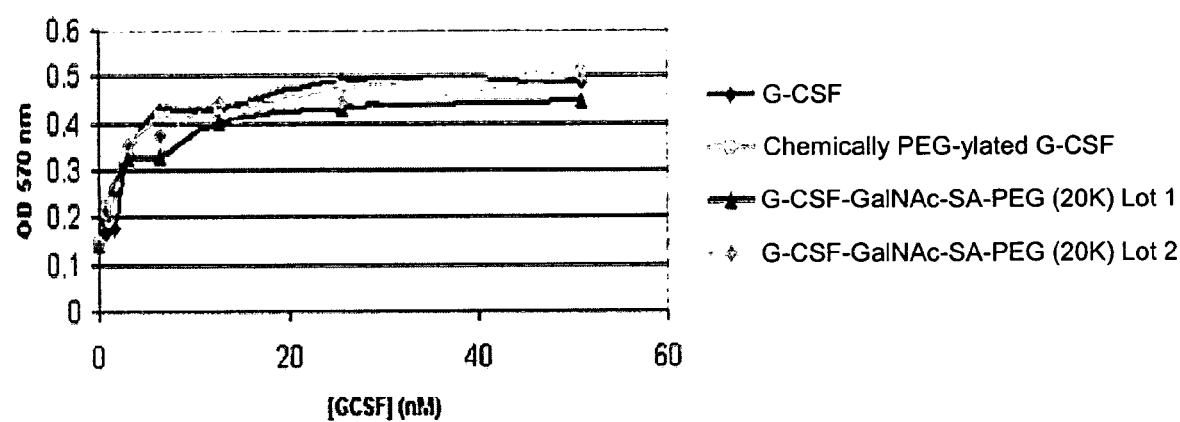
FIG. 1 is a plot of absorbance vs. GCSF concentration for unmodified G-CSF and glyco-PEG-ylated analogues in a NSF-60 cell proliferation assay.

PEG, poly(ethyleneglycol); m-PEG, methoxy-poly(ethylene glycol); PPG, poly(propyleneglycol); m-PPG, methoxy-poly(propylene glycol); Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Sia, sialic acid; and NeuAc, N-acetylneuraminyl.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the most N-terminal residue, which is numbered 1, in an unmodified wild-type polypeptide sequence.

"Peptide" refers to a polymer in which the monomers are amino acids and are joined together through amide bonds. Peptides of the present invention can vary in size, e.g., from two amino acids to hundreds or thousands of amino acids, which alternatively is referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

In the present application, amino acid residues are numbered according to their relative positions from the N-terminal, e.g., the left most residue, which is numbered 1, in a peptide sequence.

The term "mutant polypeptide" or "mutein" refers to a form of a peptide that differs from its corresponding wild-type form or naturally existing form. A mutant peptide can contain one or more mutations, e.g., replacement, insertion, deletion, etc. which result in the mutant peptide.

The term "peptide conjugate," refers to species of the invention in which a peptide is glycoconjugated with a modified sugar as set forth herein. In a representative example, the peptide is a mutant peptide having an O-linked glycosylation site not present in the wild-type peptide.

"Proximate a proline residue," as used herein refers to an amino acid that is less than about 10 amino acids removed from a proline residue, preferably, less than about 9, 8, 7, 6 or 5 amino acids removed from a proline residue, more preferably, less than about 4, 3, 2 or 1 residues removed from a proline residue. The amino acid "proximate a proline residue" may be on the C- or N-terminal side of the proline residue.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, water-soluble polymers, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(—PEG-OH)$_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term "glycoconjugation," as used herein, refers to the enzymatically mediated conjugation of a modified sugar species to an amino acid or glycosyl residue of a polypeptide, e.g., a mutant human growth hormone of the present invention. A subgenus of "glycoconjugation" is "glycol-PEGylation," in which the modifying group of the modified sugar is poly(ethylene glycol), and alkyl derivative (e.g., m-PEG) or reactive derivative (e.g., H$_2$N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Erythropoietin (EPO), Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of 1n Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., Bioconjugate Chem., 9: 108-117 (1998); Song et al., Bioconjugate Chem., 8: 249-255 (1997).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal for treating a disease, is sufficient to effect treatment for that disease.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where M' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR"", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

Introduction

The present invention provides conjugates of glycopeptides in which a modified sugar moiety is attached either directly or indirectly (e.g., through and intervening glycosyl residue) to an O-linked glycosylation site on the peptide. Also provided are methods for producing the conjugates of the invention.

The O-linked glycosylation site is generally the hydroxy side chain of a natural (e.g., serine, threonine) or unnatural (e.g., 5-hydroxyproline or 5-hydroxylysine) amino acid. Exemplary O-linked saccharyl residues include N-acetylgalactosamine, galactose, mannose, GlcNAc, glucose, fucose or xylose.

The methods of the invention can be practiced on any peptide having an O-linked glycosylation site. For example, the methods are of use to produce O-linked glycoconjugates in which the glycosyl moiety is attached to an O-linked glycosylation site that is present in the wild type peptide. Accordingly, the present invention provides glycoconjugates of wild-type peptides that include an O-linked glycosylation site. Exemplary peptides according to this description include G-CSF, GM-CSF, IL-2 and interferon.

In exemplary embodiments the invention also provides novel mutant peptides that include one or more O-linked glycosylation sites that are not present in the corresponding wild-type peptide. In one embodiment the mutant polypeptide is a G-CSF polypeptide. In other exemplary embodiments the mutant polypeptide is an hGH polypeptide, an IFN alpha polypeptide or a GM-CSF polypeptide. Also provided are O-linked glycosylated versions of the mutant peptides, and methods of preparing O-linked glycosylated mutant peptides. Additional methods include the elaboration, trimming back and/or modification of the O-linked glycosyl residue and glycosyl residues that are N—, rather than O-linked.

In an exemplary aspect, the invention provides a mutant peptide having the formula:

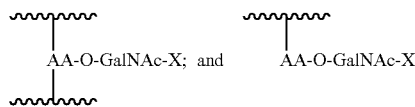

in which AA is an amino acid with a side chain that includes a hydroxyl moiety. Exemplary hydroxyamino acids are threonine and serine. The GalNAc moiety is linked to AA through the oxygen atom of the hydroxyl moiety. AA may be present in the wild type peptide or, alternatively, it is added or relocated by mutating the sequence of the wild type peptide. X is a modifying group, a saccharyl moiety, e.g., sialyl, galactosyl and Gal-Sia groups, or a saccharyl moiety and a modifying group. In an exemplary embodiment, in which X is a saccharyl moiety, it includes a modifying group, as discussed herein. The glycosylated amino acid can be at the N- or C-peptide terminus or internal to the peptide sequence.

In an exemplary embodiment, X comprises a group selected from sialyl, galactosyl and Gal-Sia moieties, wherein at least one of said sialyl, galactosyl and Gal-Sia comprises a modifying group. In a further exemplary embodiment X comprises the moiety:

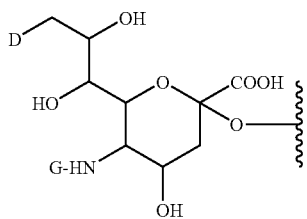

wherein D is a member selected from —OH and R'-L-HN—; G is a member selected from R'-L- and —C(O)(C$_1$-C$_6$)alkyl; R$^1$ is a moiety comprising a member selected a moiety comprising a straight-chain or branched poly(ethylene glycol) residue; and L is a linker which is a member selected from a bond, substituted or unsubstituted alkyl or substituted or unsubstituted heteroalkyl, such that when D is OH, G is R$^1$-L-, and when G is —C(O)(C$_1$-C$_6$)alkyl, D is R$^1$-L-NH—.

In another exemplary embodiment X comprises the structure:

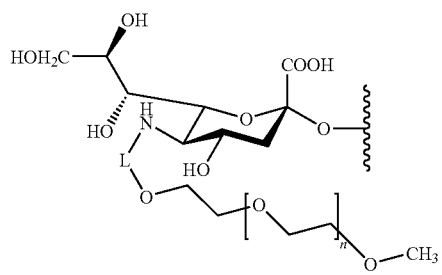

in which L is a substituted or unsubstituted alkyl or substituted or unsubstituted heteroalkyl group; and n is selected from the integers from 0 to about 2500. In yet another exemplary embodiment X comprises the structure:

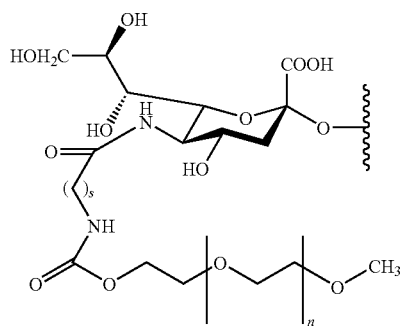

in which s is selected from the integers from 0 to 20.

In another exemplary embodiment, AA is located within a proline-rich segment of the mutant peptide and/or it is proximate to a proline residue. Appropriate sequences forming O-linked glycosylation sites are readily determined by interrogating the enzymatic O-linked glycosylation of short peptides containing one or more putative O-linked glycosylation sites.

The conjugates of the invention are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates; at least one peptide being O-glycosylated or including a mutant O-linked glycosylation site. The multi-functional conjugates of the invention can include two or more copies of the same peptide or a collection of diverse peptides with different structures, and/or properties. In exemplary conjugates according to this embodiment, the linker between the two peptides is attached to at least one of the peptides through an O-linked glycosyl residue, such as an O-linked glycosyl intact glycosyl linking group.

The conjugates of the invention are formed by the enzymatic attachment of a modified sugar to the glycosylated or unglycosylated peptide. The modified sugar is directly added to an O-linked glycosylation site, or to a glycosyl residue attached either directly or indirectly (e.g., through one or more glycosyl residue) to an O-linked glycosylation site. The invention also provides a conjugate of an O-linked glycosylated peptide in which a modified sugar is directly attached to an N-linked site, or to a glycosyl residue attached either directly or indirectly to an N-linked glycosylation site.

The modified sugar, when interposed between the peptide (or glycosyl residue) and the modifying group on the sugar becomes what is referred to herein as "an intact glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the methods of the invention, make it possible to assemble peptides and glycopeptides that have a substantially homogeneous derivatization pattern; the enzymes used in the invention are generally selective for a particular amino acid residue or combination of amino acid residues of the peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The methods of the invention also provide conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents to a peptide using an appropriate modified sugar can also be used to target a peptide to a particular tissue or cell surface receptor that is specific for the particular targeting agent. Moreover, there is provided a class of peptides that are specifically modified with a therapeutic moiety conjugated through a glycosyl linking group.

O-Glycosylation

The present invention provides O-linked glycosylated peptides, conjugates of these species and methods for forming O-linked glycosylated peptides that include a selected amino acid sequence ("an O-linked glycosylation site"). Of particular interest are mutant peptides that include an O-linked glycosylation site that is not present in the corresponding wild type peptide. The O-linked glycosylation site is a locus for attachment of a glycosyl residue that bears a modifying group.

Mucin-type O-linked glycosylation, one of the most abundant forms of protein glycosylation, is found on secreted and cell surface associated glycoproteins of all eukaryotic cells. There is great diversity in the structures created by O-linked glycosylation (hundreds of potential structures), which are produced by the catalytic activity of hundreds of glycosyltransferase enzymes that are resident in the Golgi complex. Diversity exists at the level of the glycan structure and in positions of attachment of O-glycans to protein backbones. Despite the high degree of potential diversity, it is clear that O-linked glycosylation is a highly regulated process that shows a high degree of conservation among multicellular organisms.

The first step in mucin-type O-linked glycosylation is catalysed by one or more members of a large family of UDP-GalNAc: polypeptide N-acetylgalactosaminyltransferases (GalNAc-transferases) (EC 2.4.1.41), which transfer GalNAc to serine and threonine acceptor sites (Hassan et al., *J. Biol. Chem.* 275: 38197-38205 (2000)). To date twelve members of the mammalian GalNAc-transferase family have been identified and characterized (Schwientek et al., J. Biol. Chem. 277: 22623-22638 (2002)), and several additional putative members of this gene family have been predicted from analysis of genome databases. The GalNAc-transferase isoforms have different kinetic properties and show differential expression patterns temporally and spatially, suggesting that they have distinct biological functions (Hassan et al., *J. Biol. Chem.* 275: 38197-38205 (2000)). Sequence analysis of GalNAc-transferases have led to the hypothesis that these enzymes contain two distinct subunits: a central catalytic unit, and a C-terminal unit with sequence similarity to the plant lectin ricin, designated the "lectin domain" (Hagen et al., J. Biol. Chem. 274: 6797-6803 (1999); Hazes, *Protein Eng.* 10: 1353-1356 (1997); Breton et al., *Curr. Opin. Struct. Biol.* 9: 563-571 (1999)). Previous experiments involving site-specific mutagenesis of selected conserved residues confirmed that mutations in the catalytic domain eliminated catalytic activity. In contrast, mutations in the "lectin domain" had no significant effects on catalytic activity of the GalNAc-transferase isoform, GalNAc-T1 (Tenno et al., *J. Biol. Chem.* 277(49): 47088-96 (2002)). Thus, the C-terminal "lectin domain" was believed not to be functional and not to play roles for the enzymatic functions of GalNAc-transferases (Hagen et al., J. Biol. Chem. 274: 6797-6803 (1999)).

However, recent evidence demonstrates that some GalNAc-transferases exhibit unique activities with partially GalNAc-glycosylated glycopeptides. The catalytic actions of at least three GalNAc-transferase isoforms, GalNAc-T4, -T7, and -T10, selectively act on glycopeptides corresponding to mucin tandem repeat domains where only some of the clustered potential glycosylation sites have been GalNAc glycosylated by other GalNAc-transferases (Bennett et al., *FEBS Letters* 460: 226-230 (1999); Ten Hagen et al., *J. Biol. Chem.* 276: 17395-17404 (2001); Bennett et al., *J. Biol. Chem.* 273: 30472-30481 (1998); Ten Hagen et al., *J. Biol. Chem.* 274: 27867-27874 (1999)). GalNAc-T4 and -T7 recognize different GalNAc-glycosylated peptides and catalyse transfer of GalNAc to acceptor substrate sites in addition to those that were previously utilized. One of the functions of such GalNAc-transferase activities is predicted to represent a control step of the density of O-glycan occupancy in mucins and mucin-like glycoproteins with high density of O-linked glycosylation.

One example of this is the glycosylation of the cancer-associated mucin MUC1. MUC1 contains a tandem repeat O-linked glycosylated region of 20 residues (HGVTSAPDTRPAPGSTAPPA (SEQ ID NO:138)) with five potential O-linked glycosylation sites. GalNAc-T1, -T2, and -T3 can initiate glycosylation of the MUC1 tandem repeat and incorporate at only three sites (HGV$\underline{T}$SAPDTRPAPGS$\underline{T}$APPA (SEQ ID NO:139), GalNAc attachment sites underlined). GalNAc-T4 is unique in that it is the only GalNAc-transferase isoform identified so far that can complete the O-linked glycan attachment to all five acceptor sites in the 20 amino acid tandem repeat sequence of the breast cancer associated mucin, MUC1. GalNAc-T4 transfers GalNAc to at least two sites not used by other GalNAc-transferase isoforms on the GalNAc$_4$TAP24 glycopeptide (TAPPAHGVTSAPDTRPAPGSTAPP (SEQ ID NO:140), unique GalNAc-T4 attachment sites are in bold) (Bennett et al., *J. Biol.*

Chem. 273: 30472-30481 (1998). An activity such as that exhibited by GalNAc-T4 appears to be required for production of the glycoform of MUC1 expressed by cancer cells where all potential sites are glycosylated (Muller et al., *J. Biol. Chem.* 274: 18165-18172 (1999)). Normal MUC1 from lactating mammary glands has approximately 2.6 O-linked glycans per repeat (Muller et al., *J. Biol. Chem.* 272: 24780-24793 (1997) and MUC1 derived from the cancer cell line T47D has 4.8 O-linked glycans per repeat (Muller et al., *J. Biol. Chem.* 274: 18165-18172 (1999)). The cancer-associated form of MUC1 is therefore associated with higher density of O-linked glycan occupancy and this is accomplished by a GalNAc-transferase activity identical to or similar to that of GalNAc-T4.

Polypeptide GalNAc-transferases, which have not displayed apparent GalNAc-glycopeptide specificities, also appear to be modulated by their putative lectin domains (PCT WO 01/85215 A2). Recently, it was found that mutations in the GalNAc-TI putative lectin domain, similarly to those previously analysed in GalNAc-T4 (Hassan et al., *J. Biol. Chem.* 275: 38197-38205 (2000)), modified the activity of the enzyme in a similar fashion as GalNAc-T4. Thus, while wild type GalNAc-T1 added multiple consecutive GalNAc residues to a peptide substrate with multiple acceptor sites, mutated GalNAc-TI failed to add more than one GalNAc residue to the same substrate (Tenno et al., *J. Biol. Chem.* 277(49): 47088-96 (2002)).

Since it has been demonstrated that mutations of GalNAc transferases can be utilized to produce glycosylation patterns that are distinct from those produced by the wild-type enzymes, it is within the scope of the present invention to utilize one or more mutant GalNAc transferase in preparing the O-linked glycosylated peptides of the invention.

Mutant Peptides with O-linked Glycosylation Sites

The peptides provided by the present invention include an amino acid sequence that is recognized as a GalNAc acceptor by one or more wild-type or mutant GalNac transferases. The amino acid sequence of the peptide is either the wild-type, for those peptides that include an O-linked glycosylation site, a mutant sequence in which a non-naturally occurring O-linked glycosylation site is introduced, or a polypeptide comprising both naturally occurring and non-naturally occurring O-linked glycosylation sites. Exemplary peptides with which the present invention is practiced include granulocyte colony stimulating factor (G-CSF), e.g., 175 and 178 amino acid wild types (with or without N-terminal methionine residues), interferon (e.g., interferon alpha, e.g., interferon alpha 2b, or interferon alpha 2a), granulocyte macrophage colony stimulating factor (GM-CSF), human growth hormone and interleukin (e.g., interleukin 2). The emphasis of the following discussion on G-CSF, GM-CSF and IFN-α 2β is for clarity of illustration. Any number in the superscript of an amino acid indicates the amino acid position relative to the N-terminal methionine of the polypeptide. These numbers can be readily adjusted to reflect the absence of N-terminal methionine if the N-terminal of the polypeptide starts without a methionine. It is understood that the N-terminals of the exemplary peptides can start with or without a methionine. In addition, those of skill will understand that the strategy set forth herein for preparing O-linked glycoconjugated analogues of wild-type and mutant peptides is applicable to any peptide.

In an exemplary embodiment, the peptide is a biologically active G-CSF mutant that includes one or more mutation at a site selected from the N-terminus, adjacent to or encompassing $H^{53}$, $P^{61}$, $P^{129}$, $P^{133}$ and $P^{175}$. Biologically active G-CSF mutants of the present invention include any G-CSF polypeptide, in part or in whole, with one or more mutations that do not result in substantial or entire loss of its biological activity as it is measured by any suitable functional assays known to one skilled in the art. In one embodiment, mutations within the biologically active G-CSF mutants of the present invention are located within one or more O-linked glycosylation sites that do not naturally exist in wild type G-CSF. In another embodiment, mutations within the biologically active G-CSF mutants of the present invention reside within as well as outside of one or more O-linked glycosylation sites of the G-CSF mutants.

Representative wild type and mutant G-CSF polypeptides have sequences that are selected from:

```
                                         SEQ. ID NO. 141
(178 amino acid wild type)
mtplgpasslp qsfllkcleq vrkiqgdgaa lqeklvseca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp;

SEQ. ID NO. 142
(178 amino acid wild type without N-terminal
methionine)
tplgpasslp qsfllkcleq vrkiqgdgaa lqeklvseca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp;

SEQ. ID NO. 143
(175 amino acid wild type)
mtplgpasslp qsfllkcleq vrkiqgdgaa lqeklca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp;

SEQ. ID NO. 144
(175 amino acid wild type without N-terminal
methionine)
mtplgpasslp qsfllkcleq vrkiqgdgaa lqeklca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp;

SEQ. ID NO. 145
mvtplgpasslp qsfllkcleq vrkiqgdgaa lqeklca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp;

SEQ. ID NO. 146
mvtplgpasslp qsfllkcleq vrkiqgdgaa lqeklca tyklchpeel vllghtlgip waplsscpsq alqlagclsq
```

-continued lhsglflyqg llqalegisp elgptldtlq ldvadfatti
wqqmeelgma palqptqgam pafasafqrr aggvlvashl
qsflevsyrv lrhlaqp;

SEQ. ID NO. 147
mtplgpasslp qsfllkcleq vrkiqgdgaa lqeklca
tyklchpeel vllghtlgip waplsscpsq alqlagclsq
lhsglflyqg llqalegisp elgptldtlq ldvadfatti
wqqmeelgma palqptqgam pafasafqrr aggvlvashl
qsflevsyrv lrhlaqp;

SEQ. ID NO. 148
mvtplgpasslp qsfllkcleq vrkiqgdgaa lqeklca
tyklchpeel vllgsslgip waplsscpsq alqlagclsq
lhsglflyqg llqalegisp elgptldtlq ldvadfatti
wqqmeelgma palqptqgam pafasafqrr aggvlvashl
qsflevsyrv lrhlaqp;

SEQ. ID NO. 149
mqtplgpasslp qsfllkcleq vrkiqgdgaa lqeklca
tyklchpeel vllghslgip waplsscpsq alqlagclsq
lhsglflyqg llqalegisp elgptldtlq ldvadfatti
wqqmeelgma palqptqgam pafasafqrr aggvlvashl
qsflevsyrv lrhlaqp;

SEQ. ID NO. 150
mtplgpasslp qsfllkcleq vrkiqgdgaa lqeklca
tyklchpeel vllghslgip waplsscpsq alqlagclsq
lhsglflyqg llqalegisp elgptldtlq ldvadfatti
wqqmeelgma palqptqgam pafasafqrr aggvlvashl
qsflevsyrv lrhlaqptqgamp;
and SEQ. ID NO. 151
mtplgpasslp qsfllkcleq vrkiqgdgaa lqeklca
tyklchpeel vllgsslgip waplsscpsq alqlagclsq
lhsglflyqg llqalegisp elgptldtlq ldvadfatti
wqqmeelgma palqptqgam pafasafqrr aggvlvashl
qsflevsyrv lrhlaqp SEQ ID NO: 152
maitplgpasslp qsfllkcleq vrkiqgdgaa lqeklcatyk
lchpeelvll ghslgipwap lsscpsqalq lagclsqlhs
glflyqgllq alegispelg ptldtlqldv adfattiwqq
meelgmapal qptqgampaf asafqrragg vlvashlqsf
levsyrvlrh laqp SEQ ID NO: 153
mgvtetplgpasslp qsfllkcleq vrkiqgdgaa lqeklcatyk
lchpeelvll ghslgipwap lsscpsqalq lagclsqlhs
glflyqgllq alegispelg ptldtlqldv adfattiwqq
meelgmapal qptqgampaf asafqrragg vlvashlqsf
levsyrvlrh laqp SEQ ID NO: 154
map<u>t</u>plgpasslp qsfllkcleq vrkiqgdgaa lqeklcatyk
lchpeelvll ghslgipwap lsscpsqalq lagclsqlhs
glflyqgllq alegispelg ptldtlqldv adfattiwqq
meelgmapal qptqgampaf asafqrragg vlvashlqsf
levsyrvlrh laqp SEQ ID NO: 155
Mtp<u>tq</u>glgpasslp qsfllkcleq vrkiqgdgaa lqeklcatyk
lchpeelvll ghslgipwap lsscpsqalq lagclsqlhs
glflyqgllq alegispelg ptldtlqldv adfattiwqq
meelgmapal qptqgampaf asafqrragg vlvashlqsf
levsyrvlrh laqp SEQ ID NO: 156
mtplgpasslp qsfllkcleq vrkiqgdgaa lqeklcatyk
lchpeelvll ghslgipwap lsscpsqalq lagclsqlhs
glflyqgllq alegispelg ptldtlqldv adfattiwqq
meelgmapat<u>q</u>ptqgampaf asafqrragg vlvashlqsf
levsyrvlrh laqp SEQ ID NO: 157
Mtplgpasslp qsfllkcleq vrkiqgdgaa lqeklcatyk
lchpeelvll ghslgipf<u>tp</u> lsscpsqalq lagclsqlhs
glflyqgllq alegispelg ptldtlqldv adfattiwqq
meelgmapa<u>L</u> qptqgampaf asafqrragg vlvashlqsf
levsyrvlrh laqp SEQ ID NO: 158
mtplgpasslpqsfllkcleqvrkiqgdgaalqeklcatyklchpeelvl
lghslgipwaplsscpsqalqlagclsqlhsglflyqgllqalegispel
gptldtlqldvadfattiwqqmeelgmapalqptq<u>t</u>ampafasafqrrag
gvlvashlqsflevsyrvlrhlaqp.

In another exemplary embodiment, the peptide is a biologically active hGH mutant that includes one or more mutations at a site selected from the N-terminus or adjacent to or encompassing P$^{133}$. Biologically active hGH mutants of the present invention include any hGH polypeptide, in part or in whole, with one or more mutations that do not result in substantial or entire loss of its biological activity as it is measured by any suitable functional assays known to one skilled in the art. In one embodiment, mutations within the biologically active hGH mutants of the present invention are located within one or more O-linked glycosylation sites that do not naturally exist in wild type hGH. In another embodiment, mutations within the biologically active hGH mutants of the present invention reside within as well as outside of one or more O-linked glycosylation sites of the hGH mutants.

Representative wild type and mutant hGH polypeptides have sequences that are selected from:

SEQ ID NO: 159
(192 amino acid wild-type pituitary derived hGH
comprising an N-terminal methionine)
mfptiplsrlfdnamlrahrlhqlafdtyqefeeayipkeqkysflqnpq tslcfsesiptpsnreetqqksnlellrisllliqswlepvqflrsvfan slvygasdsnvydllkdleegiqtlmgrledgsprtgqifkqtyskfdtn shnddallknygllycfrkdmdkvetflrivqcrsvegscgf SEQ ID NO: 160
(191 amino acid wild-type pituitary derived hGH
lacking an N-Terminal methionine)
fptiplsrlfdnamlrahrlhqlafdtyqefeeayipkeqkysflqnpqt slcfsesiptpsnreetqqksnlellrisllliqswlepvqflrsvfans lvygasdsnvydllkdleegiqtlmgrledgsprtgqifkqtyskfdtns hnddallknygllycfrkdmdkvetflrivqcrsvegscgf SEQ ID NO: 159
(wild type)
MFPTIPLSRLFDNAMLRAHRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGR<u>LEDGSPRTGQIFKQTYS</u>KFDTN

SHNDDALLKNYGLLYCFRKDMDKVETFLRIVQCRSVEGSCGF

The following are representative mutant peptide sequences corresponding to the region underlined in the wild type SEQ ID NO: 159: LEDGSPTTGQIFKQTYS (SEQ ID NO:161), LEDGSPTTAQIFKQTYS (SEQ ID NO:162), LEDGSPTAT-QIFKQTYS (SEQ ID NO:163), LEDGSPTQGAMFKQTYS (SEQ ID NO:164), LEDGSPTQGAIFKQTYS (SEQ ID NO:165), LEDGSPTQGQIFKQTYS (SEQ ID NO:166), LEDGSPTTLYVFKQTYS (SEQ ID NO:167), LEDGSPTINTIFKQTYS (SEQ ID NO:168), LEDGSPT-TVSIFKQTYS (SEQ ID NO:169), LEDGSPRTGQIPTQ-TYS (SEQ ID NO:170), LEDGSPRTGQIPTQAYS (SEQ ID NO:171), LEDGSPTTLQIFKQTYS (SEQ ID NO:172), LETETPRTGQIFKQTYS (SEQ ID NO:171), LVTETPRT-GQIFKQTYS (SEQ ID NO:174), LETQSPRTGQIFKQTYS (SEQ ID NO:175), LVTQSPRTGQIFKQTYS (SEQ ID NO:176), LVTETPATGQIFKQTYS (SEQ ID NO:177), LEDGSPTQGAMPKQTYS (SEQ ID NO:178), and LEDGSPTTTQIFKQTYS (SEQ ID NO:179).

In another exemplary embodiment, the peptide is a biologically active IFN alpha mutant that includes one or more mutations at a site corresponding to $T^{106}$ of INF alpha 2, e.g., adjacent to or encompassing an amino acid position in IFN alpha wild type, which corresponds to or aligns with $T^{106}$ of INF alpha 2. Biologically active IFN alpha mutants of the present invention include any IFN alpha polypeptide, in part or in whole, with one or more mutations that do not result in substantial or entire loss of its biological activity as it is measured by any suitable functional assays known to one skilled in the art. In one embodiment, mutations within the biologically active IFN alpha mutants of the present invention are located within one or more O-linked glycosylation sites that do not naturally exist in wild type IFN alpha. In another embodiment, mutations within the biologically active IFN alpha mutants of the present invention reside within as well as outside of one or more O-linked glycosylation sites of the IFN alpha mutants.

A wild type and mutant IFN alpha polypeptide is shown below:

SEQ ID NO: 180
(from wild type IDN 2b)
$^{98}$CVIQGVGVTETPLMKEDSIL$^{117}$

Other appropriate O-linked glycosylation sequences for G-CSF and peptides other than G-CSF can be determined by preparing a polypeptide incorporating a putative O-linked glycosylation site and submitting that polypeptide to suitable O-linked glycosylation conditions, thereby confirming its ability to serve as an acceptor for a GalNac transferase. Moreover, as will be apparent to one of skill in the art, peptides that include one or more mutation are within the scope of the present invention. The mutations are designed to allow the adjustment of desirable properties of the peptides, e.g., activity and number and position of O- and/or N-linked glycosylation sites on the peptide.

Acquisition of Peptide Coding Sequences
General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Entire genes can also be chemically synthesized. Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type peptide genes, polynucleotide encoding mutant peptides, and synthetic oligonucleotides can be verified after cloning using, e.g., the chain termination method for sequencing double-stranded templates of Wallace et al., *Gene* 16: 21-26 (1981).

Cloning and Subcloning of a Wild-Type Peptide Coding Sequence

Numerous polynucleotide sequences encoding wild-type peptides have been determined and are available from a commercial supplier, e.g., human growth hormone, e.g., GenBank Accession Nos. NM 000515, NM 002059, NM 022556, NM 022557, NM 022558, NM 022559, NM 022560, NM 022561, and NM 022562.

The rapid progress in the studies of human genome has made possible a cloning approach where a human DNA sequence database can be searched for any gene segment that has a certain percentage of sequence homology to a known nucleotide sequence, such as one encoding a previously identified peptide. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a peptide can be isolated from a human cDNA or genomic DNA library using standard cloning techniques such as polymerase chain reaction (PCR), where homology-based primers can often be derived from a known nucleic acid sequence encoding a peptide. Most commonly used techniques for this purpose are described in standard texts, e.g., Sambrook and Russell, supra.

cDNA libraries suitable for obtaining a coding sequence for a wild-type peptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full-length polynucleotide sequence encoding the wild-type peptide from the cDNA library. A general description of appropriate procedures can be found in Sambrook and Russell, supra.

A similar procedure can be followed to obtain a full length sequence encoding a wild-type peptide, e.g., any one of the GenBank Accession Nos mentioned above, from a human genomic library. Human genomic libraries are commercially available or can be constructed according to various art-recognized methods. In general, to construct a genomic library, the DNA is first extracted from an tissue where a peptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding a wild-type peptide is obtained.

Upon acquiring a nucleic acid sequence encoding a wild-type peptide, the coding sequence can be subcloned into a vector, for instance, an expression vector, so that a recombinant wild-type peptide can be produced from the resulting construct. Further modifications to the wild-type peptide coding sequence, e.g., nucleotide substitutions, may be subsequently made to alter the characteristics of the molecule.

Introducing Mutations into a Peptide Sequence

From an encoding polynucleotide sequence, the amino acid sequence of a wild-type peptide can be determined. Subsequently, this amino acid sequence may be modified to alter the protein's glycosylation pattern, by introducing additional glycosylation site(s) at various locations in the amino acid sequence.

Several types of protein glycosylation sites are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J*7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995). Based on this knowledge, suitable mutations can thus be introduced into a wild-type peptide sequence to form new glycosylation sites.

Although direct modification of an amino acid residue within a peptide polypeptide sequence may be suitable to introduce a new N-linked or O-linked glycosylation site, more frequently, introduction of a new glycosylation site is accomplished by mutating the polynucleotide sequence encoding a peptide. This can be achieved by using any of known mutagenesis methods, some of which are discussed below. Exemplary modifications to a G-CSF peptide include those illustrated in SEQ ID NO:5-18.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

Modification of Nucleic Acids for Preferred Codon Usage in a Host Organism

The polynucleotide sequence encoding a mutant peptide can be further altered to coincide with the preferred codon usage of a particular host. For example, the preferred codon usage of one strain of bacterial cells can be used to derive a polynucleotide that encodes a mutant peptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the mutant peptide coding sequences are verified by sequencing and are then subcloned into an appropriate expression vector for recombinant production in the same manner as the wild-type peptides.

Expression and Purification of the Mutant Peptide

Following sequence verification, the mutant peptide of the present invention can be produced using routine techniques in the field of recombinant genetics, relying on the polynucleotide sequences encoding the polypeptide disclosed herein.

Expression Systems

To obtain high-level expression of a nucleic acid encoding a mutant peptide of the present invention, one typically subclones a polynucleotide encoding the mutant peptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant peptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant peptide in host cells. A typical expression cassette thus contains a promoter operably linked to the nucleic acid sequence encoding the mutant peptide and signals required for efficient polyadenylation of the transcript, ribosome binding sites, and translation termination. The nucleic acid sequence encoding the peptide is typically linked to a cleavable signal peptide sequence to promote secretion of the peptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

In some exemplary embodiments the expression vector is chosen from pCWin1, pCWin2, pCWin2/MBP, pCWin2-MBP-SBD (PMS$_{39}$), and pCWin2-MBP-MCS-SBD (pMXS$_{39}$) as disclosed in co-owned U.S. patent application filed Apr. 9, 2004 which is incorporated herein by reference.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant peptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

When periplasmic expression of a recombinant protein (e.g., a hgh mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant peptide or its coding sequence while still retaining the biological activity of the peptide. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast or insect cell lines that express large quantities of the mutant peptide, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant peptide.
Detection of Expression of Mutant Peptide in Host Cells After the expression vector is introduced into appropriate host cells, the transfected cells are cultured under conditions favoring expression of the mutant peptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant peptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant peptide of the present invention, such as a polypeptide having the amino acid sequence of SEQ ID NO: 1-7, (e.g., Harlow and Lane, *Antibodies, A Laboratory Manual*, Chapter 14, Cold Spring Harbor, 1988; Kohler and Milstein, *Nature,* 256: 495-497 (1975)). Such techniques require antibody preparation by selecting antibodies with high specificity against the mutant peptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.,* 6: 511-519 (1976). More detailed descriptions of preparing antibody against the mutant peptide of the present invention and conducting immunological assays detecting the mutant peptide are provided in a later section.
Purification of Recombinantly Produced Mutant Peptide Once the expression of a recombinant mutant peptide in transfected host cells is confirmed, the host cells are then cultured in an appropriate scale for the purpose of purifying the recombinant polypeptide.
1. Purification of Recombinantly Produced Mutant Peptide from Bacteria When the mutant peptides of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant peptide from bacterial inclusion body, see, e.g., Patra et al., *Protein Expression and Purification* 18: 182-190 (2000).

Alternatively, it is possible to purify recombinant polypeptides, e.g., a mutant peptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., the mutant peptide of the present invention, is expressed in host cells in a soluble form, its purification can follow the standard protein purification procedure described below.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant peptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant peptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as the mutant peptide of the present invention) can also be separated from other proteins on the basis of their size, net surface charge, hydrophobicity, or affinity for ligands. In addition, antibodies raised against peptide can be conjugated to column matrices and the peptide immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant Peptide Expression

To confirm the production of a recombinant mutant peptide, immunological assays may be useful to detect in a sample the expression of the polypeptide. Immunological assays are also useful for quantifying the expression level of the recombinant hormone. Antibodies against a mutant peptide are necessary for carrying out these immunological assays.

Production of Antibodies against Mutant Peptide

Methods for producing polyclonal and monoclonal antibodies that react specifically with an immunogen of interest are known to those of skill in the art (see, e.g., Coligan, *Current Protocols in Immunology* Wiley/Greene, N Y, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant peptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant peptide of the present invention can be tested for their cross-reactivity against the wild-type peptide and thus distinguished from the antibodies against the wild-type protein. For instance, antisera obtained from an animal immunized with a mutant peptide can be run through a column on which a wild-type peptide is immobilized. The portion of the antisera that passes through the column recognizes only the mutant peptide and not the wild-type peptide. Similarly, monoclonal antibodies against a mutant peptide can also be screened for their exclusivity in recognizing only the mutant but not the wild-type peptide.

Polyclonal or monoclonal antibodies that specifically recognize only the mutant peptide of the present invention but not the wild-type peptide are useful for isolating the mutant protein from the wild-type protein, for example, by incubating a sample with a mutant peptide-specific polyclonal or monoclonal antibody immobilized on a solid support.

Immunoassays for Detecting Mutant Peptide Expression

Once antibodies specific for a mutant peptide of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

Immunoassay Formats

Immunoassays for detecting a target protein of interest (e.g., a mutant human growth hormone) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of a mutant peptide in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a mutant peptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

The Conjugates

In a representative aspect, the present invention provides a glycoconjugate between a peptide and a selected modifying group, in which the modifying group is conjugated to the peptide through a glycosyl linking group, e.g., an intact glycosyl linking group. The glycosyl linking group is directly bound to an O-linked glycosylation site on the peptide or, alternatively, it is bound to an O-linked glycosylation site through one or more additional glycosyl residues. Methods of preparing the conjugates are set forth herein and in U.S. Pat. Nos. 5,876,980; 6,030,815; 5,728,554; 5,922,577; WO 98/31826; US2003180835; and WO 03/031464.

Exemplary peptides include an O-linked GalNAc residue that is bound to the O-linked glycosylation site through the action of a GalNAc transferase. The GalNAc itself may be the intact glycosyl linking group. The GalNAc may also be further elaborated by, for example, a Gal or Sia residue, either of which can act as the intact glycosyl linking group. In representative embodiments, the O-linked saccharyl residue is GalNAc-X, GalNAc-Gal-Sia-X, or GalNAc-Gal-Gal-Sia-X, in which X is a modifying group.

In an exemplary embodiment, the peptide is a mutant peptide that includes an O-linked glycosylation site not present in the wild-type peptide. The peptide is preferably O-glycosylated at the mutated site with a GalNAc residue. The discussion immediately preceding regarding the structure of the saccharyl moiety is relevant here as well.

The link between the peptide and the selected moiety includes an intact glycosyl linking group interposed between the peptide and the modifying moiety. As discussed herein, the selected moiety is essentially any species that can be attached to a saccharide unit, resulting in a "modified sugar" that is recognized by an appropriate transferase enzyme, which appends the modified sugar onto the peptide. The saccharide component of the modified sugar, when interposed between the peptide and a selected moiety, becomes an "intact glycosyl linking group." The glycosyl linking group is formed from any mono- or oligo-saccharide that, after modification with a selected moiety, is a substrate for an appropriate transferase.

The conjugates of the invention will typically correspond to the general structure:

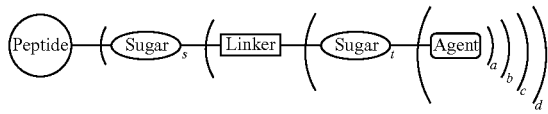

in which the symbols a, b, c, d and s represent a positive, non-zero integer; and t is either 0 or a positive integer. The "agent" is a therapeutic agent, a bioactive agent, a detectable lable, water-soluble moiety or the like. The "agent" can be a peptide, e.g., enzyme, antibody, anitgen, etc. The linker can be any of a wide array of linking groups, infra. Alternatively, the linker may be a single bond or a "zero order linker." The identity of the peptide is without limitation.

In an exemplary embodiment, the selected moiety is a water-soluble polymer, e.g., PEG, m-PEG, PPG, m-PPG, etc. The water-soluble polymer is covalently attached to the peptide via a glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group (e.g., GalNAc) is attached to an amino acid residue (e.g., Thr or Ser).

In an exemplary embodiment, the protein is an interferon. The interferons are antiviral glycoproteins that, in humans, are secreted by human primary fibroblasts after induction with virus or double-stranded RNA. Interferons are of interest as therapeutics, e.g., antiviral agents (e.g., hepatitis B and C), antitumor agents (e.g., hepatocellular carcinoma) and in the treatment of multiple sclerosis. For references relevant to interferon-α, see, Asano, et al., *Eur. J. Cancer,* 27(Suppl 4):S21-S25 (1991); Nagy, et al., *Anticancer Research,* 8(3): 467-470 (1988); Dron, et al., *J. Biol. Regul. Homeost. Agents,* 3(1):13-19 (1989); Habib, et al., *Am. Surg,* 67(3):257-260 (3/2001); and Sugyiama, et al., *Eur. J. Biochem.,* 217:921-927 (1993). For references discussing intefereon-β, see, e.g., Yu, et al., *J. Neuroimmunol.,* 64(1):91-100 (1996); Schmidt, J., *J. Neurosci. Res.,* 65(1):59-67 (2001); Wender, et al., *Folia Neuropathol.,* 39(2):91-93 (2001); Martin, et al., *Springer Semin. Immunopathol.,* 18(1): 1-24 (1996); Takane, et al., *J. Pharmacol. Exp. Ther.,* 294(2):746-752 (2000); Sburlati, et al., *Biotechnol. Prog.,* 14:189-192 (1998); Dodd, et al., *Biochimica et Biophysica Acta,* 787:183-187 (1984); Edelbaum, et al., *J. Interferon Res.,* 12:449-453 (1992); Conradt, et al., *J. Biol. Chem.,* 262(30):14600-14605 (1987); Civas, et al., *Eur. J. Biochem.,* 173:311-316 (1988); Demolder, et al., *J. Biotechnol.,* 32:179-189 (1994); Sedmak, et al., *J. Interferon Res.,* 9(Suppl 1):S61-S65 (1989); Kagawa, et al., *J. Biol. Chem.,* 263(33):17508-17515 (1988); Hershenson, et al., U.S. Pat. No. 4,894,330; Jayaram, et al., *J. Interferon Res.,* 3(2): 177-180 (1983); Menge, et al., *Develop. Biol. Standard.,* 66:391-401 (1987); Vonk, et al., *J. Interferon Res.,* 3(2):169-175 (1983); and Adolf, et al., *J. Interferon Res.,* 10:255-267 (1990).

In an exemplary interferon conjugate, interferon alpha, e.g., interferon alpha 2b and 2a, is conjugated to a water soluble polymer through an intact glycosyl linker.

In a further exemplary embodiment, the invention provides a conjugate of human granulocyte colony stimulating factor (G-CSF). G-CSF is a glycoprotein that stimulates proliferation, differentiation and activation of neutropoietic progenitor cells into functionally mature neutrophils. Injected G-CSF is rapidly cleared from the body. See, for example, Nohynek, et al., *Cancer Chemother. Pharmacol.,* 39:259-266 (1997); Lord, et al., *Clinical Cancer Research,* 7(7):2085-2090 (07/2001); Rotondaro, et al., *Molecular Biotechnology,* 11(2): 117-128 (1999); and Bönig, et al., *Bone Marrow Transplantation,* 28: 259-264 (2001).

The present invention encompasses a method for the modification of GM-CSF. GM-CSF is well known in the art as a cytokine produced by activated T-cells, macrophages, endothelial cells, and stromal fibroblasts. GM-CSF primarily acts on the bone marrow to increase the production of inflammatory leukocytes, and further functions as an endocrine hormone to initiate the replenishment of neutrophils consumed during inflammatory functions. Further GM-CSF is a macrophage-activating factor and promotes the differentiation of Lagerhans cells into dendritic cells. Like G-CSF, GM-CSF also has clinical applications in bone marrow replacement following chemotherapy In addition to providing conjugates that are formed through an enzymatically added intact glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to a structurally identical amino acid or glycosyl residue. Thus, in a second aspect, the invention provides a peptide conjugate having a population of water-soluble polymer moieties, which are covalently bound to the peptide through an intact glycosyl linking group. In another conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In another embodiment, essentially every member of the population of water soluble polymer moieties is bound to an amino acid residue of the peptide via an intact glycosyl linking group, and each amino acid residue having an intact glycosyl linking group attached thereto has the same structure.

The present invention also provides conjugates analogous to those described above in which the peptide is conjugated to a therapeutic moiety, diagnostic moiety, targeting moiety, toxin moiety or the like via a glycosyl linking group. Each of the above-recited moieties can be a small molecule, natural polymer (e.g., polypeptide) or synthetic polymer.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), IL-2 and IFN-α.

In an exemplary targeted conjugate, interferon alpha 2p (IFN-α 2β) is conjugated to transferrin via a bifunctional linker that includes an intact glycosyl linking group at each terminus of the PEG moiety (Scheme 1). For example, one terminus of the PEG linker is functionalized with an intact sialic acid linker that is attached to transferrin and the other is functionalized with an intact O-linked GalNAc linker that is attached to IFN-α 2p.

The conjugates of the invention can include glycosyl linking groups that are mono- or multi-valent (e.g., antennary structures). Thus, conjugates of the invention include both species in which a selected moiety is attached to a peptide via a monovalent glycosyl linking group. Also included within the invention are conjugates in which more than one selected moiety is attached to a peptide via a multivalent linking group.

The Methods

In addition to the conjugates discussed above, the present invention provides methods for preparing these and other conjugates. Moreover, the invention provides methods of preventing, curing or ameliorating a disease state by administering a conjugate of the invention to a subject at risk of developing the disease or a subject that has the disease. Additionally, the invention provides methods for targeting conjugates of the invention to a particular tissue or region of the body.

Thus, the invention provides a method of forming a covalent conjugate between a selected moiety and a peptide. In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via a glycosyl linking group, which is interposed between, and covalently linked to both the peptide and the modifying group (e.g. water-soluble polymer). The method includes contacting the peptide with a mixture containing a modified sugar and a glycosyltransferase for which the modified sugar is a substrate. The reaction is conducted under conditions appropriate to form a covalent bond between the modified sugar and the peptide. The sugar moiety of the modified sugar is preferably selected from nucleotide sugars, activated sugars and sugars, which are neither nucleotides nor activated.

The acceptor peptide (O-glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more N- or O-linked glycosylation sites to the peptide sequence.

In an exemplary embodiment, the peptide is O-glycosylated and functionalized with a water-soluble polymer in the following manner. The peptide is either produced with an available amino acid glycosylation site or, if glycosylated, the glycosyl moiety is trimmed off to exposed the amino acid. For example, GalNAc is added to a serine or threonine and the galactosylated peptide is sialylated with a sialic acid-modifying group cassette using ST6Gal-1. Alternatively, the galactosylated peptide is galactosylated using Core-1-GalT-1 and the product is sialylated with a sialic acid-modifying group cassette using ST3GalT1. An exemplary conjugate according to this method has the following linkages: Thr-α-1-GalNAc-β-1,3-Gal-α2,3-Sia*, in which Sia* is the sialic acid-modifying group cassette.

In the methods of the invention, such as that set forth above, using multiple enzymes and saccharyl donors, the individual glycosylation steps may be performed separately, or combined in a "single pot" reaction. For example, in the three enzyme reaction set forth above the GalNAc tranferase, GalT and SiaT and their donors may be combined in a single vessel. Alternatively, the GalNAc reaction can be performed alone and both the GalT and SiaT and the appropriate saccharyl donors added as a single step. Another mode of running the reactions involves adding each enzyme and an appropriate donor sequentially and conducting the reaction in a "single pot" motif. Combinations of each of the methods set forth above are of use in preparing the compounds of the invention.

In the conjugates of the invention, the Sia-modifying group cassette can be linked to the Gal in an α-2,6, or α-2,3 linkage.

For example, in one embodiment, G-CSF is expressed in a mammalian system and modified by treatment of sialidase to trim back terminal sialic acid residues, followed by PEGylation using ST3Gal3 and a donor of PEG-sialic acid.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Moreover, in addition to peptides, the methods of the present invention can be practiced with other biological structures (e.g., glycolipids, lipids, sphingoids, ceramides, whole cells, and the like, containing an O-linked glycosylation site).

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking two or more peptides through a linking group. The linking group is of any useful structure and may be selected from straight- and branched-chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosylunits, respectively. In practice, the (glycosyl)$^1$-PEG-(glycosyl)$^2$ linker is contacted with the first peptide and a first transferase for which the first glycosyl unit is a substrate, thereby forming (peptide)$^1$-(glycosyl)$^1$-PEG-(glycosyl)$^2$. Transferase and/or unreacted peptide is then optionally removed from the reaction mixture. The second peptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$; at least one of the glycosyl residues is either directly or indirectly O-linked. Those of skill in the art will appreciate that the method outlined above is also applicable to forming conjugates between more than two peptides by, for example, the use of a branched PEG, dendrimer, poly(amino acid), polsaccharide or the like In an exemplary embodiment, interferon alpha 2β (IFN-α 2β) is conjugated to transferrin via a bifunctional linker that includes an intact glycosyl linking group at each terminus of the PEG moiety (Scheme 1). The IFN conjugate has an in vivo half-life that is increased over that of IFN alone by virtue of the greater molecular sized of the conjugate. Moreover, the conjugation of IFN to transferrin serves to selectively target the conjugate to the brain. For example, one terminus of the PEG linker is functionalized with a CMP sialic acid and the other is functionalized with an UDP GalNAc. The linker is combined with IFN in the presence of a GalNAc transferase, resulting in the attachment of the GalNAc of the linker arm to a serine and/or threonine residue on the IFN.

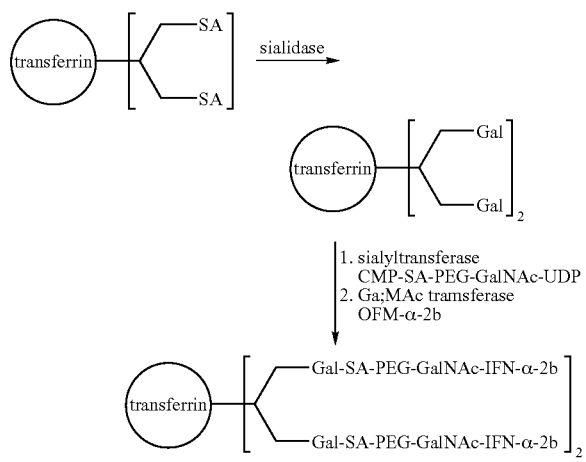

Scheme 1

The processes described above can be carried through as many cycles as desired, and is not limited to forming a conjugate between two peptides with a single linker. Moreover, those of skill in the art will appreciate that the reactions functionalizing the intact glycosyl linking groups at the termini of the PEG (or other) linker with the peptide can occur simultaneously in the same reaction vessel, or they can be carried out in a step-wise fashion. When the reactions are carried out in a step-wise manner, the conjugate produced at each step is optionally purified from one or more reaction components (e.g., enzymes, peptides).

A still further exemplary embodiment is set forth in Scheme 2. Scheme 2 shows a method of preparing a conjugate that targets a selected protein, e.g., GM-CSF, to bone and increases the circulatory half-life of the selected protein.

Scheme 2

HSGP—Gal, Gal →(CMP-SA-PEG-G, sialyltransferase)→ HSGP—Gal-SA-PEG-G, Gal-SA-PEG-G →(GM-CSF transferase)→ HSGP—Gal-SA-PEG-G-(L)$_s$-GMCSF, Gal-SA-PEG-G-(L)$_s$-GMCSF in which G is a glycosyl residue on an activated sugar moiety (e.g., sugar nucleotide), which is converted to an intact glycosyl linker group in the conjugate. When s is greater than 0, L is a saccharyl linking group such as GalNAc, or GalNAc-Gal.

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al, *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., Bioconjugate Chem., 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

In another exemplary embodiment in which a reactive PEG derivative is utilized, the invention provides a method for extending the blood-circulation half-life of a selected peptide, in essence targeting the peptide to the blood pool, by conjugating the peptide to a synthetic or natural polymer of a size sufficient to retard the filtration of the protein by the glomerulus (e.g., albumin). See, Scheme 3. This embodiment of the invention is illustrated in Scheme in which G-CSF is conjugated to albumin via a PEG linker using a combination of chemical and enzymatic modification.

Scheme 3 albumin →(X-PEG-SA-CMP)→ albumin—PEG-SA-CMP →(G-CSF)→ albumin—PEG-SA—G-CSF

X = Activating group

Thus, as shown in Scheme 3, a residue (e.g., amino acid side chain) of albumin is modified with a reactive PEG derivative, such as X-PEG-(CMP-sialic acid), in which X is an activating group (e.g., active ester, isothiocyanate, etc). The PEG derivative and G-CSF are combined and contacted with a transferase for which CMP-sialic acid is a substrate. In a further illustrative embodiment, an ε-amine of lysine is reacted with the N-hydroxysuccinimide ester of the PEG-linker to form the albumin conjugate. The CMP-sialic acid of the linker is enzymatically conjugated to an appropriate residue on GCSF, e.g., Gal, or GalNAc thereby forming the conjugate. Those of skill will appreciate that the above-described method is not limited to the reaction partners set forth. Moreover, the method can be practiced to form conjugates that include more than two protein moieties by, for example, utilizing a branched linker having more than two termini.

Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate structure can be added to a peptide using the methods of the invention. Typically, the structure will be a monosaccharide, but the present invention is not limited to the use of modified monosaccharide sugars; oligosaccharides and polysaccharides are useful as well.

The modifying group is attached to a sugar moiety by enzymatic means, chemical means or a combination thereof, thereby producing a modified sugar. The sugars are substituted at any position that allows for the attachment of the modifying moiety, yet which still allows the sugar to function as a substrate for the enzyme used to ligate the modified sugar to the peptide. In another embodiment, when sialic acid is the sugar, the sialic acid is substituted with the modifying group at either the 9-position on the pyruvyl side chain or at the 5-position on the amine moiety that is normally acetylated in sialic acid.

In certain embodiments of the present invention, a modified sugar nucleotide is utilized to add the modified sugar to the peptide. Exemplary sugar nucleotides that are used in the present invention in their modified form include nucleotide mono-, di- or triphosphates or analogs thereof. In another embodiment, the modified sugar nucleotide is selected from a UDP-glycoside, CMP-glycoside, or a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid, or CMP-NeuAc. N-acetylamine derivatives of the sugar nucletides are also of use in the method of the invention.

The invention also provides methods for synthesizing a modified peptide using a modified sugar, e.g., modified-galactose, -fucose, -GalNAc and -sialic acid. When a modified sialic acid is used, either a sialyltransferase or a trans-sialidase (for α2,3-linked sialic acid only) can be used in these methods.

In other embodiments, the modified sugar is an activated sugar. Activated modified sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups (leaving groups) include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, α-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-1-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In another embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical conjugate of the invention as set forth in the drawing above, encompasses multivalent species resulting from preparing a conjugate of the invention utilizing an antennary structure. Many antennary saccharide structures are known in the art, and the present method can be practiced with them without limitation.

Exemplary modifying groups are discussed below. The modifying groups can be selected for their ability to impart to a peptide one or more desirable property. Exemplary properties include, but are not limited to, enhanced pharmacokinetics, enhanced pharmacodynamics, improved biodistribution, providing a polyvalent species, improved water solubility, enhanced or diminished lipophilicity, and tissue targeting.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., Critical Reviews in *Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

Exemplary poly(ethylene glycol) molecules of use in the invention include, but are not limited to, those having the formula:

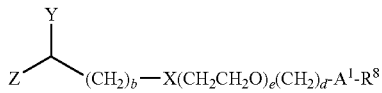

in which $R^8$ is H, OH, $NH_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N$—$(CH_2)_q$—, HS—$(CH_2)_q$, or —$(CH_2)_qC(Y)Z^1$. The index "e" represents an integer from 1 to 2500. The indices b, d, and q independently represent integers from 0 to 20. The symbols Z and $Z^1$ independently represent OH, $NH_2$, leaving groups, e.g., imidazole, p-nitrophenyl, HOBT, tetrazole, halide, S—$R^9$, the alcohol portion of activated esters; —$(CH_2)_pC(Y^1)V$, or —$(CH_2)_pU(CH_2)_nC(Y^1)_v$. The symbol Y represents H(2), =O, =S, =N—$R^{10}$. The symbols X, Y, $Y^1$, $A^1$, and U independently represent the moieties O, S, N—$R^{11}$. The symbol V represents OH, $NH_2$, halogen, S—$R^{12}$, the alcohol component of activated esters, the amine component of activated amides, sugar-nucleotides, and proteins. The indices p, q, s and v are members independently selected from the integers from 0 to 20. The symbols $R^9$, $R^{10}$, $R^{11}$ and $R^{12}$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

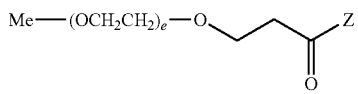

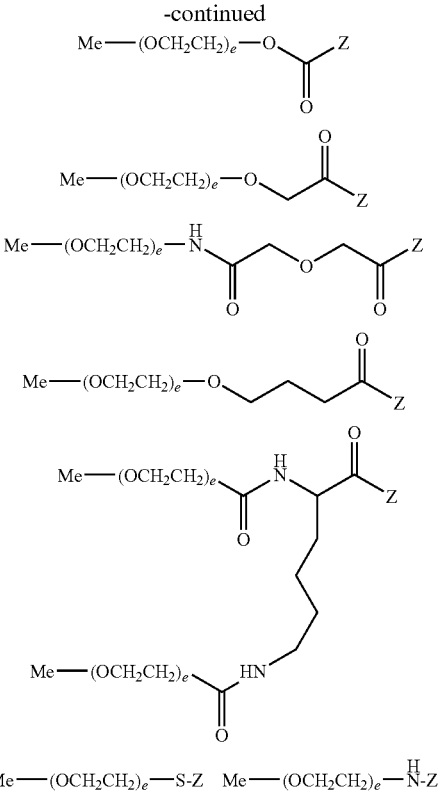

The poly(ethylene glycol) useful in forming the conjugate of the invention is either linear or branched. Branched poly (ethylene glycol) molecules suitable for use in the invention include, but are not limited to, those described by the following formula:

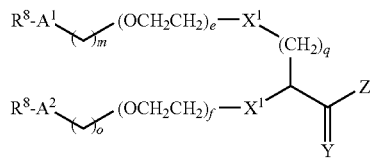

in which $R^8$ and $R^{8'}$ are members independently selected from the groups defined for $R^8$, above. $A^1$ and $A^2$ are members independently selected from the groups defined for $A^1$, above. The indices e, f, o, and q are as described above. Z and Y are as described above. $X^1$ and $X^{1'}$ are members independently selected from S, SC(O)NH, HNC(O)S, SC(O)O, O, NH, NHC(O), (O)CNH and NHC(O)O, OC(O)NH.

In other exemplary embodiments, the branched PEG is based upon a cysteine, serine or di-lysine core. Thus, further exemplary branched PEGs include:

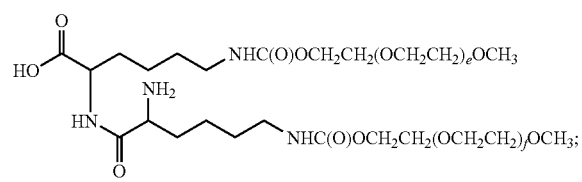

-continued

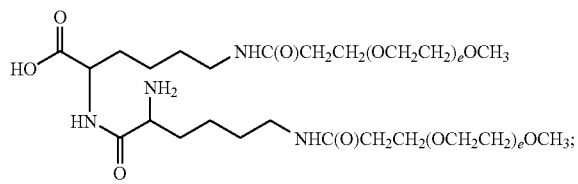

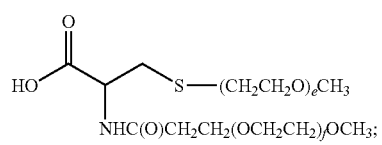

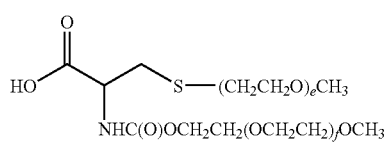

-continued

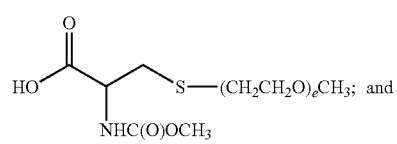

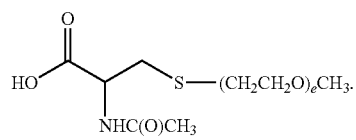

In yet another embodiment, the branched PEG moiety is based upon a tri-lysine peptide. The tri-lysine can be mono-, di-, tri-, or tetra-PEG-ylated. Exemplary species according to this embodiment have the formulae:

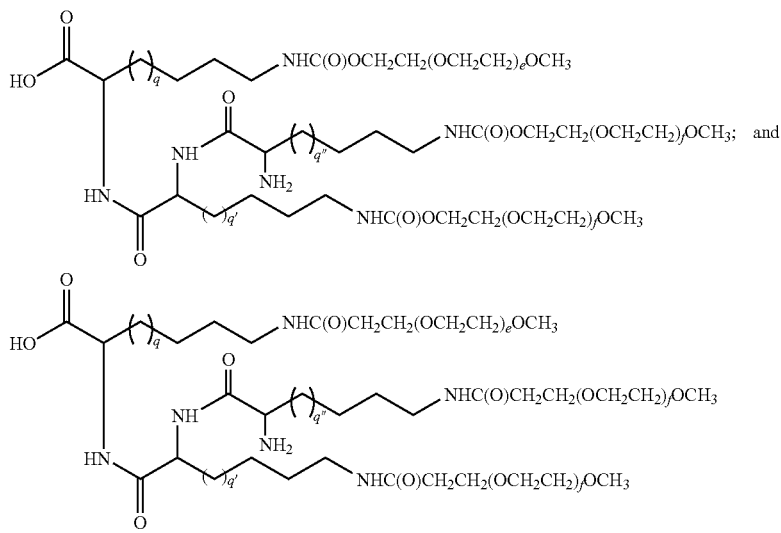

-continued

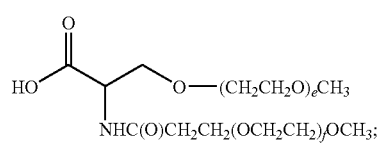

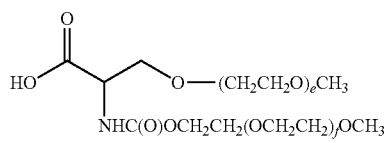

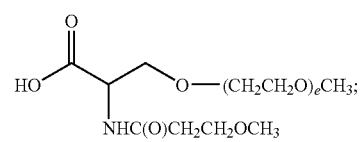

in which e, f and f' are independently selected integers from 1 to 2500; and q, q' and q" are independently selected integers from 1 to 20.

In exemplary embodiments of the invention, the PEG is m-PEG (5 kD, 10 kD, or 20 kD). An exemplary branched PEG species is a serine- or cysteine-(m-PEG)$_2$ in which the m-PEG is a 20 kD m-PEG.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits is within the scope of the invention.

Specific embodiments according to the invention include:

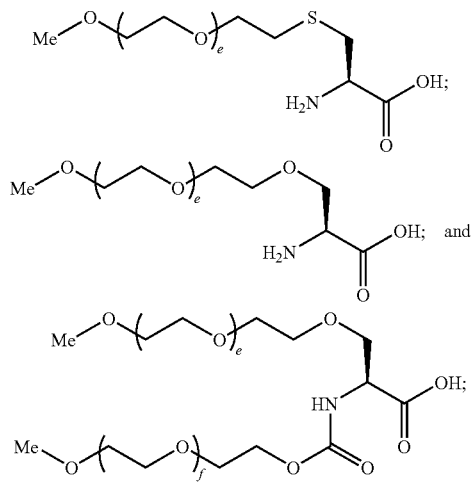

and carbonates and active esters of these species, such as:

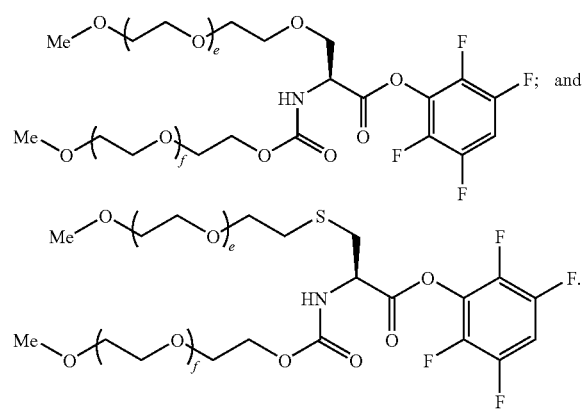

Other activating, or leaving groups, appropriate for activating linear PEGs of use in preparing the compounds set forth herein include, but are not limited to the species:

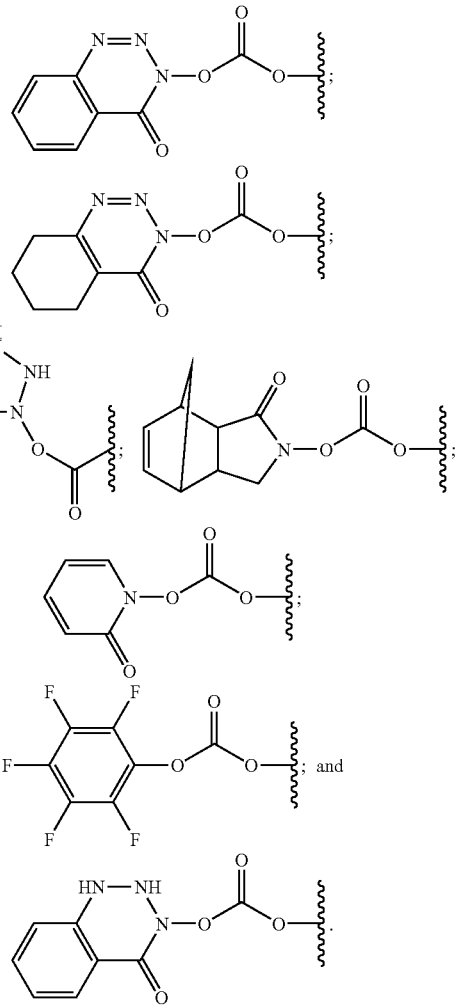

PEG molecules that are activated with these and other species and methods of making the activated PEGs are set forth in WO 04/083259.

Those of skill in the art will appreciate that one or more of the m-PEG arms of the branched polymer can be replaced by a PEG moiety with a different terminus, e.g., OH, COOH, NH$_2$, C$_2$-C$_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

The branched PEG species set forth herein are readily prepared by methods such as that set forth in the scheme below:

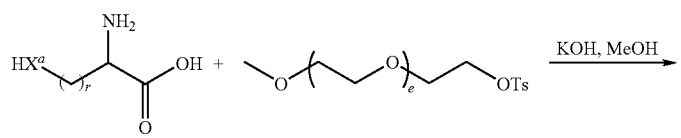

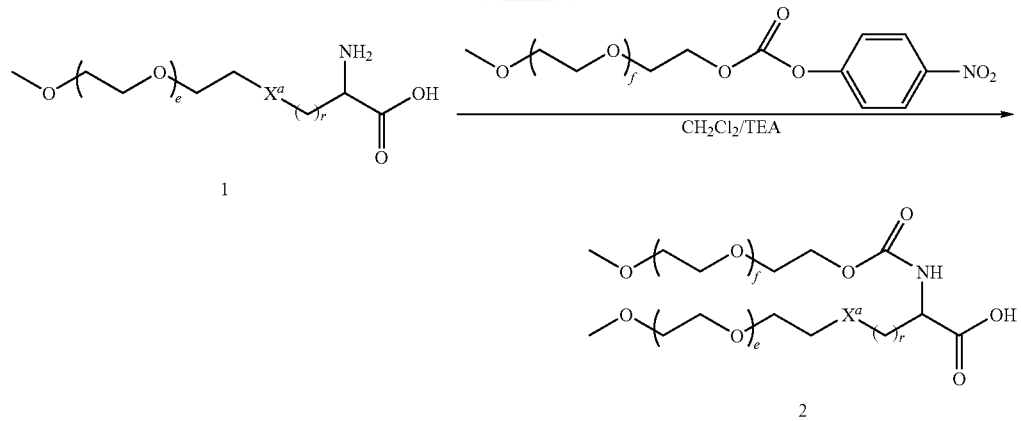

in which $X^a$ is O or S and r is an integer from 1 to 5. The indices e and f are independently selected integers from 1 to 2500.

Thus, according to this scheme, a natural or unnatural amino acid is contacted with an activated m-PEG derivative, in this case the tosylate, forming 1 by alkylating the side-chain heteroatom $X^a$. The mono-functionalized m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In an exemplary embodiment, the modifying group is a PEG moiety, however, any modifying group, e.g., water-soluble polymer, water-insoluble polymer, therapeutic moiety, etc., can be incorporated in a glycosyl moiety through an appropriate linkage. The modified sugar is formed by enzymatic means, chemical means or a combination thereof, thereby producing a modified sugar. In an exemplary embodiment, the sugars are substituted with an active amine at any position that allows for the attachment of the modifying moiety, yet still allows the sugar to function as a substrate for an enzyme capable of coupling the modified sugar to the G-CSF peptide. In an exemplary embodiment, when galactosamine is the modified sugar, the amine moiety is attached to the carbon atom at the 6-position.

Water-Soluble Polymer Modified Species

Water-soluble polymer modified nucleotide sugar species in which the sugar moiety is modified with a water-soluble polymer are of use in the present invention. An exemplary modified sugar nucleotide bears a sugar group that is modified through an amine moiety on the sugar. Modified sugar nucleotides, e.g., saccharyl-amine derivatives of a sugar nucleotide, are also of use in the methods of the invention. For example, a saccharyl amine (without the modifying group) can be enzymatically conjugated to a peptide (or other species) and the free saccharyl amine moiety subsequently conjugated to a desired modifying group. Alternatively, the modified sugar nucleotide can function as a substrate for an enzyme that transfers the modified sugar to a saccharyl acceptor on a substrate, e.g., a peptide, glycopeptide, lipid, aglycone, glycolipid, etc.

In one embodiment in which the saccharide core is galactose or glucose, $R^5$ is NHC(O)Y.

In an exemplary embodiment, the modified sugar is based upon a 6-amino-N-acetyl-glycosyl moiety. As shown below for N-acetylgalactosamine, the 6-amino-sugar moiety is readily prepared by standard methods.

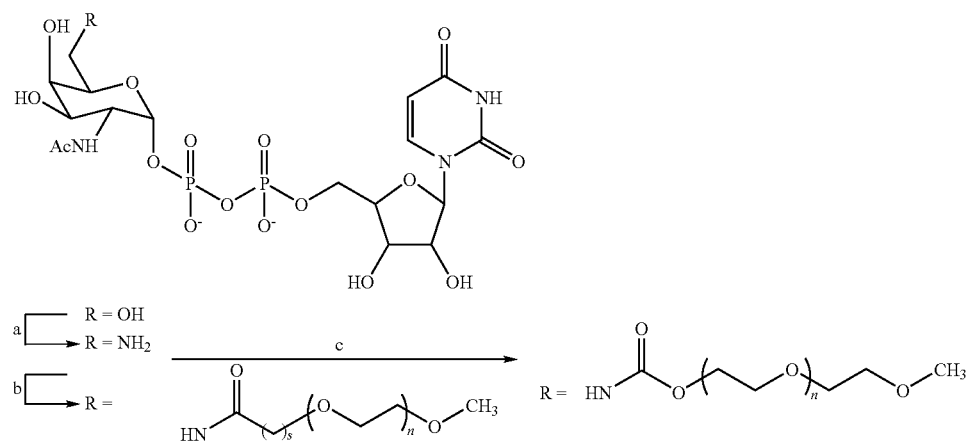

a. galactose oxidase; NH₄OAc, NaBH₃CN;
b. 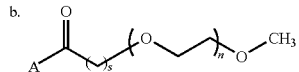
c. 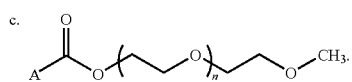

In the scheme above, the index n represents an integer from 1 to 2500, preferably from 10 to 1500, and more preferably from 10 to 1200. The symbol "A" represents an activating group, e.g., a halo, a component of an activated ester (e.g., a N-hydroxysuccinimide ester), a component of a carbonate (e.g., p-nitrophenyl carbonate) and the like. Those of skill in the art will appreciate that other PEG-amide nucleotide sugars are readily prepared by this and analogous methods.

In other exemplary embodiments, the amide moiety is replaced by a group such as a urethane or a urea.

In still further embodiments, $R^1$ is a branched PEG, for example, one of those species set forth above. Illustrative compounds according to this embodiment include:

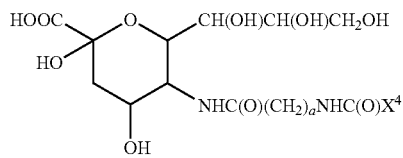 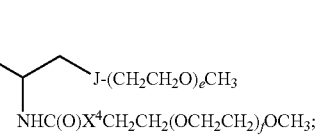

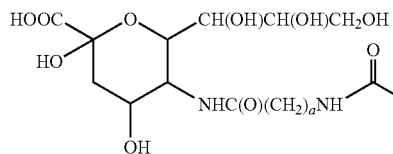 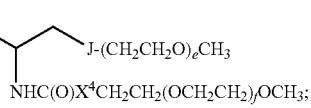

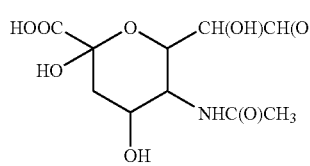 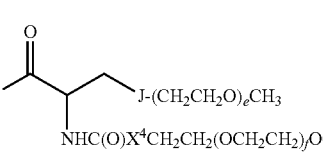

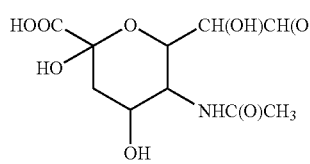 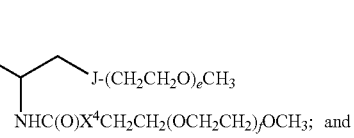; and

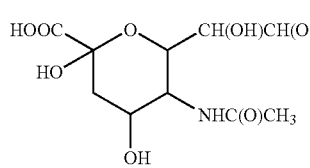 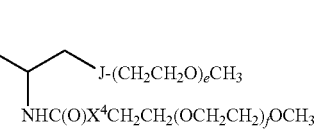

in which $X^4$ is a bond or O, and J is S or O.

Moreover, as discussed above, the present invention provides peptide conjugates that are formed using nucleotide sugars that are modified with a water-soluble polymer, which is either straight-chain or branched. For example, compounds having the formula shown below are within the scope of the present invention:

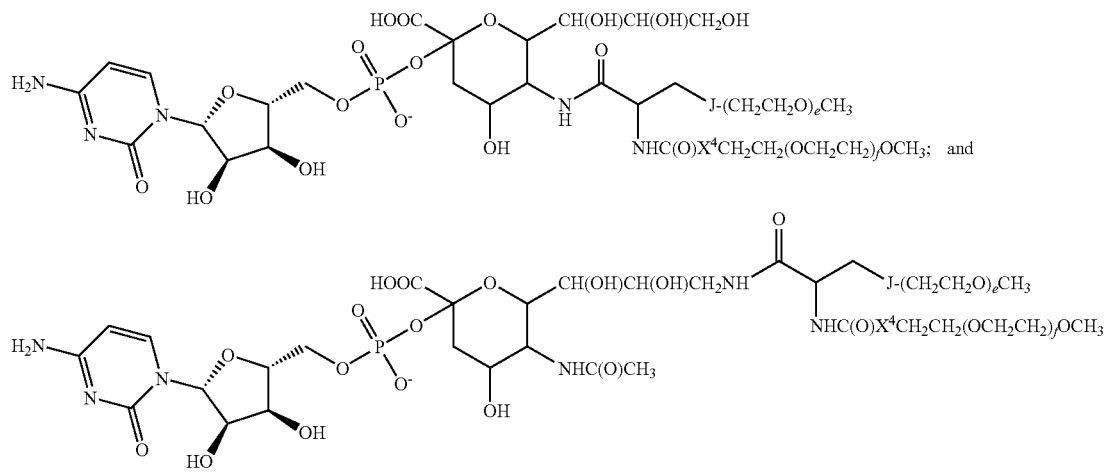

in which $X^4$ is O or a bond, and J is S or O.

Similarly, the invention provides peptide conjugates that are formed using nucleotide sugars of those modified sugar species in which the carbon at the 6-position is modified:

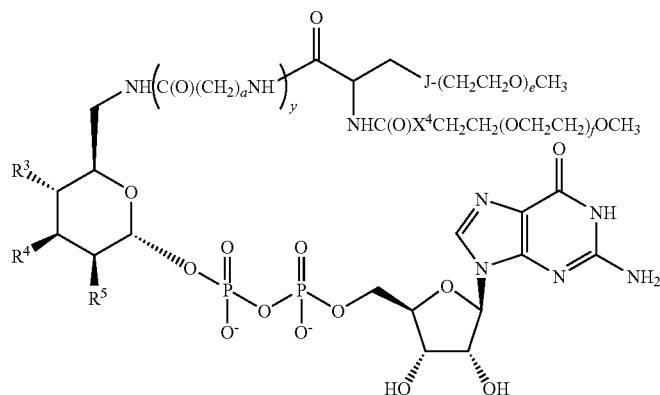

in which $X^4$ is a bond or O, J is S or O, and y is 0 or 1.

Also provided are conjugates of peptides and glycopeptides, lipids and glycolipids that include the compositions of the invention. For example, the invention provides conjugates having the following formulae:

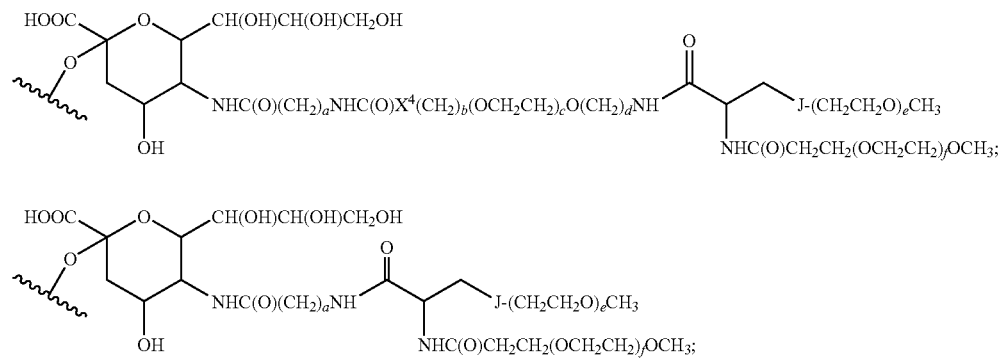

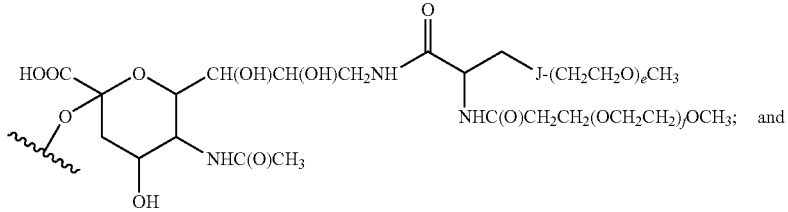

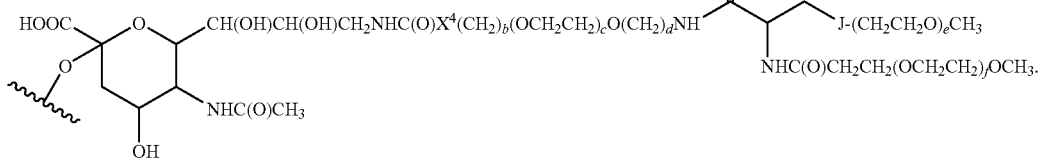

wherein J is S or O.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid' polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially nontoxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly(carbonates), poly(phosphazines), poly(phosphoesters), poly(thioesters), polysaccharides and mixtures thereof. More preferably still, the bioresorbable polymer includes a poly(hydroxy) acid component. Of the poly(hydroxy) acids, polylactic acid, polyglycolic acid, polycaproic acid, polybutyric acid, polyvaleric acid and copolymers and mixtures thereof are preferred. In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly(propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. Nos. 5,410,016, which issued on Apr. 25, 1995 and 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

The in vivo half-life of therapeutic glycopeptides can also be enhanced with PEG moieties such as polyethylene glycol (PEG). For example, chemical modification of proteins with PEG (PEGylation) increases their molecular size and decreases their surface- and functional group-accessibility, each of which are dependent on the size of the PEG attached to the protein. This results in an improvement of plasma half-lives and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a peptide derivatized with a PEG moiety by a method of the invention is increased relevant to the in vivo half-life of the non-derivatized peptide.

The increase in peptide in vivo half-life is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

Biomolecules

In another embodiment, the modified sugar bears a biomolecule. In still further embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further embodiment, the biomolecule is selected to direct the peptide modified by the methods of the invention to a specific tissue, thereby enhancing the delivery of the peptide to that tissue relative to the amount of underivatized peptide that is delivered to the tissue. In a still further embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

Therapeutic Moieties

In another embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In another embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. Preferred therapeutic moieties are essentially non-fluorescent, or emit such a minimal amount of fluorescence that they are inappropriate for use as a fluorescent marker in an assay. Moreover, it is generally preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, reductase, oxidase), light, heat and the like. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989).

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, caramiphen and carbetapentane); antipruritic drugs (e.g., methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encamide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of α-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, the duocarmycins, Chlicheamycin and related structures and analogues thereof.

The therapeutic moiety can also be a hormone (e.g., medroxyprogesterone, estradiol, leuprolide, megestrol, octreotide or somatostatin); muscle relaxant drugs (e.g., cinnanedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Preparation of Modified Sugars

In general, the sugar moiety and the modifying group are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to, e.g., esters, ethers, aldehydes, etc.
(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be, for example, converted to disulfides or reacted with acyl halides;
(h) amine or sulfhydryl groups, which can be, for example, acylated, alkylated or oxidized;
(i) alkenes, which can undergo, for example, cycloadditions, acylation, Michael addition, etc; and
(j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the peptide that is modified by a method of the invention is a glycopeptide that is produced in prokaryotic cells (e.g., *E. coli*), eukaryotic cells including yeast and mammalian cells (e.g., CHO cells), or in a transgenic animal and thus contains N- and/or O-linked oligosaccharide chains, which are incompletely sialylated. The oligosaccharide chains of the glycopeptide lacking a sialic acid and containing a terminal galactose residue can be glyco-PEG-ylated, glyco-PPG-ylated or otherwise modified with a modified sialic acid.

In Scheme 4, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG or PPG attachment by reacting compound 3 with an activated (m-) PEG or (m-) PPG derivative (e.g., PEG-C(O)NHS, PPG-C(O)NHS), producing 4 or 5, respectively.

Scheme 4

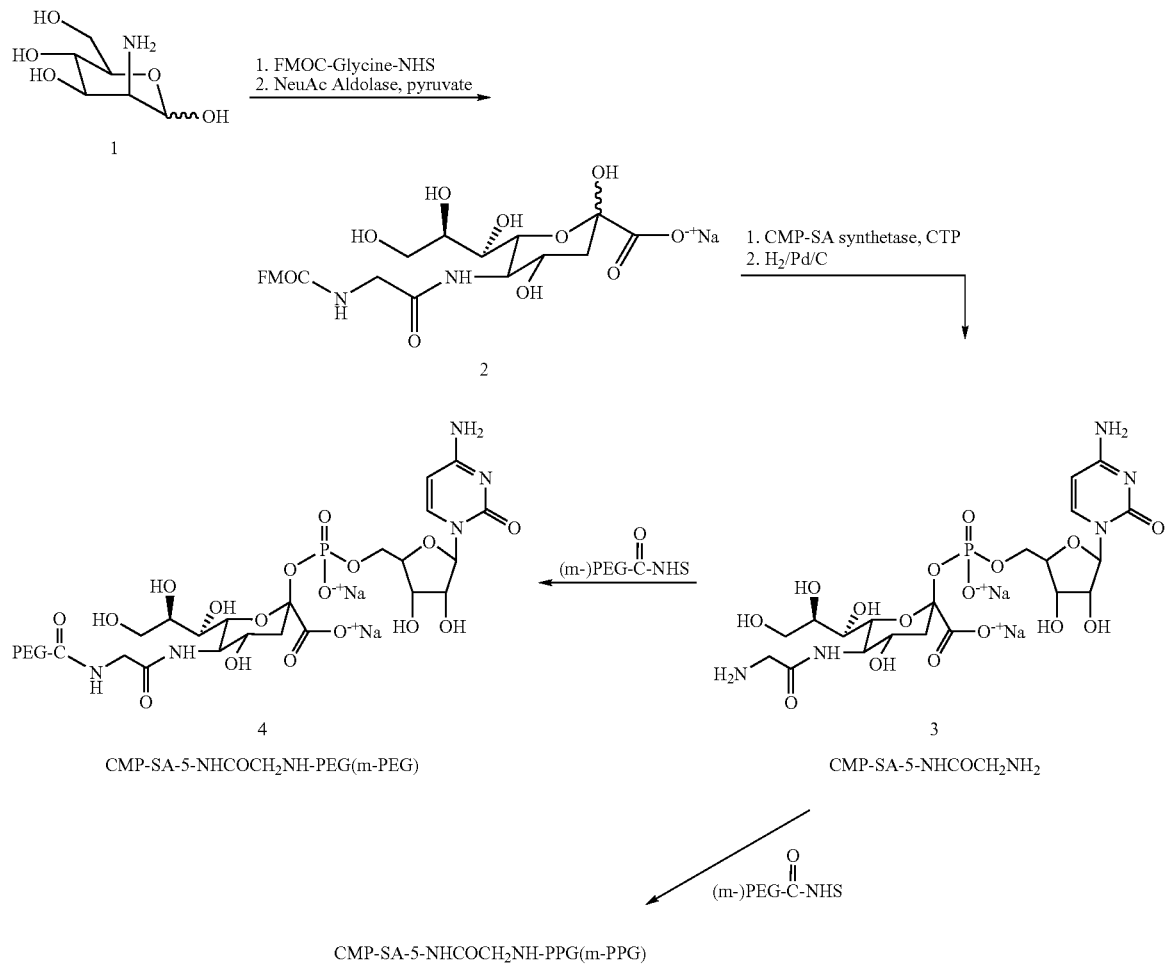

Table 2 sets forth representative examples of sugar monophosphates that are derivatized with a PEG or PPG moiety. Certain of the compounds of Table 2 are prepared by the method of Scheme 4. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 2

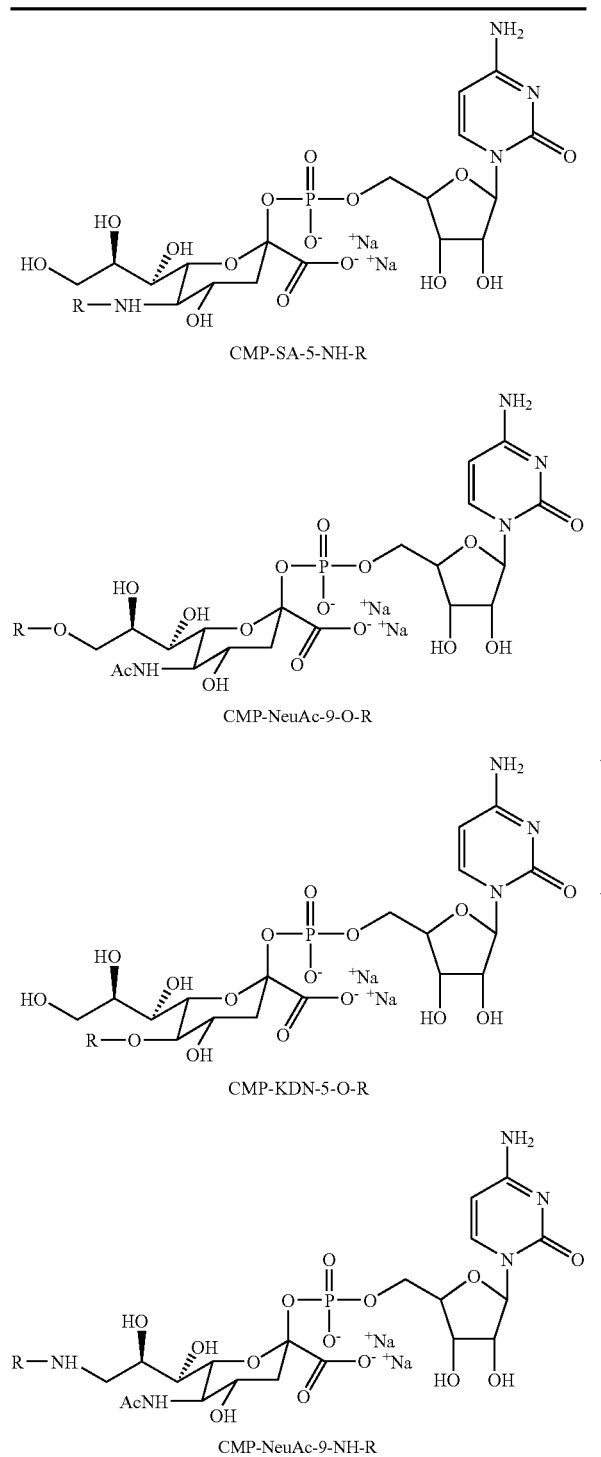

TABLE 2-continued

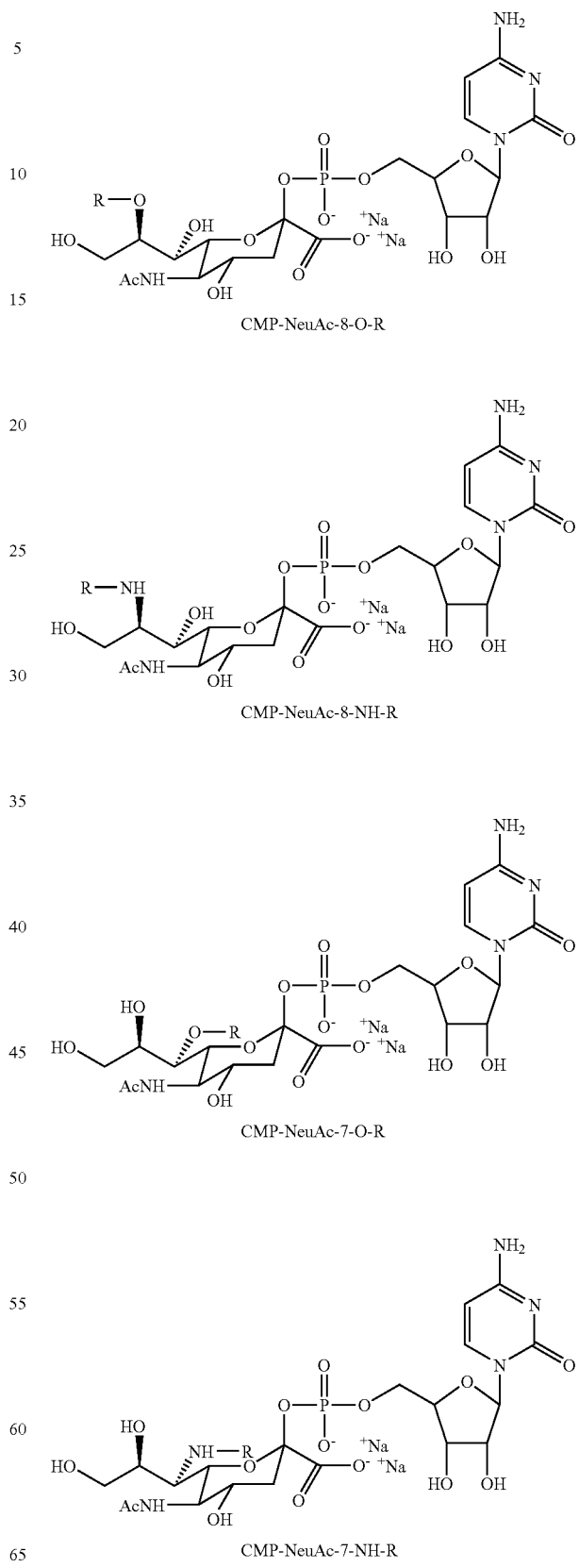

TABLE 2-continued

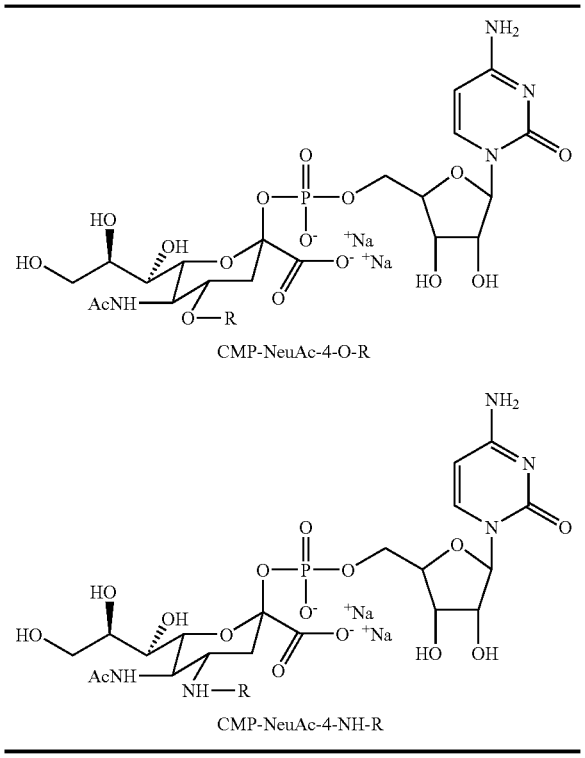

CMP-NeuAc-4-O-R

CMP-NeuAc-4-NH-R

The modified sugar phosphates of use in practicing the present invention can be substituted in other positions as well as those set forth above. Presently preferred substitutions of sialic acid are set forth in Formula I:

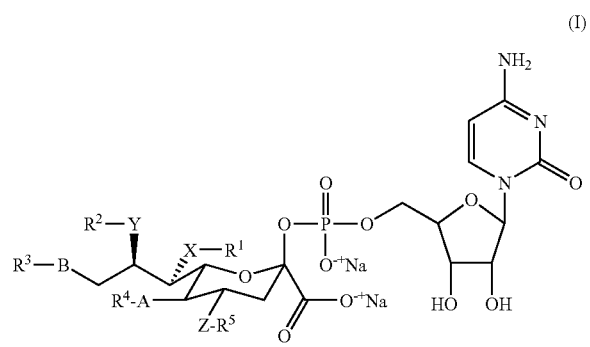

(I)

in which X is a linking group, which is preferably selected from —O—, —N(H)—, —S, $CH_2$—, and —$N(R)_2$, in which each R is a member independently selected from $R^1$-$R^5$. The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $SLe_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Cross-linking Groups

Preparation of the Modified Sugar for Use in the Methods of the Present Invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., Biochemistry 28: 1856 (1989); Bhatia et al., Anal. Biochem. 178: 408 (1989); Janda et al., J. Am. Chem. Soc. 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulthydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

2. Sulfhydryl-Reactive Groups

In another embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

3. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

ii. Preferred Nonspecific Sites in Crosslinking Reagents

In addition to the use of site-specific reactive moieties, the present invention contemplates the use of non-specific reactive groups to link the sugar to the modifying group.

Exemplary non-specific cross-linkers include photoactivatable groups, completely inert in the dark, which are converted to reactive species upon absorption of a photon of appropriate energy. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

iii. Homobifunctional Reagents

1. Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy)ethylsulfone (BSOCOES), bis-2-(sulfosuccinimidooxy-carbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis(succinimidyl-propionate) (DSP), and dithiobis(sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether. Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

iv. HeteroBifunctional Reagents

1. Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

2. Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4((iodoacetyl)-amino)methylcyclohexane-1-carboxylate (SIAC).

An example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

v. Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352, 670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In another embodiment, each of the first and second enzyme is a glycosyltransferase. In another embodiment, one enzyme is an endoglycosidase. In an additional embodiment, more than two enzymes are used to assemble the modified glycoprotein of the invention. The enzymes are used to alter a saccharide structure on the peptide at any point either before or after the addition of the modified sugar to the peptide.

The O-linked glycosyl moieties of the conjugates of the invention are generally originate with a GalNAc moiety that is attached to the peptide. Any member of the family of GalNAc transferases can be used to bind a GalNAc moiety to the peptide (Hassan H, Bennett E P, Mandel U, Hollingsworth M A, and Clausen H (2000). Control of Mucin-Type O-Glycosylation: O-Glycan Occupancy is Directed by Substrate Specificities of Polypeptide GalNAc-Transferases. (Eds. Ernst, Hart, and Sinay). Wiley-VCH chapter "Carbohydrates in Chemistry and Biology—a Comprehension Handbook", 273-292). The GalNAc moiety itself can be the intact glycosyl linker. Alternatively, the saccharyl residue is built out using one more enzyme and one or more appropriate glycosyl substrate for the enzyme, the modified sugar being added to the built out glycosyl moiety.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In another embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with (m-) PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of (m-) PEG-ylated or (m-) PPG-ylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as GalNAc, Galβ1,4GlcNAc, Galβ11,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added to an O-linked glycosylation site by the action of a GalNAc transferase. Hassan H, Bennett E P, Mandel U, Hollingsworth M A, and Clausen H (2000). Control of Mucin-Type O-Glycosylation: O-Glycan Occupancy is Directed by Substrate Specificities of Polypeptide GalNAc-Transferases. (Eds. Ernst, Hart, and Sinay). Wiley-VCH chapter "Carbohydrates in Chemistry and Biology—a Comprehension Handbook", 273-292.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment, an O-linked carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming." In one example, a glycopeptide is "trimmed" and a water-soluble polymer is added to the resulting O-side chain amino acid or glycopeptide glycan via a saccharyl moiety, e.g., Sia, Gal or GalNAc moiety conjugated to the In yet a further example, a water-soluble polymer is added onto a Gal residue using a modified sialic acid.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

The exemplary embodiments discussed above provide an illustration of the power of the methods set forth herein. Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the water-soluble polymer is added to a terminal Gal residue using a polymer modified sialic acid. An appropriate sialyltransferase is used to add a modified sialic acid. The approach is summarized in Scheme 5.

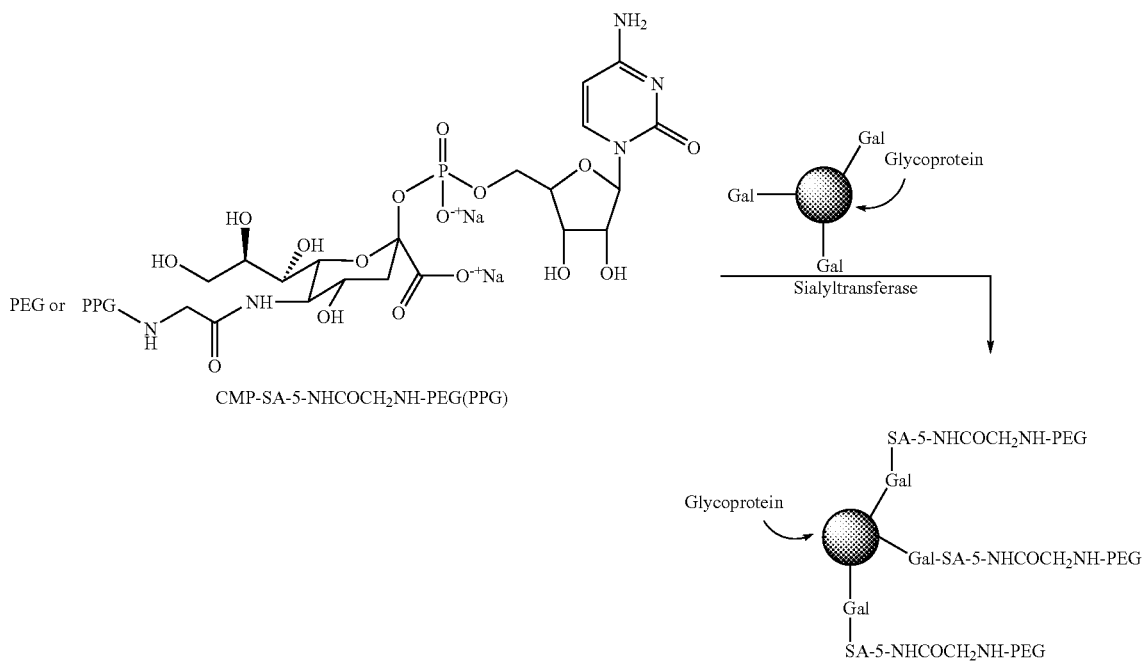

Scheme 5 water-soluble polymer. The modified saccharyl moiety is attached to an acceptor site on the "trimmed" glycopeptide. Alternatively, an unmodified saccharyl moiety, e.g., Gal can be added the terminus of the O-linked glycan.

In another exemplary embodiment, a water-soluble polymer is added to a GalNAc residue via a modified sugar having a galactose residue. Alternatively, an unmodified Gal can be added to the terminal GalNAc residue.

In yet a further approach, summarized in Scheme 6, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

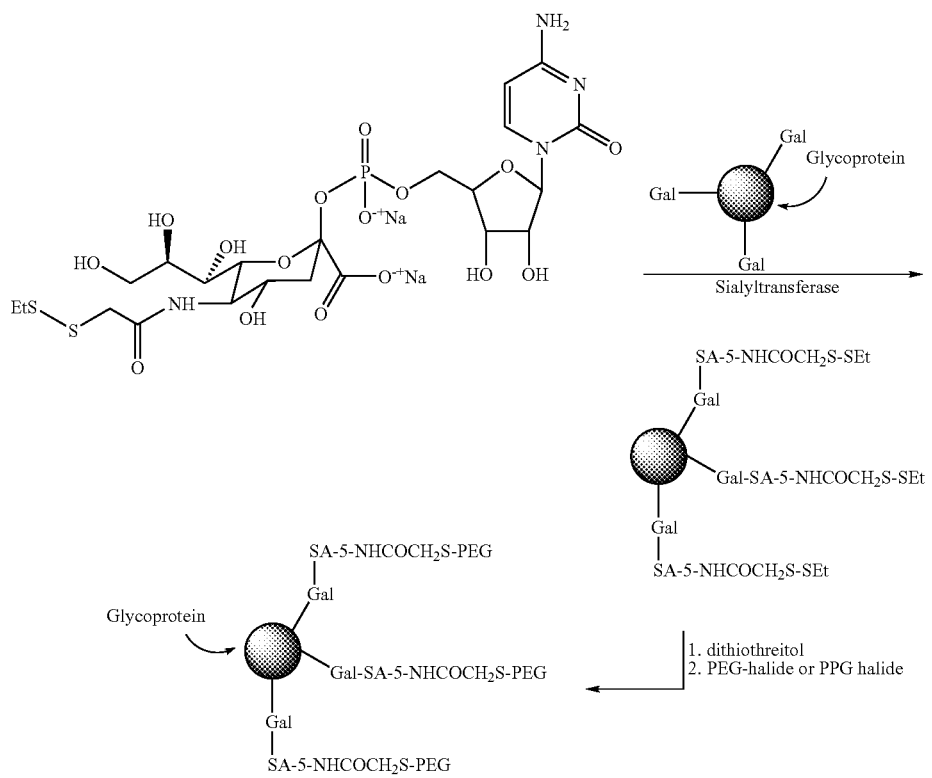

Scheme 6

Any modified sugar can be used with its appropriate glycosyltransferase, depending on the terminal sugars of the oligosaccharide side chains of the glycopeptide (Table 3). As discussed above, the terminal sugar of the glycopeptide required for introduction of the PEG-ylated or PPGylated structure can be introduced naturally during expression or it can be produced post expression using the appropriate glycosidase(s), glycosyltransferase(s) or mix of glycosidase(s) and glycosyltransferase(s).

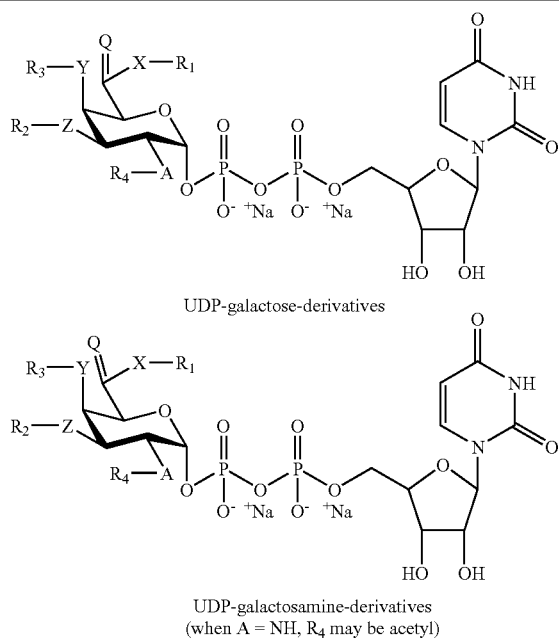

UDP-galactose-derivatives

UDP-galactosamine-derivatives
(when A = NH, R$_4$ may be acetyl)

-continued

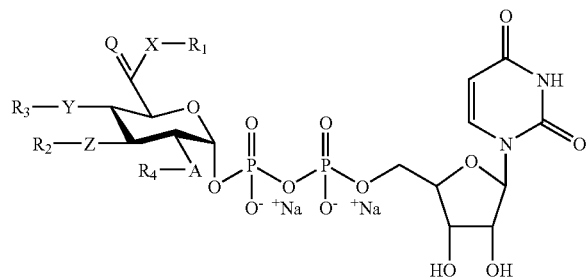
UDP-Glucose-derivatives

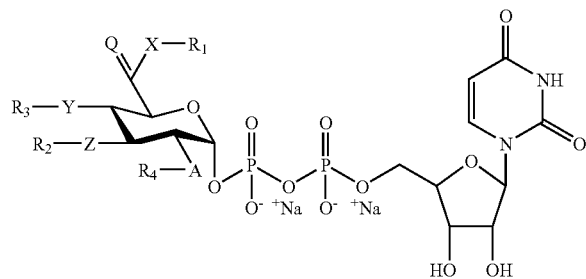
UDP-Glucosamine-derivatives
(when A = NH, R$_4$ may be acetyl)

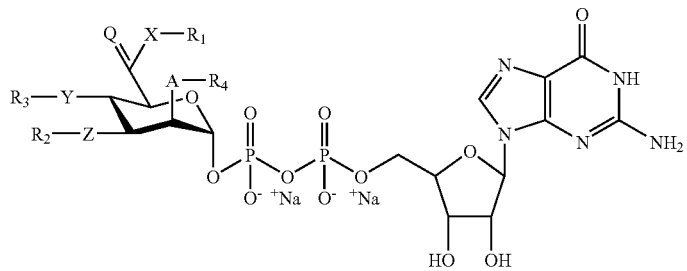
GDP-Mannose-derivatives

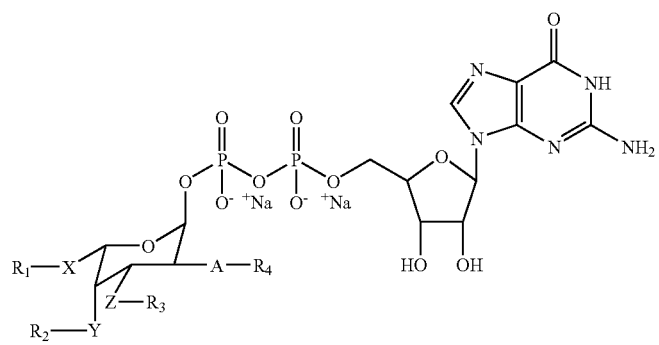
GDP-fucose-derivatives

X = O, NH, S, CH$_2$, N—(R$_{1-5}$)$_2$.
Y = X;
Z = X;
A = X;
B = X.
Q = H$_2$, O, S, NH, N—R.
R, R$_{1-4}$ = H, Linker-M, M.
M = Ligand of interest
Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-$_6$-phosphate, heparin, heparan, SLex, Mannose, FGF, VFGF, protein, chondroitin, keratan, dermatan, albumin, integrins, peptides, etc.

In an alternative embodiment, the modified sugar is added directly to the peptide backbone using a glycosyltransferase known to transfer sugar residues to the O-linked glycosylation site on the peptide backbone. This exemplary embodiment is set forth in Scheme 7. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

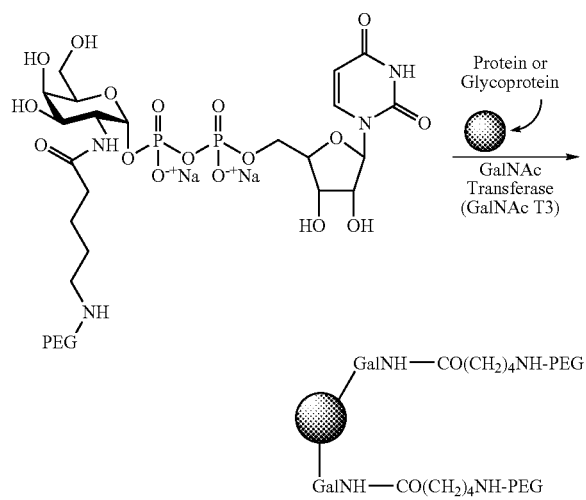

Scheme 7

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

In another exemplary embodiment, the glycopeptide is conjugated to a targeting agent, e.g., transferrin (to deliver the peptide across the blood-brain barrier, and to endosomes), carnitine (to deliver the peptide to muscle cells; see, for example, LeBorgne et al., *Biochem. Pharmacol.* 59: 1357-63 (2000), and phosphonates, e.g., bisphosphonate (to target the peptide to bone and other calciferous tissues; see, for example, Modern Drug Discovery, August 2002, page 10). Other agents useful for targeting are apparent to those of skill in the art. For example, glucose, glutamine and IGF are also useful to target muscle.

The targeting moiety and therapeutic peptide are conjugated by any method discussed herein or otherwise known in the art. Those of skill will appreciate that peptides in addition to those set forth above can also be derivatized as set forth herein. Exemplary peptides are set forth in the Appendix attached to copending, commonly owned U.S. Provisional Patent Application No. 60/328,523 filed Oct. 10, 2001.

In an exemplary embodiment, the targeting agent and the therapeutic peptide are coupled via a linker moiety. In this embodiment, at least one of the therapeutic peptide or the targeting agent is coupled to the linker moiety via an intact glycosyl linking group according to a method of the invention. In an exemplary embodiment, the linker moiety includes a poly(ether) such as poly(ethylene glycol). In another exemplary embodiment, the linker moiety includes at least one bond that is degraded in vivo, releasing the therapeutic peptide from the targeting agent, following delivery of the conjugate to the targeted tissue or region of the body.

In yet another exemplary embodiment, the in vivo distribution of the therapeutic moiety is altered via altering a glycoform on the therapeutic moiety without conjugating the therapeutic peptide to a targeting moiety. For example, the therapeutic peptide can be shunted away from uptake by the reticuloendothelial system by capping a terminal galactose moiety of a glycosyl group with sialic acid (or a derivative thereof).

i. Enzymes

1. Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., Critical Reviews in Microbiology 23(3): 139-180 (1996)). Such enzymes include, but are not limited to, the proteins of the rfa operons of species such as E. coli and Salmonella typhimurium, which include a β1,6 galactosyltransferase and a β1,3 galactosyltransferase (see, e.g., EMBL Accession Nos. M80599 and M86935 (E. coli); EMBL Accession No. S56361 (S. typhimurium)), a glucosyltransferase (Swiss-Prot Accession No. P25740 (E. coli), an β1,2-glucosyltransferase (rfaJ)(Swiss-Prot Accession No. P27129 (E. coli) and Swiss-Prot Accession No. P19817 (S. typhimurium)), and an D 1,2-N-acetylglucosaminyltransferase (rfaK) (EMBL Accession No. U00039 (E. coli). Other glycosyltransferases for which amino acid sequences are known include those that are encoded by operons such as rfaB, which have been characterized in organisms such as Klebsiellapneumoniae, E. coli, Salmonella typhimurium, Salmonella enterica, Yersinia enterocolitica, Mycobacterium leprosum, and the rh1 operon of Pseudomonas aeruginosa.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens Neisseria gonnorhoeae and N. meningitidis (Scholten et al., J. Med. Microbiol. 41: 236-243 (1994)). The genes from N. meningitidis and N. gonorrhoeae that encode the glycosyltransferases involved in the biosynthesis of these structures have been identified from N. meningitidis immunotypes L3 and L1 (Jennings et al., Mol. Microbiol. 18: 729-740 (1995)) and the N. gonorrhoeae mutant F62 (Gotshlich, J. Exp. Med. 180: 2181-2190 (1994)). In N. meningitidis, a locus consisting of three genes, lgtA, lgtB and lg E, encodes the glycosyltransferase enzymes required for addition of the last three of the sugars in the lacto-N-neotetraose chain (Wakarchuk et al., J. Biol. Chem. 271: 19166-73 (1996)). Recently the enzymatic activity of the lgtB and lgtA gene product was demonstrated, providing the first direct evidence for their proposed glycosyltransferase function (Wakarchuk et al., J. Biol. Chem. 271(45): 28271-276 (1996)). In N. gonorrhoeae, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In N. meningitidis, a separate immunotype L1 also expresses the $P^k$ blood group antigen and has been shown to carry an lgtC gene (Jennings et al., (1995), supra.). Neisseria glycosyltransferases and associated genes are also described in U.S. Pat. No. 5,545,553 (Gotschlich). Genes for α1,2-fucosyltransferase and α1,3-fucosyltransferase from Helicobacter pylori has also been characterized (Martin et al., J. Biol. Chem. 272: 21349-21356 (1997)). Also of use in the present invention are the glycosyltransferases of Campylobacter jejuni (see, for example, http://afmb.cnrs-mrs.fr/~pedro/CAZY/gtf_42.html).

a) Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., Carbohydrate Res. 190:1-11 (1989); Prieels, et al., J. Biol. Chem. 256: 10456-10463 (1981); and Nunez, et al., Can. J. Chem. 59: 2086-2095 (1981)) and the Galβ(14)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α(1→3,4)fucosyltransferase has also been characterized (see, Dumas, et al., Bioorg. Med. Letters 1: 425-428 (1991) and Kukowska-Latallo, et al., Genes and Development 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., Eur. J. Biochem. 191: 169-176 (1990) or U.S. Pat. No. 5,374,655. Cells that are used to produce a fucosyltransferase will also include an enzymatic system for synthesizing GDP-fucose.

b) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

Also suitable in the practice of the invention are r soluble forms of α1,3-galactosyltransferase such as that reported by Cho, S. K. and Cummings, R. D. (1997) J. Biol. Chem., 272, 13622-13628.

c) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal 11, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 5).

TABLE 5

Sialyltransferases which use the Galβ1,4GlcNAc sequence as an acceptor substrate

| Sialyltransferase | Source | Sequence(s) formed | Ref. |
|---|---|---|---|
| ST6Gal I | Mammalian | NeuAcα2,6Galβ1,4GlcNAc— | 1 |
| ST3Gal III | Mammalian | NeuAcα2,3Galβ1,4GlcNAc—<br>NeuAcα2,3Galβ1,3GlcNAc— | 1 |
| ST3Gal IV | Mammalian | NeuAcα2,3Galβ1,4GlcNAc—<br>NeuAcα2,3Galβ1,3GlcNAc— | 1 |
| ST6Gal II | Mammalian | NeuAcα2,6Galβ1,4GlcNAc |  |
| ST6Gal II | photobacterium | NeuAcα2,6Galβ1,4GlcNAc— | 2 |
| ST3Gal V | N. meningitides<br>N. gonorrhoeae | NeuAcα2,3Galβ1,4GlcNAc— | 3 |

1 Goochee et al., Bio/Technology 9: 1347-1355 (1991)
2 Yamamoto et al., J. Biochem. 120: 104-110 (1996)
3 Gilbert et al., J. Biol Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In another embodiment, the claimed sialylation methods use a rat ST3Gal III.

Other exemplary sialyltransferases of use in the present invention include those isolated from *Campylobacter jejuni*, including the α(2,3). See, e.g., WO99/49051.

Sialyltransferases other those listed in Table 5, are also useful in an economic and efficient large-scale process for sialylation of commercially important glycopeptides. As a simple test to find out the utility of these other enzymes, various amounts of each enzyme (1-100 mU/mg protein) are reacted with asialo-$α_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$α_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3 Gal III in this disclosure). Other exemplary sialyltransferases are shown in FIG. 10.

d) GalNAc Transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J. Biol. Chem.* 269: 15162 (1994)) and polypeptide N-acetylgalactosaminyltransferase (Homa et al., *J. Biol. Chem.* 268: 12609 (1993)).

Production of proteins such as the enzyme GalNAc T$_{1-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

2. Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

3. Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for a 1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

4. Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

5. Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Purification of Peptide Conjugates

The products produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used.

Thus, in a typical application, saccharides prepared by the methods of the present invention will be retained in the membrane and contaminating salts will pass through.

If the modified glycoprotein is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO—S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps, e.g., SP Sepharose. Additionally, the modified glycoprotein may be purified by affinity chromatography. HPLC may also be employed for one or more purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which sproduce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

Pharmaceutical Compositions

Polypeptides modified at various O-linked glycosylation site according to the method of the present invention have a broad range of pharmaceutical applications. For example, modified erythropoietin (EPO) may be used for treating general anemia, aplastic anemia, chemo-induced injury (such as injury to bone marrow), chronic renal failure, nephritis, and thalassernia. Modified EPO may be further used for treating neurological disorders such as brain/spine injury, multiple sclerosis, and Alzheimer's disease.

A second example is interferon-α (IFN-α), which may be used for treating AIDS and hepatitis B or C, viral infections caused by a variety of viruses such as human papilloma virus (HBV), coronavirus, human immunodeficiency virus (HIV), herpes simplex virus (HSV), and varicella-zoster virus (VZV), cancers such as hairy cell leukemia, AIDS-related Kaposi's sarcoma, malignant melanoma, follicular non-Hodgkins lymphoma, Philladephia chromosome (Ph)-positive, chronic phase myelogenous leukemia (CML), renal cancer, myeloma, chronic myelogenous leukemia, cancers of the head and neck, bone cancers, as well as cervical dysplasia and disorders of the central nervous system (CNS) such as multiple sclerosis. In addition, IFN-α modified according to the methods of the present invention is useful for treating an assortment of other diseases and conditions such as Sjogren's syndrome (an autoimmune disease), Behcet's disease (an autoimmune inflammatory disease), fibromyalgia (a musculoskeletal pain/fatigue disorder), aphthous ulcer (canker sores), chronic fatigue syndrome, and pulmonary fibrosis.

Another example is interferon-β, which is useful for treating CNS disorders such as multiple sclerosis (either relapsing/remitting or chronic progressive), AIDS and hepatitis B or C, viral infections caused by a variety of viruses such as human papilloma virus (HBV), human immunodeficiency virus (HIV), herpes simplex virus (HSV), and varicella-zoster virus (VZV), otological infections, musculoskeletal infections, as well as cancers including breast cancer, brain cancer, colorectal cancer, non-small cell lung cancer, head and neck cancer, basal cell cancer, cervical dysplasia, melanoma, skin cancer, and liver cancer. IFN-β modified according to the methods of the present invention is also used in treating other diseases and conditions such as transplant rejection (e.g., bone marrow transplant), Huntington's chorea, colitis, brain inflammation, pulmonary fibrosis, macular degeneration, hepatic cirrhosis, and keratoconjunctivitis.

Granulocyte colony stimulating factor (G-CSF) is a further example. G-CSF modified according to the methods of the present invention may be used as an adjunct in chemotherapy for treating cancers, and to prevent or alleviate conditions or complications associated with certain medical procedures, e.g., chemo-induced bone marrow injury; leucopenia (general); chemo-induced febrile neutropenia; neutropenia associated with bone marrow transplants; and severe, chronic neutropenia. Modified G-CSF may also be used for transplantation; peripheral blood cell mobilization; mobilization of peripheral; blood progenitor cells for collection in patients who will receive myeloablative or myelosuppressive chemotherapy; and reduction in duration of neutropenia, fever, antibiotic use, hospitalization following induction/consolidation treatment for acute myeloid leukemia (AML). Other conditions or disorders may be treated with modified G-CSF include asthma and allergic rhinitis.

As one additional example, human growth hormone (hGH) modified according to the methods of the present invention may be used to treat growth-related conditions such as dwarfism, short-stature in children and adults, cachexia/muscle wasting, general muscular atrophy, and sex chromosome abnormality (e.g., Turner's Syndrome). Other conditions may be treated using modified hGH include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomnia. Moreover, modified hGH may also be used to promote various processes, e.g., general tissue regeneration, bone regeneration, and wound healing, or as a vaccine adjunct.

Thus, in another aspect, the invention provides a pharmaceutical composition. The pharmaceutical composition includes a pharmaceutically acceptable diluent and a covalent conjugate between a non-naturally-occurring, water-soluble polymer, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, Science 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as manruitol, lactose, starch, magnesium stearate, sodium saccharine, talcum, cellulose, glucose, sucrose, and magnesium carbonate, may be employed. Biodegradable matrises, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235, 871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

The following examples are provided to illustrate the conjugates, and methods and of the present invention, but not to limit the claimed invention.

EXAMPLES

Example 1

1.1a Preparation of Interferon alpha-2β-GalNAc (pH 6.2)

Interferon alpha-2β was reconstituted by adding 200 μL water to 4 mg of IFN alpha-2β. When the solid was dissolved, 1.92 mL reaction buffer (20 mM MES, pH 6.2, 150 mM NaCl, 5 mM $MgCl_2$, 5 mM $MnCl_2$, 0.05% polysorbate, and 0.05% $NaN_3$), was added. UDP-GalNAc (4.16 mg; 3 mM) and GalNAc T2 (80 mU; 80 μL) were then added and the reaction mixture was incubated at 32° C. with slow rotary movement. The reaction was monitored using MALDI analysis and was essentially complete after 72 h Once complete, the reaction mixture was submitted for peptide mapping, and analysis of site occupancy.

1.1b Preparation of Interferon alpha-2β-GalNAc (pH 7.4)

The interferon alpha 2β was reconstituted as described by the manufacturer. Water, 50 μL, was added to 50 μg of IFN alpha-2β. When the solid was dissolved, the reaction buffer (20 mM MES, pH 7.4, 150 mM NaCl, 5 mM MgCl$_2$, 5 mM MnCl$_2$, 0.05% polysorbate, and 0.05% NaN$_3$), 50 μL was added. The UDP-GalNAc (100 μg; 3 mM) and GalNAc T2 (8 mU; 8 μL) were then added and the reaction mixture incubated at 32° C. under a slow rotary movement. The reaction was monitored using MALDI analysis and was found to be complete within about 48 to 72 h

1.2 Preparation of Interferon-alpha-2βGalNAc-SA-PEG-20 kilodalton Using CMP-SA-PEG and ST6GalNAcI The IFN-alpha-2β-GalNAc (1.0 mL, 2 mg, 0.1 mole) from 1.1 (above) was buffer exchanged (2×) using a 5 kilodalton MWCO Filter Centricon cartridge and a second buffer (20 mM MES, pH 7.4, 150 mM NaCl, 5 mM MgCl$_2$, 5 mM MnCl$_2$, 0.05% polysorbate, and 0.05% NaN$_3$). The IFN-alpha-2β-GalNAc was reconstituted from the spin cartridge using the second buffer, 1.0 mL, and both CMP-SA-PEG-20 kilodalton (10 mg, 0.5 micromoles) and ST6GalNAc1 (200 μL) were added to the reaction mixture. The reaction was incubated at 32° C. for 96 h with slow rotary movement. The product, IFN-alpha-2β-GalNAc-SA-PEG-20 kilodalton was purified using SP Sepharose and SEC (Superdex 75) chromatography. The addition of sialic acid-PEG was verified using MALDI analysis.

1.3. Preparation of Interferon-alpha-2β-GalNAc-Gal-SA-PEG-20 kilodalton Using CMP-SA-PEG, core-1-,β1,3-galactosyl-transferase, and ST3Gal2

The IFN-alpha-2β-GalNAc (1.0 mL, ~2 mg, 0.1 μmole) from the addition of GalNAc described above (pH 6.2) was buffer exchanged (2×) using a 5 kilodalton MWCO Filter Centricon cartridge and a second buffer (20 mM MES, pH 7.4, 150 mM NaCl, 5 mM MgCl$_2$, 5 mM MnCl$_2$, 0.05% polysorbate, and 0.05% NaN$_3$). The IFN-alpha-2β-GalNAc was reconstituted from the spin cartridge using 1.0 mL of the second buffer, containing CMP-SA-PEG-20 kilodalton (10 mg, 0.5 micromoles), UDP-Galactose (1.8 mg, 3 mM), core-1-β1,3-galactosyl-transferase (200 mU on resin) and ST3Gal2 (200 mU, α2,3-(O)-sialyltransferase). The reaction mixture was incubated at 32° C. for 96 h with slow rotary movement. The product, IFN-alpha-2β-GalNAc-Gal-SA-PEG-20 kilodalton, was purified by SP Sepharose and SEC (Superdex 75) chromatography. The addition of sialic acid-PEG was verified using MALDI analysis.

1.9 Protein Concentration Assay

Protein concentration was determined using a spectrophotometer at a fixed absorbance of 280 nm with 1 cm path length of cell. Triplicate readings were measured for a tested sample with water and buffer as controls. Protein concentration was determined using extinction coefficient at 0.799 mL/mg protein.

1.10 Formulation of Final Product

The formulation buffer contained pyrogen-free PBS, pH 6.5, 2.5% mannitol, and 0.05% Polysorbate 80 that was degassed by vacuum and sterile filtered (0.2 μm).
Endotoxin was removed using a Detoxi-Gel™ equilibrated with 5 column beds of the formulation buffer (PBS, pH 6.5, 2.5% mannitol, and 0.05% Polysorbate 80). The flow rate was controlled by gravity at ~0.3 mL/min. Product samples were applied onto the gel, and the product eluted using the formulation buffer. The volume of the collected product was adjusted with additional formulation buffer to provide a protein concentration of about 100 μg/mL.
The peptide formulations were sterile filtered (0.2μ) and the effluent was dispensed as 1 mL aliquots into 2.0 mL pyrogen-free vials. In addition, aliquots were taken for endotoxin and protein analysis. All products were stored at 4° C.

1.13 Pharmacokinetic Study

The pharmacokinetic analysis was performed using radioiodinated protein. After administration of the labeled interferons by IV tail vein injections into the rats, the clearance rate was measured as the reduction in radioactivity in blood drawn at specific intervals over 72 h. Each time point is a measure of at least five rats.

1.14 Results

The reaction rate of GalNAc-T2 was measured at two pH's, a neutral pH (7.4) and a slightly acidic pH (6.2). Glycosylation with GalNAc proceeded successfully at both pH 6.2 and pH 7.4. As can be seen in the MALDI analysis of the reaction progress, the reaction rate was faster at pH 7.4 than at pH 6.2.
GalNAc-T2 and GalNAc were added to interferon alpha-2β quantitatively at either pH 6.2 or pH 7.4. The reaction was followed by MALDI. During the enzymatic reaction, a new interferon alpha mass ion formed (IFN-alpha-2b 19,281 Da and IFN-alpha-2β-GalNAc, 19,485 Da).
The product of the reaction at pH 6.2, IFN-alpha-2b-GalNAc, was submitted to analysis to determine the position of substitution of the GalNAc on the protein. Peptide mapping and site occupancy mapping were used for this purpose. Peptide mapping using TIC of LC-MS/MS and a GluC digest of IFN-alpha-2b produced a peptide fragment of mass 1018.69. MS/MS peptide amino acid sequencing of the peptide mass ion of 1018.69 containing the GalNAc indicated that sugar was attached to $T^{106}$.
The sialyl-PEGylation of IFN-alpha-2b-GalNAc was examined using ST6GalNAc-1 and CMP-SA-PEG-20 kilodalton. The reaction of IFN-alpha-2b-GalNAc produced the PEG-ylated protein, which was visible by SDS PAGE. In general, the reaction proceeded at 32° C. for 96 h. The reaction was monitored by SDS PAGE. SDS PAGE indicated that about 70% of the IFN-alpha-2b-GalNAc was converted to IFN-alpha-2b-GalNAc-SA-PEG-20 kilodalton. The MALDI analysis of the new band indicated a mass ion of 41,500 Daltons, the mass of IFN-alpha-2b-GalNAc-SA-PEG-20 kilodalton.
The glycoform of PEG-ylated interferon alpha-2b containing the GalNAc-Gal-SA-PEG structure was also produced. The reaction was performed using the conditions described above. The desired product was detected by SDS PAGE. A one pot, two-step reaction was used to produce the desired product, beginning with IFN-alpha-2β-GalNAc with core-1-β3-galactosyltransferase-1, ST3Gal2, UDP-galactose and CMP-SA-PEG-20 kilodalton. The reaction was incubated at 32° C. for 96 h. The reaction was monitored by SDS PAGE. After 24 h, the reaction was about 70% complete. The MALDI of the product indicated a mass ion of 41,900 Da, which originates from the desired IFN-alpha-2β-GalNAc-Gal-SA-PEG-20 kilodalton product.
Both glycoforms of the PEG-ylated interferon alpha-2b products were purified using a two-step process. In the first step, ion-exchange chromatography was performed using SP Sepharose. This procedure removed unreacted PEG materials and provided some separation of other proteins. The ion exchange step was followed by separation on SEC. A Superdex 75 column was used to remove remaining smaller proteins including the glycosyltransferases and unPEG-ylated interferon alpha. Both PEG-ylated glycoforms of interferon alpha were purified to greater than 90% as shown by SDS PAGE).

The antiviral data indicates that PEG-ylated glycoforms A and B retain their antiviral effects).

The radioiodinated PEG-ylated proteins were injected into rats via their tail veins, the AUC for both proteins was 5-7 fold greater un-PEG-ylated interferon alpha-2β.

Glycoform A (IFN-alpha-2β-GalNAc-SA-PEG-20 kilodalton) and B (IFN-alpha-2β-GalNAc-Gal-SA-PEG-20 kilodalton) were both bioactive.

Example 2

2.1 Preparation of G-CSF-GalNAc (pH 6.2)

960 µg of G-CSF in 3.2 mL of buffer was concentrated by ultrafiltration using a UF filter (5 kilodalton) and reconstituted with 1 mL of 25 mM MES buffer (pH 6.2, 0.005% NaN$_3$). UDP-GalNAc (6 mg, 9.24 mM), GalNAc-T2 (40 µL, 0.04 U), and 100 mM MnCl$_2$ (40 µL, 4 mM) were then added and the resulting solution was incubated at room temperature for 48 hours. After 48 hours, MALDI indicated the reaction was complete (shift of the mass ion from 18800 to 19023 mass units). The reaction mixture was purified by HPLC using SEC (Superdex 75 and Superdex 200). The column was eluted using phosphate buffered saline, pH 4.9 and 0.005% Tween 80. The peak corresponding to G-CSF-GalNAc was collected and concentrated to about 150 µL using a Centricon 5 kilodalton filter and the volume was adjusted to 1 mL using PBS (phosphate buffered saline, pH 4.9 and 0.005% Tween 80); protein concentration was 1 mg/mL $A_{280}$).

2.2 Preparation of G-CSF-GalNAc-Gal (pH 6.0)

G-CSF-GalNAc (100 µg) was added to a 100 µL of a solution containing 25 mM MES buffer, pH 6.0, 1.5 mM UDP-GalNAc, 10 mM MgCl$_2$ and 80 mU GalNAc-T2. The CMP-SA-PEG-20 kilodalton (0.5 mg, 0.025 µmole), UDP-galactose 75 µg (0.125 µmole), core-1-Gal-T 20 µL (10 mU) were then added and the solution which was slowly rocked at 32° C. for 24 hours. MALDI indicated complete conversion of G-CSF-GalNAc into G-CCSF-GalNAc-Gal.

2.3 Preparation of G-CSF-GalNAc-SA-PEG-20 Kilodalton (C)

2.3a Sequential Process (pH 6.2).

A G-CSF-GalNAc solution containing 1 mg of protein was buffer exchanged into 25 mM MES buffer (pH 6.2, 0.005% NaN$_3$) then 5 mg, (0.25 µmole) CMP-SA-PEG (20 kilodalton) was added. Finally, 100 µL, of a 100 mM MnCl$_2$ solution and ST6GalNAc-I (100 µL) were added and the reaction mixture was rocked slowly at 32° C. Aliquots were taken at time points (24, 48 and 72 h) and analyzed by SDS-PAGE. After 24 h, no further reaction was observed. The reaction mixture was concentrated by spin filtration (5 kilodalton), buffer exchanged against 25 mM NaOAc (pH 4.9) and concentrated to 1 mL. The product was purified using ion exchange (SP-Sepharose, 25 mM NaOAc, pH 4.9) and SEC (Superdex 75; PBS-pH 7.2, 0.005% tween 80, 1 ml/min). The desired fraction was collected, concentrated to 0.5 mL and stored at 4° C.

2.3b One Pot Process Using ST6GalNAc-I (pH 6.0)

960 µg of G-CSF protein dissolved in 3.2 mL of product formulation buffer was concentrated by spin filtration (5 kilodalton) to 0.5 mL and reconstituted in 25 mM MES buffer (pH 6.0, 0.005% NaN$_3$) to a total volume of about 1 mL, or a protein concentration of 1 mg/mL. Following reconstitution UDP-GalNAc (6 mg, 9.21 µmol), GalNAc-T2 (80 µL, 80 mU), CMP-SA-PEG-20 kilodalton (6 mg, 0.3 µmol) and mouse enzyme ST6GalNAc-I (120 µL) were added. The solution was rocked at 32° C. for 48 hours. Following the reaction the product was purified using standard chromatography conditions on SP-Sepharose and SEC as described above. A total of 0.5 mg of protein ($A_{280}$) was obtained, for about a 50% overall yield. The product structure was confirmed by analysis with both MALDI and SDS-PAGE 2.4 Preparation of G-CSF-GalNAc-Gal-SA-PEG-20 Kilodalton (D)

2.4a Starting from G-CSF-GalNAc

UDP-galactose (4 mg, 6.5 µmole), core-1-Gal-T$_1$ (320 µL, 160 mU), CMP-SA-PEG-20 kilodalton (8 mg, 0.4 µmole), ST3Gal2 (80 µL, 0.07 mU) and 80 µL of 100 mM MnCl$_2$ were directly added to the crude 1.5 mL of reaction mixture of the G-CSF-GalNAc (1.5 mg) in 25 mM MES buffer (pH 6.0) from Example 2.1 (above). The resulting mixture was incubated at 32° C. for 60 hours, however, the reaction was complete after 24 h. The reaction mixture was centrifuged and the solution was concentrated to 0.2 mL using ultrafiltration (5 kilodalton) and then redissolved in 25 mM NaOAc (pH 4.5) to a final volume of 1 mL. The product was purified using SP-Sepharose, the peak fractions were concentrated using a spin filter (5 kilodalton) and the residue purified further using SEC (Superdex 75). After concentration using a spin filter (5 kilodalton), the protein was diluted to 1 mL using formulation buffer consisting of PBS, 2.5% mannitol, 0.005% polysorbate, pH 6.5, and formulated at a protein concentration of 850 µg protein per mL ($A_{280}$). The overall yield was 55%. The MALDI analysis is shown in FIG. 28.

2.4b Starting from G-CSF

960 µg, of G-CSF (3.2 mL) was concentrated by spin filter (5 kilodalton) and reconstituted with 25 mM MES buffer (pH 6.0, 0.005% NaN$_3$). The total volume of the G-CSF solution was adjusted to about 1 mg/mL and UDP-GalNAc (6 mg), GalNAc-T2 (80 µL), UDP-galactose (6 mg), core-1-Gal-T$_1$ (160 µL, 80 µU), CMP-SA-PEG (20 kilodalton) (6 mg), ST3Gal-2 (160 µL, 120 µU) and MnCl$_2$ (40 µL of a 100 mM solution) were added. The resulting mixture was incubated at 32° C. for 48 h.

2.5 SP Sepharose HPLC Chromatography

The SP Sepharose was performed as described in Example 1.4.

2.6 Size Exclusion Chromatography

SEC was performed as described in Example 1.5. The purified samples were stored at 4° C.

2.6a Hydrophobic Interaction Chromatography (HIC)

Following the first step of chromatographic chromatography HIC can be used as a second purification step to remove contaminants other than un-Pegylated G-CSF. Thus, a method is available for the purification of glycopegylated G-CSF that has been through an initial purificatio on a gel permeation column.

2.7 SDS PAGE Analysis

The SDS PAGE was performed as set forth in Example 1.6.

2.8 MALDI Analysis

MALDI analysis was performed as described in Example 1.7.

2.9 Peptide Mapping Analysis

Protein mapping analysis was performed as illustrated in Example 1.8

2.10 Protein Concentration Assay

Protein concentration was determined as described in Example 1.9.

2.11 Product Formulation

The product was formulated as set forth in Example 1.10

2.12 Endotoxin Determination

Endotoxin was determined as set forth in Example 1.11.

2.13 Cell proliferation assay

A G-CSF proliferation assay with a NFS-60 cell line and a Tf-1 cell line were performed according to standard procedures. The cells were plated into a 96 well plate at 25000 cell/ml in the presence of different concentrations of G-CSF (51 nM, 25.5 nM, 12.75 nM, 3.2 nM, 1.6 nM, 0.8 nM, 0 nM), a chemically PEG-ylated G-CSF analogue, and PEGylated G-CSF C from Example 2.3 (above), and PEGylated G-CSF D from Example 2.4 (above). The cells were incubated at 37° C. for 48 hours. A colorimetric MTT assay was used to determine the cell viability.

2.14 In Vivo Activity

White Blood Cell (WBC) Production in the Rat

Figure 4:
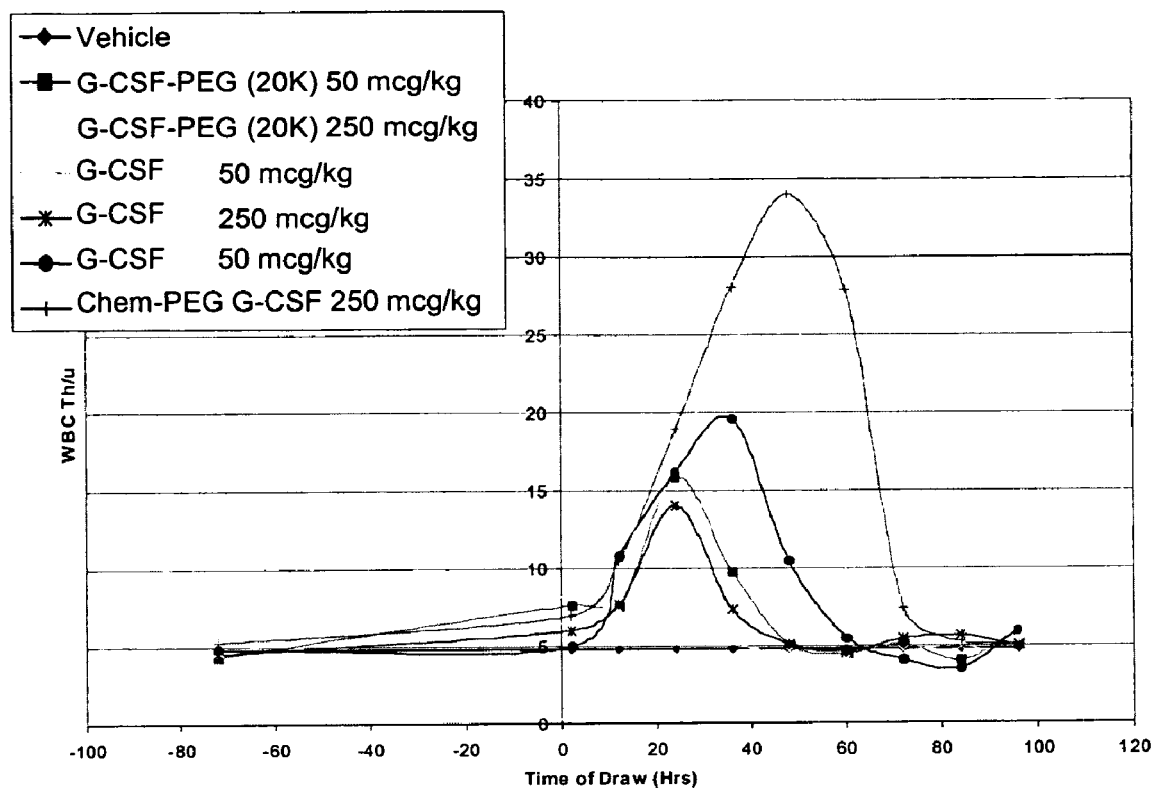
FIG. 4 is a plot showing the induction of white blood cells in mice using unmodified G-CSF and chemically- and glyco-PEG-ylated G-CSF.

Two doses of drug (50 μg/kg, 250 μg/kg) were examined for each of C, G-CSF and a chemically PEG-ylated G-CSF using mice. Blood was drawn at time points of 2 hour, 12 hour, 24 hour, 36 hour, 48 hour, 60 hour, 72 hour, 84 hour and 96 hour, and the WBC and neutrophil counts were measured (FIG. 4).

2.15 Accelerated Stability Study

An accelerated stability study of PEGylated G-CSF, C, from Example 2.3, and PEGylated G-CSF, D, from Example 2.4 was performed using a buffer at pH 8.0 heated to 40° C. 72 μg of PEGylated G-CSF C, was diluted to 8 mL with formulation buffer (PBS, 2.5% mannitol, 0.005% polysorbate 80). 1 mg of PEGylated G-CSF D, was diluted with 16 mL of formulation buffer. Both solutions were adjusted to pH 8.0 with NaOH and the resulting solution was sterile filtered into pyrogen-free tubes. The samples were slowly rotated at 40° C. and aliquots (0.8 mL) were taken at timepoints of 0 hour, 72 hours and 168 hours. Analysis was performed using SEC (Superdex 200) as described above (FIG. 6 and FIG. 7).

2.16 Protein Radiolabeling

G-CSF was radiolabeled using the Bolton Hunter reagent. This reaction was performed at pH 7.4 for 15 minutes and was followed by a SEC (Superdex 200) purification. Once purified, the formulation buffer pH was adjusted to 5.0 and the protein concentration was determined by $A_{280}$.

2.17 ELISA Assay

Figure 9:
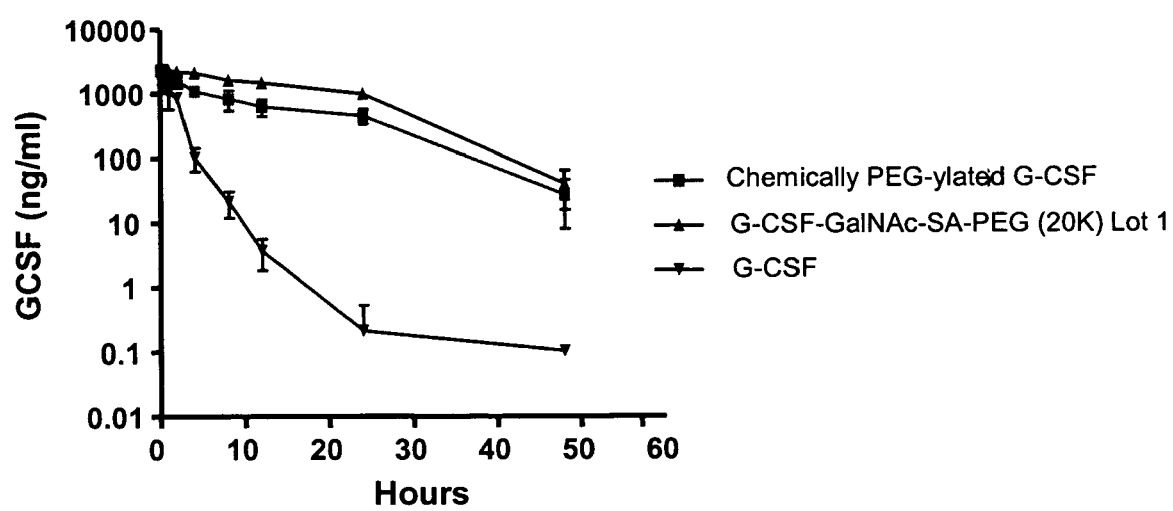
FIG. 9 is a plot of the results of a rat IV pK Study using unlabeled G-CSF, chemically- and glyco-PEG-ylated G-CSF detected by ELISA.

An Elisa assay was utilized to quantify the G-CSF derivatives in rat plasma. The pharmacokinetic results are shown in FIG. 9.

2.18 Pharmacokinetic Study

Two pharmacokinetic studies were performed. For the first pharmacokinetic study proteins were radiolabeled and administered by IV tail vein injections into rats. Clearance rate was measured as the reduction in radioactivity in blood drawn at specific intervals over 48 hours. Each time point was a measure of at least five rats.

Figure 2:
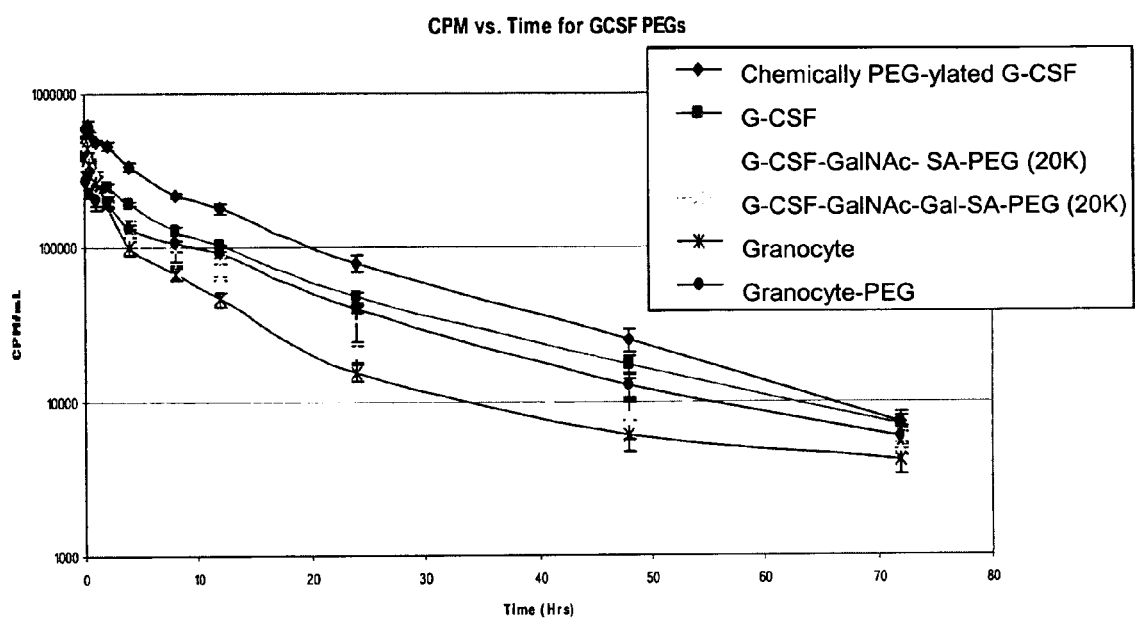
FIG. 2 is a plot of counts per minute (CPM) vs. time for a rat pharmacokinetic study using radioiodinated G-CSF and glycol-PEG-lated derivatives thereof.

Specifically, 10 μg of G-CSF derivative was injected per animal (~1 μg of labeled protein and 9 μg of unlabeled protein). In addition to the blood being drawn and counted as described above, plasma was also collected and the protein acid was precipitated. The protein pellets were then also counted for radioactivity. The data from these studies is shown is FIG. 2, FIG. 3 and FIG. 8.

In the second pharmacokinetic study the unlabeled G-CSF derivatives (30 μg per animal) were administered by IV tail vein injections into rats. Blood samples were drawn at the time points indicated and the samples analzed by the G-CSF ELISA assay. The data is shown in FIG. 9.

2.19 Results

Human GalNAc T2 transferred GalNAc to G-CSF expressed in E. coli\ using UDP-GalNAc as the donor. Depending on the pH of the reaction buffer, one or two GalNAc moieties were added to G-CSF as determined by MALDI. Addition of the second GalNAc proceeded slowly amounting to about 10-15% of the total product. One GalNAc could be selectively added to G-CSF, in conversion yields of over 90%, by adjusting the pH of the reaction solution to 6.0-6.2. Addition of the second GalNAc occurred when the reaction was performed at a pH between about 7.2 and 7.4. Both $Co^{+2}$ and $Mn^{+2}$ are useful divalent metal ions in the reaction. Peptide mapping of the reaction products indicated that the predominant product of the reaction was addition of GalNAc to threonine-133, the natural site of O-linked glycosylation in mammalian systems \. The second GalNAc was observed in the amino terminal peptide fragment of G-CSF and is postulated to occur at threonine-2.

The reaction of G-CSF-GalNAc with ST6GalNAc-1 (chicken or mouse) and CMP-SA-PEG-20 kilodalton provided the product G-CSF-GalNAc-SA-PEG-20 kilodalton, which was verified by MALDI\, with conversion yields of about 50% as determined by SDS-PAGE \. The G-CSF-GalNAc could also be further elongated using core-1-Gal-T and UDP-galactose to provide complete conversion to G-CSF-GalNAc-Gal. Glyco-PEG-ylation of this intermediate with ST3Gal2 and CMP-SA-PEG-20 kilodalton then provided the product G-CSF-GalNAc-Gal-SA-PEG-20 kilodalton in overall yields of about 50% \. These reactions were performed either sequentially in one pot or simultaneously in one pot starting from G-CSF or its glycosylated intermediates. In these studies, little or no difference was observed in overall yield by using either approach.

The products of the glycosylation or glyco-PEG-ylation reactions were purified using a combination of ion exchange and SEC. The ion exchange step removes the unreacted G-CSF or its glycosylated intermediates (GalNAc or Gal-NAc-Gal) as well as any unreacted CMP-SA-PEG-20 kilodalton\. The SEC step removed remaining unreacted G-CSF and other protein contaminants from the glycosyltransferases used in the process\. The G-CSF's containing the GalNAc-SA-PEG-20 kilodalton or the GalNAc-Gal-SA-PEG-20 kilodalton had identical properties and retention times using these purification methods. The final products had typical profiles as shown in.

Once purified, the PEG-ylated proteins were formulated in a PBS buffer containing 2.5% mannitol and 0.005% Tween 80. Initially, pH 6.5 was used in the formulation but aggregation of the glyco-PEG-ylated protein was a concern (see below) so the formulation buffer pH was lowered to 5.0. Literature reports have indicated that G-CSF aggregation is prevented by maintaining a solution pH between 4-5. Endotoxin was removed using an endotoxin removal cartridge using sterile technique. Protein concentrations were typically adjusted to concentrations between 100 µg/mL to 1 mg/mL as required for biological studies. Endotoxin calculations were typically below 3EU/ml by this process. The formulated products are stored at 4.

The products were tested in an in vitro cell proliferation assay using NSF-60 cells sensitive to G-CSF. It was observed that both the GalNAc-SA-PEG-20 kilodalton and GalNAc-Gal-SA-20 kilodalton products were effective at initiating cell proliferation (FIG. 1).

Figure 6:
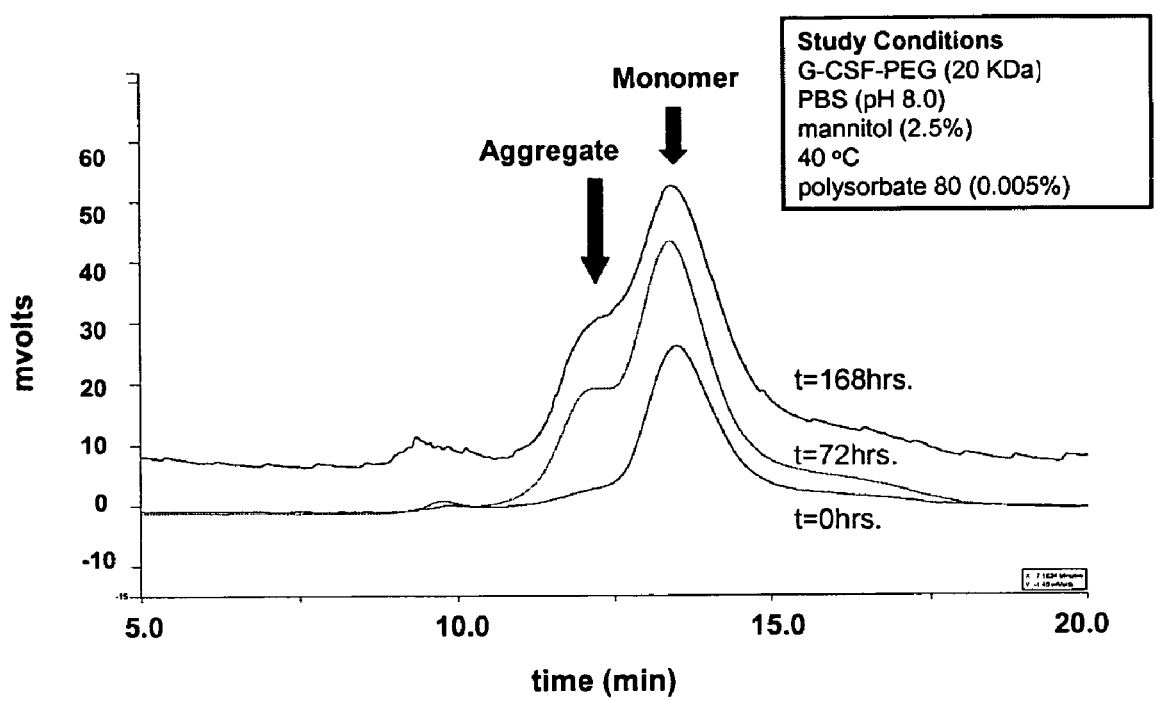
FIG. 6 is a plot of the results of an accelerated stability study of glyco-PEG-ylated G-CSF.
Figure 7:
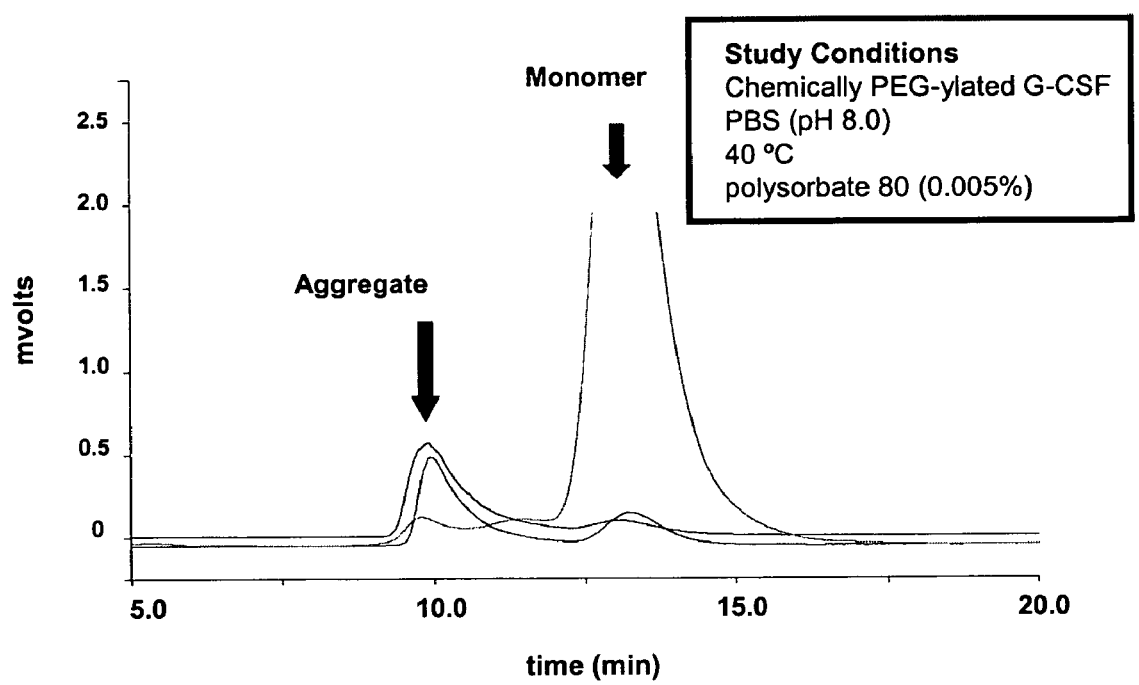
FIG. 7 is an expanded view of FIG. 6.

An accelerated stability study was performed on a chemically PEG-ylate G-CSF and C (G-CSF-GalNAc-SA-PEG-20 kilodalton). The formulation buffer pH was adjusted to 8.0 and the temperature was raised to 40° C. Samples were taken of each protein at times 0, 72 and 168 h (FIG. 6 and FIG. 7). Chemically PEG-ylated G-CSF was observed to aggregate entirely under these conditions within 168 h. SEC using a Superdex 200 chromatography was used to separate the aggregates. Although the glycoconjugate G-CSF-GalNAc-SA-PEG-20 kilodalton also formed aggregates that were separable using SEC, the aggregation occurred at a much slower rate.

Figure 5:
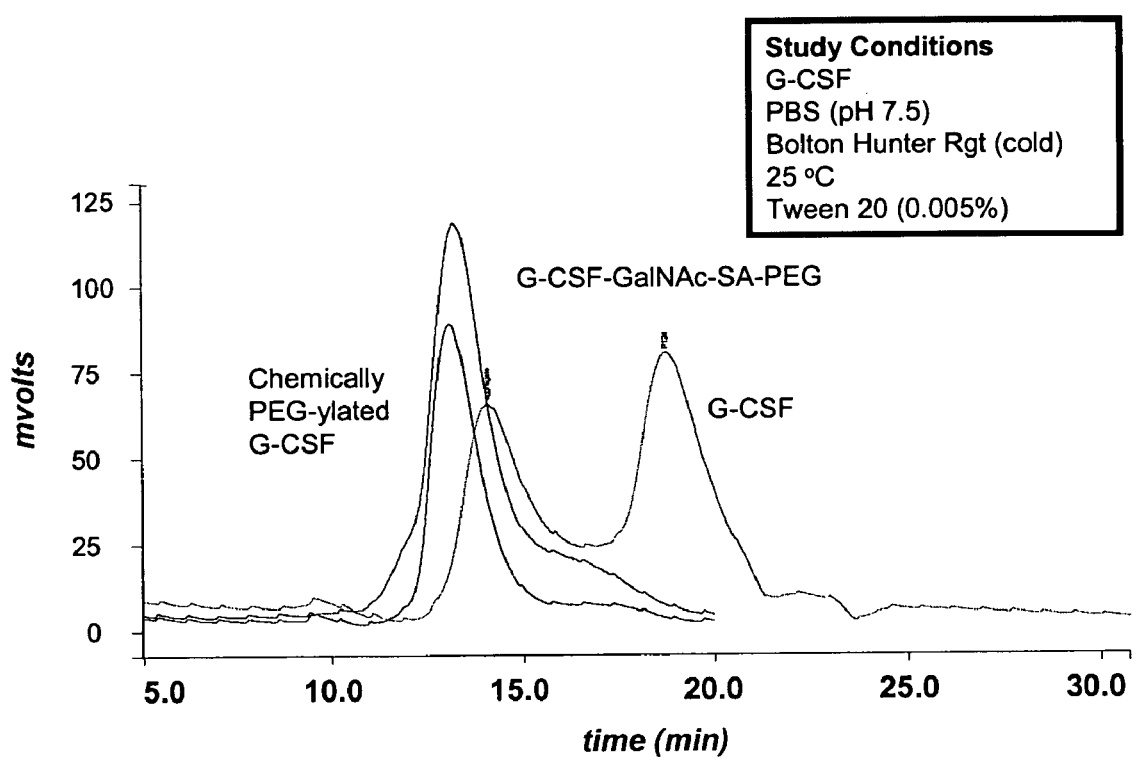
FIG. 5 is a plot of the results of an aggregation assay following radioiodination with the Bolton-Hunter reagent.

The glyco-PEG-ylated G-CSF was radioiodinated using the Bolton Hunter reagent. A cold labeling study was also performed prior to the actual radiolabeling to determine the extent of aggregation and to establish a methodology for removing any aggregates formed. Use of the Bolton Hunter reagent (cold) did provide some aggregates as shown in FIG. 5. SEC using a Superdex 200 column removed the aggregates and provided the monomeric, labeled material. Similar results were obtained using $^{125}$I labeled reagent. The use of the formulation minimized aggregation on storage. Protein content was measured by measuring the absorbance at $A_{280}$.

Figure 3:
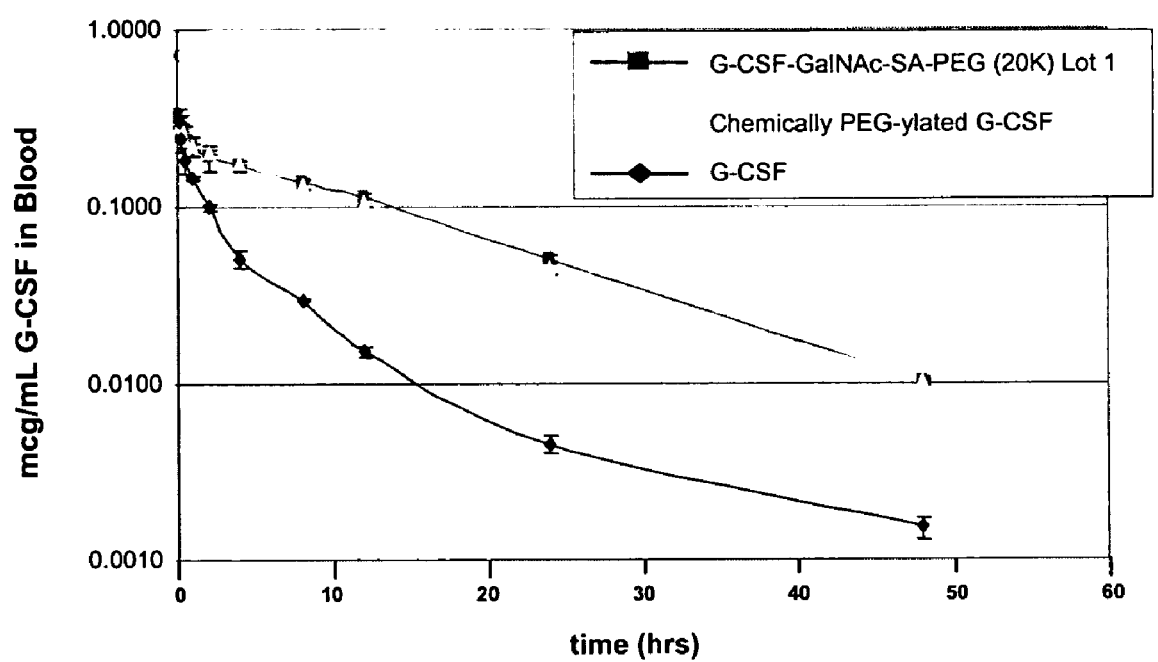
FIG. 3 is a plot of μg/mL G-CSF in blood vs. time (h) for a rat pharmacokinetic study using radioiodinated G-CSF and glycol-PEG-lated derivatives thereof.
Figure 8:
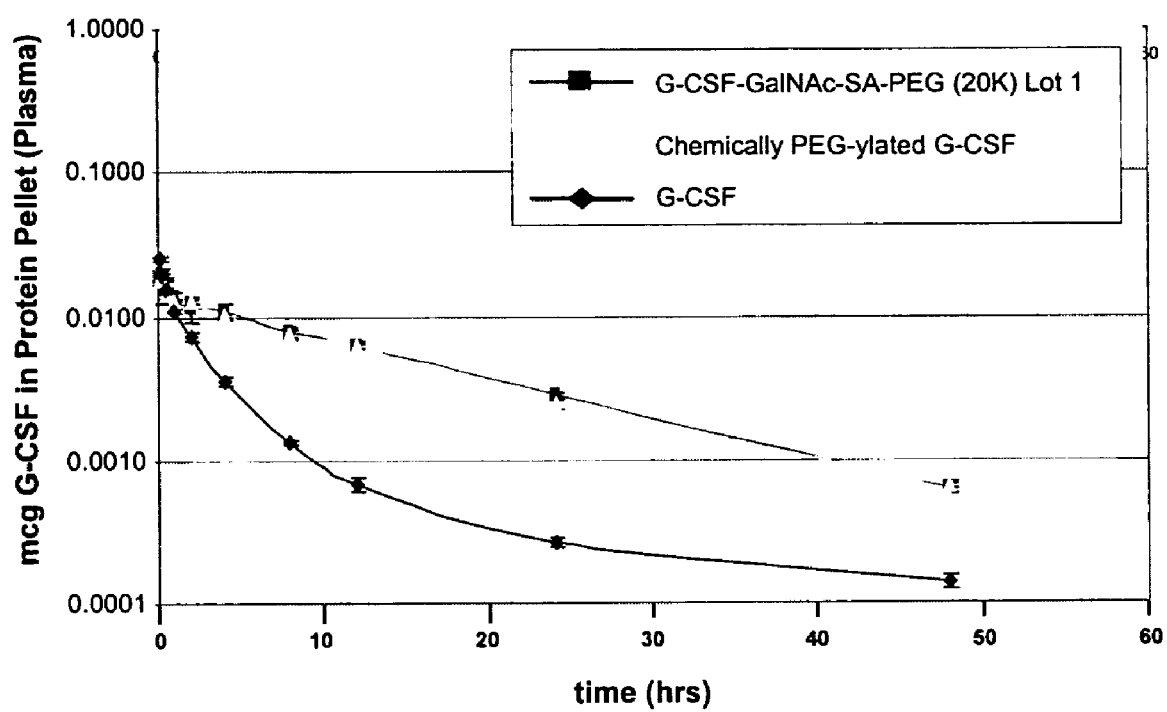
FIG. 8 is a plot of the results of a rat IV pK Study using the Bolton Hunter radiolabeling process (precipitated plasma protein).

The results of the rat pK study incorporating G-CSF, chemically PEG-ylated G-CSF and the PEG-G-CSF conjugate labeled with the Bolton Hunter reagent are shown in FIG. 3. In this study, blood and protein precipitated from plasma were counted for radioactivity after IV administration of 10 µg of G-CSF conjugate per rat. The data from both blood and plasma protein clearly indicate that the PEG conjugate and Chemically PEG-ylated G-CSF have identical clearance rates (FIG. 3 and FIG. 8).

The ability of the G-CSF derivatives to initiate WBC production was then examined in a mouse model. Each test compound was injected IV as a single bolus and the induction of WBC and neutrophils was monitored over time. Chemically PEG-ylated G-CSF was the most potent protein tested when administered at 250 µg/kg. The PEG conjugate (G-CSF-GalNAc-SA-PEG-20 kilodalton) induced WBC production to almost the same degree as Chemically PEG-ylated G-CSF at 250 µg/kg, and far greater than G-CSF at a similar concentration.

Example 3

This example discloses amino acid sequence mutations that introduce changes introduce O-linked glycosylation sites, i.e., serine or threonine residues, into a preferably proline-containing site in the 175 amino acid wild-type sequence of G-CSF or any modified version thereof. As a reference the 175 amino acid wild-type G-CSF sequence is shown below:

```
                                      (SEQ ID NO: 143)
MTPLGPASSLP QSFLLKCLEQ VRKIQGDGAA LQEKLCA

TYKLCHPEEL VLLGHSLGIP WAPLSSCPSQ ALQLAGCLSQ

LHSGLFLYQG LLQALEGISP ELGPTLDTLQ LDVADFATTI

WQQMEELGMA PALQPTQGAM PAFASAFQRR AGGVLVASHL

QSFLEVSYRV LRHLAQP
```

3.1 N-Terminal Mutations

In the N-terminal mutants, the N-terminus of a wild-type G-CSF, M$^1$TPLGPA (SEQ ID NO: 181), is replaced with either M$^1$X$_n$TPLGPA (SEQ ID NO: 226) or M$^1$B$_o$Z$_m$X$_n$TPLGPA (SEQ ID NO: 227). Wherein n, o and m are integers selected from 0 to 3, and at least one of X, B and O is Thr or Ser. When more than one of X, B and O is Thr or Ser, the identity of these moieties is independently selected. Where they appear, superscripts denote the position of the amino acid in the wild-type starting sequence.

Preferred examples include:

| | |
|---|---|
| M$^1$VTPL$^4$GPA | (SEQ ID NO: 182) |
| M$^1$QTPL$^4$GPA | (SEQ ID NO: 183) |
| M$^1$ATPL$^4$GPA | (SEQ ID NO: 184) |
| M$^1$PTQGAMPL$^4$GPA | (SEQ ID NO: 185) |
| M$^1$VQTPL$^4$GPA | (SEQ ID NO: 186) |
| M$^1$QSTPL$^4$GPA | (SEQ ID NO: 187) |
| M$^1$GQTPL$^4$GPA | (SEQ ID NO: 188) |
| M$^1$APTSSSPL$^4$GPA | (SEQ ID NO: 189) |
| M$^1$APTPL$^4$GPA | (SEQ ID NO: 10) |

3.2 Internal Mutation Site 1

In these mutants, the N-terminus of a wild-type GCSF, M$^1$TPLGP (SEQ ID NO: 190), is replaced with M¹TPX$_n$B$_o$O$_r$P (SEQ ID NO: 216). Wherein n, o and r are integers selected from 0 to 3, and at least one of X, B and O is Thr or Ser. When more than one of X, B and O is Thr or Ser, the identity of these moieties is independently selected. Where they appear, superscripts denote the position of the amino acid in the wild-type starting sequence.

Preferred mutations include:

| | |
|---|---|
| M ¹TPTLGP | (SEQ ID NO: 11) |
| M ¹TPTQLGP | (SEQ ID NO: 12) |
| M ¹TPTSLGP | (SEQ ID NO: 13) |
| M ¹TPTQGP | (SEQ ID NO: 14) |
| M ¹TPTSSP | (SEQ ID NO: 15) |
| M¹TPQTP | (SEQ ID NO: 16) |
| M¹TPTGP | (SEQ ID NO: 17) |
| M¹TPLTP | (SEQ ID NO: 18) |
| M¹TPNTGP | (SEQ ID NO: 19) |
| M¹TPVTP | (SEQ ID NO: 20) |
| M¹TPMVTP | (SEQ ID NO: 21) |
| MT¹P²TQGL³G⁴P⁵A⁶S⁷ | (SEQ ID NO: 22) |

3.3 Internal Mutation Site 2

This mutation is made for the purpose of maintaining G-CSF activity. In these mutants, the amino acid sequence containing H⁵³, LGH⁵³SLGI (SEQ ID NO: 191) is mutated to LGX⁵³B$_o$LGI (SEQ ID NO: 217), where X is H, S, R, E or Y, and B is either Thr or Ser.

Preferred examples include:

| | |
|---|---|
| LGHTLGI | (SEQ ID NO: 23) |
| LGSSLGI | (SEQ ID NO: 24) |
| LGYSLGI | (SEQ ID NO: 25) |
| LGESLGI | (SEQ ID NO: 26) |
| LGSTLGI | (SEQ ID NO: 27) |

3.4 Internal Mutation Site 3

In this type of mutant, the amino acid sequence encompassing P¹²⁹, P¹²⁹ALQPT (SEQ ID NO: 192), is mutated to P¹²⁹Z$_m$J$_q$O$_r$X$_n$PT (SEQ ID NO: 218), wherein Z, J, O and X are independently selected from Thr or Ser, and m, q, r, and n are integers sleeted selected from 0 to 3.

Preferred examples include:

| | |
|---|---|
| P¹²⁹TLGPT | (SEQ ID NO: 29) |
| P¹²⁹TQGPT | (SEQ ID NO: 30) |
| P¹²⁹TSSPT | (SEQ ID NO: 31) |
| P¹²⁹TQGAPT | (SEQ ID NO: 32) |
| P¹²⁹NTGPT | (SEQ ID NO: 33) |
| P¹²⁹ALTPT | (SEQ ID NO: 35) |
| P¹²⁹MVTPT | (SEQ ID NO: 36) |
| P¹²⁹ASSTPT | (SEQ ID NO: 37) |
| P¹²⁹TTQP | (SEQ ID NO: 38) |
| P¹²⁹NTLP | (SEQ ID NO: 39) |
| P¹²⁹TLQP | (SEQ ID NO: 40) |
| MAP¹²⁹ATQPTQGAM | (SEQ ID NO: 41) |
| MP¹²⁹ATTQPTQGAM | (SEQ ID NO: 42) |

3.5 Internal Site 4

In this type of mutant, the amino acid sequence surrounding P⁶¹, LGIPWAP⁶¹LSSC (SEQ ID NO: 213), is replaced with PZ$_m$U$_s$J$_q$P⁶¹O$_r$X$_n$B$_o$C (SEQ ID NO: 219), wherein m, s, q, r, n, and o are integers selected from 0 to 3, and at least one of Z, J, O, X, B and U is selected as either Thr or Ser. When more than one of Z, J, O X, B and U is Thr or Ser, each is independently selected.

Preferred examples include:

| | |
|---|---|
| P⁶¹TSSC | (SEQ ID NO: 43) |
| P⁶¹TSSAC | (SEQ ID NO: 44) |
| LGIPTA P⁶¹LSSC | (SEQ ID NO: 45) |
| LGIPTQ P⁶¹LSSC | (SEQ ID NO: 46) |
| LGIPTQG P⁶¹LSSC | (SEQ ID NO: 47) |
| LGIPQT P⁶¹LSSC | (SEQ ID NO: 48) |
| LGIPTS P⁶¹LSSC | (SEQ ID NO: 49) |
| LGIPTQP⁶¹LSSC | (SEQ ID NO: 50) |
| LGTPWAP⁶¹LSSC | (SEQ ID NO: 51) |
| LGTPFA P⁶¹LSSC | (SEQ ID NO: 52) |
| P⁶¹FTP | (SEQ ID NO: 53) |
| SLGAP⁵⁸TAP⁶¹LSS | (SEQ ID NO: 54) |

3.6 C-Terminal Mutations

In this type of mutant, the amino acid sequence at the C-terminus of a wild-type G-CSF, RHLAQP¹⁷⁵ (SEQ ID NO: 193) is replaced with Ø$_a$G$_p$J$_q$O$_r$P¹⁷⁵X$_n$B$_o$Z$_m$U$_s$Ψ$_t$ (SEQ ID NO: 220), wherein a, p, q, r, n, o, m, s, and t are integers selected from 0 to 3, and at least one of Z, U, O, J, G, Ø, B and X is Thr or Ser and when more than one of Z, U, O, J, G, Ø, B and X are Thr or Ser, they are independently selected. Ø is optionally R, and G is optionally H. The symbol Ψ represents any uncharged amino acid residue or E (glutamate).

Preferred examples include:

| | |
|---|---|
| RHLAQTP¹⁷⁵ | SEQ ID NO: 55) |
| RHLAGQTP¹⁷⁵ | (SEQ ID NO: 56) |
| QP¹⁷⁵TQGAMP | (SEQ ID NO: 57) |

```
RHLAQTP¹⁷⁵AM          (SEQ ID NO: 58)

QP¹⁷⁵TSSAP            (SEQ ID NO: 59)

QP¹⁷⁵TSSAP            (SEQ ID NO: 60)

QP¹⁷⁵TQGAMP           (SEQ ID NO: 61)

QP¹⁷⁵TQGAM            (SEQ ID NO: 62)

QP¹⁷⁵TQGA             (SEQ ID NO: 63)

QP¹⁷⁵TVM              (SEQ ID NO: 64)

QP¹⁷⁵NTGP             (SEQ ID NO: 65)

QP¹⁷⁵QTLP             (SEQ ID NO: 66)
```

3.7 Internal Mutations surrounding $P^{133}$

Additional G-CSF mutants include those with internal mutations surrounding the amino acid $P^{133}$. Examples include:

```
P¹³³TQTAMP¹³⁹         (SEQ ID NO: 67)

P¹³³TQGTMP            (SEQ ID NO: 68)

P¹³³TQGTNP            (SEQ ID NO: 69)

P¹³³TQGTLP            (SEQ ID NO: 70)

PALQP¹³³TQTAMPA       (SEQ ID NO: 71)
```

Example 4

Mutations in the amino acid sequence of granulocyte colony stimulating factor (G-CSF) can introduce additional sites for O-linked glycosylation, such that the protein may be modified at these sites using the method of the present invention. This example sets forth selected representative mutants of the invention.

4.1 G-CSF (wild type 178 aa variant)
(SEQ ID NO: 141)
mtplgpasslp qsfllkcleq vrkiqgdgaa lqeklvseca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp 4.2 G-CSF (wild type 175 aa variant)
(SEQ ID NO: 143)
mtplgpasslp qsfllkcleq vrkiqgdgaa lqeklca tyklchpeel vllghslgip waplsscpsq alqlagclsq lhsglflyqg llqalegisp elgptldtlq ldvadfatti wqqmeelgma palqptqgam pafasafqrr aggvlvashl qsflevsyrv lrhlaqp 4.9 G-CSF Mutant 1 (Amino Terminal mutation)
(SEQ ID NO: 195)
miatplgpasslp qsfllkcleq vrkiqgdgaa lqeklcatyk lchpeelvll ghslgipwap lsscpsqalq lagclsqlhs glflyqgllq alegispelg ptldtlqldv adfattiwqq meelgmapal qptqgampaf asafqrragg vlvashlqsf levsyrvlrh laqp 4.10 G-CSF Mutant 2 (Amino Terminal mutation)
(SEQ ID NO: 153)
mgvtetplgpasslp qsfllkcleq vrkiqgdgaa lqeklcatyk lchpeelvll ghslgipwap lsscpsqalq lagclsqlhs glflyqgllq alegispelg ptldtlqldv adfattiwqq meelgmapal qptqgampaf asafqrragg vlvashlqsf levsyrvlrh laqp 4.11 G-CSF Mutant 3 (Amino Terminal mutation)
(SEQ ID NO: 154)
maptplgpasslp qsfllkcleq vrkiqgdgaa lqeklcatyk lchpeelvll ghslgipwap lsscpsqalq lagclsqlhs glflyqgllq alegispelg ptldtlqldv adfattiwqq meelgmapal qptqgampaf asafqrragg vlvashlqsf levsyrvlrh laqp 4.12 G-CSF Mutant 4 (Site 1)
(SEQ ID NO: 155)
mtp³tqglgpasslp qsfllkcleq vrkiqgdgaa lqeklcatyk lchpeelvll ghslgipwap lsscpsqalq lagclsqlhs glflyqgllq alegispelg ptldtlqldv adfattiwqq meelgmapal qptqgampaf asafqrragg vlvashlqsf levsyrvlrh laqp 4.13 G-CSF Mutant 5 (Site 3)
(SEQ ID NO: 156)
Mtplgpasslp qsfllkcleq vrkiqgdgaa lqeklcatyk lchpeelvll ghslgipwap lsscpsqalq lagclsqlhs glflyqgllq alegispelg ptldtlqldv adfattiwqq meelgmap¹²⁹at qptqgampaf asafqrragg vlvashlqsf levsyrvlrh laqp 4.14 G-CSF Mutant 6 (Site 4)
(SEQ ID NO: 157)
Mtplgpasslp qsfllkcleq vrkiqgdgaa lqeklcatyk lchpeelvll ghslgip⁵⁸ftp lsscpsqalq lagclsqlhs glflyqgllq alegispelg ptldtlqldv adfattiwqq meelgmapaL qptqgampaf asafqrragg vlvashlqsf levsyrvlrh laqp
```

Example 5

GlycoPEGylation of G-CSF Produced in CHO Cells

5a. Preparation of Asialo-Granulocyte-Colony Stimulation Factor (G-CSF)

G-CSF produced in CHO cells was dissolved at 2.5 mg/mL in 50 mM Tris 50 mM Tris-HCl pH 7.4, 0.15 M NaCl, 5 mM $CaCl_2$ and concentrated to 500 μL in a Centricon Plus 20 centrifugal filter. The solution was incubated with 300 mU/mL Neuraminidase II (*Vibrio cholerae*) for 16 hours at 32° C. To monitor the reaction a small aliquot of the reaction was diluted with the appropriate buffer and a IEF gel performed. The reaction mixture was then added to prewashed N-(p-aminophenyl)oxamic acid-agarose conjugate (800 μL/mL reaction volume) and the washed beads gently rotated for 24 hours at 4° C. The mixture was centrifuged at 10,000 rpm and the supernatant was collected. The beads were washed 3 times with Tris-EDTA buffer, once with 0.4 mL Tris-EDTA buffer and once with 0.2 mL of the Tris-EDTA buffer and all supernatants were pooled. The supernatant was dialyzed at 4° C. against 50 mM Tris —HCl pH 7.4, 1 M NaCl, 0.05% $NaN_3$ and then twice more against 50 mM Tris —HCl pH 7.4, 1 M NaCl, 0.05% $NaN_3$. The dialyzed solution was then concentrated using a Centricon Plus 20 centrifugal filter and stored at −20° C. The conditions for the IEF gel were run according to the procedures and reagents provided by Invitrogen. Samples of native and desialylated G-CSF were dialyzed against water and analyzed by MALDI-TOF MS.

5b. Preparation of G-CSF-(alpha-2,3)-Sialyl-PEG

Desialylated G-CSF was dissolved at 2.5 mg/mL in 50 mM Tris-HCl, 0.15 M NaCl, 0.05% $NaN_3$, pH 7.2. The solution was incubated with 1 mM CMP-sialic acid-PEG and 0.1 U/mL of ST3Gall at 32° C. for 2 days. To monitor the incorporation of sialic acid-PEG, a small aliquot of the reaction had CMP-SA-PEG-fluorescent ligand added; the label incorporated into the peptide was separated from the free label by gel filtration on a Toso Haas G3000SW analytical column using PBS buffer (pH 7.1). The fluorescent label incorporation into the peptide was quantitated using an in-line fluorescent detector. After 2 days, the reaction mixture was purified using a Toso Haas G3000SW preparative column using PBS buffer (pH 7.1) and collecting fractions based on UV absorption. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

5c. Preparation of G-CSF-(alpha-2,8)-Sialyl-PEG

G-CSF produced in CHO cells, which contains an alpha 2,3-sialylated O-linked glycan, was dissolved at 2.5 mg/mL in 50 mM Tris-HCl, 0.15 M NaCl, 0.05% $NaN_3$, pH 7.2. The solution was incubated with 1 mM CMP-sialic acid-PEG and 0.1 U/mL of CST-II at 32° C. for 2 days. To monitor the incorporation of sialic acid-PEG, a small aliquot of the reaction has CMP-SA-PEG-fluorescent ligand added; the label incorporated into the peptide was separated from the free label by gel filtration on a Toso Haas G3000SW analytical column using PBS buffer (pH 7.1). The fluorescent label incorporation into the peptide was quantitated using an in-line fluorescent detector. After 2 days, the reaction mixture was purified using a Toso Haas G3000SW preparative column using PBS buffer (pH 7.1) and collecting fractions based on UV absorption. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

5d Preparation of G-CSF-(alpha 2,6)-Sialyl-PEG

G-CSF, containing only O-linked GalNAc, was dissolved at 2.5 mg/mL in 50 mM Tris-HCl, 0.15 M NaCl, 0.05% $NaN_3$, pH 7.2. The solution was incubated with 1 mM CMP-sialic acid-PEG and 0.1 U/mL of ST6GalNAcI or II at 32° C. for 2 days. To monitor the incorporation of sialic acid-PEG, a small aliquot of the reaction has CMP-SA-PEG-fluorescent ligand added; the label incorporated into the peptide was separated from the free label by gel filtration on a Toso Haas G3000SW analytical column using PBS buffer (pH 7.1). The fluorescent label incorporation into the peptide was quantitated using an in-line fluorescent detector. After 2 days, the reaction mixture was purified using a Toso Haas G3000SW preparative column using PBS buffer (pH 7.1) and collecting fractions based on UV absorption. The product of the reaction was analyzed using SDS-PAGE and IEF analysis according to the procedures and reagents supplied by Invitrogen. Samples of native and PEGylated G-CSF were dialyzed against water and analyzed by MALDI-TOF MS.

G-CSF produced in CHO cells was treated with *Arthrobacter sialidase* and was then purified by size exclusion on Superdex 75 and was treated with ST3Gal1 or ST3 Gal2 and then with CMP-SA-PEG 20 Kda. The resulting molecule was purified by ion exchange and gel filtration and analysis by SDS PAGE demonstrated that the PEGylation was complete. This was the first demonstration of glycoPEGylation of an O-linked glycan.

Example 6

Recombinant GCSF

Expression, refolding and purification

Harvest cells by centrifugation, discard supernatant. Results of growth on various media are shown in FIG. 9.
Resuspend cell pellet in 10 mM Tris pH7.4, 75 mM NaCl, 5 mM EDTA-use 10 ml/g (lysis buffer)
Microlluidize cells (French press works as well)
Centrifuge 30 min, 4° C. at 5,000 RPM-discard supernatant
Resuspend pellet in lysis buffer and centrifuge as above
Wash IB's in 25 mM Tris pH8, 100 mM NaCl, 1% TX-100, 1% NaDOC, 5 mM EDTA. Pellets are resuspended by pipetting and vortexing. Centrifuge 15 min 4° C. 5,000 RPM. Repeat this step once more (total of two washes)
Wash pellets two times in 25 mM Tris pH8, 100 mM NaCl, 5 mM EDTA to remove detergents, centrifuge as above
Resuspend pellets in $dH_2O$ to aliquot and centrifuge as above. Pellets are frozen at −2° C.
IB's are resuspended at 20 mg/ml in 6M guanidine HCl, 5 mM EDTA, 100 mM NaCl, 100 mM Tris pH8, 10 mM DTT using a pipettor, followed by rotation for 2-4 h at room temperature.
Centrifuge solubilized IB's for 1 min at room temperature at 14,000 RPM. Save supernatant.
Dilute supernatant 1:20 with refold buffer 50 mM MES pH6, 240 mM NaCl, 10mM
KCl, 0.3 mM lauryl maltoside, 0.055% PEG3350, 1 mM GSH, 0.1M GSSG, 0.5M arginine and refold on rotator overnight at 4° C.
Transfer refold to Pierce snakeskin 7 kDa MWCO for dialysis. Dialysis buffer 20 mM NaOAc pH4, 50 mM NaCl, 0.005% Tween-80, 0.1 mM EDTA. Dialyze a total of 3 times versus at least a 200 fold excess at 4° C.
After dialysis pass material through a 0.45 μM filter.
Equlibrate SP-sepharose column with the dialysis buffer and apply sample. Wash column with dialysis buffer and elute with dialysis buffer containing a salt gradient up to 1M NaCl. Protein typically is eluted at 300-400 mM NaCl.

Check material on SDS-PAGE (see e.g., FIG. 10).

Example 7

The Two Enzyme Method in Two Pots

The following example illustrates the preparation of G-CSF-GalNAc-SA-PEG in two sequential steps wherein each intermediate product is purified before it is used in the next step.

7a. Preparation of GCSF-GalNAc (pH 6.2) from G-CSF and UDP-GalNAc using GalNAc-T2.

G-CSF (960 μg) in 3.2 mL of packaged buffer was concentrated by utrafiltration using an UF filter (MWCO 5K) and then reconstituted with 1 mL of 25 mM MES buffer (pH 6.2, 0.005% NaN$_3$). UDP-GalNAc (6 mg, 9.24 mM), GalNAc-T2 (40 μL, 0.04 U), and 100 mM MnCl$_2$ (40 μL, 4 mM) were then added and the resulting solution was incubated at room temperature.

After 24 hrs, MALDI indicated the reaction was complete. The reaction mixture was directly subjected to HPLC purification using SEC (Superdex 75 and Superdex 200) and an elution buffer comprising of PBS (phosphate buffered saline, pH 4.9 and 0.005% Tween 80). The collected peak of G-CSF-GalNAc was concentrated using a Centricon 5 KDa MWCO filter to about 150 μL and the volume adjusted to 1 ml using PBS (phosphate buffered saline, pH 4.9 and 0.005% Tween 80). Final protein concentration 1 mg/mL (A$_{280}$), yield 100%. The sample was stored at 4° C.

7b. Preparation of G-CSF-GalNAc-SA-PEG using purified G-CSF-GalNAc, CMP-SA-PEG (20 KDa) and mouse ST6GalNAc-TI (pH 6.2).

The G-CSF-GalNAc solution containing 1 mg of protein was buffer exchanged into 25 mM MES buffer (pH 6.2, 0.005% NaN$_3$) and CMP-SA-PEG (20 KDa) (5 mg, 0.25 umol) was added. After dissolving, MnCl$_2$ (100 mcL, 100 mM solution) and ST6GalNAc-I (100 mcL, mouse enzyme) was added and the reaction mixture rocked slowly at 32° C. for three days. The reaction mixture was concentrated by ultrifiltration (MWCO 5K) and buffer exchanged with 25 mM NaOAc (pH 4.9) one time and then concentrated to 1 mL of total volume. The product was then purified using SP-sepharose (A: 25 mM NaOAc+0.005% tween-80 pH 4.5; B: 25 mM NaOAc+0.005% tween-80 pH 4.5+2M NaCl) at retention time 13-18 mins and SEC (Superdex 75; PBS-pH 7.2, 0.005% Tween 80) at retention time 8.6 mins (superdex 75, flow 1 ml/min) The desired fractions were collected, concentrated to 0.5 mL and stored at 4° C.

Example 8

One Pot Method to Make G-CSF-GalNAc-SA-PEG with Simultaneous Addition of Enzymes The following example illustrates the preparation of G-CSF-GalNAc-SA-PEG in one pot using simultaneous addition of enzymes 8a. One Pot Process Using Mouse ST6GalNAc-I (pH 6.0)

G-CSF (960 μg of protein dissolved in 3.2 mL of the product formulation buffer) was concentrated by ultrafiltration (MWCO 5K) to 0.5 ml and reconstituted with 25 mM MES buffer (pH 6.0, 0.005% NaN$_3$) to a total volume of about 1 mL or a protein concentration of 1 mg/mL. UDP-GalNAc (6 mg, 9.21 μmol), GalNAc-T2 (80 μL, 80 mU), CMP-SA-PEG (20 KDa) (6 mg, 0.3 μmol) and mouse enzyme ST6GalNAc-I (120 μL) and 100 mM MnCl$_2$ (50 μL) were then added. The solution was rocked at 32° C. for 48 hrs and purified using standard chromatography conditions on SP-sepharose. A total of 0.5 mg of protein (A$_{280}$) was obtained or about a 50% overall yield. The product structure was confirmed by analysis with both MALDI and SDS-PAGE.

8b. One Pot Process Using Chicken ST6GalNAc-I (Ph 60)

14.4 mg of G-CSF; was concentrated to 3 mL final volume, buffer exchanged with 25 mM MES buffer (pH 6.0, 0.05% NaN$_3$, 0.004% Tween 80) and the volume was adjusted to 13 mL. The UDP-GalNAc (90 mg, 150 μmole), GalNAc-T2 (0.59 U), CMP-SA-PEG-20 KDa (90 mg), chicken ST6GalNAc-I (0.44 U), and 100 mM MnCl$_2$ (600 mcL) were then added. The resulting mixture stood at room temperature for 60 hrs. The reaction mixture was then concentrated using a UF (MWCO 5K) and centrifugation. The residue (about 2 mL) was dissolved in 25 mM NaOAc buffer (pH 4.5) and concentrated again to 5 mL final volume. This sample was purified using SP-sepharose for about 10-23 min, SEC (Superdex 75, 17 min, flow rate 0.5 ml/min) and an additional SEC (Superdex 200, 23 min, flow rate 0.5 ml/min), to yield 3.6 mg (25% overall yield) of G-CSF-GalNAc-SA-PEG-20 KDa (A$_{280}$ and BCA method).

Example 9

One Pot Method to Make G-CSF-GalNAc-Gal-SA-PEG with Sequential Addition of Enzymes The following example illustrates a method for making G-CSF-GalNAc-Gal-SA-PEG in one pot with sequential addition of enzymes.

9.1 Starting from GalNAc-G-CSF a. Preparation of G-CSF-GalNAc (pH 6.2) from G-CSF and UDP-GalNAc using GalNAc-T2.

G-CSF (960 mcg) in 3.2 mL of packaged buffer was concentrated by utrafiltration using an UF filter (MWCO 5K) and then reconstituted with 1 mL of 25 mM MES buffer (pH 6.2, 0.005% NaN$_3$). UDP-GalNAc (6 mg, 9.24 mM), GalNAc-T2 (40 μL, 0.04 U), and 100 mM MnCl$_2$ (40 μL, 4 mM) were then added and the resulting solution was incubated at room temperature.

b. Preparation of G-CSF-GalNAc-Gal-SA-PEG from G-CSF-GalNAc; UDP-Galactose, SA-PEG-20Kdalton, and the Appropriate Enzymes The UDP-Galactose (4 mg, 6.5 μmoles), core-1-Gal-T (320 μL, 160 mU), CMP-SA-PEG-20 KDa (8 mg, 0.4 μmole), ST3Gal2 (80 μL, 0.07 mU) and 100 mM MnCl$_2$ (80 μL) were directly added to the crude reaction mixture of the G-CSF-GalNAc (1.5 mg) in 1.5 ml 25 mM MES buffer (pH 6.0) from step a, above. The resulting mixture was incubated at 32° C. for 60 hrs. The reaction mixture was centrifuged and the solution was concentrated using ultrafiltration (MWCO 5K) to 0.2 mL, and then redissolved with 25 mM NaOAc (pH 4.5) to a final volume of 1 mL. The product was purified using SP-sepharose (retention time of between 10-15 min), the peak fraction were concentrated using a spin filter (MWCO 5K) and the residue purified further using SEC (Superdex 75, retention time of 10.2 min). After concentration using a spin filter (MWCO 5K), the protein was diluted to 1 mL using formulation buffer with PBS, 2.5% mannitol, 0.005% polysorbate, pH 6.5 and formulated at a protein concentration of 850 mcg protein per mL ($A_{280}$). The overall yield was 55%.

Example 10

One Pot Method to Make G-CSF-GalNAc-Gal-SA-PEG with Simultaneous Addition of Enzymes a. Starting from G-CSF.

G-CSF (960 mcg, 3.2 ml) was concentrated by ultrafiltration (MWCO 5K) and reconstituted with 25 mM Mes buffer (pH 6.0, 0.005% $NaN_3$). The total volume of the G-CSF solution was about 1 mg/ml. UDP-GalNAc (6 mg), GalNAc-T2 (80 µL, ~80 µU), UDP-Gal (6 mg), Corel GalT (160 µL, 80 µU), CMP-SA-PEG(20K) (6 mg) and a 2,3-(O)-sialyltransferase (160 µL, 120 µU), 100 mM $MnCl_2$ (40 µL) were added. The resulting mixture was incubated at 32° C. for 48 h. Purification was performed as described below using IEX and SEC. The resulting fraction containing the product were concentrated using ultrafiltration (MWCO 5K) and the volume was adjusted to about 1 mL with buffer. The protein concentration was determined to be 0.392 mg/ml by A280, giving an overall yield of 40% from G-CSF.

Example 11

The following Example illustrates an alternative enzymatic method to obtain large quantities of GlycoPEGylated G-CSF.

Granulocyte Colony Stimulating Factor (G-CSF) protein was expressed in *E. coli* and refolded from inclusion bodies as disclosed in Example X (above).

11a. Priming the Reaction by Addition of GalNAc

GalNAc-ylation of G-CSF was carried out at 33° C. in 50 mM Bis-Tris pH 6.5 buffer containing 1 mM $MnCl_2$ using refolded GalNAcT2 in the presence UDP-GalNAc. This step primes the reaction enabling both GalNAc transferase and sialyltransferase to work together in subsequent steps to very efficiently produce maximum amount of GCSF-PEG in a short period of time.

11b. PEGylation Process

PEGylation was started 2 (+/−1) hour after GalNAc-ylation by directly adding CMP-SA-PEG (20K) and ST6GalNAcI (chicken or human) to the priming reaction. This step produces substrate (GCSF-O-GalNAc) for the sialyltransferases to drive the reaction faster in a shorter period of time than can be achieved in a two step reaction wherein the GCSF-O-GalNAc is first purified from the UDP-GalNAc and other reaction components (see e.g., Example X, above). Furthermore the primed one pot reaction produces a higher yield of product than does a one pot reaction in which all components are added simultaneously.

Indeed, comparison of several types of one pot reactions shows that when all the components were added simultaneously and incubated for 23 hours, the GCSF-PEG produced was 77%. In contrast, when addition of all the enzymes required for the PEGylation reaction was preceded by the 2 hr GalNAc-ylation step described above, product yield was 85%. Therefore, the sequential addition of reaction components resulted in a 10% higher yield than was obtained when all reaction components are added simultaneously.

Example 12

This Example describes the results of O-linked GalNAcylation of six mutant G-CSF proteins.

12.1. GalNAcsylation of Mutant G-CSF Protein

All the sequences of mutant G-CSF proteins are listed below. Having these proteins, O-linked glycosylation was examined. Under the same condition for glycosylation of native G-CSF, GalNAc-$T_2$ (BV) was used in vitro with UDP-GalNAc in 25 mM MES buffer (pH 6.0). MALDI was used to monitor the reaction. Measurement of increasing molecular weight of proteins provided GalNAc addition number. For one addition of GalNAc, increased molecular weight should be 203 Da. Based on MALDI results, we found that mutant G-CSF-2, -3, -4, accepted one GalNAc; and mutant G-CSF-5 some addition was also observed, and mutant G-CSF-1 accepted two GalNAcs, forming MAPT-G-CSF$(GalNAc)_2$ (Molecular weight increasing from 18965 to 19369 Daltons).

TABLE X

GalNAc addition of Mutant G-CSF (MW measured by MALDI)

| Peptide | MW (Intact material) | MW (GalNAc— adduct) | Number of GalNAc addition |
|---|---|---|---|
| MutantG-CSF-1 (SEQ ID NO: 154) (MAPT-G-CSF) | 18965 | 19369 | 2 |
| MutantG-CSF-2 (SEQ ID NO: 156) | 18766 | 19029 | 1 |
| MutantG-CSF-3 (SED ID NO: 158) | 18822 | 19026 | 1 |
| MutantG-CSF-4 (SEQ ID NO: 150) | 19369 | 19574 | 1 |
| MutantG-CSF-5 (SEQ ID NO: 194) | 18957 | 18853 | 1 |
| MutantG-CSF-6 (SEQ ID NO: 141) | | | NT |
| Native G-CSF (SEQ ID NO: 195) | 18800 | 19023 | 1 |

Peptide mapping and N-terminal analysis were used for determination of glycosylation sites of MAPT-G-CSF-$(GalNAc)_2$. In the Glu C-digested peptide mapping a G-1+GalNAc peak was found, indicating one GalNAc was added at G-1 sequence. N-terminal Edman degdation analysis suggested the normal T was lost indicting that GalNAc was added onto T residue.

12.2 GlycoPEGylation of Mutant G-CSF Sequences a. GlycoPEGylation of mutant G-CSF sequence and buffer impact on the glycoPEGylation of MAPT-G-CSF An examination of glycoPEGylation (20K) of 5 mutants was undertaken. GlycoPEGylation was performed using three enzyme/three nucleotides system. (UDP-GalNAc/GalNAc-$T_2$/UDP-Gal/Core GalT/CMP-SA-PEG/O-sialyltransferase) in 25 mM MES buffer (pH 6.0). All mutants can be monoglycoPEGylated. No appreciable diPEGYlation in this condition was detected by SDS-PAGE gel by Comassie Blue Stain.

Since MAPT-G-CSF accept two GalNAcs, this mutant should receive two PEGs in theory. Accordingly, we examined the buffer impact on the PEGylation of MAPT-G-CSF as a starting material. Four different buffers (1.1 M MES buffer;

2.25 mM MES buffer (pH 6.0); 3.50 mM Bis-tris buffer(pH 6.0); 4.1M HEPS buffer (pH 7.4) were investigated for this reaction. It was found that MAPT-G-CSF can be PEGylated in all of the buffer system tested. However, monoPEGylation product was still a major one. In case 1M MES and 1 M HEPS buffer were used, some diPEGYylation product was formed, indicating that high concentration buffer improves the glycoPEGylation.

b. Comparison of GlycoPEGylation efficiency by forming MAPT-G-CSF(GalNAc-SA-PEG)$_2$ and MAPT-G-CSF(GalNAc-Gal-SA-PEG)$_2$ In order to see glycoPEGylation efficiency of Muant G-CSF-1 catalyzed by different enzymes, two enzymes (St6GalNAcI and O-siayltransferase) were examined for sialylPEGylation. Accordingly, MAPT-G-CSF was converted into MAPT-G-CSF(GalNAc)$_2$ and MAPT-G-CSF(GalNAc-Gal)$_2$ for siaylPEGylation. The former was treated with CMP-SA-lys-PEG(20K)/St6GalNAc I and the latter was treated with CMP-SA-PEG(20K)/O-sialyltransferase. Both reactions were performed in 25 mM MES buffer(pH 6.0) and 1 mg/ml protein concentration. The PEGylation efficiency can be seen in SDS-Page gel. It appeared that two enzymes were pretty similar in glycoPEGylation of this protein using CMP-SA-Lys-PEG (20 KDa) under the condition tested.

c. High Protein Concentration LED to Formation of MAPT-G-CSF((GalNAc-SA-PEG(20 KDa))$_2$ as a major product.

After examining the impact of enzyme and buffer on glycoPEGylation, as described above, the influence of protein concentration on the PEGylation by combining with a factor of high buffer concentration using $ST_6GalNAcI$ as GlycoPEGylation enzyme. So we applied UDP-GalNAc/GalNAc-T$_2$ and CMP-SA-PEG(20 KDa)/St6GalNAcI for glycoPEGylation of MAPT-G-CSF using 8~10 mg/ml protein concentration for reaction in 1 M MES buffer(pH 6.0). The result suggested that under this condition, the desired diPEGylation product became the major. Over 90% conversion was also achieved by applying more CMP-SA-PEG (20K) and enzyme. PEGylated G-CSF product, MAPT-G-CSF((GalNAc-SA-PEG(20 KDa))$_2$ was purified by combining SP-Sepharose and SEC purification on Supderdex 200.

12.3. Cell Proliferation Activity of MAPT-G-CSF-(GalNAc-SA-PEG)$_2$

Cell proliferation assay of MAPT-G-CSF-(GalNAc-SA-PEG)$_2$ with NFS-60 cell line and Tf-1 cell line were performed. The assay was performed using protein concentration between 0 ng/ml to 1000 ng/ml. MAPT-G-CSF(GalNAc-SA-PEG(20K))$_2$ was active in this assay.

12.4 Experimental Details 12.4a General Procedure of GalNAcsylation of Mutant G-CSF Certain volume of mutant G-CSF solution (for 100 ug protein) was buffer exchanged with MES buffer (25 mM+0.005% NaN$_3$, pH 6.0). The final volume was adjusted to 100 ug/100 ul. To this solution was added 5 ul 100 mM MnCl$_2$ and GalNAc-T$_2$ (1 mU). The resulting mixture was rocked at rt for a period of time required for MALDI or QTOF analysis.

12.4b Preparation of MAPTP-G-CSF-(GalNAc)$_2$)

MAPTP-G-CSF 5.4 mg (KJ-675-159, 0.18 mg/ml, 0.053 umol) was exchanged with MES buffer (25 mM+0.005% NaN$_3$, pH 6.0). The final volume was adjusted to 5.4 ml. To this solution, UDP-GalNAc (5 mg, 0.15 umol), 100 mM MnCl$_2$ 0.25 ml and GalNAc-T$_2$ (1.0 U/ml, 50 ul) were added. The resulting mixture was rocked at 32° C. for 24 h. M$^+$ (MALDI): 19364 (MAPT-G-CSF-(GalNAc)$_2$ verse 18951 (MVPTP-G-CSF).

12.4c General Procedure of glycoPEGylation of Mutant G-CSF Sequences by One-Pot Reaction)

Mutant G-CSF 100 ug(Mutant G-CSF-1,2,3,4,5) was mixted with UDP-GalNAc (0.6 mg, 0.923 umol), GalNAc-T$_2$ (20 ul, 8 mU), UDP-Gal (0.6 mg, 0.923 umol), Core 1 Gal T(20 ul, 10 mU), CMP-SA-PEG(20K) (1 mg, 0.05 umol), St3GalII (20 ul, 28 mU), 100 mM MnCl2 3 ul in 100 ul 25 mM MES buffer(pH 6.0+0.005% NaN$_3$). The resulting mixture was rocked at rt for 24 h. GlycoPEGylation was followed by SDS-PAGE.

12.4d Comparison of Mutant G-CSF-1 glycoPEGyaltion (20 KDa) in Various Buffer System GalNAc$_2$-MATP-G-CSF (54 ug) was buffer exchanged to the following four buffer system(1.1 M MES buffer(pH 6.0); 2.25 mM MES buffer(pH 6.0); 3.50 mM Bis-Tris buffer (pH 6.5); 4.1M HEPS buffer (pH 7.4). Then CMP-SA-PEG (20K) (216 ug) ST6GalNAcI(BV, 1 U/mL, 2.5 ul), 100 mM MnCl$_2$ 2.5 ul were added. The resulting mixture was rocked at rt for 24 h. SDS-PAGE gel was used to follow the reaction.

12.4e Comparison of GlycoPEGylation of MAPT-G-CSF by Using ST$_6$GalNAc$_I$ and O-Sialyltransferase (Wang787-29 and 787-40)

12.4e1 Using St6GalNAc I

First step: 30 ml KJ-675-159 solution (0.18 mg/ml, 5.4 mg protein in total) was concentrated by ultrifiltration (MWCO 5K) at 3500 g, and then buffer exchanged with 25 mM MES buffer(pH 6.0). Final volume was adjusted to 5.4 ml in a plastic tube. GalNAc-T$_2$ (1.0 U/ml, 50 ul) was added, followed by addition of 0.25 mL MnCl$_2$. The resulting mixture was rocked at 32° C. for 24 h. MALDI suggested that the reaction went to completion. The reaction mixture was concentrated by UF(MWCO 5K) and diluted with 25 mM MES buffer to 5 ml, then CMP-SA-PEG(20K) (2×25 mg), ST$_6$GalNAc$_I$ (BV, 1 U/ml), 100 mM MnCl$_2$ 0.25 ml were added. The resulting mixture was rocked at 32° C. overnight. SDS-PAGE was used for the reaction.

12.4e2 Using O-Silyltransferase(St$_3$Gal$_{III}$): 200 ug GalNAc$_2$-MATP-G-CSF in 200 ul 25 mM MES buffer (pH 6.0) was mixed with UDP-Gal 0.6 mg and core GalT (0.2 U/ml, 10 ul) and 10 ul 100 mM MnCl$_2$. The resulting mixture was rocked at 32° C. for 24 h. The reaction mixture was concentrated by UF (MWCO 5K) and diluted with 25 mM MES buffer to 200 ul. CMP-SA-PEG (800 ug), St$_3$GalII (1.0 U/ml, 10 ul), 10 ul 100 mM MnCl$_2$ were added. The resulting mixture was rocked at rt for 24 h. The resulting mixture was rocked at 32° C. overnight. SDS-PAGE gel was used to follow the reaction.

12.4f MAPTP-G-CSF-(GalNAc-SA-PEG(20K))$_2$ from glycoPEGylation of MAPT-G-CSF-(GalNAc)$_2$ (Wang 787-42)

MAPTP-G-CSF solution (540 ug) was concentrated and exchanged with 1M MES buffer (pH 6.0) and adjusted to 50 ul. Then UDP-GalNAc (100 ug, 0.15 umol, 5 eq), GalNAcT$_2$ (5.0 U/ml, 5 ul) and 100 mM MnCl$_2$ (5 ul) was added. The resulting mixture was rocked at RT overnight. Then CMP-SA-PEG (20K) (2.16 mg, 0.108 umol) and St$_6$GalNAcI (1.0 U/ml, 50 ul) were added. The solution was rocked at rt for 60 h. Additional CMP-SA-PEG(20K) (2.16 mg, 0.108 umol) and St6GalNAcI (1.0 U/ml, 50 ul) were added, followed by slow rotation at rt for 24 h. Reaction mixture was exchanged with buffer A (25 mM NaOAc, 0.005% polysorbate 80, pH 4.5), then purified on an Amersham SP-FF (5 mL) column with an isocratic elution of 100% A for 10 minutes followed by a linear gradient of 100% A to 20% B over 20 minutes at a flow rate of 3 mL min$^{-1}$, where B=25 mM NaOAc, 2 M NaCl 0.005% polysorbate 80, pH 4.5. The peak at retention time 17 mins was pooled and concentrated to 0.5 ml, which was further purified on an Amersham HiLoad Superdex 200 (16× 600 mm, 34 μm) with phosphate buffered saline, pH 5.0, 0.005% Tween80, at a flow rate of 0.4 mL min$^{-1}$. Product fractions at retention time 160 mins was pooled, concentrated to provide 30 ug of MAPT-G-CSF(GalNAc-SA-PEG (20K))$_2$(BCA). The yield was not optimized.

12.4 g Sequences of G-CSF Mutants

```
Mutant G-CSF-1:
                                        (SEQ ID NO: 154)
MAPTPLGPASSLPQSFLLKCLEQVRKIQGDGAALQEKLCATYKLCHPEEL

VLLGHSLGIPWAPLSSCPSQALQLAGCLSQLHSGLFLYQGLLQALEGISP

ELGPTLDTLQLDVADFATTIWQQMEELGMAPALQPTQGAMPAFASAFQRR

AGGVLVASHLQSFLEVSYRVLRHLAQP

Mutant G-CSF-2:
                                        (SEQ ID NO: 156)
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPATQPTQGAMPAFASAFQRRAG

GVLVASHLQSFLEvSYRvLRHLAQP

Mutant G-CSF-3:
                                        (SEQ ID NO: 158)
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQTAMPAFASAFQRRAG

GVLVASHLQSFLEVSYRVLRHLAQP

Mutant G-CSF-4 (C-terminal tag):
                                        (SEQ ID NO: 150)
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQGAMPAFASAFQRRAG

GVLVASHLQSFLEVSYRVLRHLAQPTQGAMP

Mutant G-CSF-5 (N-terminal MIATP):
                                        (SEQ ID NO: 194)
MIATPLGPASSLPQSFLLKCLEQVRKIQGDGAALQEKLCATYKLCHPEEL

VLLGHSLGIPWAPLSSCPSQALQLAGCLSQLHSGLFLYQGLLQALEGISP

ELGPTLDTLQLDVADFATTIWQQMEELGMAPALQPTQGAMPAFASAFQRR

AGGVLVASHLQSFLEVSYRVLRHLAQP

Mutant G-CSF-6 (177 Mer):
                                        (SEQ ID NO: 141)
MTPLGPASSLPQSFLLKCLEQVRKIQGDGAALQEKLVSECATYKLCHPEE

LVLLGHSLGIPWAPLSSCPSQALQLAGCLSQLHSGLFLYQGLLQALEGIS

PELGPTLDTLQLDVADFATTIWQQMEELGMAPALQPTQGAMPAFASAFQR

RAGGVLVASHLQSFLEVSYRVLRHLAQP

Human recombinant G-CSF expressed in E coli:
                                        (SEQ ID NO: 195)
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDYADFATTIWQQMEELGMAPALQPT¹³⁴QGAMPAFASAFQR

RAGGVLVASHLQSFLEVSYRVLRHLAQP
```

Example 13

The following Example illustrates preparation of a Glyco-PEGylated hGH protein The wild-type hGH has no natural glycosylation site, therefore a de novo O-glycosylation site was engineered into a mutant hGH protein which was then be glycosylated with a GalNAc transferase and sialylPEGylated at the mutant site. Five mutant hGH proteins were designed to incorporate an O-glycosylation site at either the amino terminus or in the loop region of the protein molecule. The five mutant proteins were produced and each was tested for hGH activity in a Nb2-11 cell proliferation assay.

13.1 Mutant hGH Amino Acid Sequences

```
192 amino acid Wild-type pituitary derived hGH
comprising an N-Terminal methionine
                                        (SEQ ID NO: 159)
MFPTIPLSRLFDNAMLRAHRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGRLEDGSPRTGQIFKQTYSKFDTN

SHNDDALLKNYGLLYCFRKDMDKVETFLRIVQCRSVEGSCGF 191 amino acid Wild-type pituitary derived hGH
lacking an N-Terminal methionine
                                        (SEQ ID NO: 160)
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF

MVTP mutant:
                                        (SEQ ID NO: 196)
(M)VTPTIPLSRLFDNAMLRAHRLHQLAFDTYQEFEEAYIPKEQKYSFLQ

NPQTSLCFSESIPTPSNREETQQKSNLELLRISLLLIQSWLEPVQFLRSV

FANSLVYGASDSNVYDLLKDLEEGIQTLMGRLEDGSPRTGQIFKQTYSKF

DTNSHNDDALLKNYGLLYCFRKDMDKVETFLRIVQCRSVEGSCGF

PTQGAMP mutant:
                                        (SEQ ID NO: 197)
MFPTIPLSRLFDNAMLRAHRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGRLEDGSPTQGAMPKQTYSKYDTN

SHNDDALLKNYGLLYCFRKDMDKVETFLRIVQCRSVEGSCGF

TTT mutant:
                                        (SEQ ID NO: 198)
MFPTIPLSRLFDNAMLRAHRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGRLEDGSPTTTQIFKQTYSKFDTN

SHNDDALLKNYGLLYCFRKDMDKVETFLRIVQCRSVEGSCGF
```

-continued

MAPT mutant:

(SEQ ID NO: 199)
MAPTSSPTIPLSRLFDNAMLRAHRLHQLAFDTYQEFEEAYIPKEQKYSFL

QNPQTSLCFSESIPTPSNREETQQKSNLELLRISLLLIQSWLEPVQFLRS

VFANSLVYGASDSNVYDLLKDLEEGIQTLMGRLEDGSPRTGQIFKQTYSK

FDTNSHNDDALLKNYGLLYCFRKDMDKVETFLRIVQCRSVEGSCGF

NTG mutant:

(SEQ ID NO: 200)
MFPTIPLSRLFDNAMLRAHRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGRLEDGSPNTGQIFKQTYSKFDTN

SHNDDALLKNYGLLYCFRKDMDKVETFLRIVQCRSVEGSCGF

The four hGH mutants were tested for the ability to act as substrates for glycosyltransferase GalNAcT2. Of the four hGH mutants, two were found to be glycosylated by GalNAcT2 by MALDI-MS analysis.

13.2 Preparation of
hGH-(TTT)-GalNAc-SA-PEG-30 KDa

For the TTT mutant (SEQ ID NO: 198), GalNAc addition gave rise to a complex mixture of unglycosylated, and 1-GalNAc and 2-GalNAc species. Peptide mapping experiments (trypsin digest) showed that the two GalNAc's were added to the T12 peptide (L129-K141) containing the TTT mutation. The (M)VTP mutant (SEQ ID NO: 196) showed only a trace of GalNAc added by MALDI-MS.

The hGH-TTT-mutant (SEQ ID NO: 198) (4.0 mL, 6.0 mg, 0.27 micromoles) was buffer exchanged twice with 15 mL of Washing Buffer (20 mM HEPES, 150 mM NaCl, 0.02% $NaN_3$, pH 7.4) and once with Reaction Buffer (20 mM HEPES, 150 mM NaCl, 5 mM $MnCl_2$, 5 mM $MgCl_2$, 0.02% $NaN_3$, pH 7.4) then concentrated to 2.0 mL using a Centricon centrifugal filter, 5 KDa MWCO.

The hGH-TTT mutant (SEQ ID NO: 198) was combined with UDP-GalNAc (1.38 micromoles, 0.90 mg) and GalNAc-T2 (0.12 mL, 120 mU). The reaction was incubated at 32° C. with gentle shaking for 19 hours. The reaction was analyzed by MALDI-MS and partial addition of GalNAc to the hGH-TTT mutant (SEQ ID NO: 198) was observed (approximately 40%). CMP-SA-PEG-30K (16 mg, 0.533 micromoles) and ST6GalNAc1 (0.375 mL, 375 mU) were added to the reaction mixture to bring the total volume to 2.85 mL. The reaction was incubated at 32° C. with gentle shaking for 22 h. The reaction was monitored by SDS PAGE at 0 h and 22 h. The extent of reaction was determined by SDS-PAGE gel. The product, hGH-(TTT)-GalNAc-SA-PEG-30 KDa, was purified using SP Sepharose and analyzed by SDS-PAGE. Very low yield of the desired hGH-(TTT)-GalNAc-SA-PEG-30 KDa was observed.

13.3 Preparation of
hGH-(PTQGAMP)-GalNAc-SA-PEG-30 KDa

The PTQGAMP mutant (SEQ ID NO: 197) was readily glycosylated with UDP-GalNAc and GalNAc T2, then GlycoPEGylated using CMP-SA-PEG-30 KDa and ST6GalNAc1 on 10 mg scale to yield 1.45 mg of purified hGH-(PTQGAMP)-GalNAc-SA-PEG-30 KDa. Peptide mapping experiments (trypsin digest) located the GalNAc on the trypsin T12 peptide (L129-K141) containing the PTQGAMP mutation.

The hGH-PTQGAMP-mutant (SEQ ID NO: 197) (4.55 mL, 10.0 mg, 0.45 micromoles) was buffer exchanged twice with 15 mL of Washing Buffer (20 mM HEPES, 150 mM NaCl, 0.02% $NaN_3$, pH 7.4) and once with Reaction Buffer (20 mM HEPES, 150 mM NaCl, 5 mM $MnCl_2$, 5 mM $MgCl_2$, 0.02% $NaN_3$, pH 7.4) then concentrated to 3 mL using a Centricon centrifugal filter, 5 KDa MWCO.

The hGH-PTQGAMP mutant (SEQ ID NO: 197) was combined with UDP-GalNAc (2.26 micromoles, 1.47 mg) and GalNAc-T2 (0.1 mL, 100 mU). The reaction was incubated at 32° C. with gentle shaking for 22 hours. The reaction was analyzed by MALDI-MS and complete addition of GalNAc to the hGH-PTQGAMP mutant (SEQ ID NO: 197) was observed. CMP-SA-PEG-30K (27 mg, 0.9 micromoles) and ST6GalNAc1 (0.350 mL, 350 mU) were added to the reaction mixture to bring the total volume to 3.4 mL. The reaction was incubated at 32° C. with gentle shaking for 24 h. The reaction was monitored by SDS PAGE at 0 hours and 16.5 hours. The extent of reaction was determined by SDS-PAGE gel. The product, hGH-(PTQGAMP)-GalNAc-SA-PEG-30 KDa, was purified using SP Sepharose and SEC (Superdex 200) chromatography and then formulated. The final product was analyzed by MALDI, peptide map and SDS-PAGE (silver stain). Protein was determined by BCA vs. BSA standard. The overall isolated yield (1.45 mg) was 12.5% based on protein.

Example 14

This example sets forth the preparation of a GM-CSF PEG glycoconjugate of the invention.

14.1 Preparation of (PEG(20K)-SA-Gal-GalNAc)-2-GM-CSF and PEG(20k)-SA-Gal-GalNAc-GM-CSF GM-CSF (1 mg) was dissolved in 25 mM MES buffer (1 mL) (pH 6.0, 0.005% $NaN_3$), then UDP-GalNAc (1 mg), GalNAc-$T_2$ (200 μL, 0.38 U/mL, 0.076 U), 100 mM $MnCl_2$ (80 μL) were added. The resulting mixture was incubated at room temperature for 72 h. MALDI indicated GalNAc2-GM-CSF was formed.

UDP-Gal (6 mg, 9.8 mmol), core-1-Gal-$T_1$ (0.5 U/mL, 80 μL), CMP-SA-PEG (20 kilodalton) (6 mg, 0.3 μmol), α-(O)-sialyltransferase (1 U/mL, 120 μL), 100 mM $MnCl_2$ (50 μL) were added. The resulting mixture was slowly rotated at 32° C. for 48 h. The reaction mixture was centrifuged at 2 rpm for 5 min. The protein solution was taken. The remain resin was mixed with 1 mL 25 mM MES buffer (pH 6.0) and vibrated for 30 sec. The suspension was concentrated in again; the protein solutions were combined and concentrated to 200 μL. HPLC Purification provided glyco-PEG-ylated GM-CSF.

Example 15

An O-linked glycosylation site similar to that of interferon alpha-2 can be incorporated into any interferon alpha protein at the same relative position. This can be performed by aligning the amino acid sequence of interest with the IFN-alpha-2b sequence (10-20 amino acids long) and modifying the amino acid sequence to incorporate the glycosylation site. Mutation with any amino acid, deletion or insertion can be used to create the site. Exemplary mutants maintain as high an homology as possible with the IFN-alpha-2 sequence in this region with an emphasis on the T at position 106 (shown below in bold). An example of how this is performed is shown below.

Alignments of Interferon Alpha's in the NCBI Protein Database

| Alignments of Interferon alpha's in the NCBI ProteinDatabase | | | | |
|---|---|---|---|---|
| GI# | AA# | AA Sequence | Name | |
| IFN-a-2β | 1 | CVIQGVGVTETPLMKEDSIL 20 | (SEQ ID NO: 180) | |
| 124449 | 98 | .................... 117 | IFN-alpha 2 (a,b,c) | (SEQ ID NO: 180) |
| 20178265 | 99 | ....E...E.....N..... 118 | IFN-alpha 14 | (SEQ ID NO: 202) |
| 124453 | 99 | ....E...E.....N..... 118 | IFN-alpha 10 | (SEQ ID NO: 203) |
| 585316 | 99 | ....E..ME.....N..... 118 | IFN-alpha 17 | (SEQ ID NO: 204) |
| 124442 | 99 | ....E...E.....N..F.. 118 | IFN-alpha 7 | (SEQ ID NO: 205) |
| 124438 | 99 | ....E...E.....NV.... 118 | IFN-alpha 4 | (SEQ ID NO: 206) |
| 417188 | 99 | ..M.E...I.S...Y..... 118 | IFN-alpha 8 | (SEQ ID NO: 207) |
| 20178289 | 99 | ....E...E.....NV.... 118 | IFN-alpha 21 | (SEQ ID NO: 208) |
| 124457 | 99 | .MM.E...ED....NV.... 118 | IFN-alpha 5 | (SEQ ID NO: 209) |
| 124463 | 99 | ..T.E...E.IA..N..... 118 | IFN-alpha 16 | (SEQ ID NO: 210) |
| 124460 | 99 | ..M.E.W.GG....N..... 118 | IFN-alpha 6 | (SEQ ID NO: 211) |
| 124455 | 99 | ..M.EER.G.....NA.... 118 | IFN-alpha 1/13 | (SEQ ID NO: 212) |

Glycosylation/Glyco-PEG-ylation occurs at $T^{106}$ (IFN-alpha-2). Protein numbering begins with the first amino acid after removal of the protein leader sequence of the naturally expressed pre-pro form.

Interferon alpha mutations to introduce O-Linked Glycosylation Sites in IFN-alpha's that lack this site.

| GI# | AA# | AA Sequ

-continued

| GI# | AA# | AA Sequence | | Name | |
|---|---|---|---|---|---|
| 20178289 | 99 | ....E...T.....NV.... | 118 | IFN-alpha 21 ($E^{107}T$) | (SEQ ID NO: 136) |
| 20178289 | 99 | ....G...T.....NV.... | 118 | IFN-alpha 21 ($E^{103}G$; $E^{107}T$) | (SEQ ID NO: 137) |
| 124457 | 99 | .MM.E...TD....NV.... | 118 | IFN-alpha 5 ($E^{107}T$) | (SEQ ID NO: 116) |
| 124457 | 99 | .MM.E...TE....NV.... | 118 | IFN-alpha 5 ($ED^{108}TE$) | (SEQ ID NO: 117) |
| 124457 | 99 | .MM.G...TD....NV.... | 118 | IFN-alpha 5 ($E^{103}G$; $E^{107}T$) | (SEQ ID NO: 118) |
| 124463 | 99 | ..T.E...T.IP..N..... | 118 | IFN-alpha 16 ($E^{107}T$; $A^{110}P$) | (SEQ ID NO: 130) |
| 124463 | 99 | ..T.E...T.TP..N..... | 118 | IFN-alpha 16 ($E^{107}T$; $IA^{110}TP$) | (SEQ ID NO: 131) |
| 124463 | 99 | ..T.G...T.TP..N..... | 118 | IFN-alpha 16 ($E^{103}G$; $E^{107}T$; $IA^{110}TP$) | (SEQ ID NO: 132) |
| 124460 | 99 | ..M.E.W.TG....N..... | 118 | IFN-alpha 6 ( $G^{107}T$) | (SEQ ID NO: 119) |
| 124460 | 99 | ..M.E.G.TG....N..... | 118 | IFN-alpha 6 ($W^{105}G$; $G^{107}T$) | (SEQ ID NO: 120) |
| 124460 | 99 | ..M.G.G.TE....N..... | 118 | ($E^{103}G$; $W^{105}G$; $GG^{108}TE$) | (SEQ ID NO: 121) |
| 124455 | 99 | ..M.EER.T.....NA.... | 118 | IFN-alpha1/13 ($G^{107}T$) | (SEQ ID NO: 111) |
| 124455 | 99 | ..M.EEG.T.....NA.... | 118 | IFN-alpha1/13 ($R^{105}G$; $G^{107}T$) | (SEQ ID NO: 112) |
| 124455 | 99 | ..M.GVG.T.....NA.... | 118 | IFN-alpha1/13 ($EER^{105}GVG$; $G^{107}T$) | (SEQ ID NO: 113) |

The GI numbers in the above table, except the first number 124449, refer to those of the unmodified wild-type proteins.

The O-linked glycosylation site can be created in any interferon alpha isoform by placing a T or S at the appropriate amino acid site as shown above. The substitution is T as shown in the above table. The amino acid sequences between the various interferon alpha forms are similar. Any amino acid mutation, insertion, deletion can be made in this region as long as the T or S is at the appropriate position for glycosylation/glyco-PEG-ylation relative to $P^{109}$ (IFN-alpha-2) in the alignment sequence shown above.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

SEQUENCE LISTING

<160> NUMBER OF SEQ ID NOS: 228

<210> SEQ ID NO 1
<211> LENGTH: 7
<212> TYPE: PRT
<213> ORGANISM: Homo sapiens

<400> SEQUENCE: 1

Met Val Thr Pro Leu Gly Pro
1               5

<210> SEQ ID NO 2
<211> LENGTH: 7
<212> TYPE: PRT
<213> ORGANISM: Homo sapiens

<400> SEQUENCE: 2

Met Gln Thr Pro Leu Gly Pro
1               5

<210> SEQ ID NO 3
<211> LENGTH: 8
<212> TYPE: PRT

<213> ORGANISM: Homo sapiens

<400> SEQUENCE: 3

Met Ile Ala Thr Pro Leu Gly Pro
1               5

<210> SEQ ID NO 4
<211> LENGTH: 7
<212> TYPE: PRT
<213> ORGANISM: Homo sapiens

<400> SEQUENCE: 4

Met Ala Thr Pro Leu Gly Pro
1               5

<210> SEQ ID NO 5
<211> LENGTH: 11
<212> TYPE: PRT
<213> ORGANISM: Homo sapiens

<400> SEQUENCE: 5

Met Pro Thr Gln Gly Ala Met Pro Leu Gly Pro
1               5                   10

<210> SEQ ID NO 6
<211> LENGTH: 8
<212> TYPE: PRT
<213> ORGANISM: Homo sapiens

<400> SEQUENCE: 6

Met Val Gln Thr Pro Leu Gly Pro
1               5

<210> SEQ ID NO 7
<211> LENGTH: 8
<212> TYPE: PRT
<213> ORGANISM: Homo sapiens

<400> SEQUENCE: 7

Met Gln Ser Thr Pro Leu Gly Pro
1               5

<210> SEQ ID NO 8
<211> LENGTH: 8
<212> TYPE: PRT
<213> ORGANISM: Homo sapiens

<400> SEQUENCE: 8

Met Gly Gln Thr Pro Leu Gly Pro
1               5

<210> SEQ ID NO 9
<211> LENGTH: 11
<212> TYPE: PRT
<213> ORGANISM: Homo sapiens

<400> SEQUENCE: 9

Met Ala Pro Thr Ser Ser Ser Pro Leu Gly Pro
1               5                   10

<210> SEQ ID NO 10
<211> LENGTH: 9
<212> TYPE: PRT
<213> ORGANISM: Homo sapiens

<400> SEQUENCE: 10

Met Ala Pro Thr Pro Leu Gly Pro Ala
1               5

<210> SEQ ID NO 11
<211> LENGTH: 7
<212> TYPE: PRT
<213> ORGANISM: Homo sapiens

<400> SEQUENCE: 11

Met Thr Pro Thr Leu Gly Pro
1               5

<210> SEQ ID NO 12
<211> LENGTH: 8
<212> TYPE: PRT
<213> ORGANISM: Homo sapiens

<400> SEQUENCE: 12

Met Thr Pro Thr Gln Leu Gly Pro
1               5

<210> SEQ ID NO 13
<211> LENGTH: 8
<212> TYPE: PRT
<213> ORGANISM: Homo sapiens

<400> SEQUENCE: 13

Met Thr Pro Thr Ser Leu Gly Pro
1               5

<210> SEQ ID NO 14
<211> LENGTH: 7
<212> TYPE: PRT
<213> ORGANISM: Homo sapiens

<400> SEQUENCE: 14

Met Thr Pro Thr Gln Gly Pro
1               5

<210> SEQ ID NO 15
<211> LENGTH: 7
<212> TYPE: PRT
<213> ORGANISM: Homo sapiens

<400> SEQUENCE: 15

Met Thr Pro Thr Ser Ser Pro
1               5

<210> SEQ ID NO 16
<211> LENGTH: 6
<212> TYPE: PRT
<213> ORGANISM: Homo sapiens

<400> SEQUENCE: 16

Met Thr Pro Gln Thr Pro
1               5

<210> SEQ ID NO 17
<211> LENGTH: 6
<212> TYPE: PRT
<213> ORGANISM: Homo sapiens

<400> SEQUENCE: 17

Met Thr Pro Thr Gly Pro
1               5

```
<210> SEQ ID NO 18
<211> LENGTH: 6
<212> TYPE: PRT
<213> ORGANISM: Homo sapiens

<400> SEQUENCE: 18

Met Thr Pro Leu Thr Pro
1               5

<210> SEQ ID NO 19
<211> LENGTH: 7
<212> TYPE: PRT
<213> ORGANISM: Homo sapiens

<400> SEQUENCE: 19

Met Thr Pro Asn Thr Gly Pro
1               5

<210> SEQ ID NO 20
<211> LENGTH: 6
<212> TYPE: PRT
<213> ORGANISM: Homo sapiens

<400> SEQUENCE: 20

Met Thr Pro Val Thr Pro
1               5

<210> SEQ ID NO 21
<211> LENGTH: 7
<212> TYPE: PRT
<213> ORGANISM: Homo sapiens

<400> SEQUENCE: 21

Met Thr Pro Met Val Thr Pro
1               5

<210> SEQ ID NO 22
<211> LENGTH: 11
<212> TYPE: PRT
<213> ORGANISM: Homo sapiens

<400> SEQUENCE: 22

Met Thr Pro Thr Gln Gly Leu Gly Pro Ala Ser
1               5                   10

<210> SEQ ID NO 23
<211> LENGTH: 7
<212> TYPE: PRT
<213> ORGANISM: Homo sapiens

<400> SEQUENCE: 23

Leu Gly His Thr Leu Gly Ile
1               5

<210> SEQ ID NO 24
<211> LENGTH: 7
<212> TYPE: PRT
<213> ORGANISM: Homo sapiens

<400> SEQUENCE: 24

Leu Gly Ser Ser Leu Gly Ile
1               5

<210> SEQ ID NO 25
```

```
<211> LENGTH: 7
<212> TYPE: PRT
<213> ORGANISM: Homo sapiens

<400> SEQUENCE: 25

Leu Gly Tyr Ser Leu Gly Ile
1               5

<210> SEQ ID NO 26
<211> LENGTH: 7
<212> TYPE: PRT
<213> ORGANISM: Homo sapiens

<400> SEQUENCE: 26

Leu Gly Glu Ser Leu Gly Ile
1               5

<210> SEQ ID NO 27
<211> LENGTH: 7
<212> TYPE: PRT
<213> ORGANISM: Homo sapiens

<400> SEQUENCE: 27

Leu Gly Ser Thr Leu Gly Ile
1               5

<210> SEQ ID NO 28
<211> LENGTH: 6
<212> TYPE: PRT
<213> ORGANISM: Homo sapiens

<400> SEQUENCE: 28

Pro Ala Thr Gln Pro Thr
1               5

<210> SEQ ID NO 29
<211> LENGTH: 6
<212> TYPE: PRT
<213> ORGANISM: Homo sapiens

<400> SEQUENCE: 29

Pro Thr Leu Gly Pro Thr
1               5

<210> SEQ ID NO 30
<211> LENGTH: 6
<212> TYPE: PRT
<213> ORGANISM: Homo sapiens

<400> SEQUENCE: 30

Pro Thr Gln Gly Pro Thr
1               5

<210> SEQ ID NO 31
<211> LENGTH: 6
<212> TYPE: PRT
<213> ORGANISM: Homo sapiens

<400> SEQUENCE: 31

Pro Thr Ser Ser Pro Thr
1               5

<210> SEQ ID NO 32
<211> LENGTH: 7
<212> TYPE: PRT
<213> ORGANISM: Homo sapiens
```

```
<400> SEQUENCE: 32

Pro Thr Gln Gly Ala Pro Thr
1               5

<210> SEQ ID NO 33
<211> LENGTH: 6
<212> TYPE: PRT
<213> ORGANISM: Homo sapiens

<400> SEQUENCE: 33

Pro Asn Thr Gly Pro Thr
1               5

<210> SEQ ID NO 34
<211> LENGTH: 8
<212> TYPE: PRT
<213> ORGANISM: Homo sapiens

<400> SEQUENCE: 34

Pro Ala Leu Gln Pro Thr Gln Thr
1               5

<210> SEQ ID NO 35
<211> LENGTH: 6
<212> TYPE: PRT
<213> ORGANISM: Homo sapiens

<400> SEQUENCE: 35

Pro Ala Leu Thr Pro Thr
1               5

<210> SEQ ID NO 36
<211> LENGTH: 6
<212> TYPE: PRT
<213> ORGANISM: Homo sapiens

<400> SEQUENCE: 36

Pro Met Val Thr Pro Thr
1               5

<210> SEQ ID NO 37
<211> LENGTH: 7
<212> TYPE: PRT
<213> ORGANISM: Homo sapiens

<400> SEQUENCE: 37

Pro Ala Ser Ser Thr Pro Thr
1               5

<210> SEQ ID NO 38
<211> LENGTH: 5
<212> TYPE: PRT
<213> ORGANISM: Homo sapiens

<400> SEQUENCE: 38

Pro Thr Thr Gln Pro
1               5

<210> SEQ ID NO 39
<211> LENGTH: 5
<212> TYPE: PRT
<213> ORGANISM: Homo sapiens

<400> SEQUENCE: 39
```

```
Pro Asn Thr Leu Pro
1               5

<210> SEQ ID NO 40
<211> LENGTH: 5
<212> TYPE: PRT
<213> ORGANISM: Homo sapiens

<400> SEQUENCE: 40

Pro Thr Leu Gln Pro
1               5

<210> SEQ ID NO 41
<211> LENGTH: 12
<212> TYPE: PRT
<213> ORGANISM: Homo sapiens

<400> SEQUENCE: 41

Met Ala Pro Ala Thr Gln Pro Thr Gln Gly Ala Met
1               5                   10

<210> SEQ ID NO 42
<211> LENGTH: 12
<212> TYPE: PRT
<213> ORGANISM: Homo sapiens

<400> SEQUENCE: 42

Met Pro Ala Thr Thr Gln Pro Thr Gln Gly Ala Met
1               5                   10

<210> SEQ ID NO 43
<211> LENGTH: 5
<212> TYPE: PRT
<213> ORGANISM: Homo sapiens

<400> SEQUENCE: 43

Pro Thr Ser Ser Cys
1               5

<210> SEQ ID NO 44
<211> LENGTH: 6
<212> TYPE: PRT
<213> ORGANISM: Homo sapiens

<400> SEQUENCE: 44

Pro Thr Ser Ser Ala Cys
1               5

<210> SEQ ID NO 45
<211> LENGTH: 11
<212> TYPE: PRT
<213> ORGANISM: Homo sapiens

<400> SEQUENCE: 45

Leu Gly Ile Pro Thr Ala Pro Leu Ser Ser Cys
1               5                   10

<210> SEQ ID NO 46
<211> LENGTH: 11
<212> TYPE: PRT
<213> ORGANISM: Homo sapiens

<400> SEQUENCE: 46

Leu Gly Ile Pro Thr Gln Pro Leu Ser Ser Cys
1               5                   10
```

```
<210> SEQ ID NO 47
<211> LENGTH: 12
<212> TYPE: PRT
<213> ORGANISM: Homo sapiens

<400> SEQUENCE: 47

Leu Gly Ile Pro Thr Gln Gly Pro Leu Ser Ser Cys
1               5                   10

<210> SEQ ID NO 48
<211> LENGTH: 11
<212> TYPE: PRT
<213> ORGANISM: Homo sapiens

<400> SEQUENCE: 48

Leu Gly Ile Pro Gln Thr Pro Leu Ser Ser Cys
1               5                   10

<210> SEQ ID NO 49
<211> LENGTH: 11
<212> TYPE: PRT
<213> ORGANISM: Homo sapiens

<400> SEQUENCE: 49

Leu Gly Ile Pro Thr Ser Pro Leu Ser Ser Cys
1               5                   10

<210> SEQ ID NO 50
<211> LENGTH: 11
<212> TYPE: PRT
<213> ORGANISM: Homo sapiens

<400> SEQUENCE: 50

Leu Gly Ile Pro Thr Gln Pro Leu Ser Ser Cys
1               5                   10

<210> SEQ ID NO 51
<211> LENGTH: 11
<212> TYPE: PRT
<213> ORGANISM: Homo sapiens

<400> SEQUENCE: 51

Leu Gly Thr Pro Trp Ala Pro Leu Ser Ser Cys
1               5                   10

<210> SEQ ID NO 52
<211> LENGTH: 11
<212> TYPE: PRT
<213> ORGANISM: Homo sapiens

<400> SEQUENCE: 52

Leu Gly Thr Pro Phe Ala Pro Leu Ser Ser Cys
1               5                   10

<210> SEQ ID NO 53
<211> LENGTH: 4
<212> TYPE: PRT
<213> ORGANISM: Homo sapiens

<400> SEQUENCE: 53

Pro Phe Thr Pro
1

<210> SEQ ID NO 54
<211> LENGTH: 11
```

```
<212> TYPE: PRT
<213> ORGANISM: Homo sapiens

<400> SEQUENCE: 54

Ser Leu Gly Ala Pro Thr Ala Pro Leu Ser Ser
1               5                   10

<210> SEQ ID NO 55
<211> LENGTH: 7
<212> TYPE: PRT
<213> ORGANISM: Homo sapiens

<400> SEQUENCE: 55

Arg His Leu Ala Gln Thr Pro
1               5

<210> SEQ ID NO 56
<211> LENGTH: 8
<212> TYPE: PRT
<213> ORGANISM: Homo sapiens

<400> SEQUENCE: 56

Arg His Leu Ala Gly Gln Thr Pro
1               5

<210> SEQ ID NO 57
<211> LENGTH: 8
<212> TYPE: PRT
<213> ORGANISM: Homo sapiens

<400> SEQUENCE: 57

Gln Pro Thr Gln Gly Ala Met Pro
1               5

<210> SEQ ID NO 58
<211> LENGTH: 9
<212> TYPE: PRT
<213> ORGANISM: Homo sapiens

<400> SEQUENCE: 58

Arg His Leu Ala Gln Thr Pro Ala Met
1               5

<210> SEQ ID NO 59
<211> LENGTH: 7
<212> TYPE: PRT
<213> ORGANISM: Homo sapiens

<400> SEQUENCE: 59

Gln Pro Thr Ser Ser Ala Pro
1               5

<210> SEQ ID NO 60
<211> LENGTH: 7
<212> TYPE: PRT
<213> ORGANISM: Homo sapiens

<400> SEQUENCE: 60

Gln Pro Thr Ser Ser Ala Pro
1               5

<210> SEQ ID NO 61
<211> LENGTH: 8
<212> TYPE: PRT
<213> ORGANISM: Homo sapiens
```

```
<400> SEQUENCE: 61

Gln Pro Thr Gln Gly Ala Met Pro
1               5

<210> SEQ ID NO 62
<211> LENGTH: 7
<212> TYPE: PRT
<213> ORGANISM: Homo sapiens

<400> SEQUENCE: 62

Gln Pro Thr Gln Gly Ala Met
1               5

<210> SEQ ID NO 63
<211> LENGTH: 6
<212> TYPE: PRT
<213> ORGANISM: Homo sapiens

<400> SEQUENCE: 63

Gln Pro Thr Gln Gly Ala
1               5

<210> SEQ ID NO 64
<211> LENGTH: 5
<212> TYPE: PRT
<213> ORGANISM: Homo sapiens

<400> SEQUENCE: 64

Gln Pro Thr Val Met
1               5

<210> SEQ ID NO 65
<211> LENGTH: 6
<212> TYPE: PRT
<213> ORGANISM: Homo sapiens

<400> SEQUENCE: 65

Gln Pro Asn Thr Gly Pro
1               5

<210> SEQ ID NO 66
<211> LENGTH: 6
<212> TYPE: PRT
<213> ORGANISM: Homo sapiens

<400> SEQUENCE: 66

Gln Pro Gln Thr Leu Pro
1               5

<210> SEQ ID NO 67
<211> LENGTH: 7
<212> TYPE: PRT
<213> ORGANISM: Homo sapiens

<400> SEQUENCE: 67

Pro Thr Gln Thr Ala Met Pro
1               5

<210> SEQ ID NO 68
<211> LENGTH: 7
<212> TYPE: PRT
<213> ORGANISM: Homo sapiens

<400> SEQUENCE: 68

Pro Thr Gln Gly Thr Met Pro
```

```
<210> SEQ ID NO 69
<211> LENGTH: 7
<212> TYPE: PRT
<213> ORGANISM: Homo sapiens

<400> SEQUENCE: 69

Pro Thr Gln Gly Thr Asn Pro
1               5

<210> SEQ ID NO 70
<211> LENGTH: 7
<212> TYPE: PRT
<213> ORGANISM: Homo sapiens

<400> SEQUENCE: 70

Pro Thr Gln Gly Thr Leu Pro
1               5

<210> SEQ ID NO 71
<211> LENGTH: 12
<212> TYPE: PRT
<213> ORGANISM: Homo sapiens

<400> SEQUENCE: 71

Pro Ala Leu Gln Pro Thr Gln Thr Ala Met Pro Ala
1               5                   10

<210> SEQ ID NO 72
<211> LENGTH: 8
<212> TYPE: PRT
<213> ORGANISM: Homo sapiens

<400> SEQUENCE: 72

Pro Thr Thr Gly Gln Ile Phe Lys
1               5

<210> SEQ ID NO 73
<211> LENGTH: 8
<212> TYPE: PRT
<213> ORGANISM: Homo sapiens

<400> SEQUENCE: 73

Pro Thr Thr Ala Gln Ile Phe Lys
1               5

<210> SEQ ID NO 74
<211> LENGTH: 8
<212> TYPE: PRT
<213> ORGANISM: Homo sapiens

<400> SEQUENCE: 74

Pro Thr Thr Leu Gln Ile Phe Lys
1               5

<210> SEQ ID NO 75
<211> LENGTH: 8
<212> TYPE: PRT
<213> ORGANISM: Homo sapiens

<400> SEQUENCE: 75

Pro Thr Thr Leu Tyr Val Phe Lys
1               5
```

```
<210> SEQ ID NO 76
<211> LENGTH: 8
<212> TYPE: PRT
<213> ORGANISM: Homo sapiens

<400> SEQUENCE: 76

Pro Thr Thr Val Gln Ile Phe Lys
1               5

<210> SEQ ID NO 77
<211> LENGTH: 8
<212> TYPE: PRT
<213> ORGANISM: Homo sapiens

<400> SEQUENCE: 77

Pro Thr Thr Val Ser Ile Phe Lys
1               5

<210> SEQ ID NO 78
<211> LENGTH: 8
<212> TYPE: PRT
<213> ORGANISM: Homo sapiens

<400> SEQUENCE: 78

Pro Thr Thr Asn Gln Ile Phe Lys
1               5

<210> SEQ ID NO 79
<211> LENGTH: 8
<212> TYPE: PRT
<213> ORGANISM: Homo sapiens

<400> SEQUENCE: 79

Pro Thr Thr Gln Gln Ile Phe Lys
1               5

<210> SEQ ID NO 80
<211> LENGTH: 8
<212> TYPE: PRT
<213> ORGANISM: Homo sapiens

<400> SEQUENCE: 80

Pro Thr Ala Thr Gln Ile Phe Lys
1               5

<210> SEQ ID NO 81
<211> LENGTH: 8
<212> TYPE: PRT
<213> ORGANISM: Homo sapiens

<400> SEQUENCE: 81

Pro Thr Gln Gly Gln Ile Phe Lys
1               5

<210> SEQ ID NO 82
<211> LENGTH: 8
<212> TYPE: PRT
<213> ORGANISM: Homo sapiens

<400> SEQUENCE: 82

Pro Thr Gln Gly Ala Ile Phe Lys
1               5

<210> SEQ ID NO 83
<211> LENGTH: 8
<212> TYPE: PRT
```

<213> ORGANISM: Homo sapiens

<400> SEQUENCE: 83

Pro Thr Gln Gly Ala Met Phe Lys
1               5

<210> SEQ ID NO 84
<211> LENGTH: 8
<212> TYPE: PRT
<213> ORGANISM: Homo sapiens

<400> SEQUENCE: 84

Pro Thr Ile Gly Gln Ile Phe Lys
1               5

<210> SEQ ID NO 85
<211> LENGTH: 8
<212> TYPE: PRT
<213> ORGANISM: Homo sapiens

<400> SEQUENCE: 85

Pro Thr Ile Asn Gln Ile Phe Lys
1               5

<210> SEQ ID NO 86
<211> LENGTH: 8
<212> TYPE: PRT
<213> ORGANISM: Homo sapiens

<400> SEQUENCE: 86

Pro Thr Ile Asn Thr Ile Phe Lys
1               5

<210> SEQ ID NO 87
<211> LENGTH: 8
<212> TYPE: PRT
<213> ORGANISM: Homo sapiens

<400> SEQUENCE: 87

Pro Thr Ile Leu Gln Ile Phe Lys
1               5

<210> SEQ ID NO 88
<211> LENGTH: 8
<212> TYPE: PRT
<213> ORGANISM: Homo sapiens

<400> SEQUENCE: 88

Pro Thr Ile Val Gln Ile Phe Lys
1               5

<210> SEQ ID NO 89
<211> LENGTH: 8
<212> TYPE: PRT
<213> ORGANISM: Homo sapiens

<400> SEQUENCE: 89

Pro Thr Ile Gln Gln Ile Phe Lys
1               5

<210> SEQ ID NO 90
<211> LENGTH: 8
<212> TYPE: PRT
<213> ORGANISM: Homo sapiens

<400> SEQUENCE: 90

```
Pro Thr Ile Ala Gln Ile Phe Lys
1               5

<210> SEQ ID NO 91
<211> LENGTH: 12
<212> TYPE: PRT
<213> ORGANISM: Homo sapiens

<400> SEQUENCE: 91

Pro Thr Thr Thr Gln Ile Phe Lys Gln Thr Tyr Ser
1               5                   10

<210> SEQ ID NO 92
<211> LENGTH: 12
<212> TYPE: PRT
<213> ORGANISM: Homo sapiens

<400> SEQUENCE: 92

Pro Thr Gln Gly Ala Met Pro Lys Gln Thr Tyr Ser
1               5                   10

<210> SEQ ID NO 93
<211> LENGTH: 12
<212> TYPE: PRT
<213> ORGANISM: Homo sapiens

<400> SEQUENCE: 93

Pro Arg Thr Gly Gln Ile Pro Thr Gln Thr Tyr Ser
1               5                   10

<210> SEQ ID NO 94
<211> LENGTH: 12
<212> TYPE: PRT
<213> ORGANISM: Homo sapiens

<400> SEQUENCE: 94

Pro Arg Thr Gly Gln Ile Pro Thr Gln Ala Tyr Ser
1               5                   10

<210> SEQ ID NO 95
<211> LENGTH: 9
<212> TYPE: PRT
<213> ORGANISM: Homo sapiens

<400> SEQUENCE: 95

Leu Glu Thr Gln Ser Pro Arg Thr Gly
1               5

<210> SEQ ID NO 96
<211> LENGTH: 9
<212> TYPE: PRT
<213> ORGANISM: Homo sapiens

<400> SEQUENCE: 96

Leu Glu Thr Gln Ser Pro Ser Thr Gly
1               5

<210> SEQ ID NO 97
<211> LENGTH: 9
<212> TYPE: PRT
<213> ORGANISM: Homo sapiens

<400> SEQUENCE: 97

Leu Glu Thr Gln Ser Pro Ala Thr Gly
1               5
```

```
<210> SEQ ID NO 98
<211> LENGTH: 9
<212> TYPE: PRT
<213> ORGANISM: Homo sapiens

<400> SEQUENCE: 98

Leu Glu Thr Gln Ser Pro Leu Thr Gly
1               5

<210> SEQ ID NO 99
<211> LENGTH: 7
<212> TYPE: PRT
<213> ORGANISM: Homo sapiens

<400> SEQUENCE: 99

Leu Glu Thr Glu Thr Pro Arg
1               5

<210> SEQ ID NO 100
<211> LENGTH: 7
<212> TYPE: PRT
<213> ORGANISM: Homo sapiens

<400> SEQUENCE: 100

Leu Glu Thr Glu Thr Pro Ala
1               5

<210> SEQ ID NO 101
<211> LENGTH: 9
<212> TYPE: PRT
<213> ORGANISM: Homo sapiens

<400> SEQUENCE: 101

Leu Val Thr Gln Ser Pro Arg Thr Gly
1               5

<210> SEQ ID NO 102
<211> LENGTH: 9
<212> TYPE: PRT
<213> ORGANISM: Homo sapiens

<400> SEQUENCE: 102

Leu Val Thr Glu Thr Pro Arg Thr Gly
1               5

<210> SEQ ID NO 103
<211> LENGTH: 9
<212> TYPE: PRT
<213> ORGANISM: Homo sapiens

<400> SEQUENCE: 103

Leu Val Thr Glu Thr Pro Ala Thr Gly
1               5

<210> SEQ ID NO 104
<211> LENGTH: 9
<212> TYPE: PRT
<213> ORGANISM: Homo sapiens

<400> SEQUENCE: 104

Leu Ala Thr Gly Ser Pro Arg Thr Gly
1               5

<210> SEQ ID NO 105
```

```
<211> LENGTH: 11
<212> TYPE: PRT
<213> ORGANISM: Homo sapiens

<400> SEQUENCE: 105

Met Phe Pro Thr Glu Ile Pro Leu Ser Arg Leu
1               5                   10

<210> SEQ ID NO 106
<211> LENGTH: 11
<212> TYPE: PRT
<213> ORGANISM: Homo sapiens

<400> SEQUENCE: 106

Met Phe Pro Thr Val Leu Pro Leu Ser Arg Leu
1               5                   10

<210> SEQ ID NO 107
<211> LENGTH: 12
<212> TYPE: PRT
<213> ORGANISM: Homo sapiens

<400> SEQUENCE: 107

Met Ala Pro Thr Pro Thr Ile Pro Leu Ser Arg Leu
1               5                   10

<210> SEQ ID NO 108
<211> LENGTH: 11
<212> TYPE: PRT
<213> ORGANISM: Homo sapiens

<400> SEQUENCE: 108

Met Val Thr Pro Thr Ile Pro Leu Ser Arg Leu
1               5                   10

<210> SEQ ID NO 109
<211> LENGTH: 13
<212> TYPE: PRT
<213> ORGANISM: Homo sapiens

<400> SEQUENCE: 109

Met Ala Pro Thr Ser Ser Pro Thr Ile Pro Leu Ser Arg
1               5                   10

<210> SEQ ID NO 110
<211> LENGTH: 11
<212> TYPE: PRT
<213> ORGANISM: Homo sapiens

<400> SEQUENCE: 110

Asp Gly Ser Pro Asn Thr Gly Gln Ile Phe Lys
1               5                   10

<210> SEQ ID NO 111
<211> LENGTH: 20
<212> TYPE: PRT
<213> ORGANISM: Homo sapiens

<400> SEQUENCE: 111

Cys Val Met Gln Glu Glu Arg Val Thr Glu Thr Pro Leu Met Asn Ala
1               5                   10                  15

Asp Ser Ile Leu
            20

<210> SEQ ID NO 112
```

```
<211> LENGTH: 20
<212> TYPE: PRT
<213> ORGANISM: Homo sapiens

<400> SEQUENCE: 112

Cys Val Met Gln Glu Glu Gly Val Thr Glu Thr Pro Leu Met Asn Ala
1               5                   10                  15

Asp Ser Ile Leu
            20

<210> SEQ ID NO 113
<211> LENGTH: 20
<212> TYPE: PRT
<213> ORGANISM: Homo sapiens

<400> SEQUENCE: 113

Cys Val Met Gln Gly Val Gly Val Thr Glu Thr Pro Leu Met Asn Ala
1               5                   10                  15

Asp Ser Ile Leu
            20

<210> SEQ ID NO 114
<211> LENGTH: 20
<212> TYPE: PRT
<213> ORGANISM: Homo sapiens

<400> SEQUENCE: 114

Cys Val Ile Gln Glu Val Gly Val Thr Glu Thr Pro Leu Met Asn Val
1               5                   10                  15

Asp Ser Ile Leu
            20

<210> SEQ ID NO 115
<211> LENGTH: 20
<212> TYPE: PRT
<213> ORGANISM: Homo sapiens

<400> SEQUENCE: 115

Cys Val Ile Gln Gly Val Gly Val Thr Glu Thr Pro Leu Met Asn Val
1               5                   10                  15

Asp Ser Ile Leu
            20

<210> SEQ ID NO 116
<211> LENGTH: 20
<212> TYPE: PRT
<213> ORGANISM: Homo sapiens

<400> SEQUENCE: 116

Cys Met Met Gln Glu Val Gly Val Thr Asp Thr Pro Leu Met Asn Val
1               5                   10                  15

Asp Ser Ile Leu
            20

<210> SEQ ID NO 117
<211> LENGTH: 20
<212> TYPE: PRT
<213> ORGANISM: Homo sapiens

<400> SEQUENCE: 117

Cys Met Met Gln Glu Val Gly Val Thr Glu Thr Pro Leu Met Asn Val
1               5                   10                  15

Asp Ser Ile Leu
```

20

<210> SEQ ID NO 118
<211> LENGTH: 20
<212> TYPE: PRT
<213> ORGANISM: Homo sapiens

<400> SEQUENCE: 118

Cys Met Met Gln Gly Val Gly Val Thr Asp Thr Pro Leu Met Asn Val
1               5                   10                  15

Asp Ser Ile Leu
            20

<210> SEQ ID NO 119
<211> LENGTH: 20
<212> TYPE: PRT
<213> ORGANISM: Homo sapiens

<400> SEQUENCE: 119

Cys Val Met Gln Glu Val Trp Val Thr Gly Thr Pro Leu Met Asn Glu
1               5                   10                  15

Asp Ser Ile Leu
            20

<210> SEQ ID NO 120
<211> LENGTH: 20
<212> TYPE: PRT
<213> ORGANISM: Homo sapiens

<400> SEQUENCE: 120

Cys Val Met Gln Glu Val Gly Val Thr Gly Thr Pro Leu Met Asn Glu
1               5                   10                  15

Asp Ser Ile Leu
            20

<210> SEQ ID NO 121
<211> LENGTH: 20
<212> TYPE: PRT
<213> ORGANISM: Homo sapiens

<400> SEQUENCE: 121

Cys Val Met Gln Gly Val Gly Val Thr Glu Thr Pro Leu Met Asn Glu
1               5                   10                  15

Asp Ser Ile Leu
            20

<210> SEQ ID NO 122
<211> LENGTH: 20
<212> TYPE: PRT
<213> ORGANISM: Homo sapiens

<400> SEQUENCE: 122

Cys Val Ile Gln Glu Val Gly Val Thr Glu Thr Pro Leu Met Asn Glu
1               5                   10                  15

Asp Phe Ile Leu
            20

<210> SEQ ID NO 123
<211> LENGTH: 20
<212> TYPE: PRT
<213> ORGANISM: Homo sapiens

<400> SEQUENCE: 123

Cys Val Ile Gln Gly Val Gly Val Thr Glu Thr Pro Leu Met Asn Glu
1               5                   10                  15

Asp Phe Ile Leu
            20

<210> SEQ ID NO 124
<211> LENGTH: 20
<212> TYPE: PRT
<213> ORGANISM: Homo sapiens

<400> SEQUENCE: 124

Cys Val Met Gln Glu Val Gly Val Thr Glu Ser Pro Leu Met Tyr Glu
1               5                   10                  15

Asp Ser Ile Leu
            20

<210> SEQ ID NO 125
<211> LENGTH: 20
<212> TYPE: PRT
<213> ORGANISM: Homo sapiens

<400> SEQUENCE: 125

Cys Val Met Gln Gly Val Gly Val Thr Glu Ser Pro Leu Met Tyr Glu
1               5                   10                  15

Asp Ser Ile Leu
            20

<210> SEQ ID NO 126
<211> LENGTH: 20
<212> TYPE: PRT
<213> ORGANISM: Homo sapiens

<400> SEQUENCE: 126

Cys Val Ile Gln Glu Val Gly Val Thr Glu Thr Pro Leu Met Asn Glu
1               5                   10                  15

Asp Ser Ile Leu
            20

<210> SEQ ID NO 127
<211> LENGTH: 20
<212> TYPE: PRT
<213> ORGANISM: Homo sapiens

<400> SEQUENCE: 127

Cys Val Ile Gln Gly Val Gly Val Thr Glu Thr Pro Leu Met Asn Glu
1               5                   10                  15

Asp Ser Ile Leu
            20

<210> SEQ ID NO 128
<211> LENGTH: 20
<212> TYPE: PRT
<213> ORGANISM: Homo sapiens

<400> SEQUENCE: 128

Cys Val Ile Gln Glu Val Gly Val Thr Glu Thr Pro Leu Met Asn Glu
1               5                   10                  15

Asp Ser Ile Leu
            20

<210> SEQ ID NO 129
<211> LENGTH: 20
<212> TYPE: PRT

<213> ORGANISM: Homo sapiens

<400> SEQUENCE: 129

Cys Val Ile Gln Gly Val Gly Val Thr Glu Thr Pro Leu Met Asn Glu
1               5                   10                  15

Asp Ser Ile Leu
            20

<210> SEQ ID NO 130
<211> LENGTH: 20
<212> TYPE: PRT
<213> ORGANISM: Homo sapiens

<400> SEQUENCE: 130

Cys Val Thr Gln Glu Val Gly Val Thr Glu Ile Pro Leu Met Asn Glu
1               5                   10                  15

Asp Ser Ile Leu
            20

<210> SEQ ID NO 131
<211> LENGTH: 20
<212> TYPE: PRT
<213> ORGANISM: Homo sapiens

<400> SEQUENCE: 131

Cys Val Thr Gln Glu Val Gly Val Thr Glu Thr Pro Leu Met Asn Glu
1               5                   10                  15

Asp Ser Ile Leu
            20

<210> SEQ ID NO 132
<211> LENGTH: 20
<212> TYPE: PRT
<213> ORGANISM: Homo sapiens

<400> SEQUENCE: 132

Cys Val Thr Gln Gly Val Gly Val Thr Glu Thr Pro Leu Met Asn Glu
1               5                   10                  15

Asp Ser Ile Leu
            20

<210> SEQ ID NO 133
<211> LENGTH: 20
<212> TYPE: PRT
<213> ORGANISM: Homo sapiens

<400> SEQUENCE: 133

Cys Val Ile Gln Glu Val Gly Met Thr Glu Thr Pro Leu Met Asn Glu
1               5                   10                  15

Asp Ser Ile Leu
            20

<210> SEQ ID NO 134
<211> LENGTH: 20
<212> TYPE: PRT
<213> ORGANISM: Homo sapiens

<400> SEQUENCE: 134

Cys Val Ile Gln Glu Val Gly Val Thr Glu Thr Pro Leu Met Asn Glu
1               5                   10                  15

Asp Ser Ile Leu
            20

```
<210> SEQ ID NO 135
<211> LENGTH: 20
<212> TYPE: PRT
<213> ORGANISM: Homo sapiens

<400> SEQUENCE: 135

Cys Val Ile Gln Gly Val Gly Met Thr Glu Thr Pro Leu Met Asn Glu
1               5                   10                  15

Asp Ser Ile Leu
            20

<210> SEQ ID NO 136
<211> LENGTH: 20
<212> TYPE: PRT
<213> ORGANISM: Homo sapiens

<400> SEQUENCE: 136

Cys Val Ile Gln Glu Val Gly Val Thr Glu Thr Pro Leu Met Asn Val
1               5                   10                  15

Asp Ser Ile Leu
            20

<210> SEQ ID NO 137
<211> LENGTH: 20
<212> TYPE: PRT
<213> ORGANISM: Homo sapiens

<400> SEQUENCE: 137

Cys Val Ile Gln Gly Val Gly Val Thr Glu Thr Pro Leu Met Asn Val
1               5                   10                  15

Asp Ser Ile Leu
            20

<210> SEQ ID NO 138
<211> LENGTH: 20
<212> TYPE: PRT
<213> ORGANISM: Homo sapiens

<400> SEQUENCE: 138

His Gly Val Thr Ser Ala Pro Asp Thr Arg Pro Ala Pro Gly Ser Thr
1               5                   10                  15

Ala Pro Pro Ala
            20

<210> SEQ ID NO 139
<211> LENGTH: 20
<212> TYPE: PRT
<213> ORGANISM: Homo sapiens

<400> SEQUENCE: 139

His Gly Val Thr Ser Ala Pro Asp Thr Arg Pro Ala Pro Gly Ser Thr
1               5                   10                  15

Ala Pro Pro Ala
            20

<210> SEQ ID NO 140
<211> LENGTH: 24
<212> TYPE: PRT
<213> ORGANISM: Homo sapiens

<400> SEQUENCE: 140

Thr Ala Pro Pro Ala His Gly Val Thr Ser Ala Pro Asp Thr Arg Pro
1               5                   10                  15
```

```
Ala Pro Gly Ser Thr Ala Pro Pro
            20

<210> SEQ ID NO 141
<211> LENGTH: 178
<212> TYPE: PRT
<213> ORGANISM: Homo sapiens

<400> SEQUENCE: 141

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Val Ser Glu Cys Ala Thr Tyr Lys Leu Cys His Pro
        35                  40                  45

Glu Glu Leu Val Leu Leu Gly His Ser Leu Gly Ile Pro Trp Ala Pro
    50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
    130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 142
<211> LENGTH: 177
<212> TYPE: PRT
<213> ORGANISM: Homo sapiens

<400> SEQUENCE: 142

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
                85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
```

```
                130                 135                 140
Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 143
<211> LENGTH: 175
<212> TYPE: PRT
<213> ORGANISM: Homo sapiens

<400> SEQUENCE: 143

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 144
<211> LENGTH: 174
<212> TYPE: PRT
<213> ORGANISM: Homo sapiens

<400> SEQUENCE: 144

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110
```

```
Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 145
<211> LENGTH: 176
<212> TYPE: PRT
<213> ORGANISM: Homo sapiens

<400> SEQUENCE: 145

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 146
<211> LENGTH: 176
<212> TYPE: PRT
<213> ORGANISM: Homo sapiens

<400> SEQUENCE: 146

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Thr Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
```

```
                        100                 105                 110
Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 147
<211> LENGTH: 175
<212> TYPE: PRT
<213> ORGANISM: Homo sapiens

<400> SEQUENCE: 147

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Thr Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 148
<211> LENGTH: 176
<212> TYPE: PRT
<213> ORGANISM: Homo sapiens

<400> SEQUENCE: 148

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly Ser Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95
```

```
Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 149
<211> LENGTH: 176
<212> TYPE: PRT
<213> ORGANISM: Homo sapiens

<400> SEQUENCE: 149

Met Gln Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 150
<211> LENGTH: 181
<212> TYPE: PRT
<213> ORGANISM: Homo sapiens

<400> SEQUENCE: 150

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80
```

```
Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Thr
                165                 170                 175

Gln Gly Ala Met Pro
            180

<210> SEQ ID NO 151
<211> LENGTH: 175
<212> TYPE: PRT
<213> ORGANISM: Homo sapiens

<400> SEQUENCE: 151

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
            35                  40                  45

Val Leu Leu Gly Ser Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
            85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 152
<211> LENGTH: 177
<212> TYPE: PRT
<213> ORGANISM: Homo sapiens

<400> SEQUENCE: 152

Met Ala Ile Thr Pro Leu Gly Pro Ala Ser Ser Leu Pro Gln Ser Phe
1               5                   10                  15

Leu Leu Lys Cys Leu Glu Gln Val Arg Lys Ile Gln Gly Asp Gly Ala
            20                  25                  30

Ala Leu Gln Glu Lys Leu Cys Ala Thr Tyr Lys Leu Cys His Pro Glu
            35                  40                  45

Glu Leu Val Leu Leu Gly His Ser Leu Gly Ile Pro Trp Ala Pro Leu
```

```
                 50                  55                  60
Ser Ser Cys Pro Ser Gln Ala Leu Gln Leu Ala Gly Cys Leu Ser Gln
 65                  70                  75                  80

Leu His Ser Gly Leu Phe Leu Tyr Gln Gly Leu Leu Gln Ala Leu Glu
                 85                  90                  95

Gly Ile Ser Pro Glu Leu Gly Pro Thr Leu Asp Thr Leu Gln Leu Asp
                100                 105                 110

Val Ala Asp Phe Ala Thr Thr Ile Trp Gln Gln Met Glu Glu Leu Gly
                115                 120                 125

Met Ala Pro Ala Leu Gln Pro Thr Gln Gly Ala Met Pro Ala Phe Ala
                130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 153
<211> LENGTH: 179
<212> TYPE: PRT
<213> ORGANISM: Homo sapiens

<400> SEQUENCE: 153

Met Gly Val Thr Glu Thr Pro Leu Gly Pro Ala Ser Ser Leu Pro Gln
  1               5                  10                  15

Ser Phe Leu Leu Lys Cys Leu Glu Gln Val Arg Lys Ile Gln Gly Asp
                 20                  25                  30

Gly Ala Ala Leu Gln Glu Lys Leu Cys Ala Thr Tyr Lys Leu Cys His
                 35                  40                  45

Pro Glu Glu Leu Val Leu Leu Gly His Ser Leu Gly Ile Pro Trp Ala
                 50                  55                  60

Pro Leu Ser Ser Cys Pro Ser Gln Ala Leu Gln Leu Ala Gly Cys Leu
 65                  70                  75                  80

Ser Gln Leu His Ser Gly Leu Phe Leu Tyr Gln Gly Leu Leu Gln Ala
                 85                  90                  95

Leu Glu Gly Ile Ser Pro Glu Leu Gly Pro Thr Leu Asp Thr Leu Gln
                100                 105                 110

Leu Asp Val Ala Asp Phe Ala Thr Thr Ile Trp Gln Gln Met Glu Glu
                115                 120                 125

Leu Gly Met Ala Pro Ala Leu Gln Pro Thr Gln Gly Ala Met Pro Ala
                130                 135                 140

Phe Ala Ser Ala Phe Gln Arg Arg Ala Gly Gly Val Leu Val Ala Ser
145                 150                 155                 160

His Leu Gln Ser Phe Leu Glu Val Ser Tyr Arg Val Leu Arg His Leu
                165                 170                 175

Ala Gln Pro

<210> SEQ ID NO 154
<211> LENGTH: 177
<212> TYPE: PRT
<213> ORGANISM: Homo sapiens

<400> SEQUENCE: 154

Met Ala Pro Thr Pro Leu Gly Pro Ala Ser Ser Leu Pro Gln Ser Phe
  1               5                  10                  15

Leu Leu Lys Cys Leu Glu Gln Val Arg Lys Ile Gln Gly Asp Gly Ala
```

-continued

```
            20                  25                  30
Ala Leu Gln Glu Lys Leu Cys Ala Thr Tyr Lys Leu Cys His Pro Glu
         35                  40                  45
Glu Leu Val Leu Leu Gly His Ser Leu Gly Ile Pro Trp Ala Pro Leu
     50                  55                  60
Ser Ser Cys Pro Ser Gln Ala Leu Gln Leu Ala Gly Cys Leu Ser Gln
 65                  70                  75                  80
Leu His Ser Gly Leu Phe Leu Tyr Gln Gly Leu Leu Gln Ala Leu Glu
                 85                  90                  95
Gly Ile Ser Pro Glu Leu Gly Pro Thr Leu Asp Thr Leu Gln Leu Asp
                100                 105                 110
Val Ala Asp Phe Ala Thr Thr Ile Trp Gln Gln Met Glu Glu Leu Gly
             115                 120                 125
Met Ala Pro Ala Leu Gln Pro Thr Gln Gly Ala Met Pro Ala Phe Ala
         130                 135                 140
Ser Ala Phe Gln Arg Arg Ala Gly Gly Val Leu Val Ala Ser His Leu
145                 150                 155                 160
Gln Ser Phe Leu Glu Val Ser Tyr Arg Val Leu Arg His Leu Ala Gln
                165                 170                 175
Pro
```

```
<210> SEQ ID NO 155
<211> LENGTH: 178
<212> TYPE: PRT
<213> ORGANISM: Homo sapiens

<400> SEQUENCE: 155

Met Thr Pro Thr Gln Gly Leu Gly Pro Ala Ser Ser Leu Pro Gln Ser
 1                   5                  10                  15
Phe Leu Leu Lys Cys Leu Glu Gln Val Arg Lys Ile Gln Gly Asp Gly
                 20                  25                  30
Ala Ala Leu Gln Glu Lys Leu Cys Ala Thr Tyr Lys Leu Cys His Pro
             35                  40                  45
Glu Glu Leu Val Leu Leu Gly His Ser Leu Gly Ile Pro Trp Ala Pro
         50                  55                  60
Leu Ser Ser Cys Pro Ser Gln Ala Leu Gln Leu Ala Gly Cys Leu Ser
 65                  70                  75                  80
Gln Leu His Ser Gly Leu Phe Leu Tyr Gln Gly Leu Leu Gln Ala Leu
                 85                  90                  95
Glu Gly Ile Ser Pro Glu Leu Gly Pro Thr Leu Asp Thr Leu Gln Leu
            100                 105                 110
Asp Val Ala Asp Phe Ala Thr Thr Ile Trp Gln Gln Met Glu Glu Leu
        115                 120                 125
Gly Met Ala Pro Ala Leu Gln Pro Thr Gln Gly Ala Met Pro Ala Phe
    130                 135                 140
Ala Ser Ala Phe Gln Arg Arg Ala Gly Gly Val Leu Val Ala Ser His
145                 150                 155                 160
Leu Gln Ser Phe Leu Glu Val Ser Tyr Arg Val Leu Arg His Leu Ala
                165                 170                 175
Gln Pro
```

```
<210> SEQ ID NO 156
<211> LENGTH: 175
<212> TYPE: PRT
<213> ORGANISM: Homo sapiens
```

<400> SEQUENCE: 156

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Thr Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 157
<211> LENGTH: 175
<212> TYPE: PRT
<213> ORGANISM: Homo sapiens

<400> SEQUENCE: 157

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Phe Thr Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 158
<211> LENGTH: 175
<212> TYPE: PRT

<213> ORGANISM: Homo sapiens

<400> SEQUENCE: 158

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Thr Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 159
<211> LENGTH: 192
<212> TYPE: PRT
<213> ORGANISM: Homo sapiens

<400> SEQUENCE: 159

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 160
<211> LENGTH: 191
<212> TYPE: PRT
<213> ORGANISM: Homo sapiens

<400> SEQUENCE: 160

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 161
<211> LENGTH: 17
<212> TYPE: PRT
<213> ORGANISM: Homo sapiens

<400> SEQUENCE: 161

Leu Glu Asp Gly Ser Pro Thr Thr Gly Gln Ile Phe Lys Gln Thr Tyr
1               5                   10                  15

Ser

<210> SEQ ID NO 162
<211> LENGTH: 17
<212> TYPE: PRT
<213> ORGANISM: Homo sapiens

<400> SEQUENCE: 162

Leu Glu Asp Gly Ser Pro Thr Thr Ala Gln Ile Phe Lys Gln Thr Tyr
1               5                   10                  15

Ser

<210> SEQ ID NO 163
<211> LENGTH: 17
<212> TYPE: PRT
<213> ORGANISM: Homo sapiens

<400> SEQUENCE: 163

Leu Glu Asp Gly Ser Pro Thr Ala Thr Gln Ile Phe Lys Gln Thr Tyr
1               5                   10                  15

```
                 1               5                  10                 15
Ser

<210> SEQ ID NO 164
<211> LENGTH: 17
<212> TYPE: PRT
<213> ORGANISM: Homo sapiens

<400> SEQUENCE: 164

Leu Glu Asp Gly Ser Pro Thr Gln Gly Ala Met Phe Lys Gln Thr Tyr
 1               5                  10                 15
Ser

<210> SEQ ID NO 165
<211> LENGTH: 17
<212> TYPE: PRT
<213> ORGANISM: Homo sapiens

<400> SEQUENCE: 165

Leu Glu Asp Gly Ser Pro Thr Gln Gly Ala Ile Phe Lys Gln Thr Tyr
 1               5                  10                 15
Ser

<210> SEQ ID NO 166
<211> LENGTH: 17
<212> TYPE: PRT
<213> ORGANISM: Homo sapiens

<400> SEQUENCE: 166

Leu Glu Asp Gly Ser Pro Thr Gln Gly Gln Ile Phe Lys Gln Thr Tyr
 1               5                  10                 15
Ser

<210> SEQ ID NO 167
<211> LENGTH: 17
<212> TYPE: PRT
<213> ORGANISM: Homo sapiens

<400> SEQUENCE: 167

Leu Glu Asp Gly Ser Pro Thr Thr Leu Tyr Val Phe Lys Gln Thr Tyr
 1               5                  10                 15
Ser

<210> SEQ ID NO 168
<211> LENGTH: 17
<212> TYPE: PRT
<213> ORGANISM: Homo sapiens

<400> SEQUENCE: 168

Leu Glu Asp Gly Ser Pro Thr Ile Asn Thr Ile Phe Lys Gln Thr Tyr
 1               5                  10                 15
Ser

<210> SEQ ID NO 169
<211> LENGTH: 17
<212> TYPE: PRT
<213> ORGANISM: Homo sapiens

<400> SEQUENCE: 169

Leu Glu Asp Gly Ser Pro Thr Thr Val Ser Ile Phe Lys Gln Thr Tyr
 1               5                  10                 15
```

Ser

<210> SEQ ID NO 170
<211> LENGTH: 17
<212> TYPE: PRT
<213> ORGANISM: Homo sapiens

<400> SEQUENCE: 170

Leu Glu Asp Gly Ser Pro Arg Thr Gly Gln Ile Pro Thr Gln Thr Tyr
1               5                   10                  15

Ser

<210> SEQ ID NO 171
<211> LENGTH: 17
<212> TYPE: PRT
<213> ORGANISM: Homo sapiens

<400> SEQUENCE: 171

Leu Glu Asp Gly Ser Pro Arg Thr Gly Gln Ile Pro Thr Gln Ala Tyr
1               5                   10                  15

Ser

<210> SEQ ID NO 172
<211> LENGTH: 17
<212> TYPE: PRT
<213> ORGANISM: Homo sapiens

<400> SEQUENCE: 172

Leu Glu Asp Gly Ser Pro Thr Thr Leu Gln Ile Phe Lys Gln Thr Tyr
1               5                   10                  15

Ser

<210> SEQ ID NO 173
<211> LENGTH: 17
<212> TYPE: PRT
<213> ORGANISM: Homo sapiens

<400> SEQUENCE: 173

Leu Glu Thr Glu Thr Pro Arg Thr Gly Gln Ile Phe Lys Gln Thr Tyr
1               5                   10                  15

Ser

<210> SEQ ID NO 174
<211> LENGTH: 17
<212> TYPE: PRT
<213> ORGANISM: Homo sapiens

<400> SEQUENCE: 174

Leu Val Thr Glu Thr Pro Arg Thr Gly Gln Ile Phe Lys Gln Thr Tyr
1               5                   10                  15

Ser

<210> SEQ ID NO 175
<211> LENGTH: 17
<212> TYPE: PRT
<213> ORGANISM: Homo sapiens

<400> SEQUENCE: 175

Leu Glu Thr Gln Ser Pro Arg Thr Gly Gln Ile Phe Lys Gln Thr Tyr
1               5                   10                  15

Ser

<210> SEQ ID NO 176
<211> LENGTH: 17
<212> TYPE: PRT
<213> ORGANISM: Homo sapiens

<400> SEQUENCE: 176

Leu Val Thr Gln Ser Pro Arg Thr Gly Gln Ile Phe Lys Gln Thr Tyr
1               5                   10                  15

Ser

<210> SEQ ID NO 177
<211> LENGTH: 17
<212> TYPE: PRT
<213> ORGANISM: Homo sapiens

<400> SEQUENCE: 177

Leu Val Thr Glu Thr Pro Ala Thr Gly Gln Ile Phe Lys Gln Thr Tyr
1               5                   10                  15

Ser

<210> SEQ ID NO 178
<211> LENGTH: 17
<212> TYPE: PRT
<213> ORGANISM: Homo sapiens

<400> SEQUENCE: 178

Leu Glu Asp Gly Ser Pro Thr Gln Gly Ala Met Pro Lys Gln Thr Tyr
1               5                   10                  15

Ser

<210> SEQ ID NO 179
<211> LENGTH: 17
<212> TYPE: PRT
<213> ORGANISM: Homo sapiens

<400> SEQUENCE: 179

Leu Glu Asp Gly Ser Pro Thr Thr Thr Gln Ile Phe Lys Gln Thr Tyr
1               5                   10                  15

Ser

<210> SEQ ID NO 180
<211> LENGTH: 20
<212> TYPE: PRT
<213> ORGANISM: Homo sapiens

<400> SEQUENCE: 180

Cys Val Ile Gln Gly Val Gly Val Thr Glu Thr Pro Leu Met Lys Glu
1               5                   10                  15

Asp Ser Ile Leu
            20

<210> SEQ ID NO 181
<211> LENGTH: 7
<212> TYPE: PRT
<213> ORGANISM: Homo sapiens

<400> SEQUENCE: 181

Met Thr Pro Leu Gly Pro Ala
1               5

<210> SEQ ID NO 182
<211> LENGTH: 8

```
<212> TYPE: PRT
<213> ORGANISM: Homo sapiens

<400> SEQUENCE: 182

Met Val Thr Pro Leu Gly Pro Ala
1               5

<210> SEQ ID NO 183
<211> LENGTH: 8
<212> TYPE: PRT
<213> ORGANISM: Homo sapiens

<400> SEQUENCE: 183

Met Gln Thr Pro Leu Gly Pro Ala
1               5

<210> SEQ ID NO 184
<211> LENGTH: 8
<212> TYPE: PRT
<213> ORGANISM: Homo sapiens

<400> SEQUENCE: 184

Met Ala Thr Pro Leu Gly Pro Ala
1               5

<210> SEQ ID NO 185
<211> LENGTH: 12
<212> TYPE: PRT
<213> ORGANISM: Homo sapiens

<400> SEQUENCE: 185

Met Pro Thr Gln Gly Ala Met Pro Leu Gly Pro Ala
1               5                   10

<210> SEQ ID NO 186
<211> LENGTH: 9
<212> TYPE: PRT
<213> ORGANISM: Homo sapiens

<400> SEQUENCE: 186

Met Val Gln Thr Pro Leu Gly Pro Ala
1               5

<210> SEQ ID NO 187
<211> LENGTH: 9
<212> TYPE: PRT
<213> ORGANISM: Homo sapiens

<400> SEQUENCE: 187

Met Gln Ser Thr Pro Leu Gly Pro Ala
1               5

<210> SEQ ID NO 188
<211> LENGTH: 9
<212> TYPE: PRT
<213> ORGANISM: Homo sapiens

<400> SEQUENCE: 188

Met Gly Gln Thr Pro Leu Gly Pro Ala
1               5

<210> SEQ ID NO 189
<211> LENGTH: 12
<212> TYPE: PRT
<213> ORGANISM: Homo sapiens
```

<400> SEQUENCE: 189

Met Ala Pro Thr Ser Ser Ser Pro Leu Gly Pro Ala
1               5                   10

<210> SEQ ID NO 190
<211> LENGTH: 6
<212> TYPE: PRT
<213> ORGANISM: Homo sapiens

<400> SEQUENCE: 190

Met Thr Pro Leu Gly Pro
1               5

<210> SEQ ID NO 191
<211> LENGTH: 7
<212> TYPE: PRT
<213> ORGANISM: Homo sapiens

<400> SEQUENCE: 191

Leu Gly His Ser Leu Gly Ile
1               5

<210> SEQ ID NO 192
<211> LENGTH: 6
<212> TYPE: PRT
<213> ORGANISM: Homo sapiens

<400> SEQUENCE: 192

Pro Ala Leu Gln Pro Thr
1               5

<210> SEQ ID NO 193
<211> LENGTH: 6
<212> TYPE: PRT
<213> ORGANISM: Homo sapiens

<400> SEQUENCE: 193

Arg His Leu Ala Gln Pro
1               5

<210> SEQ ID NO 194
<211> LENGTH: 177
<212> TYPE: PRT
<213> ORGANISM: Homo sapiens

<400> SEQUENCE: 194

Met Ile Ala Thr Pro Leu Gly Pro Ala Ser Ser Leu Pro Gln Ser Phe
1               5                   10                  15

Leu Leu Lys Cys Leu Glu Gln Val Arg Lys Ile Gln Gly Asp Gly Ala
            20                  25                  30

Ala Leu Gln Glu Lys Leu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
                85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

```
Met Ala Pro Ala Leu Gln Pro Thr Gln Gly Ala Met Pro Ala Phe Ala
        130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 195
<211> LENGTH: 175
<212> TYPE: PRT
<213> ORGANISM: Homo sapiens

<400> SEQUENCE: 195

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Tyr Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 196
<211> LENGTH: 193
<212> TYPE: PRT
<213> ORGANISM: Homo sapiens

<400> SEQUENCE: 196

Met Val Thr Pro Thr Ile Pro Leu Ser Arg Leu Phe Asp Asn Ala Met
1               5                   10                  15

Leu Arg Ala His Arg Leu His Gln Leu Ala Phe Asp Thr Tyr Gln Glu
                20                  25                  30

Phe Glu Glu Ala Tyr Ile Pro Lys Glu Gln Lys Tyr Ser Phe Leu Gln
            35                  40                  45

Asn Pro Gln Thr Ser Leu Cys Phe Ser Glu Ser Ile Pro Thr Pro Ser
    50                  55                  60

Asn Arg Glu Glu Thr Gln Gln Lys Ser Asn Leu Glu Leu Leu Arg Ile
65                  70                  75                  80

Ser Leu Leu Leu Ile Gln Ser Trp Leu Glu Pro Val Gln Phe Leu Arg
                85                  90                  95

Ser Val Phe Ala Asn Ser Leu Val Tyr Gly Ala Ser Asp Ser Asn Val
```

```
            100             105             110
Tyr Asp Leu Leu Lys Asp Leu Glu Glu Gly Ile Gln Thr Leu Met Gly
        115                 120                 125

Arg Leu Glu Asp Gly Ser Pro Arg Thr Gly Gln Ile Phe Lys Gln Thr
    130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
            180                 185                 190

Phe

<210> SEQ ID NO 197
<211> LENGTH: 192
<212> TYPE: PRT
<213> ORGANISM: Homo sapiens

<400> SEQUENCE: 197

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Gln Gly Ala Met Pro Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 198
<211> LENGTH: 192
<212> TYPE: PRT
<213> ORGANISM: Homo sapiens

<400> SEQUENCE: 198

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45
```

```
Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Thr Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 199
<211> LENGTH: 196
<212> TYPE: PRT
<213> ORGANISM: Homo sapiens

<400> SEQUENCE: 199

```
Met Ala Pro Thr Ser Ser Pro Thr Ile Pro Leu Ser Arg Leu Phe Asp
1               5                   10                  15

Asn Ala Met Leu Arg Ala His Arg Leu His Gln Leu Ala Phe Asp Thr
                20                  25                  30

Tyr Gln Glu Phe Glu Glu Ala Tyr Ile Pro Lys Glu Gln Lys Tyr Ser
            35                  40                  45

Phe Leu Gln Asn Pro Gln Thr Ser Leu Cys Phe Ser Glu Ser Ile Pro
    50                  55                  60

Thr Pro Ser Asn Arg Glu Glu Thr Gln Gln Lys Ser Asn Leu Glu Leu
65                  70                  75                  80

Leu Arg Ile Ser Leu Leu Leu Ile Gln Ser Trp Leu Glu Pro Val Gln
                85                  90                  95

Phe Leu Arg Ser Val Phe Ala Asn Ser Leu Val Tyr Gly Ala Ser Asp
            100                 105                 110

Ser Asn Val Tyr Asp Leu Leu Lys Asp Leu Glu Glu Gly Ile Gln Thr
        115                 120                 125

Leu Met Gly Arg Leu Glu Asp Gly Ser Pro Arg Thr Gly Gln Ile Phe
    130                 135                 140

Lys Gln Thr Tyr Ser Lys Phe Asp Thr Asn Ser His Asn Asp Asp Ala
145                 150                 155                 160

Leu Leu Lys Asn Tyr Gly Leu Leu Tyr Cys Phe Arg Lys Asp Met Asp
                165                 170                 175

Lys Val Glu Thr Phe Leu Arg Ile Val Gln Cys Arg Ser Val Glu Gly
            180                 185                 190

Ser Cys Gly Phe
        195
```

<210> SEQ ID NO 200
<211> LENGTH: 192
<212> TYPE: PRT
<213> ORGANISM: Homo sapiens

<400> SEQUENCE: 200

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Asn Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 201
<211> LENGTH: 7
<212> TYPE: PRT
<213> ORGANISM: Homo sapiens

<400> SEQUENCE: 201

Pro Thr Gln Gly Ala Met Pro
1               5

<210> SEQ ID NO 202
<211> LENGTH: 20
<212> TYPE: PRT
<213> ORGANISM: Homo sapiens

<400> SEQUENCE: 202

Cys Val Ile Gln Glu Val Gly Val Glu Glu Thr Pro Leu Met Asn Glu
1               5                   10                  15

Asp Ser Ile Leu
            20

<210> SEQ ID NO 203
<211> LENGTH: 20
<212> TYPE: PRT
<213> ORGANISM: Homo sapiens

<400> SEQUENCE: 203

Cys Val Ile Gln Glu Val Gly Val Glu Glu Thr Pro Leu Met Asn Glu
1               5                   10                  15

Asp Ser Ile Leu
            20

<210> SEQ ID NO 204
<211> LENGTH: 20

```
<212> TYPE: PRT
<213> ORGANISM: Homo sapiens

<400> SEQUENCE: 204

Cys Val Ile Gln Glu Val Gly Met Glu Glu Thr Pro Leu Met Asn Glu
1               5                   10                  15

Asp Ser Ile Leu
            20

<210> SEQ ID NO 205
<211> LENGTH: 20
<212> TYPE: PRT
<213> ORGANISM: Homo sapiens

<400> SEQUENCE: 205

Cys Val Ile Gln Glu Val Gly Val Glu Glu Thr Pro Leu Met Asn Val
1               5                   10                  15

Asp Phe Ile Leu
            20

<210> SEQ ID NO 206
<211> LENGTH: 20
<212> TYPE: PRT
<213> ORGANISM: Homo sapiens

<400> SEQUENCE: 206

Cys Val Ile Gln Glu Val Gly Val Glu Glu Thr Pro Leu Met Asn Val
1               5                   10                  15

Asp Ser Ile Leu
            20

<210> SEQ ID NO 207
<211> LENGTH: 20
<212> TYPE: PRT
<213> ORGANISM: Homo sapiens

<400> SEQUENCE: 207

Cys Val Met Gln Glu Val Gly Val Ile Glu Ser Pro Leu Met Tyr Glu
1               5                   10                  15

Asp Ser Ile Leu
            20

<210> SEQ ID NO 208
<211> LENGTH: 20
<212> TYPE: PRT
<213> ORGANISM: Homo sapiens

<400> SEQUENCE: 208

Cys Val Ile Gln Glu Val Gly Val Glu Glu Thr Pro Leu Met Asn Val
1               5                   10                  15

Asp Ser Ile Leu
            20

<210> SEQ ID NO 209
<211> LENGTH: 20
<212> TYPE: PRT
<213> ORGANISM: Homo sapiens

<400> SEQUENCE: 209

Cys Met Met Gln Glu Val Gly Val Glu Asp Thr Pro Leu Met Asn Val
1               5                   10                  15

Asp Ser Ile Leu
            20
```

```
<210> SEQ ID NO 210
<211> LENGTH: 20
<212> TYPE: PRT
<213> ORGANISM: Homo sapiens

<400> SEQUENCE: 210

Cys Val Thr Gln Glu Val Gly Val Glu Glu Ile Ala Leu Met Asn Glu
1               5                   10                  15

Asp Ser Ile Leu
            20

<210> SEQ ID NO 211
<211> LENGTH: 20
<212> TYPE: PRT
<213> ORGANISM: Homo sapiens

<400> SEQUENCE: 211

Cys Val Met Gln Glu Val Trp Val Gly Gly Thr Pro Leu Met Asn Glu
1               5                   10                  15

Asp Ser Ile Leu
            20

<210> SEQ ID NO 212
<211> LENGTH: 20
<212> TYPE: PRT
<213> ORGANISM: Homo sapiens

<400> SEQUENCE: 212

Cys Val Met Gln Glu Glu Arg Val Gly Glu Thr Pro Leu Met Asn Ala
1               5                   10                  15

Asp Ser Ile Leu
            20

<210> SEQ ID NO 213
<211> LENGTH: 11
<212> TYPE: PRT
<213> ORGANISM: Homo sapiens

<400> SEQUENCE: 213

Leu Gly Ile Pro Trp Ala Pro Leu Ser Ser Cys
1               5                   10

<210> SEQ ID NO 214
<211> LENGTH: 9
<212> TYPE: PRT
<213> ORGANISM: Artificial Sequence
<220> FEATURE:
<223> OTHER INFORMATION: G-CSF Mutant-1
<220> FEATURE:
<221> NAME/KEY: VARIANT
<222> LOCATION: (2)..(2)
<223> OTHER INFORMATION: Xaa is Thr or Ser
<220> FEATURE:
<221> NAME/KEY: VARIANT
<222> LOCATION: (3)..(3)
<223> OTHER INFORMATION: Xaa may be present or absent; when present, Xaa
      is Thr or Ser
<220> FEATURE:
<221> NAME/KEY: VARIANT
<222> LOCATION: (4)..(4)
<223> OTHER INFORMATION: Xaa may be present or absent; when present, Xaa
      is Thr or Ser

<400> SEQUENCE: 214

Met Xaa Xaa Xaa Thr Pro Leu Gly Pro
1               5
```

```
<210> SEQ ID NO 215
<211> LENGTH: 16
<212> TYPE: PRT
<213> ORGANISM: Artificial Sequence
<220> FEATURE:
<223> OTHER INFORMATION: G-CSF Mutant-2
<220> FEATURE:
<221> NAME/KEY: VARIANT
<222> LOCATION: (2)..(2)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (3)..(3)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (4)..(4)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (6)..(6)
<223> OTHER INFORMATION: Xaa may be present or absent; when present, Xaa
      is Glu or an uncharged amino acid
<220> FEATURE:
<221> NAME/KEY: VARIANT
<222> LOCATION: (7)..(7)
<223> OTHER INFORMATION: Xaa may be present or absent; when present, Xaa
      is Glu or an uncharged amino acid
<220> FEATURE:
<221> NAME/KEY: VARIANT
<222> LOCATION: (8)..(8)
<223> OTHER INFORMATION: Xaa may be present or absent; when present, Xaa
      is Glu or an uncharged amino acid
<220> FEATURE:
<221> NAME/KEY: VARIANT
<222> LOCATION: (9)..(9)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (10)..(10)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (11)..(11)
<223> OTHER INFORMATION: Xaa may be present or absent; when present, Xaa
      is any amino acid with the proviso that at least one of Xaa at
      position 2-4 or 9-11 is Thr or Ser

<400> SEQUENCE: 215

Met Xaa Xaa Xaa Pro Xaa Xaa Xaa Xaa Xaa Xaa Thr Pro Leu Gly Pro
1               5                   10                  15

<210> SEQ ID NO 216
<211> LENGTH: 13
<212> TYPE: PRT
<213> ORGANISM: Artificial Sequence
<220> FEATURE:
<223> OTHER INFORMATION: G-CSF Mutant-3
<220> FEATURE:
<221> NAME/KEY: VARIANT
<222> LOCATION: (4)..(4)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
```

```
<222> LOCATION: (5)..(5)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (6)..(6)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (7)..(7)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (8)..(8)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (9)..(9)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (10)..(10)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (11)..(11)
<223> OTHER INFORMATION: Xaa may be present or absent and may be any
      amino acid with the proviso that at least one of Xaa at position
      4-12 is Thr or Ser
<220> FEATURE:
<221> NAME/KEY: VARIANT
<222> LOCATION: (12)..(12)
<223> OTHER INFORMATION: Xaa may be present or absent and may be any
      amino acid with the proviso that at least one of Xaa at position
      4-12 is Thr or Ser

<400> SEQUENCE: 216

Met Thr Pro Xaa Xaa Xaa Xaa Xaa Xaa Xaa Xaa Xaa Pro
1               5                   10

<210> SEQ ID NO 217
<211> LENGTH: 9
<212> TYPE: PRT
<213> ORGANISM: Artificial Sequence
<220> FEATURE:
<223> OTHER INFORMATION: G-CSF Mutant-4
<220> FEATURE:
<221> NAME/KEY: VARIANT
<222> LOCATION: (3)..(3)
<223> OTHER INFORMATION: Xaa is His, Ser, Arg, Glu, or Tyr
<220> FEATURE:
<221> NAME/KEY: VARIANT
<222> LOCATION: (4)..(4)
<223> OTHER INFORMATION: Xaa may be present or absent; when present, Xaa
      is Thr or Ser
<220> FEATURE:
<221> NAME/KEY: VARIANT
<222> LOCATION: (5)..(5)
<223> OTHER INFORMATION: Xaa may be present or absent; when present, Xaa
      is Thr or Ser
<220> FEATURE:
<221> NAME/KEY: VARIANT
<222> LOCATION: (6)..(6)
<223> OTHER INFORMATION: Xaa may be present or absent; when present, Xaa
      is Thr or Ser

<400> SEQUENCE: 217
```

Leu Gly Xaa Xaa Xaa Xaa Leu Gly Ile
1               5

<210> SEQ ID NO 218
<211> LENGTH: 15
<212> TYPE: PRT
<213> ORGANISM: Artificial Sequence
<220> FEATURE:
<223> OTHER INFORMATION: G-CSF Mutant-5
<220> FEATURE:
<221> NAME/KEY: VARIANT
<222> LOCATION: (2)..(2)
<223> OTHER INFORMATION: Xaa may be present or absent; when present, Xaa is Thr or Ser
<220> FEATURE:
<221> NAME/KEY: VARIANT
<222> LOCATION: (3)..(3)
<223> OTHER INFORMATION: Xaa may be present or absent; when present, Xaa is Thr or Ser
<220> FEATURE:
<221> NAME/KEY: VARIANT
<222> LOCATION: (4)..(4)
<223> OTHER INFORMATION: Xaa may be present or absent; when present, Xaa is Thr or Ser
<220> FEATURE:
<221> NAME/KEY: VARIANT
<222> LOCATION: (5)..(5)
<223> OTHER INFORMATION: Xaa may be present or absent; when present, Xaa is Thr or Ser
<220> FEATURE:
<221> NAME/KEY: VARIANT
<222> LOCATION: (6)..(6)
<223> OTHER INFORMATION: Xaa may be present or absent; when present, Xaa is Thr or Ser
<220> FEATURE:
<221> NAME/KEY: VARIANT
<222> LOCATION: (7)..(7)
<223> OTHER INFORMATION: Xaa may be present or absent; when present, Xaa is Thr or Ser
<220> FEATURE:
<221> NAME/KEY: VARIANT
<222> LOCATION: (8)..(8)
<223> OTHER INFORMATION: Xaa may be present or absent; when present, Xaa is Thr or Ser
<220> FEATURE:
<221> NAME/KEY: VARIANT
<222> LOCATION: (9)..(9)
<223> OTHER INFORMATION: Xaa may be present or absent; when present, Xaa is Thr or Ser
<220> FEATURE:
<221> NAME/KEY: VARIANT
<222> LOCATION: (10)..(10)
<223> OTHER INFORMATION: Xaa may be present or absent; when present, Xaa is Thr or Ser
<220> FEATURE:
<221> NAME/KEY: VARIANT
<222> LOCATION: (11)..(11)
<223> OTHER INFORMATION: Xaa may be present or absent; when present, Xaa is Thr or Ser
<220> FEATURE:
<221> NAME/KEY: VARIANT
<222> LOCATION: (12)..(12)
<223> OTHER INFORMATION: Xaa may be present or absent; when present, Xaa is Thr or Ser
<220> FEATURE:
<221> NAME/KEY: VARIANT
<222> LOCATION: (13)..(13)
<223> OTHER INFORMATION: Xaa may be present or absent; when present, Xaa is Thr or Ser

<400> SEQUENCE: 218

Pro Xaa Xaa Xaa Xaa Xaa Xaa Xaa Xaa Xaa Xaa Xaa Pro Thr
1               5                   10                  15

<210> SEQ ID NO 219
<211> LENGTH: 21

```
<212> TYPE: PRT
<213> ORGANISM: Artificial Sequence
<220> FEATURE:
<223> OTHER INFORMATION: G-CSF Mutant-6
<220> FEATURE:
<221> NAME/KEY: VARIANT
<222> LOCATION: (2)..(2)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (3)..(3)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (4)..(4)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (5)..(5)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (6)..(6)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (7)..(7)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (8)..(8)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (9)..(9)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (10)..(10)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (12)..(12)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (13)..(13)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (14)..(14)
<223> OTHER INFORMATION: Xaa is Thr or Ser and may be present or absent,
      with the proviso that at least one of Xaa at position 2-10 or
      12-14 is Thr or Ser
<220> FEATURE:
<221> NAME/KEY: VARIANT
<222> LOCATION: (15)..(15)
<223> OTHER INFORMATION: Xaa may be present or absent; when present, Xaa
```

-continued

```
      is Glu or any uncharged amino acid
<220> FEATURE:
<221> NAME/KEY: VARIANT
<222> LOCATION: (16)..(16)
<223> OTHER INFORMATION: Xaa may be present or absent; when present, Xaa
      is Glu or any uncharged amino acid
<220> FEATURE:
<221> NAME/KEY: VARIANT
<222> LOCATION: (17)..(17)
<223> OTHER INFORMATION: Xaa may be present or absent; when present, Xaa
      is Glu or any uncharged amino acid
<220> FEATURE:
<221> NAME/KEY: VARIANT
<222> LOCATION: (18)..(18)
<223> OTHER INFORMATION: Xaa may be present or absent; when present, Xaa
      is Glu or any uncharged amino acid
<220> FEATURE:
<221> NAME/KEY: VARIANT
<222> LOCATION: (19)..(19)
<223> OTHER INFORMATION: Xaa may be present or absent; when present, Xaa
      is Glu or any uncharged amino acid
<220> FEATURE:
<221> NAME/KEY: VARIANT
<222> LOCATION: (20)..(20)
<223> OTHER INFORMATION: Xaa may be present or absent; when present, Xaa
      is Glu or any uncharged amino acid

<400> SEQUENCE: 219

Pro Xaa Xaa Xaa Xaa Xaa Xaa Xaa Xaa Xaa Pro Xaa Xaa Xaa Xaa Xaa
1               5                   10                  15

Xaa Xaa Xaa Xaa Cys
            20

<210> SEQ ID NO 220
<211> LENGTH: 28
<212> TYPE: PRT
<213> ORGANISM: Artificial Sequence
<220> FEATURE:
<223> OTHER INFORMATION: G-CSF Mutant-7
<220> FEATURE:
<221> NAME/KEY: VARIANT
<222> LOCATION: (1)..(1)
<223> OTHER INFORMATION: Xaa may be present or absent; when present, Xaa
      is Arg, Thr, or Ser, with the proviso that at least one of Xaa at
      positions 1-12 or 14-25 is Thr or Ser
<220> FEATURE:
<221> NAME/KEY: VARIANT
<222> LOCATION: (2)..(2)
<223> OTHER INFORMATION: Xaa may be present or absent; when present, Xaa
      is Arg, Thr, or Ser, with the proviso that at least one of Xaa at
      positions 1-12 or 14-25 is Thr or Ser
<220> FEATURE:
<221> NAME/KEY: VARIANT
<222> LOCATION: (3)..(3)
<223> OTHER INFORMATION: Xaa may be present or absent; when present, Xaa
      is Arg, Thr, or Ser, with the proviso that at least one of Xaa at
      positions 1-12 or 14-25 is Thr or Ser
<220> FEATURE:
<221> NAME/KEY: VARIANT
<222> LOCATION: (4)..(4)
<223> OTHER INFORMATION: Xaa may be present or absent; when present, Xaa
      is His, Thr, or Ser, with the proviso that at least one of Xaa at
      positions 1-12 or 14-25 is Thr or Ser
<220> FEATURE:
<221> NAME/KEY: VARIANT
<222> LOCATION: (5)..(5)
<223> OTHER INFORMATION: Xaa may be present or absent; when present, Xaa
      is His, Thr, or Ser, with the proviso that at least one of Xaa at
      positions 1-12 or 14-25 is Thr or Ser
<220> FEATURE:
<221> NAME/KEY: VARIANT
<222> LOCATION: (6)..(6)
<223> OTHER INFORMATION: Xaa may be present or absent; when present, Xaa
      is His, Thr, or Ser, with the proviso that at least one of Xaa at
      positions 1-12 or 14-25 is Thr or Ser
<220> FEATURE:
<221> NAME/KEY: VARIANT
```

-continued

```
<222> LOCATION: (7)..(7)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (8)..(8)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (9)..(9)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (10)..(10)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (11)..(11)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (12)..(12)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (14)..(14)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (15)..(15)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (16)..(16)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (17)..(17)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (18)..(18)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (19)..(19)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (20)..(20)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (21)..(21)
<223> OTHER INFORMATION: Xaa may be present or absent; when present, Xaa
```

-continued

```
      is Thr or Ser, with the proviso that at least one of Xaa at
      positions 1-12 or 14-25 is Thr or Ser
<220> FEATURE:
<221> NAME/KEY: VARIANT
<222> LOCATION: (22)..(22)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (23)..(23)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (24)..(24)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (25)..(25)
<223> OTHER INFORMATION: Xaa may be present or absent; when present, Xaa
      is Thr or Ser, with the proviso that at least one of Xaa at
      positions 1-12 or 14-25 is Thr or Ser
<220> FEATURE:
<221> NAME/KEY: VARIANT
<222> LOCATION: (26)..(26)
<223> OTHER INFORMATION: Xaa may be present or absent; when present, Xaa
      is Glu or any uncharged amino acid
<220> FEATURE:
<221> NAME/KEY: VARIANT
<222> LOCATION: (27)..(27)
<223> OTHER INFORMATION: Xaa may be present or absent; when present, Xaa
      is Glu or any uncharged amino acid
<220> FEATURE:
<221> NAME/KEY: VARIANT
<222> LOCATION: (28)..(28)
<223> OTHER INFORMATION: Xaa may be present or absent; when present, Xaa
      is Glu or any uncharged amino acid

<400> SEQUENCE: 220

Xaa Xaa Xaa Xaa Xaa Xaa Xaa Xaa Xaa Xaa Xaa Xaa Pro Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 221
<211> LENGTH: 12
<212> TYPE: PRT
<213> ORGANISM: Artificial Sequence
<220> FEATURE:
<223> OTHER INFORMATION: hGH Mutant-1
<220> FEATURE:
<221> NAME/KEY: VARIANT
<222> LOCATION: (2)..(2)
<223> OTHER INFORMATION: Xaa is Thr or Arg
<220> FEATURE:
<221> NAME/KEY: VARIANT
<222> LOCATION: (3)..(3)
<223> OTHER INFORMATION: Xaa is Ala, Gln, Ile, or Thr
<220> FEATURE:
<221> NAME/KEY: VARIANT
<222> LOCATION: (4)..(4)
<223> OTHER INFORMATION: Xaa is Gly, Ala, Leu, Val, Asn, Gln, or Thr
<220> FEATURE:
<221> NAME/KEY: VARIANT
<222> LOCATION: (5)..(5)
<223> OTHER INFORMATION: Xaa is Tyr, Ser, Ala, or Thr
<220> FEATURE:
<221> NAME/KEY: VARIANT
<222> LOCATION: (6)..(6)
<223> OTHER INFORMATION: Xaa is Ile or Met
<220> FEATURE:
<221> NAME/KEY: VARIANT
<222> LOCATION: (7)..(7)
```

-continued

<223> OTHER INFORMATION: Xaa is Phe or Pro

<400> SEQUENCE: 221

Pro Xaa Xaa Xaa Xaa Xaa Xaa Lys Gln Thr Tyr Ser
1               5                   10

<210> SEQ ID NO 222
<211> LENGTH: 12
<212> TYPE: PRT
<213> ORGANISM: Artificial Sequence
<220> FEATURE:
<223> OTHER INFORMATION: hGH Mutant-2
<220> FEATURE:
<221> NAME/KEY: VARIANT
<222> LOCATION: (10)..(10)
<223> OTHER INFORMATION: Xaa is Ala or Thr

<400> SEQUENCE: 222

Pro Arg Thr Gly Gln Ile Pro Thr Gln Xaa Tyr Ser
1               5                   10

<210> SEQ ID NO 223
<211> LENGTH: 9
<212> TYPE: PRT
<213> ORGANISM: Artificial Sequence
<220> FEATURE:
<223> OTHER INFORMATION: hGH Mutant-3
<220> FEATURE:
<221> NAME/KEY: VARIANT
<222> LOCATION: (2)..(2)
<223> OTHER INFORMATION: Xaa is Glu, Val, or Ala
<220> FEATURE:
<221> NAME/KEY: VARIANT
<222> LOCATION: (4)..(4)
<223> OTHER INFORMATION: Xaa is Gln, Glu, or Gly
<220> FEATURE:
<221> NAME/KEY: VARIANT
<222> LOCATION: (5)..(5)
<223> OTHER INFORMATION: Xaa is Ser or Thr
<220> FEATURE:
<221> NAME/KEY: VARIANT
<222> LOCATION: (7)..(7)
<223> OTHER INFORMATION: Xaa is Arg, Ser, Ala, or Leu

<400> SEQUENCE: 223

Leu Xaa Thr Xaa Xaa Pro Xaa Thr Gly
1               5

<210> SEQ ID NO 224
<211> LENGTH: 16
<212> TYPE: PRT
<213> ORGANISM: Artificial Sequence
<220> FEATURE:
<223> OTHER INFORMATION: hGH Mutant-4
<220> FEATURE:
<221> NAME/KEY: VARIANT
<222> LOCATION: (2)..(2)
<223> OTHER INFORMATION: Xaa is Phe, Val, or Ala
<220> FEATURE:
<221> NAME/KEY: VARIANT
<222> LOCATION: (3)..(3)
<223> OTHER INFORMATION: Xaa may be present or absent; when present, Xaa
      is Phe, Val, or Ala
<220> FEATURE:
<221> NAME/KEY: VARIANT
<222> LOCATION: (4)..(4)
<223> OTHER INFORMATION: Xaa may be present or absent; when present, Xaa
      is Phe, Val, or Ala
<220> FEATURE:
<221> NAME/KEY: VARIANT
<222> LOCATION: (7)..(7)
<223> OTHER INFORMATION: Xaa may be present or absent; when present, Xaa
      is Glu, Val, or Pro
<220> FEATURE:

```
<221> NAME/KEY: VARIANT
<222> LOCATION: (8)..(8)
<223> OTHER INFORMATION: Xaa is Glu, Val, or Pro and may be present or
      absent, with the proviso that when Xaa at position 7 is present,
      Xaa at position 8 also is present
<220> FEATURE:
<221> NAME/KEY: VARIANT
<222> LOCATION: (9)..(9)
<223> OTHER INFORMATION: Xaa may be present or absent; when present, Xaa
      is Thr
<220> FEATURE:
<221> NAME/KEY: VARIANT
<222> LOCATION: (10)..(10)
<223> OTHER INFORMATION: Xaa is Thr and may be present or absent, with
      the provisos that when Xaa at positions 7 and 8 are Pro and Xaa at
      position 9 is present, then Xaa at position 10 also is present
<220> FEATURE:
<221> NAME/KEY: VARIANT
<222> LOCATION: (11)..(11)
<223> OTHER INFORMATION: Xaa is Leu or Ile

<400> SEQUENCE: 224

Met Xaa Xaa Xaa Pro Thr Xaa Xaa Xaa Xaa Xaa Pro Leu Ser Arg Leu
1               5                   10                  15

<210> SEQ ID NO 225
<211> LENGTH: 9
<212> TYPE: PRT
<213> ORGANISM: Artificial Sequence
<220> FEATURE:
<223> OTHER INFORMATION: G-CSF Mutant-8
<220> FEATURE:
<221> NAME/KEY: VARIANT
<222> LOCATION: (4)..(4)
<223> OTHER INFORMATION: Xaa is Thr or Ser
<220> FEATURE:
<221> NAME/KEY: VARIANT
<222> LOCATION: (5)..(5)
<223> OTHER INFORMATION: Xaa is Thr or Ser
<220> FEATURE:
<221> NAME/KEY: VARIANT
<222> LOCATION: (6)..(6)
<223> OTHER INFORMATION: Xaa may be present or absent, when present, Xaa
      is Thr or Ser
<220> FEATURE:
<221> NAME/KEY: VARIANT
<222> LOCATION: (7)..(7)
<223> OTHER INFORMATION: Xaa may be present or absent, when present, Xaa
      is Thr or Ser
<220> FEATURE:
<221> NAME/KEY: VARIANT
<222> LOCATION: (8)..(8)
<223> OTHER INFORMATION: Xaa may be present or absent, when present, Xaa
      is Thr or Ser

<400> SEQUENCE: 225

Met Thr Pro Xaa Xaa Xaa Xaa Xaa Pro
1               5

<210> SEQ ID NO 226
<211> LENGTH: 10
<212> TYPE: PRT
<213> ORGANISM: Artificial Sequence
<220> FEATURE:
<223> OTHER INFORMATION: G-CSF Mutant-9
<220> FEATURE:
<221> NAME/KEY: VARIANT
<222> LOCATION: (2)..(2)
<223> OTHER INFORMATION: Xaa is Thr or Ser
<220> FEATURE:
<221> NAME/KEY: VARIANT
<222> LOCATION: (3)..(3)
<223> OTHER INFORMATION: Xaa may be present or absent; when present, Xaa
      is Thr or Ser
<220> FEATURE:
<221> NAME/KEY: VARIANT
```

```
<222> LOCATION: (4)..(4)
<223> OTHER INFORMATION: Xaa may be present or absent; when present, Xaa
      is Thr or Ser

<400> SEQUENCE: 226

Met Xaa Xaa Xaa Thr Pro Leu Gly Pro Ala
1               5                   10

<210> SEQ ID NO 227
<211> LENGTH: 17
<212> TYPE: PRT
<213> ORGANISM: Artificial Sequence
<220> FEATURE:
<223> OTHER INFORMATION: G-CSF Mutant-10
<220> FEATURE:
<221> NAME/KEY: VARIANT
<222> LOCATION: (2)..(2)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (3)..(3)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (4)..(4)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (6)..(6)
<223> OTHER INFORMATION: Xaa may be present or absent; when present, Xaa
      is any amino acid
<220> FEATURE:
<221> NAME/KEY: VARIANT
<222> LOCATION: (7)..(7)
<223> OTHER INFORMATION: Xaa may be present or absent; when present, Xaa
      is any amino acid
<220> FEATURE:
<221> NAME/KEY: VARIANT
<222> LOCATION: (8)..(8)
<223> OTHER INFORMATION: Xaa may be present or absent; when present, Xaa
      is any amino acid
<220> FEATURE:
<221> NAME/KEY: VARIANT
<222> LOCATION: (9)..(9)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (10)..(10)
<223> OTHER INFORMATION: Xaa may be present or absent; when present, Xaa
      is any amino acid with the proviso that at least one of Xaa at
      position 2-4 or 9-11 is Thr or Ser
<220> FEATURE:
<221> NAME/KEY: VARIANT
<222> LOCATION: (11)..(11)
<223> OTHER INFORMATION: Xaa may be present or absent; when present, Xaa
      is any amino acid with the proviso that at least one of Xaa at
      position 2-4 or 9-11 is Thr or Ser

<400> SEQUENCE: 227

Met Xaa Xaa Xaa Pro Xaa Xaa Xaa Xaa Xaa Xaa Thr Pro Leu Gly Pro
1               5                   10                  15

Ala

<210> SEQ ID NO 228
<211> LENGTH: 7
<212> TYPE: PRT
<213> ORGANISM: Homo sapiens
```

<400> SEQUENCE: 228

Met Thr Pro Thr Leu Gly Pro
1               5

What is claimed is:

1. An isolated mutant G-CSF polypeptide comprising the wild-type G-CSF sequence SEQ ID NO: 143 wherein the sequence M¹TPLGP (SEQ ID NO: 190) in SEQ ID NO: 143 is replaced with a mutant peptide sequence, wherein the mutant peptide sequence encodes an O-linked glycosylation site that does not exist in the wild-type G-CSF polypeptide, and wherein the mutant peptide sequence is selected from the group consisting of: MVTPLGP (SEQ ID NO: 1), MQTPLGP (SEQ ID NO: 2), MIATPLGP (SEQ ID NO: 3), MPTQGAMPLGP (SEQ ID NO: 5), MVQTPLGP (SEQ ID NO: 6), MQSTPLGP (SEQ ID NO: 7), MGQTPLGP (SEQ ID NO: 8), MAPTSSSPLGP (SEQ ID NO: 9), MAPTPLGPA (SEQ ID NO: 10), MTPTLGP (SEQ ID NO: 11), MTPTQLGP (SEQ ID NO: 12), MTPTSLGP (SEQ ID NO: 13), MTPTQGP (SEQ ID NO: 14), MTPTSSP (SEQ ID NO: 15), MTPQTP (SEQ ID NO: 16), MTPTGP (SEQ ID NO: 17), MTPLTP (SEQ ID NO: 18), MTPNTGP (SEQ ID NO: 19), MTPVTP (SEQ ID NO: 20), MTPMVTP (SEQ ID NO: 21), and MTPTQGLGPAS (SEQ ID NO: 22).

2. The mutant G-CSF polypeptide of claim 1, wherein the mutant peptide sequence is selected from the group consisting of: MVTPLGP (SEQ ID NO: 1), MQTPLGP (SEQ ID NO: 2), MIATPLGP (SEQ ID NO: 3), MPTQGAMPLGP (SEQ ID NO: 5), MVQTPLGP (SEQ ID NO: 6), MQSTPLGP (SEQ ID NO: 7), MGQTPLGP (SEQ ID NO: 8), MAPTSSSPLGP (SEQ ID NO: 9), MAPTPLGPA (SEQ ID NO: 10).

3. The mutant G-CSF polypeptide of claim 1, wherein the mutant peptide sequence is selected from the group consisting of: MTPTLGP (SEQ ID NO: 11), MTPTQLGP (SEQ ID NO: 12), MTPTSLGP (SEQ ID NO: 13), MTPTQGP (SEQ ID NO: 14), MTPTSSP (SEQ ID NO: 15), MTPQTP (SEQ ID NO: 16), MTPTGP (SEQ ID NO: 17), MTPLTP (SEQ ID NO: 18), MTPNTGP (SEQ ID NO: 19), MTPVTP (SEQ ID NO: 20), MTPMVTP (SEQ ID NO: 21), and MTPTQGLGPAS (SEQ ID NO: 22).

4. An isolated nucleic acid encoding the mutant G-CSF polypeptide of claim 1.

5. An expression cassette comprising the nucleic acid of claim 4.

6. A cell comprising the nucleic acid of claim 4.

7. The mutant G-CSF polypeptide of claim 1, further comprising a formula selected from:

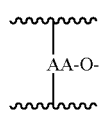 
AA-O-GalNAc-X; and    AA-O-GalNAc-X wherein AA is an amino acid with a side chain that comprises a hydroxyl moiety that is within the mutant peptide sequence; and X comprises a modifying group or a saccharyl moiety.

8. The polypeptide according to claim 7, wherein X comprises a group selected from sialyl, galactosyl and Gal-Sia moieties, wherein at least one of said sialyl, galactosyl and Gal-Sia comprises a modifying group.

9. The polypeptide according to claim 7, wherein X comprises the moiety:

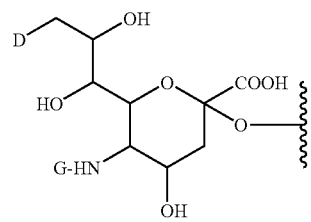

wherein

D is a member selected from —OH and R¹-L-HN—;

G is a member selected from R¹-L- and —C(O)(C₁-C₆)alkyl;

R¹ is a moiety comprising a member selected a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is R¹-L-, and when G is —C(O)(C₁-C₆)alkyl, D is R¹-L-NH—.

10. The polypeptide according to claim 7, wherein X comprises the structure:

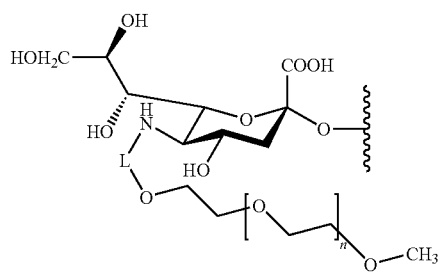

in which L is a substituted or unsubstituted alkyl or substituted or unsubstituted heteroalkyl group; and n is selected from the integers from 0 to about 500.

11. The polypeptide according to claim 7, wherein X comprises the structure:

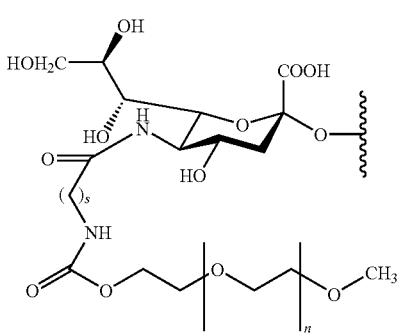

wherein s is selected from the integers from 0 to 20 and n is selected from the integers from 0 to about 500.

12. A method for making a glycoconjugate of the mutant G-CSF polypeptide of claim 1, comprising the steps of:
(a) recombinantly producing the mutant G-CSF polypeptide of claim 1, and
(b) enzymatically glycosylating the mutant G-CSF polypeptide with a modified sugar at said O-linked glycosylation site.

13. A pharmaceutical composition of a granulocyte colony stimulating factor (G-CSF) comprising: an effective amount of the mutant G-CSF polypeptide of claim 1, wherein said mutant G-CSF polypeptide is glycoconjugated with a modified sugar.

14. The pharmaceutical composition according to claim 13, wherein said modified sugar is modified with a member selected from poly(ethylene glycol) and methoxy-poly(ethylene glycol) (m-PEG).

15. A method of providing G-CSF therapy to a subject in need of said therapy, said method comprising, administering to said subject an effective amount the pharmaceutical composition of claim 13.

* * * * *